United States Patent
Marion et al.

(10) Patent No.: US 9,416,143 B2
(45) Date of Patent: Aug. 16, 2016

(54) GRISEOFULVIN DERIVATIVES

(71) Applicant: PIERRE FABRE MEDICAMENT, Boulogne-Billancourt (FR)

(72) Inventors: Frédéric Marion, Toulouse (FR); Frédéric Lieby-Muller, Portet-sur-Garonne (FR); Serge Grisoni, Portet-sur-Garonne (FR); Nicolas Rahier, Ayguesvives (FR); Michel Perez, Castres (FR); Isabelle Sartori, Toulouse (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/418,892

(22) PCT Filed: Aug. 1, 2013

(86) PCT No.: PCT/EP2013/066165
§ 371 (c)(1),
(2) Date: Jan. 30, 2015

(87) PCT Pub. No.: WO2014/020101
PCT Pub. Date: Feb. 6, 2014

(65) Prior Publication Data
US 2015/0210713 A1 Jul. 30, 2015

(30) Foreign Application Priority Data

Aug. 1, 2012 (FR) ..................... 12 57482

(51) Int. Cl.
| | | |
|---|---|---|
| C07D 493/10 | (2006.01) | |
| C07D 495/10 | (2006.01) | |
| C07D 405/14 | (2006.01) | |
| C07D 307/94 | (2006.01) | |
| C07D 405/12 | (2006.01) | |
| C07D 407/04 | (2006.01) | |
| C07D 407/12 | (2006.01) | |
| C07D 409/04 | (2006.01) | |
| C07D 491/107 | (2006.01) | |

(52) U.S. Cl.
CPC ............ *C07D 495/10* (2013.01); *C07D 307/94* (2013.01); *C07D 405/12* (2013.01); *C07D 405/14* (2013.01); *C07D 407/04* (2013.01); *C07D 407/12* (2013.01); *C07D 409/04* (2013.01); *C07D 491/107* (2013.01); *C07D 493/10* (2013.01)

(58) Field of Classification Search
USPC .......... 549/331, 236; 544/236, 116, 376, 253; 546/17, 19; 540/552
See application file for complete search history.

(56) References Cited

FOREIGN PATENT DOCUMENTS

| EP | 2008652 A1 | 12/2008 |
| EP | 2204367 A1 | 7/2010 |

OTHER PUBLICATIONS

Birch et al., "Studies in Relation to Biosynthesis. Part XIII. Griseofulvin," Journal of Chemical Society, Jan. 1, 1958, pp. 360-365.
Gregory et al., "Griseofulvin Analogues. Part II. Some 3'-Alkyl-griseofulvic Acids and Their Enol Ethers," Journal of Chemical Society, 1962, pp. 1269-1276, XP009117842.
International Search Report (Form PCT/ISA/210) for International Application No. PCT/EP2013/066165, dated Oct. 16, 2013, with an English translation.
Lesniewska et al., "Transformations of griseofulvin in strong acidic conditions—crystal structures of 2'-demethylgriseofulvin and dimerized griseofulvin," Database CA, Chemical Abstract Service, Database Access No. 2012:492352, XP-002694255, 1 page, abstract provided only.
Lesniewska et al., "Transformations of Griseofulvin in Strong Acidic Conditions—Crystal Structures of 2'-Demethylgriseofulvin and Dimerized Griseofulvin," Natural Product Communications, vol. 7, No. 3, 2012, pp. 327-332, XP008160903.
Mir et al., "Correlation between the in vivo effects of some griseofulvin derivatives and their in vitro interactions with mammalian microtubules," FEBS Letters, vol. 88, No. 2, Apr. 1978, pp. 259-263.
Newman, "E oxidation of Griseofulvin. A New Reaction of the β-Methoxyenone System," Journal of Organic Chemistry, vol. 35, No. 11, 1970, pp. 3990-3993, XP55057107.
Oda et al., "Regio- and Stereoselective Hydrogenation of 2'-Demethoxy-2'-methyldehydrogriseofulvin, a Symmetrical Substrate, to (+)-2'-Demethoxy-2'-methylgriseofulvin with a Cell-Free System of . . . ," Chemical and Pharmaceutical Bulletin, vol. 38, No. 2, Feb. 1990, pp. 525-528, XP55057104.
Panda et al., "Kinetic suppression of microtubule dynamic instability by griseofulvin: Implications for its possible use in the treatment of cancer," Proceedings of the National Academy of Sciences, vol. 102, No. 28, Jul. 12, 2005, pp. 9878-9883.

(Continued)

*Primary Examiner* — Noble Jarrell
(74) *Attorney, Agent, or Firm* — Birch, Stewart, Kolasch & Birch, LLP

(57) ABSTRACT

The present invention relates to compounds of the following general formula (I), or to a pharmaceutically acceptable salt thereof, as well as to the uses thereof as a drug, in particular in the treatment of cancerous or precancerous hyperproliferative conditions, and to the pharmaceutical compositions containing same.

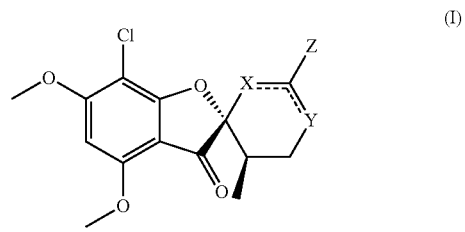

(I)

25 Claims, No Drawings

(56) References Cited

OTHER PUBLICATIONS

Rebacz et al., "Identification of Griseofulvin as an Inhibitor of Centrosomal Clustering in a Phenotype-Based Screen," Cancer Research, vol. 67, No. 13, Jul. 1, 2007, pp. 6342-6350.

Rønnest et al., "Synthesis and Structure—Activity Relationship of Griseofulvin Analogues as Inhibitors of Centrosomal Clustering in Cancer Cells," Journal of Medicinal Chemistry, vol. 52, No. 10, 2009 (Published on Web Apr. 29, 2009), pp. 3342-3347.

Wu et al., "Skraup-Doebner-Von Miller Quinoline Synthesis Revisited: Reversal of the Regiochemistry for $\gamma$-Aryl-$\beta$,$\gamma$-unsaturated $\alpha$-Ketoesters," Journal of Organic Chemistry, vol. 71, 2006 (Published on Web Jul. 19, 2006), pp. 6592-6595.

GRISEOFULVIN DERIVATIVES

The present invention relates to derivatives of griseofulvin and to the use thereof for the treatment of cancerous and pre-cancerous hyperproliferative pathologies.

Griseofulvin 1 is a natural molecule isolated from cultures of filamentous fungi *Penicilium griseofulvum* [*J. Chem. Soc.* 1958, 360-365]. It is used in the treatment of fungal skin disorders in human and is also used in veterinary medicine. It is chiefly given via oral route at doses of 0.5 to 1.0 gram per day in human.

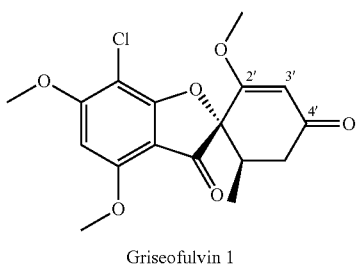

Griseofulvin 1

While the mechanism of action of griseofulvin on fungi still remains ill understood, several studies indicate possible involvement in perturbation of the microtubular network [*FEBS Letters* 1978, 259-263; *PNAS* 2005, 978-9883; *Cancer Res.*, 2007, 6342-6350] in eukaryote cells to explain its low cytotoxicity and anti-cancer potential.

With a view to improving the anti-tumour properties of griseofulvin, derivatives of griseofulvin substituted at 2' with oxygen- or sulfur-containing groups [*J. Med. Chem.* 2009, 3342-3347] have been synthesised. However none of these products has displayed sufficient potential for use as drug to treat cancerous and pre-cancerous hyperproliferative pathologies.

The inventors have surprisingly discovered that the adding of particular rings or groups at 2', 3' and/or 4' allows the obtaining of cytotoxic derivatives that are more powerful than griseofulvin and its previously described analogues.

The subject of the present invention is therefore a compound of following general formula (I):

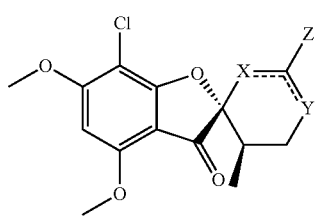

(I)

or a pharmaceutically acceptable salt thereof, where:
- ----- represents a single or double bond, it not being possible for the bonds X----- and -----Y to represent a double bond at the same time;
- either Y, together with Z and their carrier carbon atom, forms an optionally substituted carbocyle or heterocycle, and
  X----- represents a single bond X—, and
  X is $C=O$, $C=S$, $CH_2$, $CH-OR_1$, $CHN_3$, $CHNR_2R_3$, $C=N-OR_4$, or $C=N-NR_5R_6$;

or Y is $C=O$, $C=S$, $CH_2$, $CH-OR_7$, $CHN_3$, $CHNR_8R_9$, $C=N-OR_{10}$ or $C=N-NR_{11}R_{12}$, and
- ----- Y represents a single bond —Y, and either X, together with Z and their carrier carbon atom, forms an optionally substituted carbocycle or heterocycle, or Z is a hydrogen atom or an aryl, $-S(O)R_{13}$ or $-S(O)_2R_{13}$ group, and X is a $CH-R_{14}$ group when X ----- represents a single bond X—, or $C-R_{14}$ when X ----- represents a double bond $X=$, with:

$R_1$ to $R_5$ and $R_7$ to $R_{11}$ each independently representing a hydrogen atom or a $(C_1-C_6)$alkyl, aryl, $(C_1-C_6)$alkyl-aryl or aryl-$(C_1-C_6)$alkyl group;

$R_6$ and $R_{12}$ each independently representing a hydrogen atom or a $(C_1-C_6)$alkyl, aryl, $(C_1-C_6)$alkyl-aryl, aryl-$(C_1-C_6)$alkyl, $C(O)NH_2$ or $C(S)NH_2$ group;

$R_{13}$ represents a $(C_1-C_6)$alkyl, aryl, $(C_1-C_6)$alkyl-aryl or aryl-$(C_1-C_6)$alkyl group;

$R_{14}$ representing $-R_{15}$, $-NHR_{15}$, $-CH_2-NHR_{15}$, $-CH_2-NH-C(O)-R_{15}$, $-NH-CH_2-R_{15}$, $-NH-NH-R_{15}$, $-NH-C(O)-R_{15}$, $-NH-C(O)-CH_2-R_{15}$, $-NH-CH_2-C(O)-R_{15}$, $-NH-CH_2-C(O)-O-R_{15}$, $-NH-CH_2-C(O)-NH-R_{15}$, $-NH-SO_2-R_{15}$, $-S(O)-R_{15}$, $-SO_2-R_{15}$, $-S(O)-CH_2-R_{15}$, $-SO_2-CH_2-R_{15}$, or $-NR_{16}R_{17}$;

$R_{15}$ representing a hydrogen atom or a $(C_1-C_6)$alkyl, carbocycle, heterocycle, biaryl, carbocycle-$(C_1-C_6)$alkyl or heterocycle-$(C_1-C_6)$alkyl group, optionally substituted; and $R_{16}$ and $R_{17}$, together with their carrier nitrogen atom, forming a heterocycle optionally substituted with $-R_{15}$, $-OR_{15}$ or $-NHR_{15}$.

The absolute stereochemistry at the spiro ring junction and alpha carbon carrying a methyl group is such as indicated in formula (I) illustrated above. In addition, the

portion of the molecule of above-mentioned formula (I) may comprise one or more other asymmetric carbon atoms which may each be present in R or S configuration or else in the form of a mixture of both configurations R and S in any proportion, in particular in equimolar proportions.

The article of Oda et al. *Chem. Pharm. Bull.* 1990, 38(2), 525-528 describes griseofulvin derivatives without mentioning any biological activity of these derivatives. In particular it describes compounds 6 to 10 of following formulas:

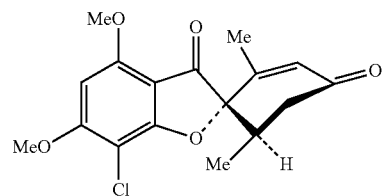

6

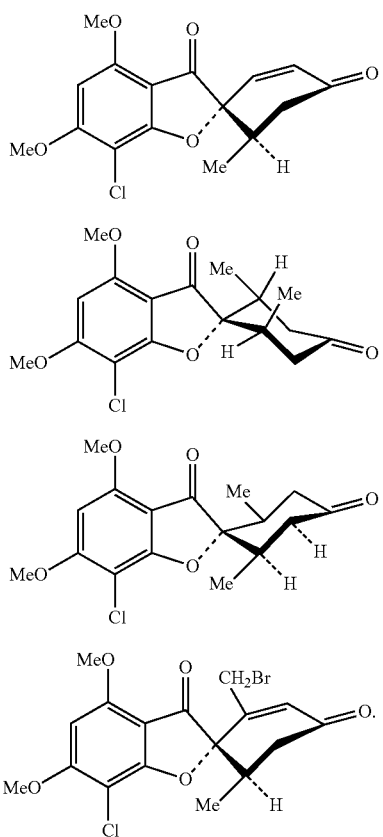

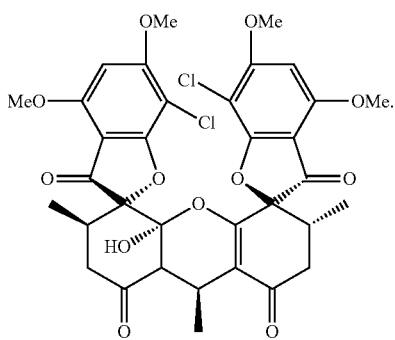

Preferably the formula (I) compound of the invention is not compounds 6 to 10 described in Oda et al.

The article of Lesniewska et al. *Nat. Prod. Comm.* 2012, 7(3), 327-332 describes griseofulvin derivatives without mentioning any biological activity of these derivatives. In particular it describes a dimer of griseofulvin (compound VI) of following formula:

Preferably, the formula (I) compound of the invention is not the dimer of griseofulvin (VI) described in Lesniewska et al.

The article of Newman *J. Org. Chem.* 1970, 35(11), 3990-3993 describes griseofulvin derivatives without mentioning any biological activity of these derivatives. In particular, it describes following compound 2:

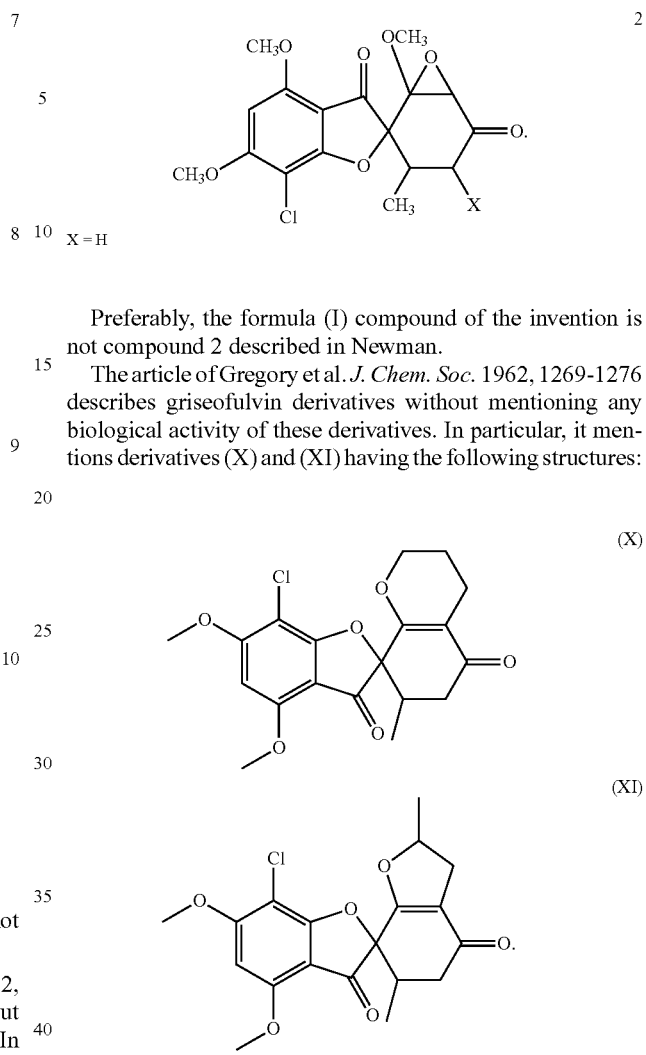

Preferably, the formula (I) compound of the invention is not compound 2 described in Newman.

The article of Gregory et al. *J. Chem. Soc.* 1962, 1269-1276 describes griseofulvin derivatives without mentioning any biological activity of these derivatives. In particular, it mentions derivatives (X) and (XI) having the following structures:

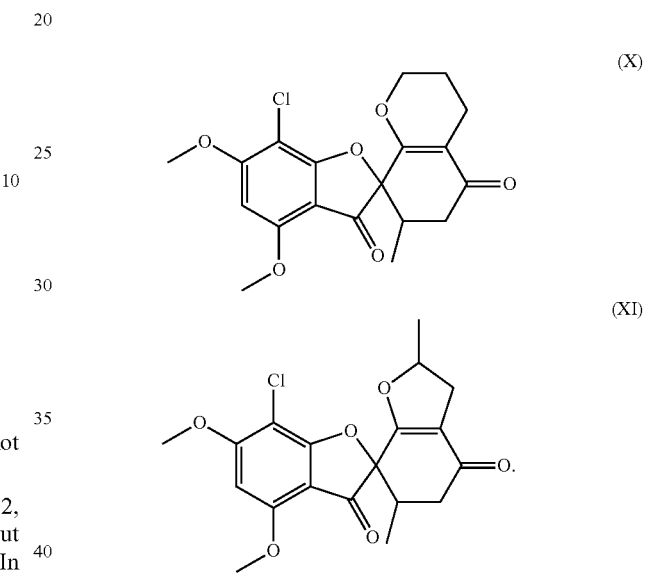

However, on reading this article it appears that the authors assume that one of these two structures corresponds to the structure of the compound obtained by rearrangement of the 2'- or 4'-allylenol ether of griseofulvin. It is therefore solely an assumption by the authors, no proof can be obtained to determine whether or not one of the compounds (X) and (XI) is indeed the compound obtained during this rearrangement reaction.

In the present invention by "pharmaceutically acceptable" is meant that which can be used to prepare a pharmaceutical composition which is generally safe, non-toxic and neither biologically nor otherwise adverse, and which is acceptable for veterinary use as well as for human pharmaceutical use.

By "pharmaceutically acceptable salts" of a compound in this invention it is meant to designate salts that are pharmaceutically acceptable as defined above and which have the desired pharmacological activity of the parent compound.

In particular these are acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like.

By "halogen atom" in the present invention is meant atoms of fluorine, chlorine, bromine and iodine.

By "$(C_1-C_6)$alkyl" in the present invention is meant a linear or branched, saturated hydrocarbon chain comprising 1 to 6 carbon atoms. In particular it may be a methyl, ethyl, n-propyl, isopropyl, n-butyl, iso-butyl, sec-butyl, tert-butyl, n-pentyl or n-hexyl group.

By "$(C_1-C_6)$alkoxy" in the present invention is meant a $(C_1-C_6)$alkyl group as defined above attached to the remainder of the molecule via an oxygen atom. It may in particular be a methoxy, ethoxy, n-propoxy, isopropoxy, n-butoxy, iso-butoxy, sec-butoxy, tert-butoxy, n-pentoxy or n-hexoxy group.

By "$(C_2-C_6)$alkenyl" in the present invention is meant a linear or branched hydrocarbon chain having at least one double bond and comprising 2 to 6 carbon atoms. For example the ethenyl or allyl groups can be cited.

By "$(C_2-C_6)$alkynyl" in the present invention is meant a linear or branched hydrocarbon chain having at least one triple bond and comprising 2 to 6 carbon atoms. For example, the ethynyl or propynyl groups can be cited.

By "aryl" in the present invention is meant an aromatic hydrocarbon group preferably having 5 to 10 carbon atoms and comprising one or more fused rings, preferably 1 or 2 rings, e.g. a phenyl or naphthyl group. Advantageously it is phenyl.

By "$(C_1-C_6)$alkyl-aryl" in the present invention is meant a $(C_1-C_6)$alkyl group as defined above attached to the remainder of the molecule via an aryl group as defined above. In particular it may be a tolyl group.

By "aryl-$(C_1-C_6)$alkyl" in the present invention is meant an aryl group as defined above attached to the remainder of the molecule via a $(C_1-C_6)$alkyl group as defined above. In particular, it may be a benzyl group.

By "biaryl" in the present invention is meant an aryl group as defined above attached to the remainder of the molecule via an aryl group as defined above. In particular it may be a biphenyl group.

By "heteroaryl" group in the present invention is meant an aryl group as defined above wherein one or more carbon atoms have been replaced by one or more heteroatoms, advantageously 1 to 4, preferably 1 or 2. Examples of heteroaryl groups are pyridine, pyrimidine, pyrazine, pyridazine, furan, thiophene, pyrrole, pyrazole, imidazole, thiazole, isothiazole, oxazole, isoxazole, triazole, tetrazole, benzofuran, benzothiophene, indole, benzimidazole, indazole, quinoline, isoquinoline, quinazoline or quinoxaline groups.

By "heteroatom" is particularly meant a sulfur, nitrogen or oxygen atom.

By "carbocycle" in the present invention is meant one or more fused rings, preferably 1 or 2 aromatic, saturated or unsaturated hydrocarbon fused rings, each ring advantageously having 3 to 8 members, preferably 3, 5, 6 or 7 members and more preferably 5 or 6 members. In particular, it may be a cyclopentyl or cyclohexyl.

By "unsaturated" in the present invention is meant that the ring comprises one or more double bonds.

By "carbocycle-$(C_1-C_6)$alkyl" in the present invention is meant a carbocycle group as defined above attached to the remainder of the molecule via a $(C_1-C_6)$alkyl group as defined above, preferably via a —$CH_2$— group. In particular, it may be a cyclopentyl-methyl or cyclohexyl-methyl group.

By "heterocycle" in the present invention is meant a carbocycle group as defined above wherein one or more carbon atoms have been replaced by one or more heteroatoms, advantageously 1 to 4, preferably 1 or 2. Examples of heterocycles comprising only 1 ring are the rings: epoxide, aziridine, furan, dihydrofuran, tetrahydrofuran, pyrrole, pyroline, pyrrolidine, thiophene, dihydrothiophene, tetrahydrothiophene, pyrazole, pyrazoline, pyrazolidine, imidazole, imidazoline, imizadolidine, thiazole, dihydrothiazole, tetrahydrothiazole, oxazole, dihydrooxazole, tetrahydrooxazole, triazoles, dihydrotriazoles, tetrahydrotriazoles, pyridine, dihydropyridine, tetrahydropyridine, piperidine, pyrimidine, pyridazine, pyrazine, dihydropyrimidine, dihydropyridazine, dihydropyrazine, tetrahydropyrimidine, tetrahydropyridazine, tetrahydropyrazine, hexahydropyrimidine, hexahydropyridazine, piperazine, pyran, dihydropyran, tetrahydropyran, oxazines, dihydrooxazines, tetrahydrooxazines (e.g. morpholine), azepine, dihydroazepine, tetrahydroazepine, azepane, diazepines, dihydrodiazepines, tetrahydrodiazepines and diazepanes. Examples of heterocycles comprising 2 fused rings are the previously mentioned 1-ring heterocycles fused with 1 phenyl core such as indole, benzofuran, benzopyran including chromene and isochromene, dihydrobenzopyrans including chromane, quinoline, dihydroquinolines, tetrahydroquinoline, isoquinoline, dihydroisoquinolines and tetrahydroisoquinoline.

By "heterocycle-$(C_1-C_6)$alkyl" in the present invention is meant a heterocycle group as defined above attached to the remainder of the molecule via a $(C_1-C_6)$alkyl group as defined above, and preferably via a —$CH_2$— group.

By "cycloalkyl" in the present invention is meant a saturated, hydrocarbon, monocycle advantageously comprising 3 to 8 carbon atoms, in particular 5 or 6. In particular, it may be a cyclohexyl.

According to a first particular embodiment of the invention, the present invention concerns a compound of following general formula (I):

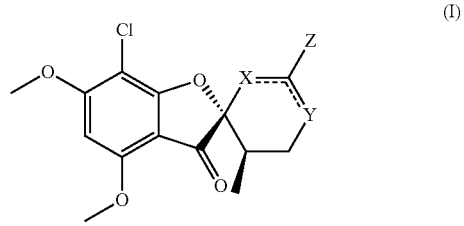

or a pharmaceutically acceptable salt thereof, where:
- ----- represents a single or double bond, it not being possible for the bonds X----- and -----Y to represent a double bond at the same time;
- either Y, together with Z and their carrier carbon atom, represents an optionally substituted carbocycle or heterocycle, and
- X----- represents a single bond X—, and
- X is C=O, C=S, $CH_2$, CH—$OR_1$, $CHN_3$, $CHNR_2R_3$, C=N—$OR_4$, or C=N—$NR_5R_6$;
- or Y is C=O, C=S, $CH_2$, CH—$OR_7$, $CHN_3$, $CHNR_8R_9$, C=N—$OR_{10}$ or C=N—$NR_{11}R_{12}$, and
- ----- Y represents a single bond —Y, and
- X, together with Z and their carrier carbon atom, represents an optionally substituted carbocycle or heterocycle,
- with $R_1$ to $R_{12}$ as previously defined.

Therefore according to this embodiment Z, together with Y or X and their carrier carbon atom, forms an optionally substituted carbocycle or heterocycle, preferably an optionally substituted heterocycle.

The heterocycle advantageously comprises 1 or 2 saturated, unsaturated or aromatic fused rings, each ring advantageously having 3 to 8 members, preferably 3, 5, 6 or 7 members, and more preferably 5 or 6 members. Advantageously it comprises 1 or 2 heteroatoms selected from among N, O and S, preferably selected from among N and O.

It may in particular be epoxide, aziridine, furan, dihydrofuran, tetrahydrofuran, pyrrole, pyroline, pyrrolidine, pyrazole, pyrazoline, pyrazolidine, imidazole, imidazoline, imizadolidine, oxazole, dihydrooxazole, tetrahydrooxazole, triazoles, dihydrotriazoles, tetrahydrotriazoles, pyridine, dihydropyridine, tetrahydropyridine, piperidine, pyrimidine, pyridazine, pyrazine, dihydropyrimidine, dihydropyridazine, dihydropyrazine, tetrahydropyrimidine, tetrahydropyridazine, tetrahydropyrazine, hexahydropyrimidine, hexahydropyridazine, piperazine, pyran, dihydropyran, tetrahydropyran, oxazines, dihydrooxazines, tetrahydrooxazines (e.g. morpholine), azepine, dihydroazepine, tetrahydroazepine, azepane, diazepines, dihydrodiazepines, tetrahydrodiazepines, diazepanes, indole, benzofuran, benzopyrans including chromene and isochromene, dihydrobenzopyrans including chromane, quinoline, dihydroquinolines, tetrahydroquinoline, isoquinoline, dihydroisoquinolines or tetrahydroisoquinoline.

Advantageously, the ring may be epoxide, aziridine, furan, dihydrofuran, tetrahydrofuran, pyrrole, pyroline, pyrrolidine, pyrazole, pyrazoline, pyrazolidine, imidazole, imidazoline, imizadolidine, pyridine, dihydropyridine, tetrahydropyridine, piperidine, pyrimidine, pyridazine, pyrazine, dihydropyrimidine, dihydropyridazine, dihydropyrazine, tetrahydropyrimidine, tetrahydropyridazine, tetrahydropyrazine, hexahydropyrimidine, hexahydropyridazine, piperazine, pyran, dihydropyran, tetrahydropyran, azepine, dihydroazepine, tetrahydroazepine, azepane, indole, benzofuran, benzopyrans including chromene and isochromene, dihydrobenzopyrans including chromane, quinoline, dihydroquinolines, tetrahydroquinoline, isoquinoline, dihydroisoquinolines or tetrahydroisoquinoline.

Preferably the ring is furan, dihydrofuran, tetrahydrofuran, pyrrole, pyroline, pyrrolidine, pyrazole, pyrazoline, pyrazolidine, imidazole, imidazoline, imidazolidine, pyridine, dihydropyridine, tetrahydropyridine, piperidine, pyrimidine, pyridazine, pyrazine, dihydropyrimidine, dihydropyridazine, dihydropyrazine, tetrahydropyrimidine, tetrahydropyridazine, tetrahydropyrazine, hexahydropyrimidine, hexahydropyridazine, piperazine, pyran, dihydropyran, tetrahydropyran, indole, benzofuran, benzopyrans including chromene and isochromene, dihydrobenzopyrans including chromane, quinoline, dihydroquinolines, tetrahydroquinoline, isoquinoline, dihydroisoquinolines or tetrahydroisoquinoline.

More preferably the ring is furan, dihydrofuran, pyrrole, pyroline, pyrazole, pyrazoline, imidazole, imidazoline, pyridine, dihydropyridine, tetrahydropyridine, pyrimidine, pyridazine, pyrazine, dihydropyrimidine, dihydropyridazine, dihydropyrazine, tetrahydropyrimidine, tetrahydropyridazine, tetrahydropyrazine, pyran, dihydropyran, indole, benzofuran, benzopyrans including chromene and isochromene, quinoline, dihydroquinolines, isoquinoline or dihydroisoquinolines.

In particular the ring may be epoxide, furan, dihydrofuran, pyrrole, pyroline, pyrazole, pyridine, dihydropyridine, tetrahydropyridine, pyrimidine, tetrahydropyrimidine, dihydropyran, tetrahydroazepine, benzofuran, isochromene, isoquinoline, or dihydroisoquinolines.

If the carbocycle or heterocycle is substituted, its carbon atoms can be substituted with one or more substituents selected from among a halogen atom; an oxo group (=O); —CN; —OR$_{18}$; —NR$_{19}$R$_{20}$; —SR$_{21}$; —S(O)R$_{22}$; —S(O)$_2$R$_{23}$; —C(O)R$_{24}$; —C(O)OR$_{25}$; —C(O)NR$_{26}$R$_{27}$; —C(O)SR$_{28}$; —S(O)$_2$NR$_{29}$R$_{30}$; —NR$_{31}$S(O)$_2$R$_{32}$; —NR$_{33}$C(O)NR$_{34}$R$_{35}$; —C(=NR$_{36}$)NR$_{37}$R$_{38}$; —NR$_{39}$C(=NR$_{42}$)NR$_{43}$R$_{44}$; (C$_1$-C$_6$)alkyl optionally substituted with one or more substituents selected from among a halogen atom (e.g. F), NR$_{45}$R$_{46}$, SR$_{47}$, OR$_{48}$ and aryl, selected in particular from among NR$_{45}$R$_{46}$, OR$_{48}$ and aryl; (C$_2$-C$_6$)alkenyl; (C$_2$-C$_6$)alkynyl; and a carbocycle, heterocycle or biaryl (preferably an aryl, heteroaryl, saturated carbocycle, saturated heterocycle or biaryl such as phenyl, naphthyl, thiophene, thiazole, piperidine, morpholine, piperazine, tetrahydropyran, tetrahydrofuran or biphenyl) optionally substituted with one or more substituents selected from among a halogen atom (e.g. F or Cl), OR$_{49}$, NR$_{50}$R$_{51}$, C(O)R$_{52}$, C(O)OR$_{53}$, C(O)NR$_{54}$R$_{55}$, an aryl and a (C$_1$-C$_6$)alkyl group optionally substituted with one or more substituents selected from among a halogen atom, OR$_{56}$ and NR$_{57}$R$_{58}$, with:

R$_{18}$ to R$_{47}$ and R$_{49}$ to R$_{56}$ each independently representing a hydrogen atom or a (C$_1$-C$_6$)alkyl, aryl, (C$_1$-C$_6$)alkyl-aryl or aryl-(C$_1$-C$_6$)alkyl group, advantageously a hydrogen atom or (C$_1$-C$_6$)alkyl or aryl group;

R$_{48}$ representing a hydrogen atom or a (C$_1$-C$_6$)alkyl, aryl, (C$_1$-C$_6$)alkyl-aryl, aryl-(C$_1$-C$_6$)alkyl or —C(O)—(C$_1$-C$_6$)alkyl group, advantageously a hydrogen atom or a (C$_1$-C$_6$)alkyl or —C(O)—(C$_1$-C$_6$)alkyl group; and R$_{57}$ and R$_{58}$ each independently representing a hydrogen atom or a (C$_1$-C$_6$)alkyl, aryl, (C$_1$-C$_6$)alkyl-aryl or aryl-(C$_1$-C$_6$)alkyl group, advantageously a hydrogen atom or a (C$_1$-C$_6$)alkyl or aryl group, or together with their carrier nitrogen atom forming a heterocycle which may contain another heteroatom such as morpholine, piperazine and piperidine, and, when it is a heterocycle comprising one or more nitrogen atoms, its nitrogen atoms may optionally be substituted with an oxygen atom (to give a N$^+$—O$^-$ group) if the nitrogen atom is engaged in a double bond, or with an OH or (C$_1$-C$_6$)alkyl group if the nitrogen atom is not engaged in a double bond.

Advantageously, when the carbocycle or heterocycle is substituted, its carbon atoms may be substituted with one or more substituents selected from among a halogen atom; an oxo group (=O); —CN; —OR$_{18}$; —NR$_{19}$R$_{20}$; —C(O)R$_{24}$; —C(O)OR$_{25}$; —C(O)NR$_{26}$R$_{27}$; (C$_1$-C$_6$)alkyl optionally substituted with one or more substituents selected from among a halogen atom (e.g. F), NR$_{45}$R$_{46}$, OR$_{48}$ and aryl, selected in particular from among NR$_{45}$R$_{46}$, OR$_{48}$ and aryl; and an aryl, heteroaryl, saturated carbocycle, saturated heterocycle or biaryl (such as phenyl, naphthyl, thiophene, thiazole, piperidine, morpholine, piperazine, tetrahydropyran, tetrahydrofuran or biphenyl) optionally substituted with one or more substituents selected from among a halogen atom (e.g. F or Cl), OR$_{49}$, NR$_{50}$R$_{51}$, C(O)R$_{52}$, C(O)OR$_{53}$, C(O)NR$_{54}$R$_{55}$, an aryl and a (C$_1$-C$_6$)alkyl group optionally substituted with one or more substituents selected from among a halogen atom, OR$_{56}$ and NR$_{57}$R$_{58}$, and if it is a heterocycle comprising one or more nitrogen atoms, its nitrogen atoms may optionally be substituted with an oxygen atom (to give a N$^+$—O$^-$ group) if the nitrogen atom is engaged in a double bond, or with an OH or (C$_1$-C$_6$)alkyl group if the nitrogen atom is not engaged in a double bond.

When Y and Z form a carbocycle or heterocycle with their carrier carbon atom, the ⸺ Y bond is preferably a double bond =Y.

X is advantageously a C=O or CH—OR$_1$ group, preferably C=O or CH—OH.

The formula (I) compounds may meet following formula (I-YZ):

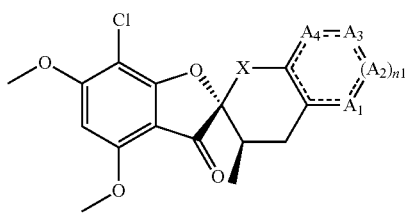

(I-YZ)

where:
- ⸺ represents a single or double bond, it not being possible for two successive ⸺ bonds to represent a double bond at the same time;
- X is C=O, C=S, CH$_2$, CH—OR$_1$, CHN$_3$, CHNR$_2$R$_3$, C=N—OR$_4$, or C=N—NR$_5$R$_6$, and is preferably C=O or CH—OR$_1$, in particular C=O or CH—OH;
- n1 equals 0 or 1;
- A$_1$ represents:
  - N when one of the ⸺ bonds starting from A$_1$ is a double bond (the other ⸺ bond being a single bond), or
  - NRa, N$^+$O$^-$ or O when the two ⸺ bonds starting from A$_1$ are single bonds;
- A$_2$ represents:
  - CRb when one of the ⸺ bonds starting from A$_2$ is a double bond (the other ⸺ bond being a single bond), or
  - CRbRb' or C=O when the two ⸺ bonds starting from A$_2$ are single bonds.
- A$_3$ represents:
  - N or CRc when one of the ⸺ bonds starting from A$_3$ is a double bond (the other ⸺ bond being a single bond), or
  - NRc (such as NRa) or CRcRc' when the two ⸺ bonds starting from A$_3$ are single bonds; and
- A$_4$ represents:
  - CRz when one of the ⸺ bonds starting from A$_4$ is a double bond (the other ⸺ bond being a single bond), or
  - CRzRz' when the two ⸺ bonds starting from A$_4$ are single bonds, with Ra, Rb, Rb', Rc, Rc', Rz, and Rz' as defined below.

The formula (I) compounds may in particular meet one of the following formulas (I-YZ-A) and (I-YZ-B):

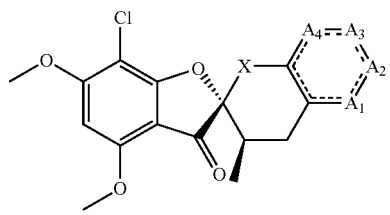

(I-YZ-A)

or

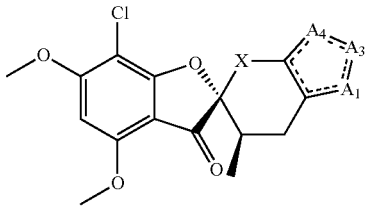

(I-YZ-B)

where ⸺, X and A$_1$ to A$_4$ are as defined above.

The formula (I) compounds may meet one of the general formulas (I-YZ-1) to (I-YZ-14) below:

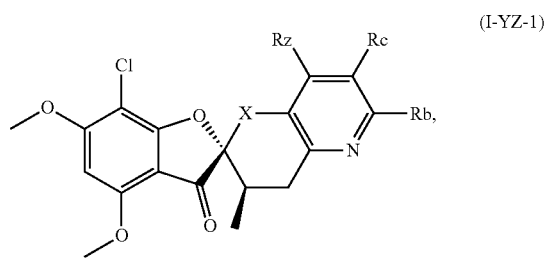

(I-YZ-1)

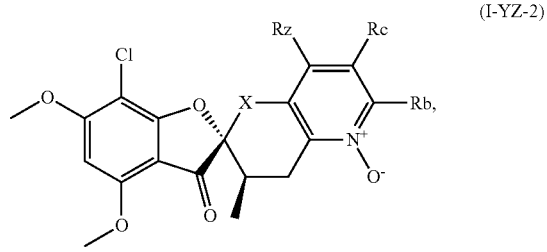

(I-YZ-2)

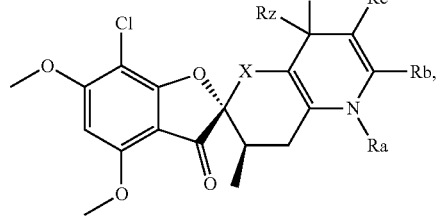

(I-YZ-3)

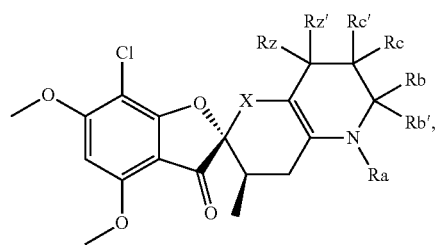

(I-YZ-4)

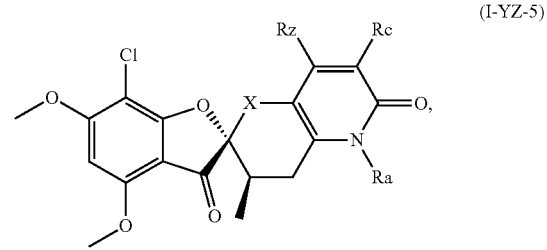

(I-YZ-5)

-continued (I-YZ-6)
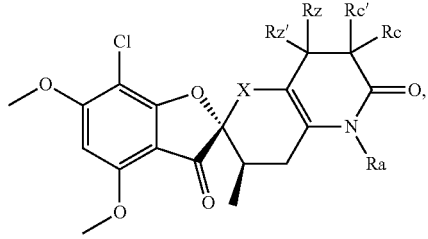

(I-YZ-7)
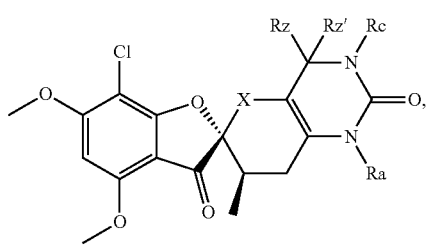

(I-YZ-8)
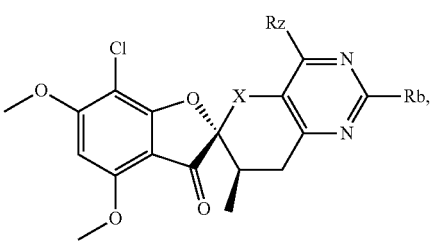

(I-YZ-9)
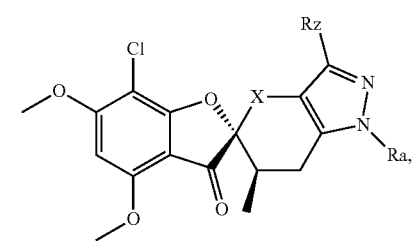

(I-YZ-10)
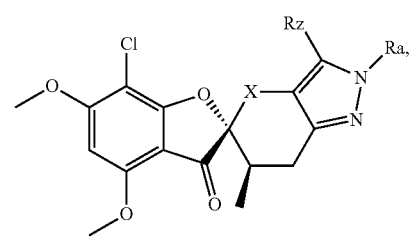

(I-YZ-11)
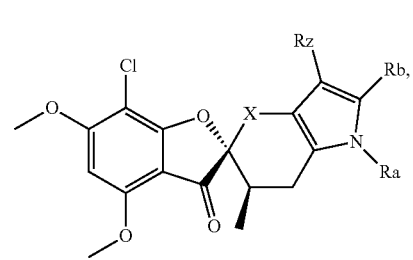

-continued (I-YZ-12)
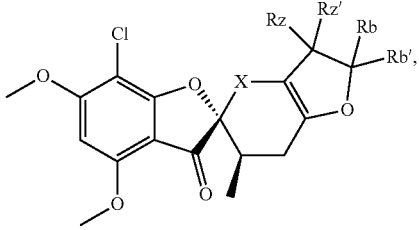

(I-YZ, 13)
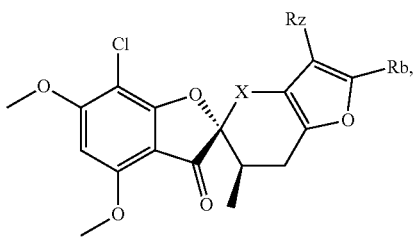

(I-YZ-14)
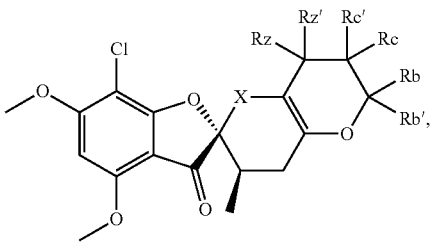

advantageously (I-YZ-1), (I-YZ-2), (I-YZ-3), (I-YZ-9), (I-YZ-10) or (I-YZ-12), where:

Ra is a hydrogen atom or an OH, ($C_1$-$C_6$)alkyl, aryl, aryl-($C_1$-$C_6$)alkyl or C(O)O—($C_1$-$C_6$)alkyl group; and Rb, Rb', Rc, Rc', Rz, and Rz' are each independently a hydrogen atom; a halogen atom; —CN; —OR$_{18}$; —NR$_{19}$R$_{20}$; —SR$_{21}$; —S(O)R$_{22}$; —S(O)$_2$R$_{23}$; —C(O)R$_{24}$; —C(O)OR$_{25}$; —C(O)NR$_{26}$R$_{27}$; —C(O)SR$_{28}$; —S(O)$_2$NR$_{29}$R$_{30}$; —NR$_{31}$S(O)$_2$R$_{32}$; —NR$_{33}$C(O)NR$_{34}$R$_{35}$; —C(=NR$_{36}$)NR$_{37}$R$_{38}$; —NR$_{39}$C(=NR$_{42}$)NR$_{43}$R$_{44}$; ($C_1$-$C_6$)alkyl optionally substituted with one or more substituents selected from among a halogen atom (e.g. F), NR$_{45}$R$_{46}$, SR$_{47}$, OR$_{48}$ and aryl, selected in particular among NR$_{45}$R$_{46}$, OR$_{48}$ and aryl; ($C_2$-$C_6$)alkenyl; ($C_2$-$C_6$)alkynyl; or a carbocycle, heterocycle or biaryl (preferably an aryl, heteroaryl, saturated carbocycle, saturated heterocycle or biaryl such as phenyl, naphthyl, thiophene, thiazole, piperidine, morpholine, piperazine, tetrahydropyran, tetrahydrofuran or biphenyl) optionally substituted with one or more substituents selected from among a halogen atom (e.g. F or Cl), OR$_{49}$, NR$_{50}$R$_{51}$, C(O)R$_{52}$, C(O)OR$_{53}$, C(O)NR$_{54}$R$_{55}$, an aryl and ($C_1$-$C_6$)alkyl group optionally substituted with one or more substituents selected from among a halogen atom, OR$_{56}$ and NR$_{57}$R$_{58}$, in particular a hydrogen atom; a halogen atom; —CN—OR$_{18}$; —NR$_{19}$R$_{20}$; —C(O)R$_{24}$; —C(O)OR$_{25}$; —C(O)NR$_{26}$R$_{27}$; ($C_1$-$C_6$)alkyl optionally substituted with one or more substituents selected from among a halogen atom (e.g. F), NR$_{45}$R$_{46}$, OR$_{48}$ and aryl, selected in particular from among NR$_{45}$R$_{46}$, OR$_{48}$ and aryl; or an aryl, heteroaryl, saturated carbocycle, saturated heterocycle or biaryl (such as phenyl, naphthyl, thiophene, thiazole, piperidine, morpholine, piperazine, tetrahydropyran, tetrahydrofuran or biphenyl) optionally substituted with one or more substituents selected from among a halogen atom (e.g. F or Cl), $OR_{49}$, $NR_5OR_{51}$, $C(O)R_{52}$, $C(O)OR_{53}$, $C(O)NR_{54}R_{55}$, an aryl and a $(C_1-C_6)$alkyl group optionally substituted with one or more substituents selected from among a halogen atom, $OR_{56}$ and $NR_{57}R_{58}$.

When X and Z form a carbocycle or heterocycle with their carrier carbon atom, the X⁓ bond is preferably a double bond X=.

Y is advantageously C=O, $CH_2$, CH—$OR_7$, $CHN_3$, $CHNR_8R_9$, C=N—$OR_{10}$ or C=N—$NR_{11}R_{12}$, in particular C=O, CH—$OR_7$, $CHN_3$, $CHNR_8R_9$, C=N—$OR_{10}$ or C=N—$NR_{11}R_{12}$, particularly C=O or CH—$OR_7$, such as C=O or CH—OH, and in particular C=O.

The formula (I) compounds may meet following formula (I-XZ):

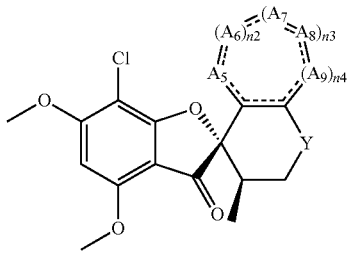
(I-XZ)

where:
⁓ represents a single or double bond, it not being possible for two successive ⁓ bonds to represent a double bond at the same time;
Y is C=O, C=S, $CH_2$, CH—$OR_7$, $CHN_3$, $CHNR_8R_9$, C=N—$OR_{10}$ or C=N—$NR_{11}R_{12}$; preferably C=O, $CH_2$, CH—$OR_7$, $CHN_3$, $CHNR_8R_9$, C=N—$OR_{10}$ or C=N—$NR_{11}R_{12}$; in particular C=O, CH—$OR_7$, $CHN_3$, $CHNR_8R_9$, C=N—$OR_{10}$ or C=N—$NR_{11}R_{12}$; particularly C=O or CH—$OR_7$, such as C=O or CH—OH, and more particularly C=O;
n2, n3 and n4 each independently equal 0 or 1;
$A_5$ represents:
  N or CRe when one of the ⁓ bonds starting from $A_5$ is a double bond (the other ⁓ bond being a single bond), or
  NRa, O or CReRe' when the two ⁓ bonds starting from $A_5$ are single bonds;
$A_6$ represents:
  CRb when one of the ⁓ bonds starting from $A_6$ is a double bond (the other ⁓ bond being a single bond), or
  NRa, CRbRb' or C=O when the two ⁓ bonds starting from $A_6$ are single bonds;
$A_7$ represents:
  CRc when one of the ⁓ bonds starting from $A_7$ is a double bond (the other ⁓ bond being a single bond), or
  CRcRc' when the two ⁓ bonds starting from $A_7$ are single bonds;
$A_8$ represents:
  CRd when one of the ⁓ bonds starting from $A_8$ is a double bond (the other ⁓ bond being a single bond), or
  CRdRd' when the two ⁓ bonds starting from $A_8$ are single bonds, or

represents

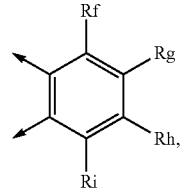

and
$A_9$ represents:
  CRz when one of the ⁓ bonds starting from $A_9$ is a double bond (the other ⁓ bond being a single bond), or
  CRzRz' when the two ⁓ bonds starting from $A_9$ are single bonds,
with Ra, Rb, Rb', Rc, Rc', Rd, Rd', Re, Rf, Rz and Rz' as defined below, and
Re', Rg, Rh and Ri each independently representing a hydrogen atom; a halogen atom; —CN; —$OR_{18}$; —$NR_{19}R_{20}$; —$SR_{21}$; —$S(O)R_{22}$; —$S(O)_2R_{23}$; —$C(O)R_{24}$; —$C(O)OR_{25}$; —$C(O)NR_{26}R_{27}$; —$C(O)SR_{28}$; —$S(O)_2NR_{29}R_{30}$; —$NR_{31}S(O)_2R_{32}$; —$NR_{33}C(O)NR_{34}R_{35}$; —$C(=NR_{36})NR_{37}R_{38}$; —$NR_{39}C(=NR_{42})NR_{43}R_{44}$; $(C_1-C_6)$alkyl optionally substituted with one or more substituents selected from among a halogen atom (e.g. F), $NR_{45}R_{46}$, $SR_{47}$, $OR_{48}$ and aryl, selected in particular from among $NR_{45}R_{46}$, $OR_{48}$ and aryl; $(C_2-C_6)$alkenyl; $(C_2-C_6)$alkynyl; or a carbocycle, heterocycle or biaryl (preferably an aryl, heteroaryl, saturated carbocycle, saturated heterocycle or biaryl such as phenyl, naphthyl, thiophene, thiazole, piperidine, morpholine, piperazine, tetrahydropyran, tetrahydrofuran or biphenyl) optionally substituted with one or more substituents selected from among a halogen atom (e.g. F or Cl), $OR_{49}$, $NR_{50}R_{51}$, $C(O)R_{52}$, $C(O)OR_{53}$, $C(O)NR_{54}R_{55}$, an aryl and a $(C_1-C_6)$alkyl group optionally substituted with one or more substituents selected from among a halogen atom, $OR_{56}$ and $NR_{57}R_{58}$,
in particular a hydrogen atom; a halogen atom; —CN; —$OR_{18}$; —$NR_{19}R_{20}$; —$C(O)R_{24}$; —$C(O)OR_{25}$; —$C(O)NR_{26}R_{27}$; $(C_1-C_6)$alkyl optionally substituted with one or more substituents selected from among a halogen atom (e.g. F), $NR_{45}R_{46}$, $OR_{48}$ and aryl, selected in particular from among $NR_{45}R_{46}$, $OR_{48}$ and aryl; or an aryl, heteroaryl, saturated carbocycle, saturated heterocycle or biaryl (such as phenyl, naphthyl, thiophene, thiazole, piperidine, morpholine, piperazine, tetrahydropyran, tetrahydrofuran or biphenyl) optionally substituted with one or more substituents selected from among a halogen atom (e.g. F or Cl), $OR_{49}$, $NR_{50}R_{51}$, $C(O)R_{52}$, $C(O)OR_{53}$, $C(O)NR_{54}R_{55}$, an aryl and a $(C_1-C_6)$alkyl group optionally substituted with one or more substituents selected from among a halogen atom, $OR_{56}$ and $NR_{57}R_{58}$.

Advantageously:
  when n2=1, then $A_5$=N, O or NRa and/or $A_6$=NRa; and
  when n2=0, then $A_5$=N, O or NRa.
Preferably, when n3=0, then n2=n4.
Advantageously, n3=0 and n2=n4=1; or n3=1, and n2 and/or n4=0.

The formula (I) compounds may in particular meet one of the following formulas (I-XZ-A) and (I-XZ-B):

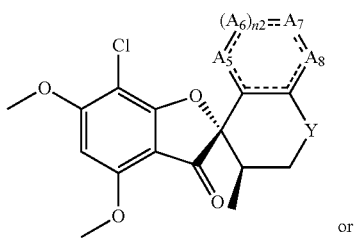
(I-XZ-A)

or

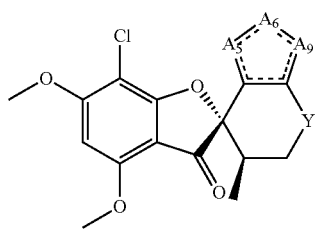
(I-XZ-B)

where ----, Y, n2 and $A_5$ to $A_9$ are as defined above.

Advantageously:
when n2=1, then $A_5$=N, O or NRa and/or $A_6$=NRa; and
when n2=0, then $A_5$=N, O, or NRa.

The formula (I) compounds may advantageously meet following formula (I-XZ-C):

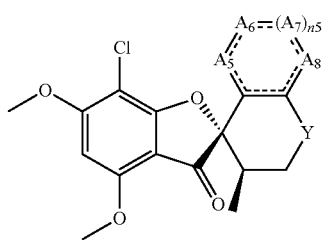
(I-XZ-C)

where:
- - - - is a single or double bond, it not being possible for two successive - - - - bonds to represent a double bond at the same time;

Y is C=O, C=S, $CH_2$, CH—$OR_7$, $CHN_3$, $CHNR_8R_9$, C=N—$OR_{10}$ or C=N—$NR_{11}R_{12}$; preferably C=O, $CH_2$, CH—$OR_7$, $CHN_3$, $CHNR_8R_9$, C=N—$OR_{10}$ or C=N—$NR_{11}R_{12}$; in particular C=O, CH—$OR_7$, $CHN_3$, $CHNR_8R_9$, C=N—$OR_{10}$ or C=N—$NR_{11}R_{12}$; particularly C=O or CH—$OR_7$, such as C=O or CH—OH, and more particularly C=O;

n5 equals 0 or 1;

$A_5$ represents:
  N or CRe when one of the ---- bonds starting from $A_5$ is a double bond (the other ---- bond being a single bond), or
  NRa, O or CReRe' when the two ---- bonds starting from $A_5$ are single bonds;

$A_6$ represents:
  CRb when one of the ---- bonds starting from $A_6$ is a double bond (the other ---- bond being a single bond), or
  NRa, CRbRb' or C=O when the two ---- bonds starting from $A_6$ are single bonds;

$A_7$ represents:
  CRc when one of the ---- bonds starting from $A_7$ is a double bond (the other ---- bond being a single bond), or
  CRcRc' when the two ---- bonds starting from $A_7$ are single bonds; and $A_8$ represents:
  CRd when one of the ---- bonds starting from $A_8$ is a double bond (the other ---- bond being a single bond), or
  CRdRd' when the two ---- bonds starting from $A_8$ are single bonds, with Ra, Rb, Rb', Rc, Rc', Rd, Rd', Re, Rf, Rz and Rz' as defined below and Re' as defined above.

Advantageously, $A_5$=N, O or NRa and/or $A_6$=NRa.

The formula (I) compounds may meet one of the general formulas (I-XZ-1) to (I-XZ-19) below:

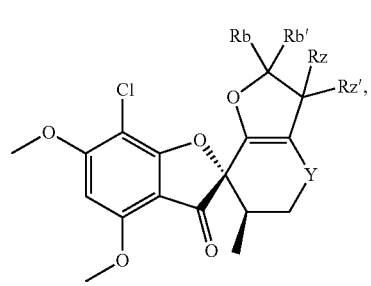
(I-XZ-1)

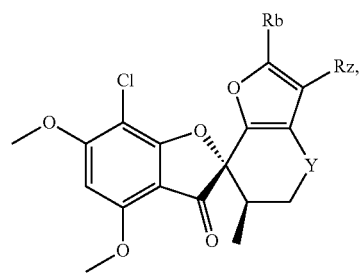
(I-XZ-2)

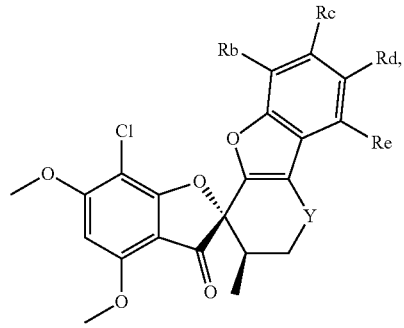
(I-XZ-3)

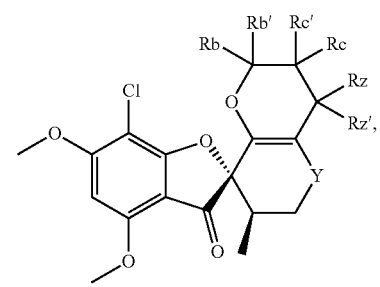
(I-XZ-4)

(I-XZ-5)
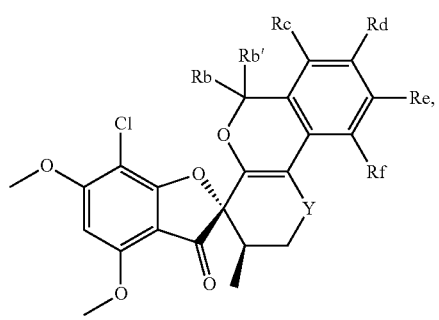
(I-XZ-6)
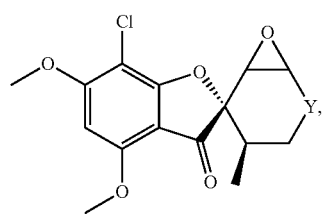
(I-XZ-7)
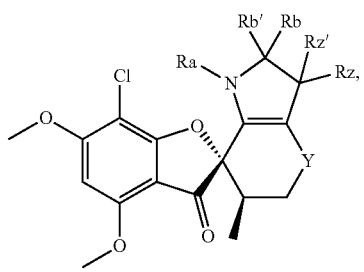
(I-XZ-8)
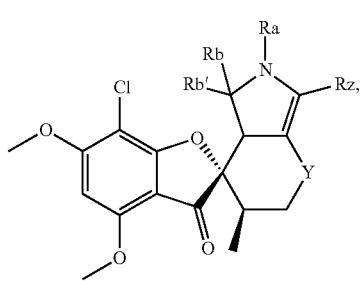
(I-XZ-9)
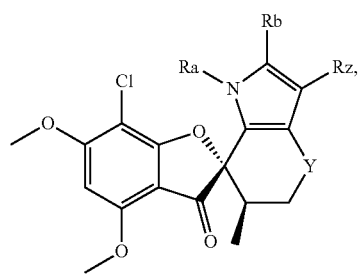
(I-XZ-10)
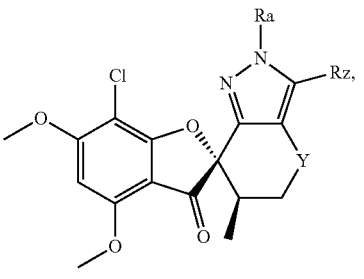
(I-XZ-11)
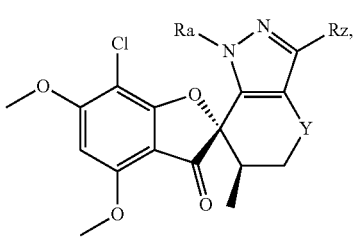
(I-XZ-12)
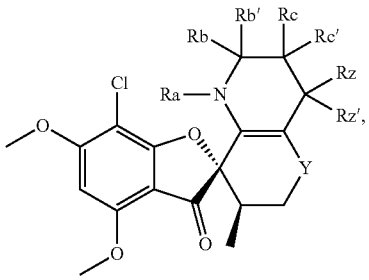
(I-XZ-13)
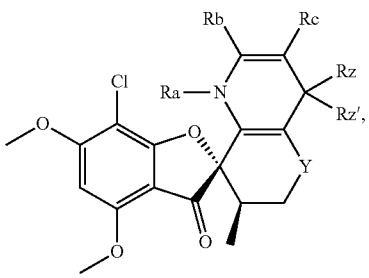
(I-XZ-14)
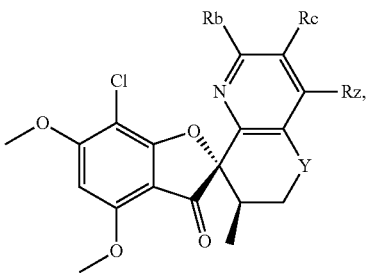
(I-XZ-15)
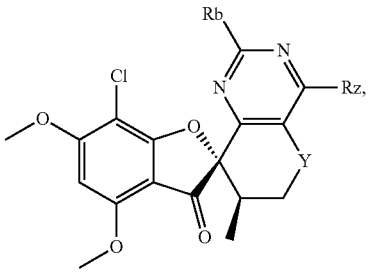
(I-XZ-16)
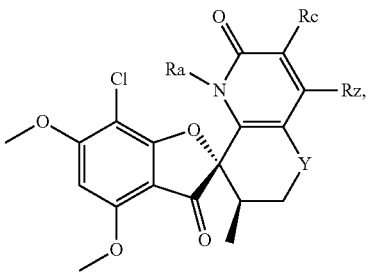

-continued

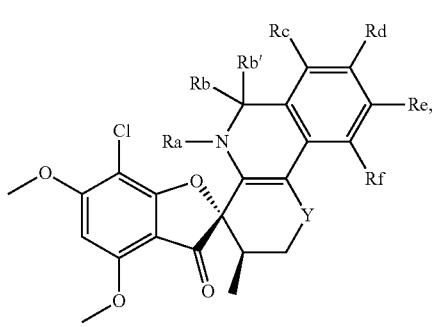
(I-XZ-17)

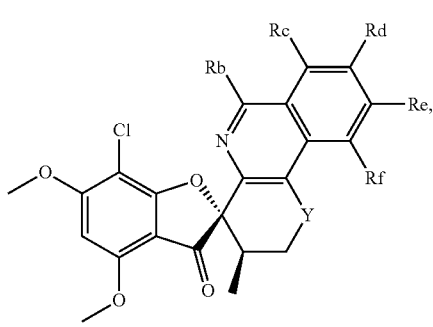
(I-XZ-18)

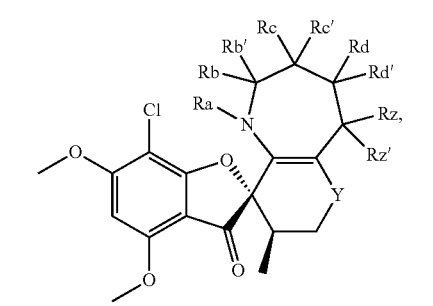
(I-XZ-19)

advantageously (I-XZ-1), (I-XZ-7), (I-XZ-8), (I-XZ-10), (I-XZ(-11) or (I-XZ-13) to (I-XZ-15),
where:
Ra is a hydrogen atom or an OH, $(C_1\text{-}C_6)$alkyl, aryl, aryl-$(C_1\text{-}C_6)$alkyl or $C(O)O$—$(C_1\text{-}C_6)$alkyl group; and
Rb, Rb', Rc, Rc', Rd, Rd', Re, Rf, Rz and Rz' are each independently a hydrogen atom; a halogen atom; —CN; —$OR_{18}$; —$NR_{19}R_{20}$; —$SR_{21}$; —$S(O)R_{22}$; —$S(O)_2R_{23}$; —$C(O)R_{24}$; —$C(O)OR_{25}$; —$C(O)NR_{26}R_{27}$; —$C(O)SR_{28}$; —$S(O)_2NR_{29}R_{30}$; —$NR_{31}S(O)_2R_{32}$; —$NR_{33}C(O)NR_{34}R_{35}$; —$C(=NR_{36})NR_{37}R_{38}$; —$NR_{39}C(=NR_{42})NR_{43}R_{44}$; $(C_1\text{-}C_6)$alkyl optionally substituted with one or more substituents selected from among a halogen atom (e.g. F), $NR_{45}R_{46}$, $SR_{47}$, $OR_{48}$ and aryl, selected in particular among $NR_{45}R_{46}$, $OR_{48}$ and aryl; $(C_2\text{-}C_6)$alkenyl; $(C_2\text{-}C_6)$alkynyl; or a carbocycle, heterocycle or biaryl (preferably an aryl, heteroaryl, saturated carbocycle, saturated heterocycle or biaryl such as phenyl, naphthyl, thiophene, thiazole, piperidine, morpholine, piperazine, tetrahydropyran, tetrahydrofuran or biphenyl) optionally substituted with one or more substituents selected from among a halogen (e.g. F or Cl), $OR_{49}$, $NR_{50}R_{51}$, $C(O)R_{52}$, $C(O)OR_{53}$, $C(O)NR_{54}R_{55}$, an aryl and a $(C_1\text{-}C_6)$alkyl group optionally substituted with one or more substituents selected from among a halogen atom, $OR_{56}$ and $NR_{57}R_{58}$,
in particular a hydrogen atom; a halogen atom; —CN; —$OR_{18}$; —$NR_{19}R_{20}$; —$C(O)R_{24}$; —$C(O)OR_{25}$; —$C(O)NR_{26}R_{27}$; $(C_1\text{-}C_6)$alkyl optionally substituted with one or more substituents selected from among a halogen atom (e.g. F), $NR_{45}R_{46}$, $OR_{48}$ and aryl, selected in particular among $NR_{45}R_{46}$, $OR_{48}$ and aryl; or an aryl, heteroaryl, saturated carbocycle, saturated heterocycle or biaryl (such as phenyl, naphthyl, thiophene, thiazole, piperidine, morpholine, piperazine, tetrahydropyran, tetrahydrofuran or biphenyl) optionally substituted with one or more substituents selected from among a halogen atom (e.g. F or Cl), $OR_{49}$, $NR_{50}R_{51}$, $C(O)R_{52}$, $C(O)OR_{53}$, $C(O)NR_{54}R_{55}$, an aryl and a $(C_1\text{-}C_6)$alkyl group optionally substituted with one or more substituents selected from among a halogen atom, $OR_{56}$ and $NR_{57}R_{58}$.

According to a second particular embodiment of the invention, neither X and Z, nor Y and Z form a carbocycle or heterocycle with their carrier carbon atom.

In this case, Y particularly represents C=O, CH—$OR_7$, $CHN_3$, $CHNR_8R_9$, C=N—$OR_{10}$ or C=N—$NR_{11}R_{12}$, advantageously C=O, CH—$OR_7$, C=N—$OR_{10}$ or C=N—$NR_{11}R_{12}$, in particular C=O or CH—$OR_7$ such as C=O or CH—OH and more particularly C=O.

Z is advantageously a hydrogen atom, a —SO—$R_{13}$ group or a —$SO_2$—$R_{13}$ group.

X⋯ is advantageously a double bond X=.

$R_{14}$ is in particular a carbocycle such as aryl, a heterocycle such as heteroaryl, —$NHR_{15}$, —$CH_2$—$NHR_{15}$, —$CH_2$—NH—C(O)—$R_{15}$, —NH—$CH_2$—$R_{15}$, —NH—NH—$R_{15}$, —NH—C(O)—$R_{15}$, —NH—C(O)—$CH_2$—$R_{15}$, —NH—$CH_2$—C(O)—$R_{15}$, —NH—$CH_2$—C(O)—O—$R_{15}$, —NH—$CH_2$—C(O)—NH—$R_{15}$, —NH—$SO_2$—$R_{15}$, —$SO_2$—$R_{15}$, —$SO_2$—$CH_2$—$R_{15}$ or —$NR_{16}R_{17}$.

$R_{14}$ is advantageously a carbocycle such as aryl, a heterocycle such as heteroaryl, —$NHR_{15}$, —NH—$CH_2$—$R_{15}$, —NH—NH—$R_{15}$, —NH—C(O)—$R_{15}$, —NH—C(O)—$CH_2$—$R_{15}$, —NH—$CH_2$—C(O)—$R_{15}$, —NH—$CH_2$—C(O)—O—$R_{15}$, —NH—$CH_2$—C(O)—NH—$R_{15}$, —NH—$SO_2$—$R_{15}$ or —$NR_{16}R_{17}$.

$R_{14}$ is in particular a carbocycle such as aryl, a heterocycle such as heteroaryl, —NH—$CH_2$—$R_{15}$, —NH—NH—$R_{15}$, —NH—C(O)—$R_{15}$, —NH—C(O)—$CH_2$—$R_{15}$, —NH—$CH_2$—C(O)—$R_{15}$, —NH—$CH_2$—C(O)—O—$R_{15}$, —NH—$CH_2$—C(O)—NH—$R_{15}$ or —NH—$SO_2$—$R_{15}$.

$R_{14}$ is more particularly —NH—$CH_2$—$R_{15}$, —NH—NH—$R_{15}$, —NH—C(O)—$R_{15}$, —NH—C(O)—$CH_2$—$R_{15}$, —NH—$CH_2$—C(O)—$R_{15}$, —NH—$CH_2$—C(O)—O—$R_{15}$ or —NH—$CH_2$—C(O)—NH—$R_{15}$.

$R_{14}$ may also represent —$NHR_{15}$, —NH—$CH_2$—$R_{15}$, —NH—NH—$R_{15}$, —NH—C(O)—$R_{15}$, —NH—C(O)—$CH_2$—$R_{15}$, —NH—$CH_2$—C(O)—$R_{15}$, —NH—$CH_2$—C(O)—O—$R_{15}$, —NH—$CH_2$—C(O)—NH—$R_{15}$, —NH—$SO_2$—$R_{15}$ or —$NR_{16}R_{17}$.

When $R_{14}$ represents a —$NR_{16}R_{17}$ group, this group is advantageously a heterocycle selected from among piperidine, piperazine and morpholine optionally substituted with a —$R_{15}$, —$OR_{15}$ or —$NHR_{15}$ group.

$R_{15}$ is advantageously an optionally substituted $(C_1\text{-}C_6)$ alkyl, carbocycle, heterocycle, biaryl, carbocycle-$(C_1\text{-}C_6)$ alkyl or heterocycle-$(C_1\text{-}C_6)$alkyl group, in particular an optionally substituted alkyl, carbocycle, heterocycle or biaryl group and in particular an optionally substituted carbocycle, heterocycle or biaryl group, the carbocycle advantageously being a cycloalkyl such as cyclohexyl or an aryl such as phenyl or naphthyl,
the heterocycle advantageously being pyridine, pyrimidine, pyridazine, pyrazine, furan, thiophene, pyrrole, pyrazole, imidazole, thiazole, oxazole, triazoles, benzofuran, benzothiophene, indole, 1,3-benzodioxolane, piperidine, morpholine or piperazine; more particularly pyridine, furane, thiophene, pyrrole, benzofuran, benzothiophene, indole, 1,3-benzodioxolane or piperidine; more particularly pyridine, furan, thiophene, benzofuran, 1,3-benzodioxolane or piperidine, and the biaryl advantageously being biphenyl.

When the ($C_1$-$C_6$)alkyl, carbocycle, heterocycle, biaryl, carbocycle-($C_1$-$C_6$)alkyl or heterocycle-($C_1$-$C_6$)alkyl group of $R_{15}$ is substituted, it is advantageously substituted with a halogen atom; an oxo group (=O); CN; $CO_2H$; $CO_2$—($C_1$-$C_6$)alkyl; OH; $NR_{59}R_{60}$; an aryl optionally substituted with one or more substituents selected from among a halogen atom, ($C_1$-$C_6$)alkyl, OH or ($C_1$-$C_6$)alkoxy; a heterocycle; or a ($C_1$-$C_6$)alkyl or ($C_1$-$C_6$)alkoxy group optionally substituted with one or more substituents selected from among a halogen atom, a ($C_1$-$C_6$)alkoxy group, a heterocycle or $NR_{61}R_{62}$, the groups $R_{59}$ to $R_{62}$ each independently representing a hydrogen atom or a ($C_1$-$C_6$)alkyl or aryl group, and the heterocycles optionally being substituted with an oxo, ($C_1$-$C_6$)alkyl or $CO_2$—($C_1$-$C_6$)alkyl group.

In particular, the compounds of the invention can be selected from among Examples 1 to 261 described in the experimental section below.

A further subject of the invention is a formula (I) compound of the invention such as defined above, for use as a drug, notably intended for the treatment of cancerous and pre-cancerous hyperproliferative pathologies.

The present invention also concerns the use of a formula (I) compound such as defined above in the manufacture of a drug, notably intended for the treatment of cancerous and pre-cancerous hyperproliferative pathologies.

The present invention also concerns a method for treating cancerous and pre-cancerous hyperproliferative pathologies, comprising the administration of an efficient dose of a formula (I) compound as defined above to a person in need thereof.

By "cancerous or pre-cancerous hyperproliferative pathologies" in the present invention is meant all types of cancerous or pre-cancerous hyperproliferative pathologies, in particular lung cancer, breast cancer, brain cancer and skin cancers.

By "skin cancer" in the present invention is meant actinic keratosis, solar keratosis, keratinocyte intraepithelial neoplasia, cutaneous papilloma, in situ epidermoid carcinoma, epidermoid carcinoma, pre-cancerous skin lesions, basal cell carcinoma including surface and nodular forms, Bowen's disease, Dubreuilh's melanoma, condylomas, Merkel cell tumour, Paget's disease, or cutaneous-mucosal lesions caused by human papilloma virus.

The present invention also concerns a pharmaceutical composition comprising at least one formula (I) compound as defined above, and at least one pharmaceutically acceptable excipient.

The pharmaceutical compositions of the invention can be formulated in particular for oral administration, for administration via topical route or via injection, the said compositions being more particularly intended for mammals including human.

The active ingredient can be administered in unit administration forms, in a mixture with conventional pharmaceutical carriers, to animals including human beings.

The compounds of the invention as active ingredients can be used at doses of between 0.01 mg and 1000 mg per day, given in a single dose once daily or administered in several doses throughout the day, for example twice a day in equal doses. The dose administered per day is advantageously between 5 mg and 500 mg, more advantageously between 10 mg and 200 mg. It may be necessary to use doses outside these ranges as can be determined by persons skilled in the art.

The pharmaceutical compositions of the invention may also comprise at least one other active ingredient such as an anti-cancer agent.

The present invention further concerns a pharmaceutical composition such as defined above for use as a drug, notably intended for the treatment of cancerous and pre-cancerous hyperproliferative pathologies The present invention is illustrated by the following non-limiting examples.

EXAMPLE 1

Synthesis of the Compounds of the Invention

Abbreviations Used

PTSA para-Toluenesulfonic acid
CAN Ceric Ammonium Nitrate
DBA Dibenzylideneacetone
DBU 1,8-Diazabicyclo[5.4.0]undec-7-ene
DEAD Diethyl Azodicarboxilate
DIEA Diisopropylethylamine
DMAP N,N-4-Dimethylaminopyridine
DMF Dimethylformamide
DMFDMA Dimethylformamide dimethyl acetal
DMSO Dimethylsulfoxide
DPPA Diphenylphosphoryl azide
EDC 1-(3-Dimethylaminopropyl)-3-ethylcarbodiimide hydrochloride
Equiv./eq. Eq.uivalent
EP Petroleum ether
ES Electrospray ionization
HOBt 1-Hydroxybenzotriazole
HPLC High Performance Liquid Chromatography
LCMS Liquid Chromatography coupled with mass spectrometry
mCPBA Meta-Chloroperbenzoic acid
MS4A 4A Molecular sieve
NBS N-Bromosuccinimide
PNBA Par-nitrobenzoic acid
PTSCl para-Toluenesulfonyl chloride
NMR Nuclear Magnetic Resonance
rt Room temperature
TEA Triethylamine
THF Tetrahydrofuran
Tol Toluene The compounds of the invention were often obtained in the form of two diastereoisomers which were able to be separated. However, among the two NMR spectra obtained it was not determined to which spectrum each of these two diastereoisomers corresponded.

1.1. Synthesis of the dihydrofurans at 2' and 4':

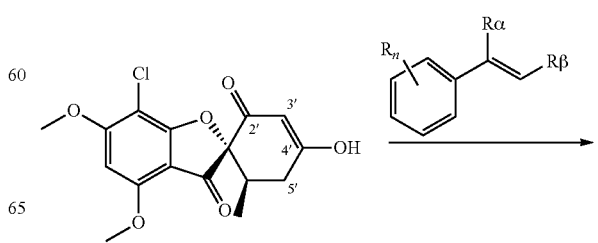

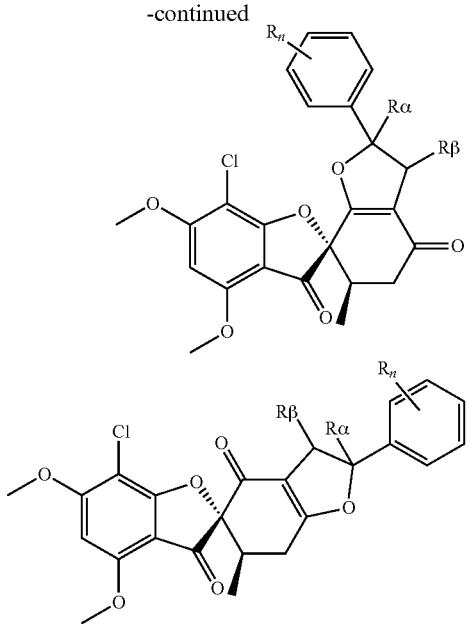

Example: $R_n=R_\alpha=R_\beta=H$

Manganese acetate dihydrate (9.45 mmol; 2.0 equiv.) was dissolved in acetic acid (50 mL) at 80° C. until a dark brown solution was formed. The temperature was reduced to 40° C., griseofulvic acid (1.6 g, 4.72 mmol; 1.0 equiv.) and styrene (5.67 mmol; 1.2 equiv.) were then successively added. The reaction medium was left under agitation until disappearance of the dark brown colouring (1 hour in this case, from 1 h to 24 h). The acetic acid was evaporated in vacuo, the residue obtained diluted in ethyl acetate (150 mL) and the organic phase successively washed with saturated aqueous bicarbonate solution (100 mL), sodium hydroxide and brine (100 mL). The organic phase was dried over magnesium sulfate, filtered and the solvents evaporated under reduced pressure. The residue was purified on silica gel (CH$_2$Cl$_2$/AcOEt 98:2 to 90:10) leading to the four isomers of the reaction with yields ranging from 12 to 22%.

(2S,2'S,6R)-7'-chloro-4',6'-dimethoxy-6-methyl-2-phenyl-6,7-dihydro-2H,3'H-2,5'-spirobi[benzofuran]-3',4(3H)-dione and (2R,2'S,6R)-7'-chloro-4',6'-dimethoxy-6-methyl-2-phenyl-6,7-dihydro-2H,3'H-2,5'-spirobi[benzofuran]-3',4(3H)-dione 1 yellow solid, 459 mg (22%) (CDCl$_3$, 400 MHz, δ, ppm): 7.39 (m, 5H), 6.10 (s, 1H), 5.85 (dd, 1H, J=10.6, 7.0 Hz), 4.02 (s, 3H), 3.94 (s, 3H), 3.36 (ddt, 1H, J=14.6, 10.6, 2.0 Hz), 3.17 (ddt, 1H, J=17.6, 11.6, 2.0 Hz), 2.97 (m, 1H), 2.82 (ddd, 1H, J=14.6, 7.0, 2.0 Hz), 2.63 (ddd, 1H, J=17.6, 6.0, 2.0 Hz), 1.08 (d, 3H, J=6.6 Hz); LCMS (ES, m/z): 441.103 [M+H]$^+$ 2 off-white solid, 377 mg (18%); $^1$H NMR (CDCl$_3$, 400 MHz, δ, ppm): 7.39 (m, 5H), 6.11 (s, 1H), 5.90 (dd, 1H, J=10.3, 8.4 Hz), 4.03 (s, 3H), 3.96 (s, 3H), 3.27 (ddd, 1H, J=14.3, 10.3, 2.0 Hz), 3.16 (ddt, 1H, J=17.6, 11.5, 2.0 Hz), 2.98 (m, 1H), 2.95 (m, 1H), 2.64 (ddd, 1H, J=17.6, 5.6, 2.0 Hz), 1.09 (d, 3H, J=6.6 Hz); LCMS (ES, m/z): 441.103 [M+H]$^+$ (2R,2'S,6R)-7'-chloro-4',6'-dimethoxy-6-methyl-2-phenyl-5,6-dihydro-2H,3'H-2,7'-spirobi[benzofuran]-3',4(3H)-dione and (2S,2'S,6R)-7'-chloro-4',6'-dimethoxy-6-methyl-2-phenyl-5,6-dihydro-2H,3'H-2,7'-spirobi[benzofuran]-3',4(3H)-dione 3 off-white solid, 297 mg (14%); $^1$H NMR (CDCl$_3$, 400 MHz, δ, ppm): 7.33 (m, 3H), 7.22 (m, 2H), 6.12 (s, 1H), 5.80 (dd, 1H, J=10.5, 8.0 Hz), 4.01 (s, 3H), 3.98 (s, 3H), 3.38 (dd, 1H, J=15.2, 10.5 Hz), 3.09 (dd, 1H, J=16.4, 13.0 Hz), 2.98 (m, 1H), 2.93 (dd, 1H, J=15.2, 8.0 Hz), 2.49 (dd, 1H, J=16.4, 4.3 Hz), 1.01 (d, 3H, J=6.6 Hz); LCMS (ES, m/z): 441.103 [M+H]$^+$ 4 white solid, 12% yield; $^1$H NMR (CDCl$_3$, 400 MHz, δ, ppm): 7.34 (m, 5H), 6.13 (s, 1H), 5.76 (dd, 1H, J=10.5, 8.0 Hz), 4.02 (s, 3H), 4.00 (s, 3H), 3.37 (dd, 1H, J=15.0, 10.5 Hz), 3.11 (dd, 1H, J=16.4, 13.0 Hz), 2.95 (m, 2H), 2.47 (dd, 1H, J=16.4, 5.0 Hz), 1.02 (d, 3H, J=6.6 Hz); LCMS (ES, m/z): 441.103 [M+H]$^+$ (2R,2'S,6R)-7'-chloro-4',6'-dimethoxy-2,6-dimethyl-2-phenyl-5,6-dihydro-2H,3'H-2,7'-spirobi[benzofuran]-3',4(3H)-dione and (2S,2'S,6R)-7'-chloro-4',6'-dimethoxy-2,6-dimethyl-2-phenyl-5,6-dihydro-2H,3'H-2,7'-spirobi[benzofuran]-3',4(3H)-dione 5 white foam, 15% yield; $^1$H NMR (400 MHz, CDCl$_3$, ppm): δ 7.31 (m, 2H), 7.24 (m, 1H), 7.19 (m, 2H), 6.15 (s, 1H), 4.04 (s, 3H), 4.00 (s, 3H), 3.13 (d, 1H, J=15.0 Hz), 3.07 (d, 1H, J=15.0 Hz), 3.03 (d, 1H, J=16.0 Hz), 2.98 (m, 1H), 2.47 (dd, 1H, J=16.0, 4.0 Hz), 1.79 (s, 3H), 1.01 (d, 3H, J=6.5 Hz); LCMS (ES, m/z): 454.92 [M+H]$^+$ 6 white foam, 10% yield; $^1$H NMR (400 MHz, CDCl$_3$, ppm): δ 7.37 (m, 4H), 7.29 (m, 1H), 6.17 (s, 1H), 4.06 (s, 3H), 4.02 (s, 3H), 3.10 (m; 3H), 2.92 (m, 1H), 2.43 (dd, 1H, J=16.5, 4.3 Hz), 1.62 (s, 3H), 1.01 (d, 3H, J=6.7 Hz); LCMS (ES, m/z): 455.23 [M+H]$^+$ (2'S,6R)-7'-chloro-4',6'-dimethoxy-6-methyl-2,2-diphenyl-6,7-dihydro-2H,3'H-2,5'-spirobi[benzofuran]-3',4(3H)-dione 7 pale yellow solid, 53% yield; $^1$H NMR (400 MHz, CDCl$_3$, ppm): δ 7.42-7.22 (m, 10H), 6.07 (s, 1H), 3.99 (s, 3H), 3.91 (s, 3H), 3.66 (d, 1H, J=14.6 Hz), 3.44 (d, 1H, J=14.6 Hz), 3.23 (dd, 1H, J=17.2, 11.7 Hz), 2.94 (m, 1H), 2.70 (dd, 1H, J=17.2, 5.5 Hz), 1.07 (d, 3H, J=6.7 Hz); LCMS (ES, m/z): 516.90 [M+H]$^+$ (2'S,6R)-7'-chloro-4',6'-dimethoxy-6-methyl-2,2-diphenyl-5,6-dihydro-2H,3'H-2,7'-spirobi[benzofuran]-3',4(3H)-dione 8 pale yellow solid, 34% yield; $^1$H NMR (400 MHz, CDCl$_3$, ppm): δ 7.43 (d, 2H, J=7.7 Hz), 7.37 (t, 2H, J=7.7 Hz), 7.30 (m, 1 h), 7.22 (m, 3H), 7.12 (d, 2H, J=7.7 Hz), 6.14 (s, 1H), 4.04 (s, 3H), 3.98 (s, 3H), 3.61 (s, 2H), 3.09 (m, 1H), 2.92 (m, 1H), 2.43 (dd, 1H, J=15.5, 4.0 Hz), 0.99 (d, 3H, J=6.6 Hz); LCMS (ES, m/z): 517.10 [M+H]$^+$ (2'S,6R)-7'-chloro-4',6'-dimethoxy-6-methyl-2-(4-(morpholinomethyl)phenyl)-5,6-dihydro-2H,3'H-2,7'-spirobi[benzofuran]-3',4(3H)-dione 9 beige solid, 7% yield; $^1$H NMR (400 MHz, CDCl$_3$, ppm): δ 7.32 (d, 2H, J=7.8 Hz), 7.17 (d, 2H, J=7.8 Hz), 6.12 (s, 1H), 5.80 (dd, 1H, J=10.7, 8.2 Hz), 4.01 (s, 3H), 3.98 (s, 3H), 3.72 (m, 4H), 3.49 (m, 2H), 3.37 (dd, 1H, J=15.2, 10.7 Hz), 3.08 (dd, 1H, J=16.2, 12.8 Hz), 2.97 (m, 1H), 2.92 (dd, 1H, J=15.2, 8.0 Hz), 2.48 (dd, 1H, J=16.2, 4.2 Hz), 2.44 (m, 4H), 1.00 (d, 3H, J=6.7 Hz); LCMS (ES, m/z): 540.29 [M+H]$^+$ Methyl 4-((2R,2'S,6R)-7'-chloro-4',6'-dimethoxy-6-methyl-3',4-dioxo-3,4,5,6-tetrahydro-2H,3'H-2,7'-spirobi[benzofuran]-2-yl)benzoate and methyl 4-((2S,2'S,6R)-7'-chloro-4',6'-dimethoxy-6-methyl-3',4-dioxo-3,4,5,6-tetrahydro-2H,3'H-2,7'-spirobi[benzofuran]-2-yl)benzoate 10 white solid, 25% yield; $^1$H NMR (400 MHz, CDCl$_3$, ppm): δ 7.93 (d, 2H, J=8.2 Hz), 7.19 (d, 2H, J=8.2 Hz), 6.08 (s, 1H), 5.80 (dd, 1H, J=10.8, 7.7 Hz), 3.93 (s, 3H), 3.92 (s, 3H), 3.84 (s, 3H), 3.37 (dd, 1H, J=16.3, 10.8 Hz), 3.01 (dd, 1H, J=15.6, 12.6 Hz), 2.92 (m, 1H), 2.83 (dd, 1H, J=15.6, 7.8 Hz), 2.43 (dd, 1H, J=16.3, 3.8 Hz), 0.95 (d, 3H, J=6.7 Hz); LCMS (ES, m/z): 499.01 [M+H]$^+$ 11 white solid, 14% yield; $^1$H NMR (400 MHz, CDCl$_3$, ppm): δ 8.02 (d, 2H, J=8.2 Hz), 7.36 (d, 2H, J=8.2 Hz), 6.13 (s, 1H), 5.78 (dd, 1H, J=10.8, 7.5 Hz), 3.99 (s, 3H), 3.97 (s, 3H), 3.89 (s, 3H), 3.38 (dd, 1H, J=15.0, 10.8 Hz), 3.08 (dd, 1H, J=16.3, 13.0 Hz), 2.94 (m, 1H), 2.86 (dd, 1H, J=15.0, 7.5 Hz), 2.44 (dd, 1H, J=16.3, 4.3 Hz), 1.00 (d, 3H, J=7.0 Hz); LCMS (ES, m/z): 498.99 [M+H]$^+$ 2-((2R,2'S,6R)-7'-chloro-4',6'-dimethoxy-6-methyl-3',4-dioxo-2-phenyl-3,4,5,6-tetrahydro-2H,3'H-2,7'-spirobi[benzofuran]-2-yl)ethyl acetate and 2-((2 S,2'S,6R)-7'-chloro-4',6'-dimethoxy-6-methyl-3',4-dioxo-2-phenyl-3,4,5,6-tetrahydro-2H,3'H-2,7'-spirobi[benzofuran]-2-yl)ethyl acetate 12 white solid, 12% yield; $^1$H NMR (400 MHz, CDCl$_3$, ppm): δ 7.41-7.28 (m, 5H), 6.19 (s, 1H), 4.08 (s, 3H), 4.02 (s, 3H), 3.87 (m, 1H), 3.76 (m, 1H), 3.22 (d, 1H, J=15.0 Hz), 3.16 (d, 1H, J=15.0 Hz), 3.07 (dd, 1H, J=16.3, 12.8 Hz), 2.90 (m, 1H), 2.42 (dd, 1H, J=16.3, 4.2 Hz), 2.29 (t, 2H, J=7.0 Hz), 1.82 (s, 3H), 1.00 (d, 3H, J=6.7 Hz); LCMS (ES, m/z): 527.26 [M+H]$^+$ 13 white solid, 12% yield; $^1$H NMR (400 MHz, CDCl$_3$, ppm): δ 7.29 (m, 2H), 7.22 (m, 1H), 7.10 (m, 2H), 6.18 (s, 1H), 4.05 (s, 1H), 4.01 (s, 1H), 3.20 (d, 1H, J=14.7 Hz), 3.09 (d, 1H, J=14.7 Hz), 3.02 (dd, 1H, J=15.6, 12.8 Hz), 2.95 (m, 1H), 2.48-2.35 (m, 3H), 1.90 (s, 3H), 0.99 (d, 3H, J=6.7 Hz); LCMS (ES, m/z): 527.00 [M+H]$^+$ (2 S,2'S,6R)-7'-chloro-2-(4-hydroxybutyl)-4',6'-dimethoxy-6-methyl-2-phenyl-5,6-dihydro-2H,3'H-2,7'-spirobi[benzofuran]-3',4(3H)-dione and (2R,2'S,6R)-7'-chloro-2-(4-hydroxybutyl)-4',6'-dimethoxy-6-methyl-2-phenyl-5,6-dihydro-2H,3'H-2,7'-spirobi[benzofuran]-3',4(3H)-dione 14 pale yellow solid, 3% yield; $^1$H NMR (400 MHz, CDCl$_3$, ppm): δ 7.28 (m, 2H), 7.20 (m, 1H), 7.09 (m, 2H), 6.17 (s, 1H), 4.04 (s, 3H), 4.01 (s, 3H), 3.58 (td, 2H, J=6.4, 2.0 Hz), 3.11 (d, 1H, J=15.2 Hz), 3.08-2.98 (m, 2H), 2.94 (m, 1H), 2.44 (dd, 1H, J=15.8, 3.7 Hz), 2.08 (ddd, 1H, J=14.2, 8.8, 5.3 Hz), 1.98 (ddd, 1H, J=14.2, 8.8, 5.3 Hz), 1.54 (m, 1H), 1.39 (m, 1H), 1.25 (m, 1H), 1.00 (d, 3H, J=6.7 Hz); LCMS (ES, m/z): 513.00 [M+H]$^+$ 15 pale yellow solid, 3% yield; $^1$H NMR (400 MHz, CDCl$_3$, ppm): δ 7.38-7.23 (m, 5H), 6.16, s, 1H), 4.05 (s, 3H), 4.00 (s, 3H), 3.48 (td, 2H, J=6.0, 2.2 Hz), 3.11 (m, 2H), 3.04 (dd, 1H, J=16.4, 12.9 Hz), 2.89 (m, 1H), 2.41 (dd, 1H, J=16.4, 4.4 Hz), 1.93 (ddd, 1H, J=14.0, 9.2, 5.0 Hz), 1.82 (ddd, 1H, J=14.0, 9.2, 5.0 Hz), 1.37 (m, 2H), 1.19 (m, 1H), 1.06 (m, 1H), 0.98 (d, 3H, J=6.7 Hz); LCMS (ES, m/z): 513.00 [M+H]$^+$ (2R,2'S,3R,6R)-7'-chloro-4',6'-dimethoxy-6-methyl-3',4-dioxo-2-phenyl-3,4,6,7-tetrahydro-2H,3'H-2,5'-spirobi[benzofuran]-3-carboxamide and (2 S,2'S,3S,6R)-7'-chloro-4',6'-dimethoxy-6-methyl-3',4-dioxo-2-phenyl-3,4,6,7-tetrahydro-2H,3'H-2,5'-spirobi[benzofuran]-3-carboxamide 16 pale yellow solid, 9% yield; $^1$H NMR (400 MHz, CDCl$_3$, ppm): δ 7.46 (bs, 1H), 7.38-7.25 (m, 5H), 6.49 (d, 1H, J=5.1 Hz), 6.09 (s, 1H), 5.98 (bs, 1H), 3.96 (s, 3H), 3.89 (s, 3H), 3.81 (d, 1H, J=5.1 Hz), 3.15 (dd, 1H, J=18.2, 11.5 Hz), 2.96 (m, 1H), 2.70 (dd, 1 h, J=18.2, 5.8 Hz), 1.03 (d, 3H, J=6.7 Hz); LCMS (ES, m/z): 484.20 [M+H]$^+$ 17 pale yellow solid, 9% yield; $^1$H NMR (400 MHz, CDCl$_3$, ppm): δ 7.40-7.27 (m, 5H), 7.18 (bs, 1H), 6.47 (d, 1H, J=6.0 Hz), 6.11 (s, 1H), 5.57 (bs, 1H), 4.02 (m, 1H), 3.99 (s, 3H), 3.91 (s, 3H), 3.22 (dd, 1H, J=17.4, 11.8 Hz), 2.96 (m, 1H), 2.70 (dd, 1H, J=17.4, 5.7 Hz), 1.07 (d, 3H, J=6.6 Hz); LCMS (ES, m/z): 484.20 [M+H]$^+$ (2R,2'S,3R,6R)-7'-chloro-4',6'-dimethoxy-6-methyl-3',4-dioxo-2-phenyl-3,4,5,6-tetrahydro-2H,3'H-2,7'-spirobi[benzofuran]-3-carboxamide and (2S,2'S,3S,6R)-7'-chloro-4',6'-dimethoxy-6-methyl-3',4-dioxo-2-phenyl-3,4,5,6-tetrahydro-2H,3'H-2,7'-spirobi[benzofuran]-3-carboxamide 18 pale yellow solid, 9% yield; $^1$H NMR (400 MHz, CDCl$_3$, ppm): δ 7.75 (bs, 1H), 7.36-7.25 (m, 3H), 7.19 (m, 2H), 6.46 (d, 1H, J=6.4 Hz), 6.09 (s, 1H), 5.59 (bs, 1H), 4.03 (d, 1H, J=6.4 Hz), 3.98 (s, 3H), 3.95 (s, 3H), 3.16 (dd, 1H, J=16.8, 13.1 Hz), 2.99 (m, 1H), 2.52 (dd, 1H, J=16.8, 4.2 Hz), 1.01 (d, 3H, J=6.7 Hz); LCMS (ES, m/z): 441.103 [M+H]$^+$ 19 pale yellow solid, 9% yield; $^1$H NMR (400 MHz, CDCl$_3$, ppm): δ 7.67 (bs, 1H), 7.42-7.29 (m, 5H), 6.44 (bs, 1H), 6.16 (s, 1H), 5.43 (bs, 1H), 4.03 (s, 3H), 4.02 (m, 1H), 4.00 (s, 3H), 3.18 (dd, 1H, J=16.7, 12.8 Hz), 2.99 (m, 1H), 2.55 (dd, 1H, J=16.7, 4.6 Hz), 1.06 (d, 3H, j=6.7 Hz); LCMS (ES, m/z): 484.20 [M+H]$^+$ (2R,2'S,6R)-2-(aminomethyl)-7'-chloro-2-(2-chlorophenyl)-4',6'-dimethoxy-6-methyl-5,6-dihydro-2H,3'H-2,7'-spirobi[benzofuran]-3',4(3H)-dione and (2S,2'S,6R)-2-(aminomethyl)-7'-chloro-2-(2-chlorophenyl)-4',6'-dimethoxy-6-methyl-5,6-dihydro-2H,3'H-2,7'-spirobi[benzofuran]-3',4(3H)-dione 20 beige solid; $^1$H NMR (400 MHz, CDCl$_3$, ppm): δ 7.37 (d, 1H, J=7.8 Hz), 7 25 (m, 1H), 7 18 (m, 2H), 6 22 (s, 1H), 4 06 (s, 3H), 4 04 (s, 3H), 3 78 (d, 1H, J=13 6 Hz), 3 64 (d, 1H, J=13.6 Hz), 3 47 (d, 1H, J=16.5 Hz), 3 31 (d, 1H, J=16.5 Hz), 2.96 (m, 2H), 2.45 (m, 1H), 0.98 (d, 3H, J=5.6 Hz); LCMS (ES, m/z): 504.29 [M+H]$^+$ 21 pale yellow solid; $^1$H NMR (400 MHz, CDCl$_3$, ppm): δ 7.77 (m, 1H), 7.47-7.31 (m, 3H), 6.14 (s, 1H), 4.04 (s, 3H), 3.97 (s, 3H), 3.96-3.80 (m, 2H), 3.53 (d, 1H, J=16.6 Hz), 3.35

(d, 1H, J=13.8 Hz), 2.89 (m, 2H), 2.043 (m, 1H), 1.00 (d, 1H, J=6.7 Hz); LCMS (ES, m/z): 504.29 [M+H]$^+$ (2S,2'S,6R)-2-(aminomethyl)-7'-chloro-2-(2-chlorophenyl)-4',6'-dimethoxy-6-methyl-6,7-dihydro-2H,3'H-2,5'-spirobi[benzofuran]-3',4(3H)-dione and (2R,2'S,6R)-2-(aminomethyl)-7'-chloro-2-(2-chlorophenyl)-4',6'-dimethoxy-6-methyl-6,7-dihydro-2H,3'H-2,5'-spirobi[benzofuran]-3',4(3H)-dione 22 beige solid; $^1$H NMR (400 MHz, CDCl$_3$, ppm): δ 7.70 (m, 1H), 7.44 (m, 1H), 7.33 (m, 2H), 6.14 (s, 1H), 4.04 (s, 3H), 3.91 (s, 3H), 3.73 (d, 1H, J=13.9 Hz), 3.66 (d, 1 h, J=13.9 Hz), 3.43 (d, 1H, J=15.9 Hz), 3.28 (d, 1H, J=15.9 Hz), 3.03 (dd, 1H, J=17.7, 11.8 Hz), 2.88 (m, 1H), 2.70 (dd, 1H, J=17.7, 5.0 Hz), 1.02 (d, 3H, J=6.7 Hz).
LCMS (ES, m/z): 504.29 [M+H]$^+$
23 pale yellow solid; $^1$H NMR (400 MHz, CDCl$_3$, ppm): δ 7.66 (m, 1H), 7.41 (m, 1H), 7.28 (m, 2H), 6.15 (s, 1H), 4.04 (s, 3H), 3.93 (s, 3H), 3.74 (d, 1H, J=13.4 Hz), 3.62 (d, 1H, J=13.4 Hz), 3.48 (m, 1H), 3.14 (d, 1H, J=15.5 Hz), 3.05 (dd, 1H, J=17.2, 11.3 Hz), 2.75 (m, 2H), 0.99 (d, 3H, J=6.7 Hz); LCMS (ES, m/z): 504.29 [M+H]$^+$ (2'S,6R)-7'-chloro-2-(3,4-dichlorophenyl)-4',6'-dimethoxy-6-methyl-6,7-dihydro-2H,3'H-2,5'-spirobi[benzofuran]-3',4(3H)-dione 24 yellow solid, 6.9% yield; $^1$H NMR (CDCl$_3$, 400 MHz, δ, ppm): δ 1.08 (d, 3H, J=6.7 Hz), 2.63 (ddd, 1H, J=17.9, 5.7, 1.6 Hz), 2.86 (ddt, 1H, J=14.7, 8.4, 2.0 Hz), 2.90-3.00 (m, 1H), 3.14 (ddt, 1H, J=17.7, 11.5, 2.0), 3.26 (ddd, 1H, J=14.6, 10.5, 2.2 Hz), 3.95 (s, 3H), 4.01 (s, 3H), 5.82 (dd, 1H, J=10.3, 8.5 Hz), 6.10 (s, 1H), 7.17 (dd, 1H, J=8.3, 2.0 Hz), 7.44 (d, 1H, J=2.0 Hz), 7.47 (d, 1H, J=8.3 Hz); LCMS (ES, m/z): 508.8 [M+H]$^+$.

(2R,2'S,6R)-7'-chloro-2-(3,4-dichlorophenyl)-4',6'-dimethoxy-6-methyl-5,6-dihydro-2H,3'H-2,7'-spirobi[benzofuran]-3',4(3H)-dione and (2S,2'S,6R)-7'-chloro-2-(3,4-dichlorophenyl)-4',6'-dimethoxy-6-methyl-5,6-dihydro-2H,3'H-2,7'-spirobi[benzofuran]-3',4(3H)-dione 25 yellow solid, 9% yield; $^1$H NMR (CDCl$_3$, 400 MHz, δ, ppm): δ 0.99 (d, 3H, J=6.6 Hz), 2.48 (dd, 1H, J=16.4, 4.2 Hz), 2.86 (dd, 1H, J=15.3, 7.7 Hz), 2.91-2.97 (m, 1H), 3.06 (dd, 1H, J=16.3, 13.0), 3.37 (dd, 1H, J=15.3, 10.6 Hz), 3.98 (s, 3H), 4.01 (s, 3H), 5.72 (dd, 1H, J=10.6, 7.7 Hz), 6.13 (s, 1H), 7.02 (dd, 1H, J=8.3, 2.0 Hz), 7.26 (d, 1H, J=2.0 Hz), 7.41 (d, 1H, J=8.3 Hz); LCMS (ES, m/z): 508.8 [M+H]$^+$
26 yellow solid, 3% yield; $^1$H NMR (CDCl$_3$, 400 MHz, δ, ppm): δ 1.02 (d, 3H, J=6.8 Hz), 2.46 (dd, 1H, J=16.4, 4.3 Hz), 2.86 (dd, 1H, J=15.1, 7.3 Hz), 2.91-2.00 (m, 1H), 3.09 (dd, 1H, J=16.4, 13.0), 3.37 (dd, 1H, J=15.1, 10.8 Hz), 3.99 (s, 3H), 4.02 (s, 3H), 5.68 (dd, 1H, J=10.7, 7.4 Hz), 6.14 (s, 1H), 7.14 (dd, 1H, J=8.3, 2.0 Hz), 7.41 (d, 1H, J=2.0 Hz), 7.45 (d, 1H, J=8.3 Hz); LCMS (ES, m/z): 508.9 [M+H]$^+$.

(2'S,6R)-7'-chloro-2-(4-((dimethylamino)methyl)phenyl)-4',6'-dimethoxy-6-methyl-6,7-dihydro-2H,3'H-2,5'-spirobi[benzofuran]-3',4(3H)-dione 27 colourless solid, 4% yield; $^1$H NMR (DMSO-d$_6$, 400 MHz, δ, ppm): δ 0.85 (d, 3H, J=6.7 Hz), 0.91 (d, 3H, J=6.5 Hz), 2.12 (s, 6H), 2.14 (s, 6H), 2.40 (dd, 1H, J=16.7, 4.8 Hz), 2.66-3.01 (m, 7H), 3.13-3.22 (m, 2H), 3.28 (dd, 2H, J=15.1, 10.7), 3.37 (s, 2H), 3.39 (s, 2H), 3.92 (s, 3H), 3.96 (s, 3H), 4.03 (s, 3H), 4.04 (s, 3H), 5.87 (dd, 1H, J=10.1, 7.8 Hz), 6.02 (dd, 1H, J=9.9, 8.2 Hz), 6.48 (s, 1H), 6.52 (s, 1H), 7.31 (s, 4H), 7.33 (d, 2H, J=7.9 Hz), 7.39 (d, 2H, J=7.9 Hz); LCMS (ES, m/z): 498.0 [M+H]$^+$ (2'S,6R)-7'-chloro-2-(4-((dimethylamino)methyl)phenyl)-4',6'-dimethoxy-6-methyl-5,6-dihydro-2H,3'H-2,7'-spirobi[benzofuran]-3',4(3H)-dione 28 yellow solid, 7% yield; $^1$H NMR (400 MHz, DMSO-d$_6$, ppm): δ 0.84 (d, 3H, J=6.6 Hz), 0.91 (d, 3H, 6.0 Hz), 2.10 (s, 6H), 2.14 (s, 6H), 2.42 (dd, 1H, J=16.7, 4.6 Hz), 2.59 (dd, 1H, J=14.5, 6.4 Hz), 2.66-2.78 (m, 3H), 2.82-2.99 (m, 3H), 3.26-3.36 (m, 2H), 3.34 (s, 2H), 3.40 (s, 2H), 3.92 (s, 3H), 3.94 (s, 3H), 4.02 (s, 3H), 4.04 (s, 3H), 5.94 (dd, 1H, J=10.1, 8.2 Hz), 6.02 (dd, 1H, J=10.5, 6.7 Hz), 6.48 (s, 1H), 6.50 (s, 1H), 7.14 (d, 2H, J=7.8 Hz), 7.26 (d, 2H, J=7.8 Hz), 7.31-7.37 (m, 2H); LCMS (ES, m/z): 498.0 [M+H]$^+$.

(2S,2'S,6R)-7'-chloro-2-(3-fluorophenyl)-4',6'-dimethoxy-6-methyl-6,7-dihydro-2H,3'H-2,5'-spirobi[benzofuran]-3',4(3H)-dione and (2R,2'S,6R)-7'-chloro-2-(3-fluorophenyl)-4',6'-dimethoxy-6-methyl-6,7-dihydro-2H,3'H-2,5'-spirobi[benzofuran]-3',4(3H)-dione 29 yellow solid, 2% yield; $^1$H NMR (400 MHz, CDCl$_3$, ppm): δ 1.08 (d, 3H, J=6.8 Hz), 2.63 (ddd, 1H, J=17.8, 5.7, 1.7 Hz), 2.78 (ddd, 1H, J=14.7, 6.9, 2.1 Hz), 2.91-3.01 (m, 1H), 3.17 (ddt, 1H, J=17.9, 11.5, 2.1 Hz), 3.36 (ddt, 1H, J=14.7, 10.8, 2.0 Hz), 3.95 (s, 3H), 4.01 (s, 3H), 5.82 (dd, 1H, J=10.6, 7.0 Hz), 6.10 (s, 1H), 7.00-7.10 (m, 2H), 7.15 (dl, 1H, J=7.7 Hz), 7.33-7.40 (m, 1H); LCMS (ES, m/z): 458.9 [M+H]$^+$
30 white solid, 3% yield; $^1$H NMR (400 MHz, CDCl$_3$, ppm): δ 1.08 (d, 3H, J=6.7 Hz), 2.64 (ddd, 1H, J=17.7, 5.6, 1.6 Hz), 2.85-3.00 (m, 2H), 3.15 (ddt, 1H, J=17.8, 11.6, 4.0 Hz), 3.27 (ddd, 1H, J=14.5, 10.6, 2.0 Hz), 3.94 (s, 3H), 4.01 (s, 3H), 5.86 (dd, 1H, J=10.3, 8.4 Hz), 6.10 (s, 1H), 7.02-7.08 (m, 2H), 7.11 (d, 1H, J=7.9 Hz), 7.34-7.40 (m, 1H); LCMS (ES, m/z): 458.9 [M+H]$^+$ (2'S,6R)-7'-chloro-2-(2-fluorophenyl)-4',6'-dimethoxy-6-methyl-6,7-dihydro-2H,3'H-2,5'-spirobi[benzofuran]-3',4(3H)-dione 31 white solid, 4% yield; $^1$H NMR (400 MHz, CDCl$_3$, ppm): δ 1.08 (d, 3H, J=6.8 Hz), 2.63 (dd, 1H, J=17.6, 5.5 Hz), 2.77 (dd, 1H, J=14.8, 6.9 Hz), 2.90-3.01 (m, 1H), 3.11-3.22 (dd, 1H, J=17.7, 11.5 Hz), 3.33-3.42 (M, 1H), 3.93 (s, 3H), 4.01 (s, 3H), 6.09 (s, 1H), 6.14 (dd, 1H, J=10.6, 6.9 Hz), 7.07 (t, 1H, J=9.0 Hz), 7.20 (t, 1H, J=7.5), 7.28-7.35 (m, 1H), 7.43 (td, 1H, J=7.4, 1.2 Hz); LCMS (ES, m/z): 458.9 [M+H]$^+$.

(2S,2'S,6R)-7'-chloro-2-(3-fluorophenyl)-4',6'-dimethoxy-6-methyl-5,6-dihydro-2H,3'H-2,7'-spirobi[benzofuran]-3',4(3H)-dione and (2R,2'S,6R)-7'-chloro-2-(3-fluorophenyl)-4',6'-dimethoxy-6-methyl-5,6-dihydro-2H,3'H-2,7'-spirobi[benzofuran]-3',4(3H)-dione 32 white solid, 3% yield; RMN $^1$H (400 MHz, CDCl$_3$, ppm): δ 0.99 (d, 3H, J=6.6 Hz), 2.47 (dd, 1H, J=16.4, 4.1 Hz), 2.89 (dd, 1H, J=15.2, 8.0 Hz), 2.93-3.00 (m, 1H), 3.06 (dd, 1H, J=16.4, 13.1 Hz), 3.38 (dd, 1H, J=15.4, 10.7 Hz), 3.98 (s, 3H), 4.01 (s, 3H), 5.77 (dd, 1H, J=10.5, 8.1), 6.12 (s, 1H), 6.88 (td, 1H, J=9.4, 2.0 Hz), 6.94-7.00 (m, 1H), 7.30 (td, 1H, J=8.0, 5.8 Hz); LCMS (ES, m/z): 458.9 [M+H]$^+$.

33 pale yellow solid, 1% yield; $^1$H NMR (400 MHz, CDCl$_3$, ppm): δ 1.02 (d, 3H, J=6.7 Hz), 2.46 (dd, 1H, J=16.4, 4.5 Hz), 2.88 (dd, 1H, J=15.0, 7.6 Hz), 2.92-3.00 (m, 1H), 3.09 (dd, 1H, J=16.4, 13.0 Hz), 3.36 (dd, 1H, J=15.0, 10.8 Hz), 3.99 (s, 3H), 4.02 (s, 3H), 5.72 (dd, 1H, J=10.8, 7.6 Hz), 6.13 (s, 1H), 6.97-7.09 (m, 3H), 7.30-7.37 (m, 1H); LCMS (ES, m/z): 458.8 [M+H]$^+$.

(2R,2'S,6R)-7'-chloro-2-(4-fluorophenyl)-4',6'-dimethoxy-6-methyl-5,6-dihydro-2H,3'H-2,7'-spirobi[benzofuran]-3',4(3H)-dione and (2S,2'S,6R)-7'-chloro-2-(4-fluorophenyl)-4',6'-dimethoxy-6-methyl-5,6-dihydro-2H,3'H-2,7'-spirobi[benzofuran]-3',4(3H)-dione 34 white solid, 2% yield; $^1$H NMR (400 MHz, CDCl$_3$, ppm): δ 7 0.98 (d, 3H, J=6.6 Hz), 2.47 (dd, 1H, J=16.3, 4.1 Hz), 2.88 (dd, 1H, J=15.4, 7.9 Hz), 2.92-2.98 (m, 1H), 3.05 (dd, 1H, J=16.2, 13.0 Hz), 3.36 (dd, 1H, J=15.4, 10.7 Hz), 3.96 (s, 3H), 3.98 (s, 3H), 5.77 (dd, 1H, J=10.5, 7.9 Hz), 6.10 (s, 1H), 7.00 (t, 2H, J=8.6 Hz), 7.14-7.20 (m, 2H); LCMS (ES, m/z): 458.9 [M+H]$^+$.

35 white solid, 3% yield; 1H NMR (400 MHz, CDCl$_3$, ppm): δ 0.99 (d, 3H, J=6.6 Hz), 2.47 (dd, 1H, J=16.3, 4.1 Hz), 2.88 (dd, 1H, J=15.4, 8.0 Hz), 2.92-2.99 (m, 1H), 3.06 (dd, 1H, J=16.2, 13.0 Hz), 3.36 (dd, 1H, J=15.3, 10.7 Hz), 3.97 (s, 3H), 4.00 (s, 3H), 5.77 (dd, 1H, J=10.6, 8.1 Hz), 6.10 (s, 1H), 7.01 (t, 2H, J=8.7 Hz), 7.15-7.20 (m, 2H); LCMS (ES, m/z): 458.81 [M+H]$^+$.

(2S,2'S,6R)-7'-chloro-2-(2-fluorophenyl)-4',6'-dimethoxy-6-methyl-5,6-dihydro-2H,3'H-2,7'-spirobi[benzofuran]-3',4(3H)-dione and (2R,2'S,6R)-7'-chloro-2-(2-fluorophenyl)-4',6'-dimethoxy-6-methyl-5,6-dihydro-2H,3'H-2,7'-spirobi[benzofuran]-3',4(3H)-dione 36 colourless solid, 86 mg (14%); $^1$H NMR (400 MHz, CDCl$_3$, ppm): δ 1.02 (d, 3H, J=6.7 Hz), 2.46 (dd, 1H, J=16.5, 4.4 Hz), 2.86 (dd, 1H, J=15.2, 7.4 Hz), 2.92-3.01 (m, 1H), 3.10 (dd, 1H, J=16.4, 13.0 Hz), 3.40 (dd, 1H, J=15.2, 10.8 Hz), 3.99 (s, 3H), 4.01 (s, 3H), 5.94 (dd, 1H, J=10.8, 7.6 Hz), 6.13 (s, 1H), 7.02-7.08 (m, 1H), 7.17 (td, 1H, J=7.6, 1.0 Hz), 7.27-7.33 (m, 1H), 7.38-7.43 (td, 1H, J=7.5, 1.5 Hz); LCMS (ES, m/z): 458.9 [M+H]$^+$ 37 light brown solid, 1% yield; $^1$H NMR (400 MHz, CDCl$_3$, ppm): δ 1.03 (d, 3H, J=6.7 Hz), 2.47 (dd, 1H, J=16.3, 4.1 Hz), 2.88 (dd, 1H, J=15.2, 8.0 Hz), 2.92-3.00 (m, 1H), 3.07 (dd, 1H, J=16.2, 8.0 Hz), 3.40 (dd, 1H, J=15.3, 10.9 Hz), 3.97 (s, 3H), 4.00 (s, 3H), 6.07 (dd, 1H, J=10.8, 8.0 Hz), 6.11 (s, 1H), 6.98-7.04 (m, 1H), 7.08-7.18 (m, 1H), 7.23-7.29 (m, 1H); LCMS (ES, m/z): 458.9 [M+H]$^+$.

(2R,2'S,6R)-7'-chloro-4',6'-dimethoxy-6-methyl-2-(4-(trifluoromethyl)phenyl)-5,6-dihydro-2H,3'H-2,7'-spirobi[benzofuran]-3',4(3H)-dione and (2S,2'S,6R)-7'-chloro-4',6'-dimethoxy-6-methyl-2-(4-(trifluoromethyl)phenyl)-5,6-dihydro-2H,3'H-2,7'-spirobi[benzofuran]-3',4(3H)-dione 38 pale yellow solid, 2% yield; $^1$H NMR (400 MHz, CDCl$_3$, ppm): δ 1.02 (d, 3H, J=6.8 Hz), 2.47 (dd, 1H, J=16.4, 4.4 Hz), 2.88 (dd, 1H, J=15.1, 7.4 Hz), 2.92-2.98 (m, 1H), 3.10 (dd, 1H, J=16.4, 12.9 Hz), 3.41 (dd, 1H, J=15.1, 10.9 Hz), 3.99 (s, 3H), 4.02 (s, 3H), 5.79 (dd, 1H, J=10.8, 7.4 Hz), 6.14 (s, 1H), 7.43 (d, 1H, J=8.2 Hz), 7.64 (d, 1H, J=8.2 Hz); LCMS (ES, m/z): 508.9 [M+H]$^+$.

39 pale yellow solid, 9% yield; $^1$H NMR (400 MHz, CDCl$_3$, ppm): δ 1.08 (d, 3H, J=6.7 Hz), 2.65 (dd, 1H, J=17.8, 5.7 Hz), 2.89 (dd, 1H, J=14.6, 8.4 Hz), 2.92-3.00 (m, 1H), 3.16 (dd, 1H, J=17.9, 11.7 Hz), 3.26-3.34 (m, 1H), 3.95 (s, 3H), 4.02 (s, 3H), 5.93 (t, 1H, J=9.6 Hz), 6.10 (s, 1H), 7.46 (d, 1H, J=8.2 Hz), 7.67 (d, 1H, J=8.2 Hz); LCMS (ES, m/z): 508.79 [M+H]$^+$.

(2R,2'S,6R)-7'-chloro-2-(4-fluorophenyl)-4',6'-dimethoxy-6-methyl-6,7-dihydro-2H,3'H-2,5'-spirobi[benzofuran]-3',4(3H)-dione and (2S,2'S,6R)-7'-chloro-2-(4-fluorophenyl)-4',6'-dimethoxy-6-methyl-6,7-dihydro-2H,3'H-2,5'-spirobi[benzofuran]-3',4(3H)-dione 40 white solid, 10% yield; $^1$H NMR (400 MHz, CDCl$_3$, ppm): δ 1.07 (d, 3H, J=6.8 Hz), 2.60 (dd, 1H, J=17.7, 5.4 Hz), 2.87-2.99 (m, 1H), 3.14 (dd, 1H, J=17.6, 11.7), 3.20-3.28 (m, 1H), 3.94 (m, 1H), 4.01 (s, 3H), 5.85 (t, 1H, J=9.4 Hz), 6.10 (s, 1H), 7.10 (t, 2H, J=8.6 Hz), 7.30-7.35 (m, 2H); LCMS (ES, m/z): 458.8 [M+H]$^+$.

41 white solid, 12% yield; $^1$H NMR (400 MHz, CDCl$_3$, ppm): δ 1.07 (d, 3H, J=6.7 Hz), 2.61 (dd, 1H, J=17.8, 5.4 Hz), 2.77 (ddd, 1H, J=14.7, 6.6, 1.9 Hz), 2.91-3.00 (m, 1H), 3.13 (dd, 1H, J=17.8, 11.6 Hz), 3.30-3.39 (m, 1H), 3.94 (s, 3H), 4.01 (s, 3H), 5.81 (dd, 1H, J=10.5, 6.7 Hz), 6.10 (s, 1H), 7.08 (t, 2H, J=8.6 Hz), 7.33-7.37 (m, 2H); LCMS (ES, m/z): 458.8 [M+H]$^+$.

Examples with a reagent carrying a triple bond instead of the double bond ($R_\alpha$ and $R_\beta$ are therefore absent): $R_n$=H (2'S,6R)-7'-chloro-4',6'-dimethoxy-6-methyl-2-phenyl-6,7-dihydro-3'H,4H-2,5'-spirobi[benzofuran]-3',4-dione 42 white solid, 27%; $^1$H NMR (400 MHz, CDCl$_3$, ppm): δ 7.68 (d, 2H, J=7.5 Hz), 7.42 (t, 2H, J=7.5 Hz), 7.33 (t, 1H, J=7.5 Hz), 6.87 (s, 1H), 6.12 (s, 1H), 4.04 (s, 3H), 3.92 (s, 3H), 3.54 (m, 1H), 3.13 (m, 1H), 3.09 (m, 1H), 1.17 (d, 3H, J=6.4 Hz); LCMS (ES, m/z): 439.09 [M+H]$^+$ (2'S,6R)-7'-chloro-4',6'-dimethoxy-6-methyl-2-phenyl-5,6-dihydro-3'H,4H-2,7'-spirobi[benzofuran]-3',4-dione 43 pale yellow solid, 21%

$^1$H NMR (400 MHz, CDCl$_3$, ppm): δ 7.57 (m, 2H), 7.33 (m, 3H), 6.92 (s, 1H), 6.21 (s, 1H), 4.09 (s, 3H), 4.01 (s, 3H), 3.27 (dd, 1H, J=16.6, 12.7 Hz), 3.08 (m, 1H), 2.64 (dd, J=16.6, 4.0 Hz), 1.09 (d, 3H, J=6.7 Hz).

LCMS (ES, m/z): 439.07 [M+H]$^+$

Particular Procedure:

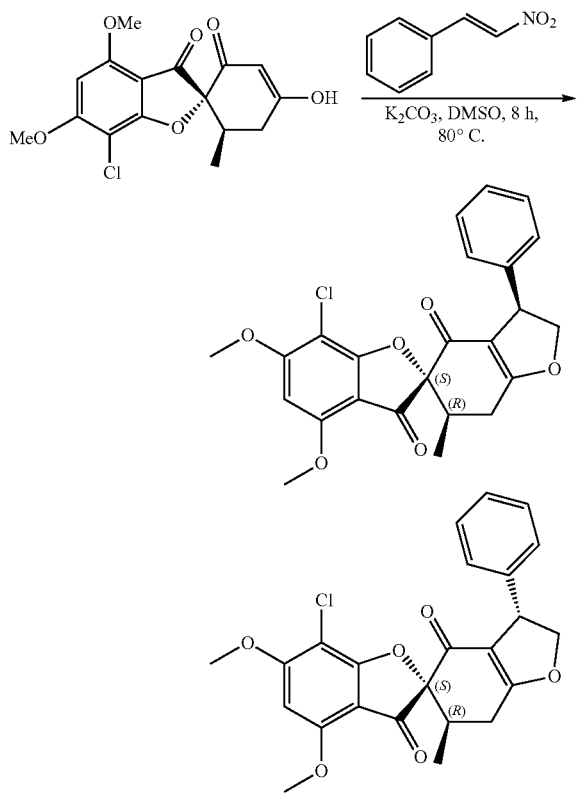

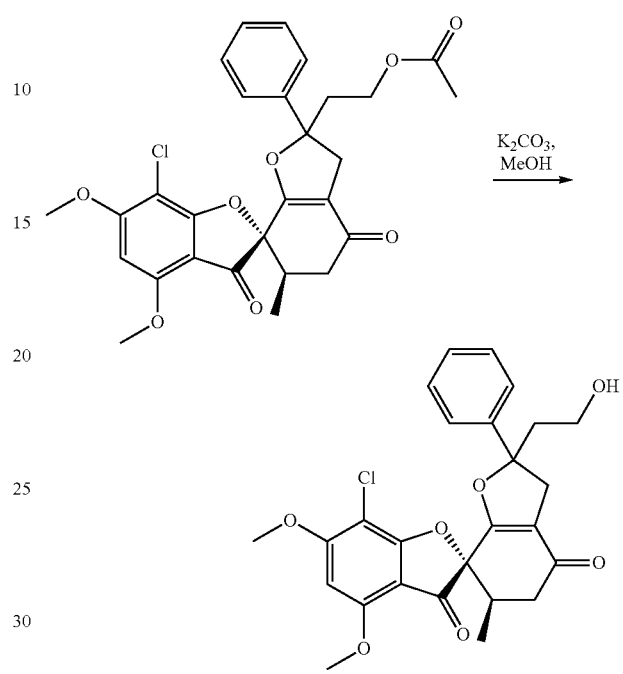

A mixture of griseofulvic acid (1.0 g; 1.0 equiv.), nitrostyrene (1.0 equiv.) and potassium carbonate (0.6 equiv.) in DMSO (16.0 mL) was left under agitation at 80° C. in a nitrogen atmosphere for 24 hours. After return to ambient temperature hydrochloric acid (1.0 M; 1.0 equiv.) was added followed by water (20 mL). The reaction medium was diluted in ethyl acetate (100 mL) and the organic phase successively washed with a saturated aqueous solution of bicarbonate (100 mL), of sodium hydroxide and brine (100 mL). The organic phase was dried over magnesium sulfate, filtered and the solvents evaporated under reduced pressure. The residue was purified on silica gel (cyclohexane/CH$_2$Cl$_2$/AcOEt 1:1:2) to give the dihydrofurans with a global yield of 54%.

(2'S,3R,6R)-7'-chloro-4',6'-dimethoxy-6-methyl-3-phenyl-6,7-dihydro-2H,3'H-2,5'-spirobi[benzofuran]-3',4(3H)-dione (2'S,3S,6R)-7'-chloro-4',6'-dimethoxy-6-methyl-3-phenyl-6,7-dihydro-2H,3'H-2,5'-spirobi[benzofuran]-3',4(3H)-dione 44 beige solid, 34% yield; $^1$H NMR (400 MHz, CDCl$_3$, ppm): δ 7.29 (m, 2H), 7.21 (m, 3H), 6.07 (s, 1H), 5.00 (t, 1H, J=9.9 Hz), 4.62 (dd, 1H, J=9.9, 4.7 Hz), 4.31 (dd, 1H, J=9.9, 4.7 Hz), 3.96 (s, 3H), 3.90 (s, 3H), 3.17 (dd, 1H, J=17.4, 11.5 Hz), 2.98 (m, 1H), 2.69 (dd, 1H, J=17.4, 5.6 Hz), 1.07 (d, 3H, J=6.6 Hz); LCMS (ES, m/z): 441.00 [M+H]$^+$ 45 beige solid, 20% yield; $^1$H NMR (400 MHz, CDCl$_3$, ppm): δ 7.28 (m, 2H), 7.19 (m, 3H), 5.87 (s, 1H), 4.98 (t, 1H, J=9.7 Hz), 4.49 (dd, 1H, J=9.2, 5.8 Hz), 4.42 (dd, 1H, J=9.2, 5.8 Hz), 3.97 (s, 3H), 3.46 (s, 3H), 3.25 (dd, 1H, J=17.5, 11.7 Hz), 2.94 (m, 1H), 2.63 (dd, 1H, J=17.5, 5.6 Hz), 1.06 (d, 3H, J=6.7 Hz); LCMS (ES, m/z): 441.00 [M+H]$^+$ 1.2. Reaction of the Dihydrofurans Saponification of an Acetate:

Potassium carbonate (190.0 mg; 1.2 equiv.) was added at ambient temperature to a solution of the acetate to be reduced (723.0 m; 1.0 equiv.) in methanol (25.0 mL). After an agitation time of thirty minutes at this temperature the methanol was evaporated and the residue diluted in water (100 mL) and ethyl acetate (100 mL). The organic phase was dried over magnesium sulfate, filtered and the solvent evaporated. The residue was purified on silica gel (CH$_2$Cl$_2$/AcOEt 1:1) to give the corresponding alcohol in the form of a white solid with a yield of 96%.

(2R,2'S,6R)-7'-chloro-2-(2-hydroxyethyl)-4',6'-dimethoxy-6-methyl-2-phenyl-5,6-dihydro-2H,3'H-2,7'-spirobi[benzofuran]-3',4(3H)-dione and (2 S,2'S,6R)-7'-chloro-2-(2-hydroxyethyl)-4',6'-dimethoxy-6-methyl-2-phenyl-5,6-dihydro-2H,3'H-2,7'-spirobi[benzofuran]-3',4(3H)-dione 46 white solid, 96% yield; $^1$H NMR (400 MHz, CDCl$_3$, ppm): δ 7.28 (m, 3H), 7.12 (d, 2H, J=7.5 Hz), 6.20 (s, 1H), 4.06 (s, 3H, 4.03 (s, 3H), 3.65 (m, 2H), 3.21 (d, 1H, J=15.0 Hz), 3.56 (m, 3H), 2.46 (m, 2H), 2.29 (m, 1H), 1.02 (d, 3H, J=6.4 Hz); LCMS (ES, m/z): 484.90 [M+H]$^+$ 47 white solid, 98% yield $^1$H NMR (400 MHz, CDCl$_3$, ppm): δ 7.35 (m, 5H), 6.18 (s, 1H), 4.07 (s, 3H), 4.02 (s, 3H), 3.47 (m, 2H), 3.25 (d, 1H, J=15.0 Hz), 3.15 (d, 1H, J=15.0 Hz), 3.07 (dd, 1H, J=16.5, 13.0 Hz), 2.90 (m, 1H), 2.44 (dd, 1H, J=16.5, 4.0 Hz), 2.22 (m, 2H), 1.01 (d, 3H, 6.7 Hz).

LCMS (ES, m/z): 485.22 [M+H]$^+$

Synthesis of Brominated Derivatives:

Substitution by an Amine:

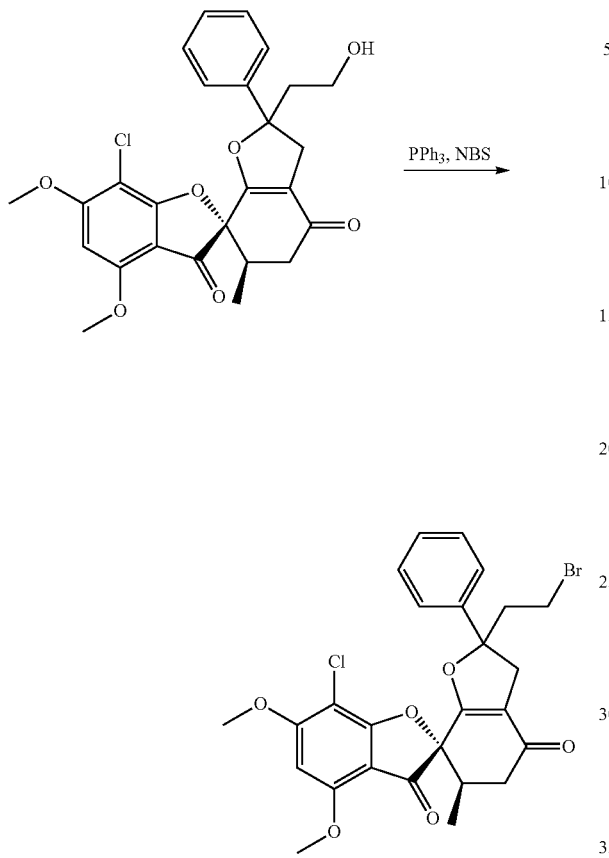

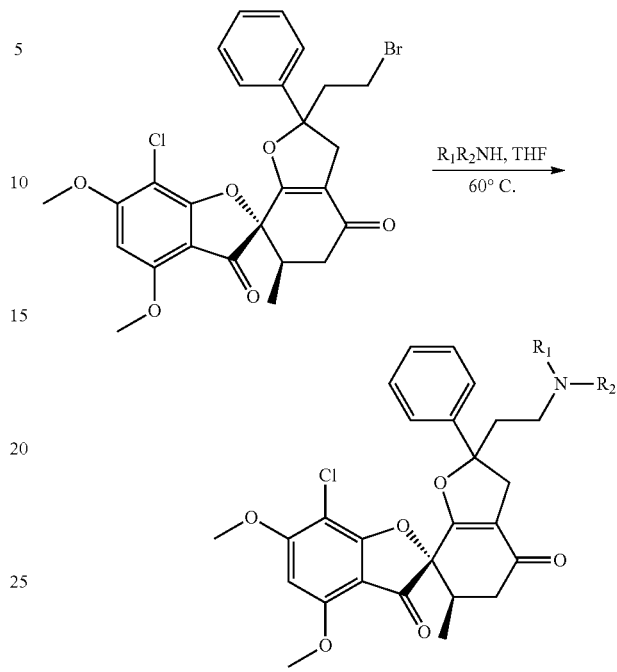

Example: $R_1=R_2=Me$

A mixture of brominated derivative 49 (400.0 mg; 1.0 equiv.) and dimethylamine (5.0 equiv.) in THF (5.0 mL) was heated to 60° C. for 24 h in a sealed tube. After evaporation in vacuo, the residue was diluted in ethyl acetate (20 mL) and the organic phase successively washed with saturated aqueous solution of bicarbonate (10 mL), of sodium hydroxide and brine (10 mL). The organic phase was dried over magnesium sulfate, filtered and the solvents evaporated under reduced pressure. The residue was purified on silica gel ($CH_2Cl_2$/MeOH 95:5 to 90:10) to give the desired amine with a yield of 74%.

NBS (48.0 mg; 1.3 equiv.) was added at 0° C. to a solution of the alcohol to be brominated (100.0 mg; 1.0 equiv.) and triphenylphosphine (81.0 mg; 1.5 equiv.) in tetrahydrofuran (2.0 mL). The temperature was brought to ambient temperature. After an agitation time of 1 hour, water was added (15 mL) and the mixture diluted with AcOEt (15 mL). The organic phase was extracted with brine, dried over $MgSO_4$, filtered and evaporated. The residue was purified on silica ($CH_2Cl_2$/cylcohexane/AcOEt 10:10 1) to give the brominated derivative in the form of a white foam with a yield of 58%.

(2R,2'S,6R)-7'-chloro-2-(2-bromoethyl)-4',6'-dimethoxy-6-methyl-2-phenyl-5,6-dihydro-2H,3'H-2,7'-spirobi[benzofuran]-3',4(3H)-dione and (2 S,2'S,6R)-7'-chloro-2-(2-bromoethyl)-4',6'-dimethoxy-6-methyl-2-phenyl-5,6-dihydro-2H,3'H-2,7'-spirobi[benzofuran]-3',4(3H)-dione 48 synthesized from 47: $^1$H NMR (400 MHz, $CDCl_3$, ppm): δ 7.40 (m, 2H), 7.33 (m, 3H), 6.20 (s, 1H), 4.08 (s, 3H), 4.04 (s, 3H), 3.16 (m, 2H), 3.12 (m, 1H), 3.08 (m, 1H), 2.89 (m, 2H), 2.51 (m, 2H), 2.42 (m, 1H), 1.01 (d, 3H, J=6.5 Hz).

49 synthesized from 46: $^1$H NMR (400 MHz, $CDCl_3$, ppm): δ 7.30 (m, 3H), 7.10 (m, 2H), 6.20 (s, 1H), 4.07 (s, 3H), 4.03 (s, 3H), 3.34 (m, 1H), 3.17 (m, 1H), 3.09 (m, 2H), 2.99 (m, 2H), 2.69 (m, 1H), 2.55 (m, 1H), 2.47 (m, 1H), 1.02 (d, 3H, J=6.5 Hz).

(2'S,6R)-7'-chloro-2-(2-(dimethylamino)ethyl)-4',6'-dimethoxy-6-methyl-2-phenyl-5,6-dihydro-2H,3'H-2,7'-spirobi[benzofuran]-3',4(3H)-dione 50 beige solid, 74% yield; $^1$H NMR (400 MHz, $CDCl_3$, ppm): δ 7.30 (m, 2H), 7.24 (m, 1H), 7.12 (m, 2H), 6.19 (s, 1H), 4.07 (s, 3H), 4.03 (s, 3H), 3.17 (d, 1H, J=15.0 Hz), 3.04 (m, 2H), 2.96 (m, 1H), 2.47 (dd, 1H, J=15.8 Hz, 4.0 Hz), 2.39 (m, 1H), 2.22 (m, 9H), 1.02 (d, 3H, J=6.5 Hz); LCMS (ES, m/z): 512.26 $[M+H]^+$ (2'S,6R)-7'-chloro-4',6'-dimethoxy-6-methyl-2-(2-(4-methylpiperazin-1-yl)ethyl)-2-phenyl-5,6-dihydro-2H,3'H-2,7'-spirobi[benzofuran]-3',4(3H)-dione 51 white solid, 76% yield; $^1$H NMR (400 MHz, $CDCl_3$, ppm): δ 7.30 (m, 2H), 7.23 (m, 1H), 7.12 (m, 2H), 6.19 (s, 1H), 4.06 (s, 3H), 4.03 (s, 3H), 3.17 (d, 1H, J=15.0 Hz), 3.06 (d, 1H, J=15.0 Hz), 3.02 (m, 1H), 2.94 (m, 1H), 2.45 (m, 9H), 2.30 (bs, 3H), 2.23 (m, 4H), 1.02 (d, 3H, J=6.6 Hz); LCMS (ES, m/z): 567.21 $[M+H]^+$ Forming of a Tetrahydroazepine Derivative:

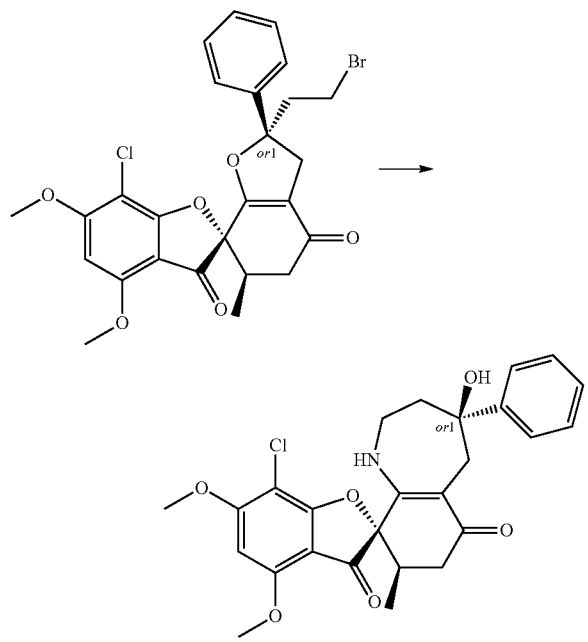

A mixture of the brominated derivative (290.0 mg, 1.0 equiv.) and ammonia (32% by weight, 10 equiv.) in dioxane (5.0 mL) was heated to 100° C. for 3 hours in a sealed tube. After evaporation in vacuo the residue was diluted in ethyl acetate (20 mL) and the organic phase successively washed with a saturated aqueous solution of bicarbonate (10 mL), of sodium hydroxide and brine (10 mL). The organic phase was dried over magnesium sulfate, filtered and the solvents evaporated under reduced pressure. The residue was purified on silica gel (CH$_2$Cl$_2$/MeOH 95:5) to give the desired product with a yield of 52%.

(2'S,4R,8R)-7'-chloro-4-hydroxy-4',6'-dimethoxy-8-methyl-4-phenyl-2,3,4,5,7,8-hexahydro-3'H-spiro[benzo[b]azepine-9,2'-benzofuran]-3',6(1H)-dione
and (2'S,4S,8R)-7'-chloro-4-hydroxy-4',6'-dimethoxy-8-methyl-4-phenyl-2,3,4,5,7,8-hexahydro-3'H-spiro[benzo[b]azepine-9,2'-benzofuran]-3',6(1H)-dione 52 (synthesized from 48) brown solid, 52% yield; $^1$H NMR (400 MHz, CDCl$_3$, ppm): δ 7.58 (d, 2H, J=7.4 Hz), 7.35 (t, 2H, J=7.4 Hz), 7.25 (t, 1H, J=7.4 Hz), 6.19 (s, 1H), 4.77 (m, 1H), 4.06 (s, 3H), 4.01 (s, 3H), 3.78 (m, 1H), 3.32 (m, 1H), 3.30 (d, 1H, J=14.5 Hz), 3.16 (d, 1H, J=14.5 Hz), 2.94 (dd, 1H, J=16.2, 13.3 Hz), 2.83 (m, 1H); LCMS (ES, m/z): 483.98 [M+H]$^+$ 53 (synthesized from 49) yellow solid, 45% yield; $^1$H NMR (400 MHz, CDCl$_3$, ppm): δ 7.54 (d, 2H, J=7.6 Hz), 7.34 (t, 2H, J=7.6 Hz), 7.25 (t, 1H, J=7.6 Hz), 6.19 (s, 1H), 4.75 (m, 1H), 4.06 (s, 3H), 4.01 (s, 3H), 3.65 (m, 1H), 3.35 (m, 1H), 3.28 (d, 1H, J=15.2 Hz), 3.23 (d, 1H, J=15.2 Hz), 2.91 (dd, 1H, J=17.0, 13.3 Hz), 2.81 (m, 1H); LCMS (ES, m/z): 484.31 [M+H]$^+$ 1.3. Synthesis of the Pyrimidines at 2'

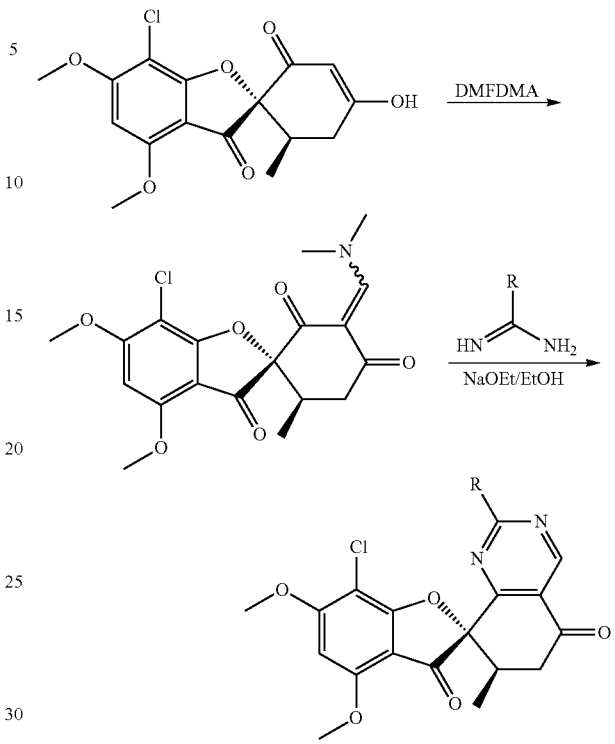

Example: R=Ph

A solution of griseofulvic acid (1.0 g; 1.0 equiv.) and DMFDMA (1.0 mL; 2.5 equiv.) in dimethylformamide (3 mL) was heated to 100° C. for 1 hour. The solvents were evaporated and the residue re-dissolved in dichloromethane then evaporated three times to obtain methylenedimethylaminodione in the form of yellow foam with a yield of 89%. To a mixture of this product (200.0 mg; 1.0 equiv.) and phenylamidine hydrochloride (119 mg; 1.5 equiv.) in methanol (3 mL) the addition was made of sodium methanolate (68 mg; 2.5 equiv.), the reaction medium was then heated to 60° C. for 2 hours. After return to ambient temperature, the pH was adjusted to 7 using hydrochloric acid (0.1 M) and the mixture then diluted with ethyl acetate (20 mL). The organic phase was dried over magnesium sulfate, filtered and the solvents evaporated under reduced pressure. The residue was purified on silica gel (cyclohexane/CH$_2$Cl$_2$/AcOEt 5:5:1) to give the desired pyrimidine in the form of a white solid with a yield of 46%.

(2S,7'R)-7-chloro-4,6-dimethoxy-7'-methyl-2'-phenyl-6',7'-dihydro-3H,5'H-spiro[benzofuran-2,8'-quinazoline]-3,5'-dione R=Ph 54 white solid, 46% yield; $^1$H NMR (400 MHz, CDCl$_3$, ppm): δ CDCl3: 9.37 (s, 1H), 8.35 (m, 2H), 7.50 (m, 1H), 7.43 (m, 2h), 6.20 (s, 1H), 4.11 (s, 3H), 3.98 (s, 3H), 3.56 (dd, 1H, J=17.4, 13.8 Hz), 3.08 (m, 1H), 2.78 (dd, 1H, J=17.4, 4.7 Hz), 1.18 (d, 3H, J=6.7 Hz); LCMS (ES, m/z): 451.28 [M+H]$^+$ (2S,7'R)-7-chloro-4,6-dimethoxy-7'-methyl-2'-morpholino-6',7'-dihydro-3H,5'H-spiro[benzofuran-2,8'-quinazoline]-3,5'-dione R=N-morpholine 55 beige solid, 43% yield; $^1$H NMR (400 MHz, CDCl$_3$, ppm): δ CDCl3: 8.94 (s, 1H), 6.16 (s, 1H), 4.08 (s, 3H), 3.98 (s, 3H), 3.96-3.51 (m, 8H), 3.37 (dd, 1H, J=17.2, 13.7 Hz), 2.94 (m, 1H), 2.63 (dd, 1H, J=17.2, 4.4 Hz), 1.09 (d, 3H, J=6.7 Hz); LCMS (ES, m/z): 460.12 [M+H]$^+$

(2S,7'R)-2'-amino-7-chloro-4,6-dimethoxy-7'-methyl-6',7'-dihydro-3H,5'H-spiro[benzofuran-2,8'-quinazoline]-3,5'-dione R=NH$_2$ 56 white solid, 20% yield; $^1$H NMR (400 MHz, CDCl$_3$, ppm): δ 8.93 (s, 1H), 6.15 (s, 1H), 5.89 (bs, 2H), 4.05 (s, 3H), 3.96 (s, 3H), 3.31 (dd, 1H, J=14.0, 17.0 Hz), 2.92 (m, 1H), 2.61 (dd, 1H, J=5.0, 17.0 Hz), 1.04 (d, 3H, J=6.0 Hz); LCMS (ES, m/z): 389.90 [M+H]$^+$ 1.4. Synthesis of Pyridines and Pyridones at 2'

Method A:

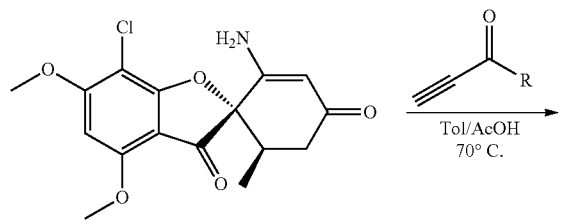

Example: R=Me

A mixture of 2'-aminogriseofulvin (4.64 g; 1.0 equiv.) and butynone (1.29 mL; 1.2 equiv.) in toluene (40 mL) and acetic acid (15 mL) was heated to 70° C. for 6 hours. After evaporation of the solvents in vacuo, the residue was triturated in methanol and then filtered. The solid obtained was dried in vacuo to obtain the desired pyridine in the form of a beige solid with a yield of 91%.

(2S,7'R)-7-chloro-4,6-dimethoxy-2',7'-dimethyl-6',7'-dihydro-3H,5'H-spiro[benzofuran-2,8'-quinoline]-3,5'-dione R=Me 57 beige solid, 65% yield; $^1$H NMR (400 MHz, CDCl$_3$, ppm): δ 8.21 (d, 1H, J=8.0 Hz), 7.21 (d, 1H, J=8.0 Hz), 6.17 (s, 1H), 4.07 (s, 3H), 3.98 (s, 3H), 3.46 (dd, 1H, J=17.0, 13.5 Hz), 3.00 (m, 1H), 2.74 (dd, 1H, J=17.0, 4.5 Hz), 2.49 (s, 3H), 1.13 (d, 3H, J=7.0 Hz); LCMS (ES, m/z): 387.94 [M+H]$^+$

(2S,7'R)-7-chloro-4,6-dimethoxy-7'-methyl-2'-phenyl-6',7'-dihydro-3H,5'H-spiro[benzofuran-2,8'-quinoline]-3,5'-dione R=Ph 58 pale yellow solid, 63% yield; $^1$H NMR (400 MHz, CDCl$_3$, ppm): δ 8.39 (d, 1H, J=8.0 Hz), 7.93 (m, 2H), 7.85 (d, 1H, J=8.0 Hz), 7.41 (m, 3H), 6.17 (s, 1H), 4.09 (s, 3H), 3.96 (s, 3H), 3.56 (dd, 1H, J=17.4, 13.8 Hz), 3.07 (m, 1H), 2.79 (dd, 1H, J=17.4, 4.2 Hz), 1.19 (d, 3H, J=6.6 Hz); LCMS (ES, m/z): 450.00 [M+H]$^+$ Method B:

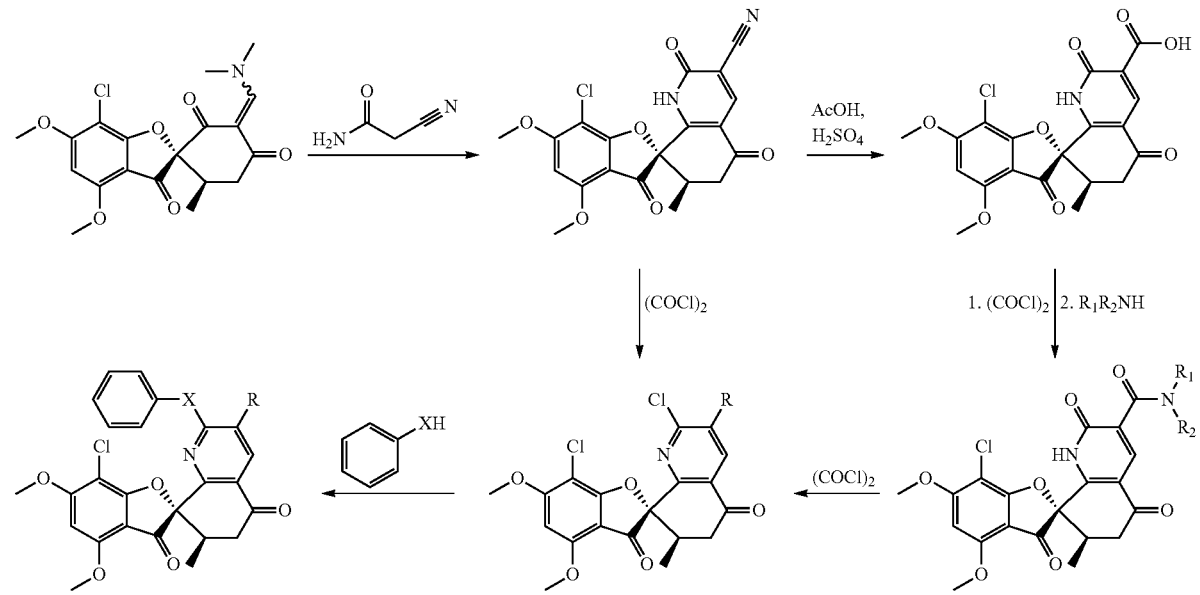

R = CN or CONR$_1$R$_2$
X = O, S or NH

Synthesis of Cyano-Pyridone:

Sodium ethanolate (9.48 mL; 21 weight 0; 1.0 equiv.) was added to a solution of preceding methylene-dimethylamino (see 1.3.) (10 g; 1.0 equiv.) and cyanoacetamide (2.135 g; 1.0 equiv.) in ethanol (100 mL). The mixture was left under agitation 3 hours at ambient temperature. The medium was then neutralised with the dropwise addition of acetic acid and concentrated under reduced pressure. The reaction medium was diluted in ethyl acetate (200 mL) and the organic phase washed with a brine solution (150 mL). The organic phase was dried over magnesium sulfate, filtered and the solvents evaporated under reduced pressure. The residue was purified on silica gel ($CH_2Cl_2$/AcOEt 8:2) to give the pyridone with a global yield of 57%.

(2S,7'R)-7-chloro-4,6-dimethoxy-7'-methyl-2',3,5'-trioxo-2',5',6',7'-tetrahydro-1'H,3H-spiro[benzofuran-2,8'-quinoline]-3'-carbonitrile 59 beige solid, 57% yield; $^1$H NMR (400 MHz, $CDCl_3$, ppm): δ 12.12 (bs, 1H), 8.45 (s, 1H), 6.25 (s, 1H), 4.08 (s, 3H), 4.00 (s, 3H), 3.18 (dd, 1H, J=17.5, 13.8 Hz), 2.98 (m, 1H), 2.63 (dd, 1H), J=17.5, 4.5 Hz), 0.98 (d, 3H, J=6.4 Hz); LCMS (ES, m/z): 415.18 [M+H]$^+$ Hydrolysis/Coupling:
Example: $R_1$=Bn, $R_2$=H A mixture of cyano-pyridone (1.31 g; 1.0 equiv.) in acetic acid (10 mL), sulfuric acid (2.5 mL) and water (2.5 mL) was heated to 110° C. for 8 hours. After return to ambient temperature water was added (30 mL) and a solid was precipitated. The precipitate was filtered and dried in vacuo to give the acid in the form of a slightly purple powder with a yield of 92%. This acid (1.3 g; 1.0 equiv.) was diluted in $CH_2Cl_2$ (15 mL), the solution held at 0° C., and oxalyl chloride added (1.62 mL; 6.2 equiv.) followed by a few drops of DMF. As soon as gas release was completed, the medium was evaporated in vacuo and re-dissolved (400 mg) in $CH_2Cl_2$ (5 mL) then added dropwise to a solution of benzylamine (5.0 equiv.), triethylamine (8.0 equiv.) and DMAP (0.3 equiv.) at 0° C. The temperature was then brought to ambient temperature and the mixture left under agitation for 4 hours. The reaction medium was diluted in ethyl acetate (20 mL) and the organic phase washed with brine solution (15 mL). The organic phase was dried over magnesium sulfate, filtered and the solvents evaporated under reduced pressure. The residue was purified on silica gel ($CH_2Cl_2$/MeOH 99:1) to give the pyridone with a global yield of 20%.

(2S,7'R)—N-benzyl-7-chloro-4,6-dimethoxy-7'-methyl-2',3,5'-trioxo-2',5',6',7'-tetrahydro-1'H,3H-spiro[benzofuran-2,8'-quinoline]-3'-carboxamide 60 beige solid, 20% yield; $^1$H NMR (400 MHz, $CDCl_3$, ppm): δ 9.63 (m, 1H), 9.04 (s, 1H), 7.30 (m, 5H), 6.12 (s, 1H), 4.59 (m, 2H), 4.03 (s, 3H), 3.95 (s, 3H), 3.19 (m, 1H), 2.97 (m, 1H), 2.67 (m, 1H), 1.00 (d, 3H, J=6.6 Hz); LCMS (ES, m/z): 523.30 [M+H]$^+$ Chlorination/Substitution:

Oxalyl chloride (2.2 mL; 5.0 equiv.) in $CH_2Cl_2$ (5.0 mL) was added over a time of 10 minutes to a suspension of pyridone (2.1 g; 1.0 equiv.) in a mixture of $CH_2Cl_2$ (20 mL) and DMF (0.5 mL). The reaction medium was then heated to 40° C. for 2 hours. The medium was diluted with dichloromethane and neutralised with sodium hydroxide (1.0 M). The organic phase was washed with brine solution. The organic phase was then dried over magnesium sulfate, filtered and the solvents evaporated under reduced pressure. The residue was purified on silica gel ($CH_2Cl_2$/AcOEt 98:2) to give the chloropyridine with a global yield of 56%.

A 50 mL round-bottomed flask was charged with sodium carbonate, DMF and then thiophenol. After an agitation time of 10 minutes the chloropyridine was added. The mixture was heated to 50° C. for 18 hours. Water was added followed by ethyl acetate. The organic phase was washed with brine solution. The organic phase was dried over magnesium sulfate, filtered and the solvents evaporated under reduced pressure. The residue was purified on silica gel ($CH_2Cl_2$/AcOEt 98:2) to give the substituted pyridine with a yield of 37%.

(2S,7'R)-7-chloro-4,6-dimethoxy-7'-methyl-3,5'-dioxo-2'-(phenylthio)-6',7'-dihydro-3H,5'H-spiro[benzofuran-2,8'-quinoline]-3'-carbonitrile X=S, R=CN 61 pale yellow solid, 37% yield; $^1$H NMR (400 MHz, $CDCl_3$, ppm): δ 8.45 (s, 1H), 7.34 (m, 2H), 7.14 (m, 3H), 6.10 (s, 1H), 4.14 (s, 3H), 3.97 (s, 3H), 3.45 (dd, 1H, J=17.2, 14.4 Hz), 2.91 (m, 1H), 2.69 (dd, 1H, J=17.2, 4.8 Hz), 1.03 (d, 3H, J=6.4 Hz); LCMS (ES, m/z): 507.16 [M+H]$^+$ (2S,7'R)-7-chloro-4,6-dimethoxy-7'-methyl-3,5'-dioxo-2'-(phenylamino)-6',7'-dihydro-3H,5'H-spiro[benzofuran-2,8'-quinoline]-3'-carboxamide X=NH, R=$CONH_2$ 62 yellow solid, 15% yield; $^1$H NMR (400 MHz, $CDCl_3$, ppm): δ 11.22 (bs, 1H), 8.43 (s, 1H), 7.56 (m, 2H), 7.14 (m, 2H), 6.98 (m, 2H), 6.115 (s, 1H), 4.11 (s, 3H), 3.94 (s, 3H), 3.49 (dd, 1H J=17.4, 13.7 Hz), 3.07 (m, 1H), 2.71 (dd, 1H, J=17.4, 4.6 Hz), 1.17 (d, 3H, J=6.5 Hz); LCMS (ES, m/z): 508.29 [M+H]$^+$

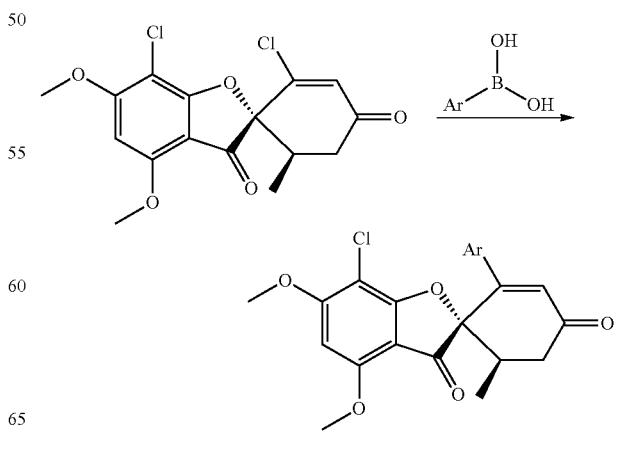

1.5. Suzuki Coupling at 2'
Example: Ar=Ph

Under argon, Pd$_2$DBA$_3$ (25 mg; 0.05 equiv.) then tri-tert-butyl phosphine (14 mg; 0.12 equiv.) were successively added to a mixture of chlorinated derivative (200 mg; 1.0 equiv.), potassium fluoride (107 mg; 3.3 equiv.) and phenylboronic acid (75 mg; 1.1 equiv.) in THF (3 mL). The reaction medium was left under agitation at 60° C. for 18 hours. The crude product was directly filtered on silica cake with AcOEt. The solvents were evaporated and the residue purified on silica gel (CH$_2$Cl$_2$/cyclohexane/AcOEt 50:50:10) to give the coupling product in the form of a white solid with a yield of 65%.

(1'S,6'R)-7-chloro-4,6-dimethoxy-6'-methyl-2'-phenyl-3H-spiro[benzofuran-2,1'-cyclohex[2]ene]-3,4'-dione Ar=Ph: 63 white solid, 65% yield; $^1$H NMR (400 MHz, CDCl$_3$, ppm): δ 7.24 (m, 5H), 6.23 (s, 1H), 6.05 (s, 1H), 3.99 (s, 3H), 3.96 (s, 3H), 3.019 (dd, 1H, J=16.7, 14.0 Hz), 3.07 (m, 1H), 2.53 (dd, 1H, J=16.7, 4.5 Hz), 0.98 (d, 3H, J=6.5 Hz); LCMS (ES, m/z): 398.90 [M+H]$^+$ (1'S,6'R)-7-chloro-4,6-dimethoxy-6'-methyl-2'-(thiophen-2-yl)-3H-spiro[benzofuran-2,1'-cyclohex[2]ene]-3,4'-dione Ar=thiophene: 64 pale yellow solid, 36% yield $^1$H NMR (400 MHz, CDCl$_3$, ppm): δ 7.36 (dd, 1H, J=5.2, 1.0 Hz), 7.26 (dd, 1H, J=3.6 1.0 Hz), 6.97 (dd, 1H, J=5.2, 3.6 Hz), 6.55 (s, 1H), 6.13 (s, 1H), 4.06 (s, 3H), 3.96 (s, 3H), 3.09 (m, 2H), 2.49 (m, 1H), 0.99 (d, 3H, J=6.5 Hz).
LCMS (ES, m/z): 405.12 [M+H]$^+$ (1'S,6'R)-2'-(benzo[d][1,3]dioxol-5-yl)-7-chloro-4,6-dimethoxy-6'-methyl-3H-spiro[benzofuran-2,1'-cyclohex[2]ene]-3,4'-dione Ar=3-dioxanylphenyl: 65 pale yellow solid, 90% yield; $^1$H NMR (400 MHz, CDCl$_3$, ppm): δ 6.79 (d, 1H, J=1.6 Hz), 6.76 (dd, 1H, J=8.1, 1.6 Hz), 6.67 (d, 1H, J=8.1 Hz), 6.20 (s, 1H), 6.08 (s, 1H), 5.93 (m, 2H), 4.01 (s, 3H), 3.96 (s, 3H), 3.15 (dd, 1H, J=16.5, 13.8 Hz), 3.04 (m, 1H), 2.50 (dd, 1H, J=16.5, 4.0 Hz), 0.97 (d, 3H, J=6.5 Hz); LCMS (ES, m/z): 443.17 [M+H]$^+$ (1'S,6'R)-2'-(benzofuran-2-yl)-7-chloro-4,6-dimethoxy-6'-methyl-3H-spiro[benzofuran-2,1'-cyclohex[2]ene]-3,4'-dione Ar=2-benzofuran: 66 pale yellow solid, 77% yield; $^1$H NMR (400 MHz, CDCl$_3$, ppm): δ 7.49 (d, 1H, J=7.6 Hz), 7.39 (d, 1H, J=7.6 Hz), 7.33 (t, 1H, J=7.6 Hz), 7.19 (t, 1H, J=7.6 Hz), 69.6 (s, 1H), 6.80 (s, 1H), 6.21 (s, 1H), 4.11 (s, 3H), 4.00 (s, 3H), 3.11 (m, 2H), 2.53 (m, 1H), 1.00 (d, 3H, J=6.0 Hz) LCMS (ES, m/z): 439.14 [M+H]$^+$ 1.6. Alkylation of an Amino Derivative of Griseofulvin and Coupling of the Derivative Obtained

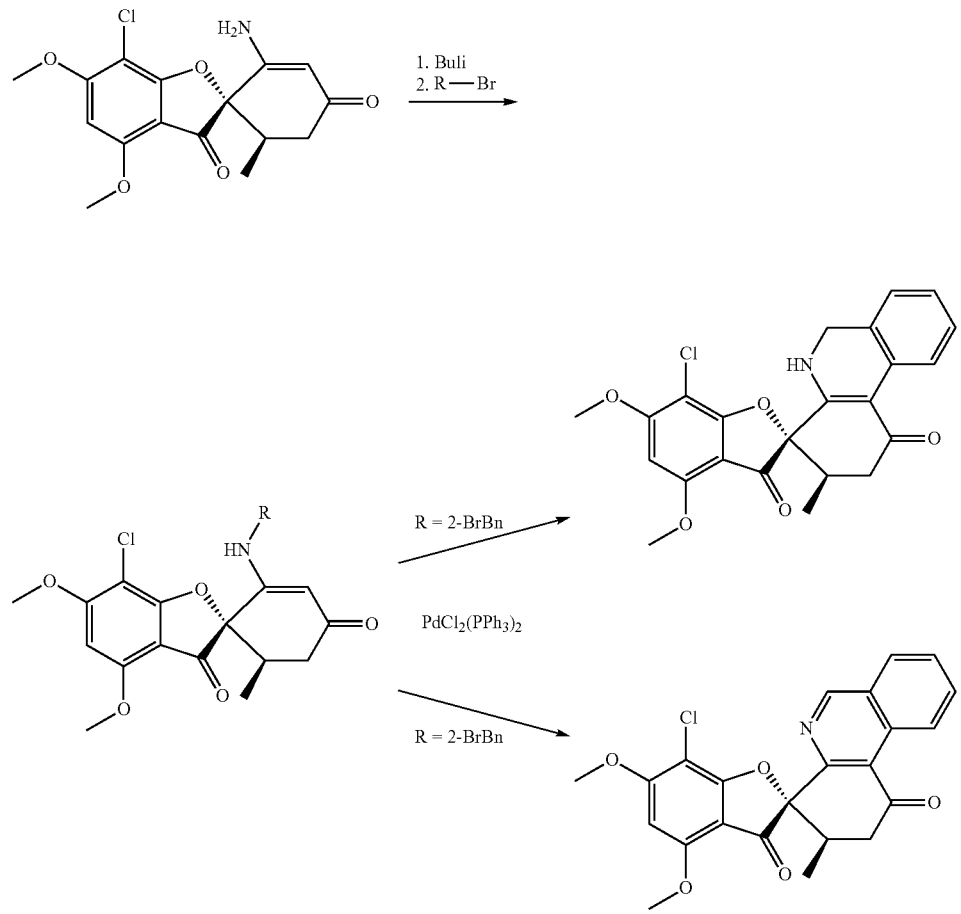

Alkylation:
Example: R=2-BrBn

To a solution of 2'-aminogriseofulvin (1.0 g; 1.0 equiv.) in 35 ml of THF at −78° C., n-butyllithium (1.6 M hexane; 1.85 mL; 1.0 equiv.) was added. After an agitation time of 10 minutes a precipitate was observed, 2-bromobenzyl bromide (740 mg; 1.0 equiv.) was then added and the mixture was allowed to return to ambient temperature before heating under reflux for 2 hours. After return to ambient temperature, a saturated NH$_4$Cl solution (100 mL) was added, and the mixture diluted with AcOEt (150 mL). The organic phase was washed with saturated sodium chloride solution and dried over MgSO$_4$, filtered and evaporated. The residue was purified on silica gel (CH$_2$Cl$_2$/AcOEt 50:50) to give the desired amine in the form of a beige solid with a yield of 45%.

(1'S,6'R)-2'-(2-bromobenzylamino)-7-chloro-4,6-dimethoxy-6'-methyl-3H-spiro[benzofuran-2,1'-cyclohex[2]ene]-3,4'-dione R=2-BrBn: 67 yellow solid, 54% yield; $^1$H NMR (400 MHz, CDCl$_3$, ppm): δ 7.55 (m, 1H), 7.30 (m, 1H), 7.17 (m, 2H), 6.19 (s, 1H), 5.33 (bs, 1H), 5.22 (m, 1H), 4.28 (m, 2H), 4.06 (s, 3H), 4.01 (s, 3H), 3.00-2.85 (m, 2H), 2.39 (dd, 1H, J=15.6, 3.5 Hz), 0.93 (d, 3H, J=6.7 Hz); LCMS (ES, m/z): 507.85 [M+H]$^+$ (1'S,6'R)-2'-(benzylamino)-7-chloro-4,6-dimethoxy-6'-methyl-3H-spiro[benzofuran-2,1'-cyclohex[2]ene]-3,4'-dione R=Bn: 68 pale yellow solid, 37% yield; $^1$H NMR (400 MHz, CDCl$_3$, ppm): δ 7.33 (m, 3H), 7.19 (d, 2H, J=6.8 Hz), 6.17 (s, 1H), 5.33 (s, 1H), 4.85 (t, 1H, J=4.8 Hz), 4.23 (dd, 1H, J=15.2, 4.8 Hz), 4.16 (dd, 1H, J=15.2, 4.8 Hz), 4.04 (s, 3H), 4.00 (s, 3H), 2.94 (m, 2H), 2.40 (m, 1H), 0.93 (d, 3H, J=6.2 Hz); LCMS (ES, m/z): 428.34 [M+H]$^+$ (1'S,6'R)-7-chloro-4,6-dimethoxy-6'-methyl-2'-(4-(morpholinomethyl)benzylamino)-3H-spiro[benzofuran-2,1'-cyclohex[2]ene]-3,4'-dione R=4-(Morpholine-CH$_2$)Bn: 69 beige solid, 76% yield; $^1$H NMR (400 MHz, CDCl$_3$, ppm): δ 7.32 (m, 2H), 7.15 (d, 2H, J=7.7 Hz), 6.19 (s, 1H), 5.31 (s, 1H), 4.87 (m, 1H), 4.19 (m, 2H), 4.05 (s, 3H), 4.01 (s, 3H), 3.75 (bs, 4H), 3.51 (bs, 2H), 2.94 (m, 2H), 2.43 (m, 5H), 0.93 (d, 3H, J=6.4 Hz); LCMS (ES, m/z): 527.27 [M+H]$^+$ (1'S,6'R)-7-chloro-4,6-dimethoxy-6'-methyl-2'-((S)-1-phenylethylamino)-3H-spiro[benzofuran-2,1'-cyclohex[2]ene]-3,4'-dione R=Ph-CHMe: 70 yellow solid, 32% yield; $^1$H NMR (400 MHz, CDCl$_3$, ppm): δ 1:1 diastereomeric mixture: 7.36 (m, 2H), 7.29 (m, 3H), 7.23 (m, 3H), 7.08 (m, 2H), 6.22 (s, 2H), 5.21 (s, 1H), 5.16 (s, 1H), 4.87 (m, 2H), 4.41 (m, 2H), 4.08 (s, 3H), 4.07 (s, 3H), 4.03 (s, 3H), 4.02 (s, 3H), 2.95-2.80 (m, 4H), 2.43-2.31 (m, 2H), 1.48 (d, 3H, J=6.7 Hz), 1.37 (d, 3H, J=6.7 Hz), 0.94-0.89 (m, 6H).
LCMS (ES, m/z): 442.35 [M+H]$^+$ (1'S,6'R)-7-chloro-2'-(cyclohexylmethylamino)-4,6-dimethoxy-6'-methyl-3H-spiro[benzofuran-2,1'-cyclohex[2]ene]-3,4'-dione R=cHex-CH$_2$: 71 white solid, 32% yield; $^1$H NMR (400 MHz, CDCl$_3$, ppm): 6.19 (s, 1H), 5.21 (s, 1H), 4.77 (m, 1H), 4.04 (s, 3H), 3.97 (s, 3H), 2.93-2.71 (m, 4H), 2.32 (m, 1H), 1.71-1.55 (m, 5H), 1.50 (m, 1H), 1.25-1.02 (m, 3H), 0.88 (d, 3H, J=6.7 Hz), 0.82 (m, 2H); LCMS (ES, m/z): 434.32 [M+H]$^+$ Coupling:
Example: R=2-BrBn Dichlorobis(triphenylphosphine) palladium (355 mg; 0.4 equiv.) was added to a solution degassed under nitrogen of benzylated derivative (640 mg; 1.0 equiv.) and sodium acetate (176 mg; 1.7 equiv.) in dimethylacetamide (20 mL). The mixture was left under agitation at 90° C. for 18 hours. The crude product was directly filtered on silica cake with AcOEt. The solvents were evaporated and the residue purified on silica gel (CH$_2$Cl$_2$/AcOEt 85:15) to give the pyridine in the form of a beige solid with a yield of 13%.

(2 S,3'R)-7-chloro-4,6-dimethoxy-3'-methyl-2',3'-dihydro-1'H,3H-spiro[benzofuran-2,4'-phenanthridine]-1',3-dione 72 brown solid, 13% yield; $^1$H NMR (400 MHz, CDCl$_3$, ppm): δ 9.48 (d, 1H, J=9.2 Hz), 9.27 (s, 1H), 7.98 (d, 1H, J=8.1 Hz), 7.92 (m, 1H), 7.71 (m, 1H), 6.20 (s, 1H), 4.08 (s, 3H), 3.99 (s, 3H), 3.63 (dd, 1H, J=16.2, 13.6 Hz), 3.13 (m, 1H), 2.85 (dd, 1H, J=16.2, 4.4 Hz), 1.18 (d, 3H, J=6.7 Hz); LCMS (ES, m/z): 424.23 [M+H]$^+$ Coupling:
R=2-BrBn Dichlorobis(triphenylphosphine) palladium (55 mg; 0.2 equiv.) was added to a solution degassed under nitrogen of benzylated derivative (200 mg; 1.0 equiv) and sodium acetate (65 mg; 2.0 equiv.) in dimethylacetamide (3 mL). The mixture was left under agitation at 90° C. for 5 hours. The crude was directly filtered on silica cake with AcOEt. The solvents were evaporated and the residue purified on silica gel (CH$_2$Cl$_2$/AcOEt 85:15) to give the coupled derivative in the form of a green solid with a yield of 24%.

(2S,3'R)-7-chloro-4,6-dimethoxy-3'-methyl-2',3',5',6'-tetrahydro-1'H,3H-spiro[benzofuran-2,4'-phenanthridine]-1',3-dione 73 greenish solid, 23% yield; $^1$H NMR (400 MHz, CDCl$_3$, ppm): δ 8.65 (d, 1H, J=7.6 Hz), 7.25 (m, 1H), 7.13 (m, 1H), 6.91 (d, 1H, J=7.4 Hz), 6.19 (s, 1H), 4.97 (m, 1H), 4.54 (d, 1H, J=14.0 Hz), 4.45 (d, 1H, J=14.0 Hz), 4.06 (s, 3H), 3.99 (s, 3H), 3.11 (dd, 1H, J=17.0, 13.0 Hz), 2.94 (m, 1H), 2.58 (dd, 1H, J=17.0, 5.0 Hz), 0.95 (d, 3H, J=6.7 Hz); LCMS (ES, m/z): 426.21 [M+H]$^+$ (2 S,3'R)-7-chloro-4,6-dimethoxy-3'-methyl-2',3'-dihydro-1'H,3H-spiro[benzofuran-2,4'-dibenzo[b,d]furan]-1',3-dione 74 beige solid, 69% yield; $^1$H NMR (400 MHz, CDCl$_3$, ppm): δ 8.13 (m, 1H), 7.43 (m, 1H), 7.37 (m, 2H), 6.22 (s, 1H), 4.09 (s, 3H), 4.01 (s, 3H), 3.37 (dd, 1H, J=16.7, 12.9 Hz), 3.16 (m, 1H), 2.70 (dd, 1H, J=16.7, 4.5 Hz), 112 (d, 3H, J=6.7 Hz); LCMS (ES, m/z): 413.23 [M+H]$^+$ (2'S,3R)-7'-chloro-4',6'-dimethoxy-3-methyl-2,3-dihydro-3'H-spiro[benzo[c]chromene-4,2'-benzofuran]-1,3'(6H)-dione 75 white solid, 10% yield; $^1$H NMR (400 MHz, CDCl$_3$, ppm): δ 8.35 (d, 1H, J=7.6 Hz), 7.35 (t, 1H, J=7.6 Hz), 7.25 (t, 1H, J=7.6 Hz), 6.99 (d, 1H, J=7.6 Hz), 6.16 (s, 1H), 5.11 (d, 1H, J=12.8 Hz), 5.02 (d, 1H, J=12.8 Hz), 4.06 (s, 3H), 4.01 (s, 3H), 3.26 (dd, 1H, J=16.3, 13.4 Hz), 2.92 (m, 1H), 2.60 (dd, 1H, J=16.3, 4.5 Hz), 1.02 (d, 3H, J=6.7 Hz); LCMS (ES, m/z): 427.12 [M+H]⁺

1.7. Acylation or Sulfonylation of an Amino Derivative of Griseofulvin

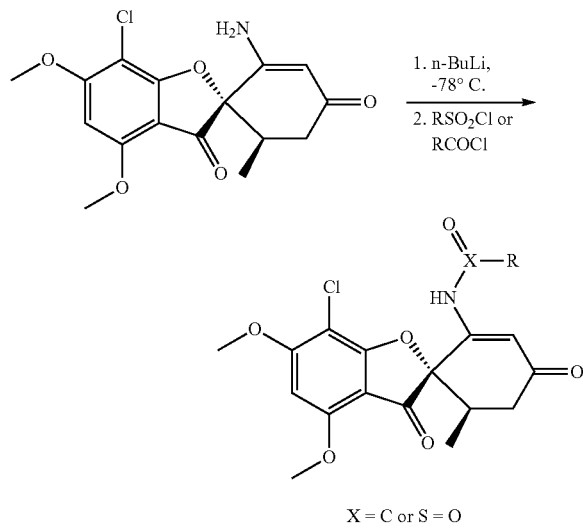

X = C or S = O

Example X=S=O, R=Ph

To a solution of 2'-aminogriseofulvin (200 mg; 1.0 equiv.) in 10 ml of THF at −78° C., n-butyllithium (1.6 M hexane; 0.370 mL; 1.0 equiv.) as added. After an agitation time of 10 minutes a precipitate was observed, benzene sulfonyl chloride (105 mg; 1.0 equiv.) was added and the mixture was allowed to return to ambient temperature. The mixture was left under agitation for 30 minutes. A saturated solution of NH₄Cl (30 mL) was added and the mixture then diluted with AcOEt (30 mL). The organic phase was washed with a saturated solution of sodium chloride then dried over MgSO₄, filtered and evaporated. The residue was purified on silica gel (CH₂Cl₂/MeOH 95:5) to give the sulfonamide in the form of a yellow solid with a yield of 36%.

X=S=O, R=Ph: 76, yellow solid, 36% yield; ¹H NMR (400 MHz, CDCl₃, ppm): δ 7.81 (d, 2H, J=7.5 Hz), 7.67 (t, 1H, J=7.5 Hz), 7.54 (t, 2H, J=7.5 Hz), 6.59 (s, 1H), 6.20 (s, 1H), 6.19 (s, 1H), 4.09 (s, 3H), 4.01 (s, 3H), 2.86 (dd, 1H, J=16.4, 13.4 Hz), 2.75 (m, 1H), 2.34 (dd, 1H, J=16.4, 5.0 Hz), 0.84 (d, 3H, J=6.7 Hz); LCMS (ES, m/z): 478.17 [M+H]⁺

X=S=O, R=Me 77, brown solid, 22% yield; ¹H NMR (400 MHz, CDCl₃, ppm): δ 6.36 (bs, 1H), 6.34 (s, 1H), 6.23 (s, 1H), 4.09 (s, 3H), 4.03 (s, 3H), 3.06 (s, 3H), 3.00-2.86 (m, 2H), 2.46 (m, 1H), 0.92 (d, 3H, J=6.4 Hz); LCMS (ES, m/z): 416.18 [M+H]⁺

X=C, R=Me 78, beige solid, 71% yield; ¹H NMR (400 MHz, CDCl₃, ppm): δ 7.23 (s, 1H), 6.83 (s, 1H), 6.23 (s, 1H), 4.09 (s, 3H), 4.02 (s, 3H), 2.98 (dd, 1H, J=16.4, 13.6 Hz), 2.90 (m, 1H), 2.45 (dd, 1H, J=16.4, 4.0 Hz), 2.05 (s, 3H), 0.93 (d, 3H, J=6.7 Hz); LCMS (ES, m/z): 380.19 [M+H]⁺

X=C, R=Ph 79, yellow solid, 65% yield; ¹H NMR (400 MHz, CDCl₃, ppm): δ 7.84 (bs, 1H), 7.65 (m, 2H), 7.55 (m, 1H), 7.45 (m, 2H), 6.22 (s, 1H), 4.08 (s, 3H), 4.00 (s, 3H), 3.06 (dd, 1H, J=16.3, 13.6 Hz), 2.99 (m, 1H), 2.52 (dd, 1H, J=16.3, 5.0 Hz), 0.99 (d, 3H, J=6.7 Hz); LCMS (ES, m/z): 442.24 [M+H]⁺

X=C, R=CH₂OMe 80, pale yellow solid, 74% yield; ¹H NMR (400 MHz, CDCl, ppm): δ 8.38 (bs, 1H), 7.25 (s, 1H), 6.22 (s, 1H), 4.08 (s, 3H), 4.02 (s, 3H), 3.86 (s, 2H), 3.32 (s, 3H), 3.04 (dd, 1H, J=16.4, 13.6 Hz), 2.93 (m, 1H), 2.48 (dd, 1H, J=16.4, 4.5 Hz), 0.97 (d, 3H, J=7.0 Hz); LCMS (ES, m/z): 410.18 [M+H]⁺

X=C, R=cyclohexyl 81, beige solid, 47% yield; ¹H NMR (400 MHz, CDCl₃, ppm): δ7.25 (s, 1H), 7.03 (bs, 1H), 6.23 (s, 1H), 4.10 (s, 3H), 4.02 (s, 3H), 2.99 (dd, 1H, J=16.2, 13.6 Hz), 2.91 (m, 1H), 2.46 (dd, 1H, J=16.2, 4.0 Hz), 2.08 (m, 1H), 1.85-1.68 (m, 4H), 1.39-1.13 (m, 6H), 0.94 (d, 3H, J=6.7 Hz); LCMS (ES, m/z): 448.27 [M+H]⁺

1.8. Coupling at 3'

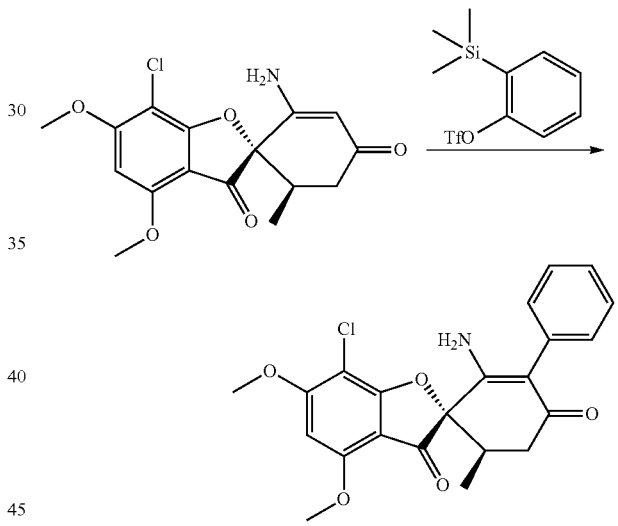

A mixture of 2'-aminogriseofulvin (337 mg; 1.0 equiv.), caesium fluoride (379 mg; 2.5 equiv.) and 2-(trimethylsilyl)phenyl-trifluoromethane-sulfonate (372 mg; 1.25 equiv.) in acetonitrile (20 mL) was left under agitation at ambient temperature for 20 hours. The solvent was evaporated and the residue purified on silica gel (CH₂Cl₂/MeOH 95:5) to give the desired derivative in the form of a pale yellow solid with a yield of 67%.

(1'S,6'R)-2'-amino-7-chloro-4,6-dimethoxy-6'-methyl-3'-phenyl-3H-spiro[benzofuran-2,1'-cyclohex[2]ene]-3,4'-dione 82 beige solid, 67% yield; ¹H NMR (400 MHz, CDCl₃, ppm): δ 7.41 (m, 2H), 7.31 (m, 1H), 7.23 (m, 2H), 6.19 (s, 1H), 4.36 (bs, 2H), 4.06 (s, 3H), 4.02 (s, 3H), 3.11 (dd, 1H, J=16.3, 13.5 Hz), 3.02 (m, 1H), 2.55 (dd, 1H, J=16.3, 4.5 Hz), 0.98 (d, 3H, J=6.5 Hz); LCMS (ES, m/z): 414.26 [M+H]⁺

1.9. Synthesis of Pyridines at 4'
Method A:

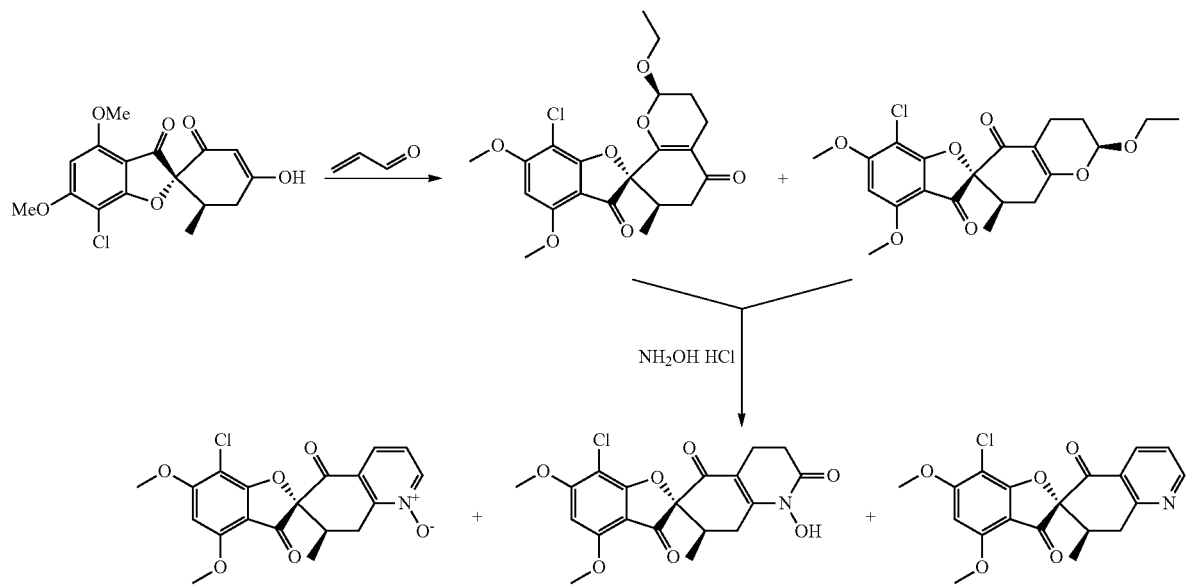

Synthesis of Dihydropyrans at 2' and 4':

A 100 ml round-bottomed flask was charged with ethanol (20 mL) and then potassium hydroxide (204 mg; 0.1 equiv.). After complete dissolution, griseofulvic acid (5.0 g; 1.0 equiv.) was added followed by the slow addition of acrolein (965 mg; 1.05 equiv.). The mixture was left under agitation at ambient temperature for 2 h then under reflux for 3 h. The reaction medium became pink. The temperature was lowered to 0° C.; the medium was acidified to pH 2 through the addition of concentrated hydrochloric acid. Water was added and the mixture extracted with AcOEt and then $CH_2Cl_2$. The organic phases were washed with 10% $NaHCO_3$ solution, dried over $Na_2SO_4$, filtered and evaporated. The residue was purified on silica gel ($CH_2Cl_2$/AcOEt 1:1) to give the dihydropyrans at 2' and 4' in the form of a mixture of diastereoisomers with a global yield of 50%.

(2S,7'R)-7-chloro-2'-ethoxy-4,6-dimethoxy-7'-methyl-3',4',7',8'-tetrahydro-3H-spiro[benzofuran-2,6'-chromene]-3,5'(2'H)-dione At 4', 83 white solid, 19% yield; $^1$H NMR (400 MHz, $CDCl_3$, ppm): δ 1:1 diastereomer mixture 6.09 (s, 2H), 5.25 (m, 1H), 5.17 (m, 1H), 4.02 (s, 6H), 3.94 (s, 6H), 3.69 (m, 2H), 3.50 (m, 1H), 3.14 (m, 2H), 2.84 (m, 2H), 2.48-2.29 (m, 5H), 2.21 (m, 2H), 2.02-1.72 (m, 4H), 1.31-1.25 (m, 6H), 1.04 (d, 6H, J=6.7 Hz); LCMS (ES, m/z): 423.00 [M+H]$^+$ (2S,7'R)-7-chloro-2'-ethoxy-4,6-dimethoxy-7'-methyl-3',4',6',7'-tetrahydro-3H-spiro[benzofuran-2,8'-chromene]-3,5'(2'H)-dione At 2', 84 white solid, 30% yield; $^1$H NMR (400 MHz, $CDCl_3$, ppm): δ 1:1 diastereomer mixture: 6.13 (s, 2H), 5.11 (bs, 1H), 5.06 (bs, 1H), 4.04 (s, 6H), 3.99 (s, 6H), 3.82 (m, 1H), 3.62-3.37 (m, 3H), 3.08 (m, 1H), 3.00 (m, 1H), 2.86 (m, 2H), 2.5-2.25 (m, 6H), 1.97-1.77 (m, 3H), 1.69 (m, 1H), 1.20 (t, 3H), J=6.7 Hz), 1.07 (t, 3H, J=6.7 Hz), 0.98 (m, 6H); LCMS (ES, m/z): 423.00 [M+H]$^+$ Synthesis of Pyridines at 4' and Analogues:

A 50 ml round-bottomed flask was charged with the mixture of dihydropyrans (500 mg; 1.0 equiv.), and then at once acetonitrile (10 mL) and hydroxylamine hydrochloride (493 mg; 6.0 equiv.). The reaction medium was left under magnetic stirring under reflux for 2 hours. After return to ambient temperature, the insolubles were filtered. The filtrate was evaporated and the residue purified on silica gel ($CH_2Cl_2$/MeOH 100:0 to 80:20) to give 40% pyridine N-oxide, pyridine and hydroxypyridone as sub-products.

(2S,7'R)-7-chloro-4,6-dimethoxy-7'-methyl-3,5'-dioxo-7',8'-dihydro-3H,5'H-spiro[benzofuran-2,6'-quinoline]1'-oxide 85 yellow solid, 41% yield; $^1$H NMR (400 MHz, $CDCl_3$, ppm): δ 8.49 (d, 1H, J=7.0 Hz), 7.79 (d, 1H, J=7.0 Hz), 7.32 (t, 1H, J=7.0 Hz), 6.13 (s, 1H), 4.03 (s, 3H), 3.92 (s, 3H), 3.65 (dd, 1H, J=19.4, 6.0 Hz), 3.47 (dd, 1H, J=19.4, 11.8 Hz), 2.96 (m, 1H), 1.20 (d, 3H), J=6.7 Hz); LCMS (ES, m/z): 390.00 [M+H]$^+$ (2S,7'R)-7-chloro-1'-hydroxy-4,6-dimethoxy-7'-methyl-3',4',7',8'-tetrahydro-1'H,3H-spiro[benzofuran-2,6'-quinoline]-2',3,5'-trione 86 beige solid, 7% yield; $^1$H NMR (400 MHz, $CDCl_3$, ppm): δ 8.57 (bs, 1H), 6.11 (s, 1H), 4.03 (s, 3H), 3.95 (s, 3H), 3.25 (ddt, 1 h, J=18.6, 11.4, 2.0), 3.06 (dd, 1H, J=18.6, 6.0 Hz), 2.89 (m, 1H), 2.75-2.69 (m, 2H), 2.61 (m, 2H), 1.10 (d, 3H, J=6.7 Hz); LCMS (ES, m/z): 408.00 [M+H]$^+$ (2S,7'R)-7-chloro-4,6-dimethoxy-7'-methyl-7',8'-dihydro-3H,5'H-spiro[benzofuran-2,6'-quinoline]-3,5'-dione 87 white solid, 3% yield; $^1$H NMR (400 MHz, $CDCl_3$, ppm): δ 8.76 (dd, 1H, J=4.7, 1.8 Hz), 8.22 (dd, 1H, J=7.9, 1.8 Hz), 7.31 (dd, 1H, 7.9, 4.7 Hz), 6.11 (s, 1H), 4.03 (s, 3H), 3.92

(s, 3H), 3.88 (dd, 1H, J=17.4, 12.0 Hz), 3.24 (dd, 1H, J=17.4, 6.0 Hz), 3.04 (m, 1H), 1.17 (d, 3H, J=6.7 Hz); LCMS (ES, m/z): 374.00 [M+H]+

Method B: See Bohlmann-Rhatz Synthesis of Pyridines 88 pale yellow solid; ¹H NMR (400 MHz, CDCl₃, ppm): δ 8.28 (d, 1H, J=8 2 Hz), 8.10 (m, 2H), 7.75 (d, 1H, J=8.2 Hz), 7.51 (m, 3H), 6.13 (s, 1H), 4.04 (s, 3H), 3.95 (m, 1H), 3.93 (s, 3H), 3.33 (dd, 1H, J=17.7, 5.3 Hz), 3.09 (m, 1H), 1.20 (d, 3H, J=6.7 Hz); LCMS (ES, m/z): 450.20 [M+H]+

Method C:

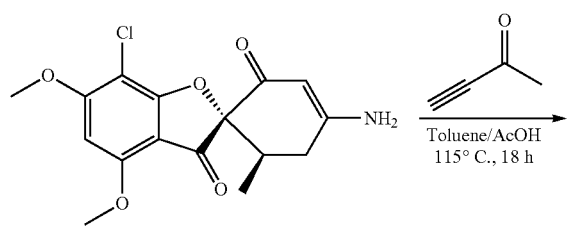

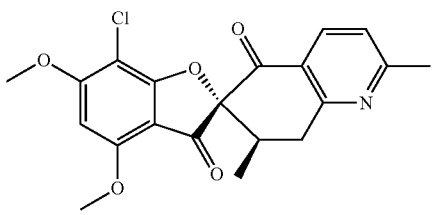

In a 100 mL round-bottomed flask, 1.2 g (3.5 mmol, 1 eq.) of (1'S,6'R)-4'-amino-7-chloro-4,6-dimethoxy-6'-methyl-3H-spiro[benzofuran-2,1'-cyclohex[3]ene]-2',3-dione were mixed with 331 μL (4.2 mmol, 1.2 eq) of 3-butyn-2-one in 12 mL of toluene and 4.0 mL of acetic acid. The mixture was heated to 115° C. and left under agitation 16 h. After return to ambient temperature the mixture was concentrated under reduced pressure. The residue was purified by chromatography on silica gel (CH₂Cl₂/MeOH 99:1). An orange oil was obtained (0.86 g) with a yield of 63%.

(2S,7'R)-7-chloro-4,6-dimethoxy-2',7'-dimethyl-7',8'-dihydro-3H,5'H-spiro[benzofuran-2,6'-quinoline]-3,5'-dione 89 ¹H NMR (CDCl₃, 400 MHz, δ, ppm): 1.15 (d, 3H, J=6.8 Hz), 2.64 (s, 3H), 3.02 (m, 1H), 3.19 (dd, 1H, J=17.0, 5.0 Hz), 3.83 (dd, 1H, J=17.0, 12.0 Hz), 3.92 (s, 3H), 4.02 (s, 3H), 6.11 (s, 1H), 7.17 (d, 1H, J=8.0 Hz), 8.11 (d, 1H, J=8.0 Hz); LCMS (ES, m/z): 388.20 [M+H]+

Method D:

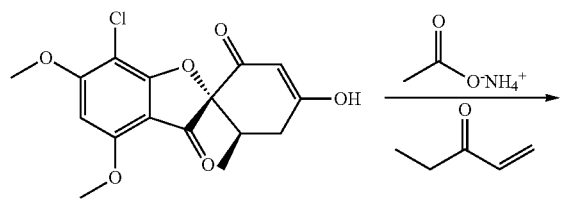

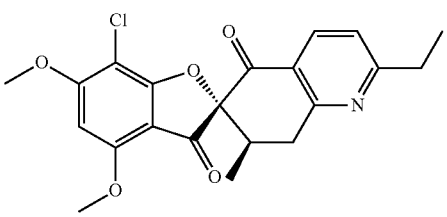

A 100 mL round-bottomed flask was charged with 1 g (2.9 mmol, 1 eq.) of griseofulvic acid, 0.34 g (4.4 mmol, 1.5 eq.) ammonium acetate and 347 μL (3.5 mmol, 1.2 eq.) of ethyl vinyl ketone in 10 mL ethanol. The mixture was left under agitation for 4 h at 80° C., cooled to ambient temperature then concentrated under reduced pressure. The residue was purified by chromatography on silica gel (CH₂Cl₂/AcOEt 98:2 to 80:20). A yellow solid (0.25 g) was obtained with a yield of 21%.

(2 S,7'R)-7-chloro-2'-ethyl-4,6-dimethoxy-7'-methyl-7',8'-dihydro-3H,5'H-spiro[benzofuran-2,6'-quinoline]-3,5'-dione 90 ¹H NMR (CD₃CN, 400 MHz, δ, ppm): 1.09 (d, 3H, J=6.6 Hz), 1.33 (t, 3H, J=7.3 Hz), 2.90 (q, 2H, J=7.3 Hz), 3.05 (m, 1H), 3.18 (dd, 1H, J=17.9, 6.0 Hz), 3.64 (dd, 1H, J=17.9, 12.4 Hz), 3.93 (s, 3H), 4.06 (s, 3H), 6.38 (s, 1H), 7.30 (d, 1H, J=8.3 Hz), 8.12 (d, 1H, J=8.3 Hz); LCMS (ES, m/z): 401.98 [M+H]+

Method E:

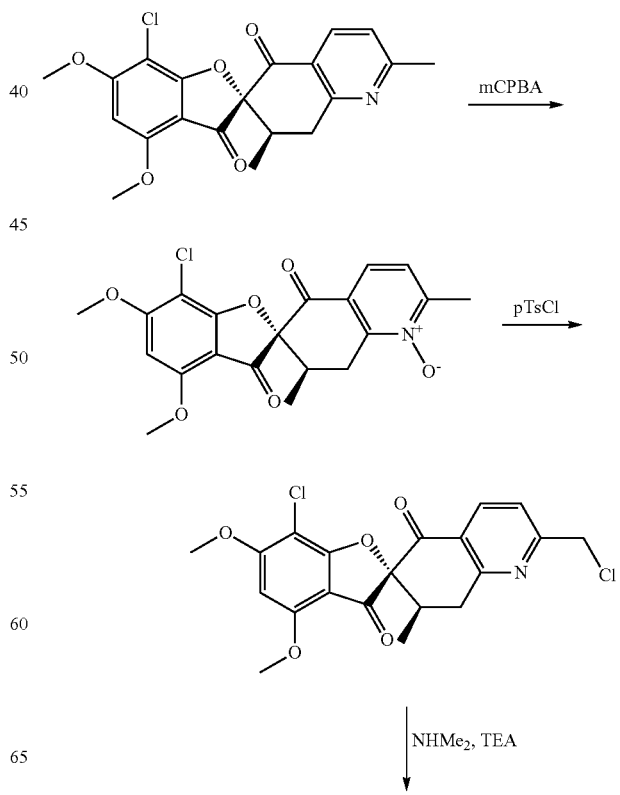

-continued

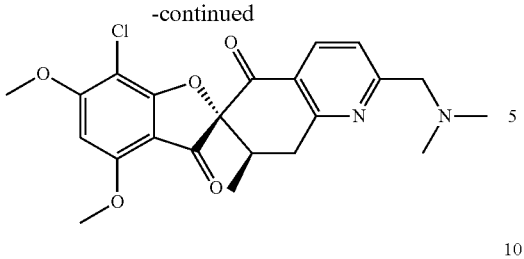

In a 250 mL round-bottomed flask 1.3 g (7.7 mmol, 2 eq.) of mCPBA was added to a solution of (2S,7'R)-7-chloro-4,6-dimethoxy-2',7'-dimethyl-7',8'-dihydro-3H,5'H-spiro[benzofuran-2,6'-quinoline]-3,5'-dione (1.5 g, 3.9 mmol, 1.0 eq) in 45 mL of dichloromethane. The mixture was left under agitation at ambient temperature for 16 h, then concentrated under reduced pressure. The residue was dissolved in AcOEt. The organic phase was washed with 10% Na$_2$S$_2$O$_3$ solution, then a saturated NaHCO$_3$ solution, then brine solution and dried over Na$_2$SO$_4$, filtered and concentrated under reduced pressure. A yellow solid (1.6 g) was obtained with a yield of 100%.

(2S,7'R)-7-chloro-4,6-dimethoxy-2',7'-dimethyl-3,5'-dioxo-7',8'-dihydro-3H,5'H-spiro[benzofuran-2,6'-quinoline]1'-oxide 91 $^1$H NMR (CD$_3$CN, 400 MHz, δ, ppm): 1.14 (d, 3H, J=6.8 Hz), 2.54 (s, 3H), 3.00 (m, 1H), 3.20 (dd, 1H, J=19.2, 11.6 Hz), 3.58 (dd, 1H, J=19.2, 6.0 Hz), 3.93 (s, 3H), 4.06 (s, 3H), 6.38 (s, 1H), 7.47 (d, 1H, J=8.2 Hz), 7.66 (d, 1H, J=8.2 Hz); LCMS (ES, m/z): 403.92 [M+H]$^+$ In a 100 mL round-bottomed flask 0.51 g (2.7 mmol, 1.2 eq.) of PTSCl was added to a solution of the product previously obtained (0.9 g, 2.2 mmol, 1 eq.) in 18 mL of toluene. The mixture was left under agitation for 18 h at 115° C., then cooled to ambient temperature and concentrated under reduced pressure. The residue was purified by chromatography on silica gel (CH$_2$Cl$_2$/AcOEt 95:5). The product was obtained with 93% yield. 0.2 g (0.48 mmol, 1 eq.) of the product previously obtained was diluted in 2 mL of acetonitrile. The addition was then made of 125 µL (0.48 mmol, 1 eq.) of dimethylamine and 67 µL (0.48 mmol, 1 eq.) of triethylamine. The mixture was left under agitation at 90° C. for 1 h, cooled to ambient temperature and concentrated under reduced pressure. The residue was purified by chromatography on silica gel (CH$_2$Cl$_2$/MeOH/NH$_4$OH 97:3:0.1). A yellow solid (68 mg) was obtained with a yield of 33%.

(2S,7'R)-7-chloro-2'-(((dimethylamino)methyl)-4,6-dimethoxy-7'-methyl-7',8'-dihydro-3H,5'H-spiro[benzofuran-2,6'-quinoline]-3,5'-dione 92 RMN $^1$H (CD$_3$CN, 400 MHz, δ, ppm): 1.09 (d, 3H, J=6.4 Hz), 2.29 (s, 6H), 3.05 (m, 1H), 3.18 (dd, 1H, J=18.0, 5.6 Hz), 3.64 (m, 3H), 3.93 (s, 3H), 4.06 (s, 3H), 6.37 (s, 1H), 7.53 (d, 1H, J=8.2 Hz), 8.17 (d, 1H, J=8.2 Hz); LCMS (ES, m/z): 430.9 [M+H]$^+$ 1.10. Synthesis of a Sulfoxide at 3'

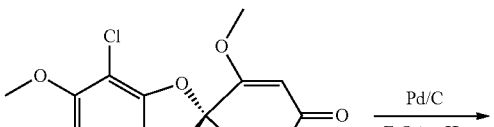

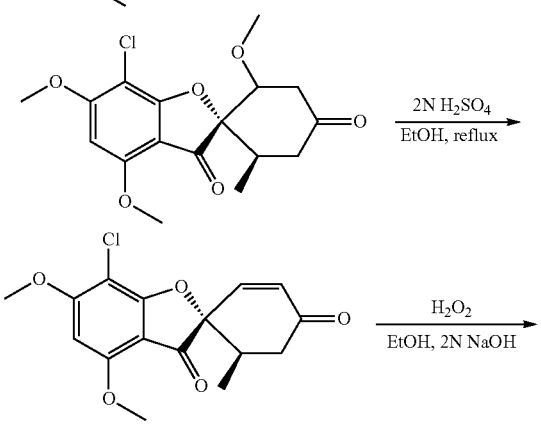

378357

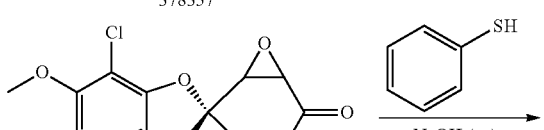

378353

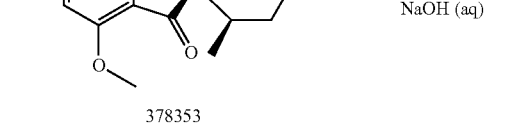

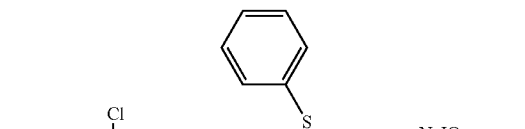

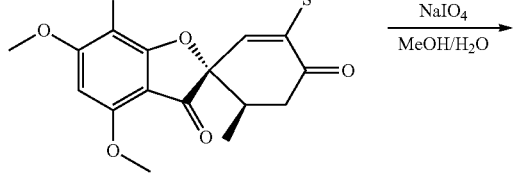

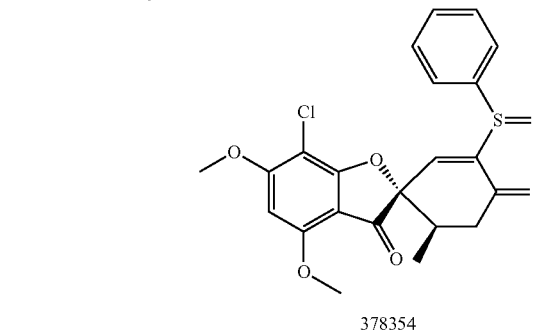

378354

A 2 L round-bottomed flask was charged with 3 g of Pd/C in a solution of griseofulvin (20 g, 5.7 mmol) in 1.2 L AcOEt. The mixture was left under agitation in a hydrogen atmosphere (1 bar) at ambient temperature for 60 h, then filtered.

The filtrate was concentrated under reduced pressure. A white solid was obtained (20 g) and used as crude product at the following step.

93

In a 2 L round-bottomed flask 600 mL of 2N sulfuric acid was added dropwise to a solution of the product previously obtained (60 g, 169.1 mmol) in 600 mL of ethanol. The resulting solution was heated under reflux for 16 h, then cooled to ambient temperature. The reaction medium was extracted with 2×400 mL of dichloromethane. The organic phases were combined, dried over anhydrous sodium sulfate and concentrated under reduced pressure. A pale yellow solid (54 g) was obtained with a yield of 99%.

$^1$H NMR (CDCl$_3$, 400 MHz, δ, ppm): 6.57 (1H, d), 6.19 (1H, d), 6.15 (1H, s), 4.04 (3H, s), 4.00 (3H, s), 3.12 (1H, dd), 2.94-2.81 (1H, m), 2.42 (1H, dd), 0.97 (3H, d) LCMS (ES, m/z): 322.90 [M+H]$^+$

94

In a 100 mL round-bottomed flask a 2N solution of NaOH was added dropwise to a solution of 0.5 g (1.55 mmol, 1 equiv.) of the product previously obtained in 20 mL of ethanol under agitation at 0° C. H$_2$O$_2$ (1 mL) was added dropwise to the agitated solution at 0° C. The reaction mixture was left under agitation 1 h at 0° C., then diluted in 100 mL of water. The solution was then extracted with 3×100 mL AcOEt. The organic phases were combined, dried over anhydrous sodium sulfate and filtered. The filtrate was concentrated under reduced pressure. A pale yellow solid (m=0.5 g) was obtained with a yield of 95%.

$^1$H NMR (DMSO-d6, 400 MHz, δ, ppm): 6.52 (1H, s), 4.05 (3H, s), 4.05-4.00 (1H, m), 3.94 (3H, s), 3.58-3.56 (1H, m), 2.80-2.68 (1H, m), 2.65-2.55 (1H, m), 2.31-2.21 (1H, m), 0.63 (3H, d) LCMS (ES, m/z): 338.85 [M+H]$^+$ In a 100 mL round-bottomed flask 4 mL of 0.1 N NaOH was added to a solution of thiophenol (176 mg, 1.6 mmol, 1.2 eq.) in 20 mL of water. The mixture was agitated 10 min at 30° C. The previously obtained product (0.45 g, 1.3 mmol, 1.0 eq.) was added and the mixture left user agitation 1 h at 30° C., then 16 h at 70° C. The reaction mixture was cooled to ambient temperature then extracted with 3×30 mL AcOEt. The organic phase were combined, dried over anhydrous sodium sulfate, filtered and concentrated under reduced pressure. The residue was purified by chromatography on silica gel (AcOEt/EP 1:2). A pale yellow solid (360 mg) was obtained with a yield of 63%.

1'S,6'R)-7-chloro-4,6-dimethoxy-6'-methyl-3'-(phenylsulfinyl)-3H-spiro[benzofuran-2,1'-cyclohex[2]ene]-3,4'-dione (95)

In a 100 mL round-bottomed flask, to a solution of the product previously obtained (0.35 g, 0.8 mmol, 1.0 eq.) in 20 mL methanol was added 261 mg (1.2 mmol, 1.5 eq.) of sodium periodate dissolved in 10 mL of water. The solution was left under agitation at 50° C. for 16 h. The reaction mixture was cooled to ambient temperature and extracted with 3×50 mL of dichloromethane. The organic phases were combined, dried over anhydrous sodium sulfate, filtered and concentrated under reduced pressure. The residue was purified by chromatography on silica gel (EtOAc/EP 1:2). A white solid (0.2 g) was obtained with a yield of 55%.

$^1$H NMR (300 MHz, CD$_3$OD, δ, ppm): 7.78-7.84 (1H, m), 7.70-7.73 (1H, dd, J=6 Hz), 7.51-7.58 (3H, m), 7.28-7.30 (1H, d, J=5.4 Hz), 6.48 (1H, s), 4.85 (3H, s), 4.09 (3H, s), 2.73-3.07 (2H, m), 2.41-2.54 (1H, m), 0.86-0.90 (3H, t, J=6.6 Hz); LCMS (ES, m/z): 447 [M+H]$^+$ The following sulfoxides were prepared following similar procedure.

(1'S,6'R)-3'-(benzylsulfonyl)-7-chloro-4,6-dimethoxy-6'-methyl-3H-spiro[benzofuran-2,1'-cyclohex[2]ene]-3,4'-dione 96 white solid 79% yield; $^1$H (CDCl$_3$, 400 MHz, δ, ppm): 0.93 (d, 3H, J=6.7 Hz), 2.63 (dd, 1H, J=17.6, 5.3 Hz), 2.80 (m, 1H), 3.21 (dd, 1H, J=17.6, 13.7 Hz), 3.98 (s, 3H), 4.03 (s, 3H), 4.56 (d, 1H, J=13.7 Hz), 4.63 (d, 1H, J=13.7 Hz), 6.14 (s, 1H), 7.27-7.34 (m, 5H); LCMS (ES, m/z): 477.1 [M+H]$^+$ (1'S,6'R)-3'-(benzylsulfinyl)-7-chloro-4,6-dimethoxy-6'-methyl-3H-spiro[benzofuran-2,1'-cyclohex[2]ene]-3,4'-dione 97 white solid 30% yield; $^1$H (CDCl$_3$, 400 MHz, δ, ppm): 0.97 (d, 3H, J=6.7 Hz), 2.60 (dd, 1H, J=17.3, 5.0 Hz), 2.88-2.96 (m, 1H), 3.27 (dd, 1H, J=17.4, 13.8 Hz), 3.90 (d, 1H, J=13.0 Hz), 4.01 (s, 3H), 4.03 (s, 3H), 4.35 (d, 1H, J=13.0 Hz), 6.14 (s, 1H), 6.87 (s, 1H), 7.20 (d, 2H, J=7.7 Hz), 7.26-7.34 (m, 3H); LCMS (ES, m/z): 461.1 [M+H]$^+$ (1'S,6'R)-7-chloro-4,6-dimethoxy-6'-methyl-3'-(phenylsulfonyl)-3H-spiro[benzofuran-2,1'-cyclohex[2]ene]-3,4'-dione 98 white solid 46% yield; $^1$H (CDCl$_3$, 400 MHz, δ, ppm): 0.92 (d, 3H, J=6.7 Hz), 2.46 (dd, 1H, J=17.2, 4.9 Hz), 2.86-2.94 (m, 1H), 3.13 (dd, 1H, J=17.2, 14.0 Hz), 4.00 (s, 3H), 4.06 (s, 3H), 6.18 (s, 1H), 7.52 (t, 2H, J=7.4 Hz), 7.62 (t, 1H, J=7.4 Hz), 7.78 (s, 1H), 8.01 (d, 2H, J=7.4 Hz); LCMS (ES, m/z): 463.0 [M+H]$^+$ 1.11. Synthesis of Dihydropyrroles at 2'

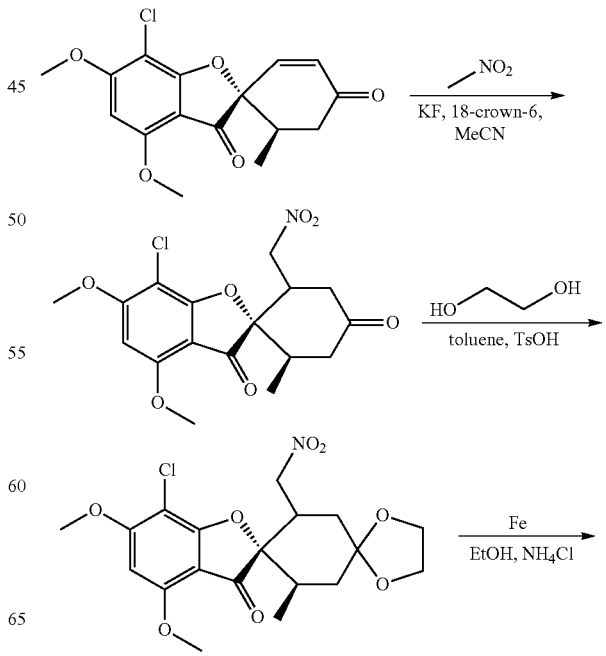

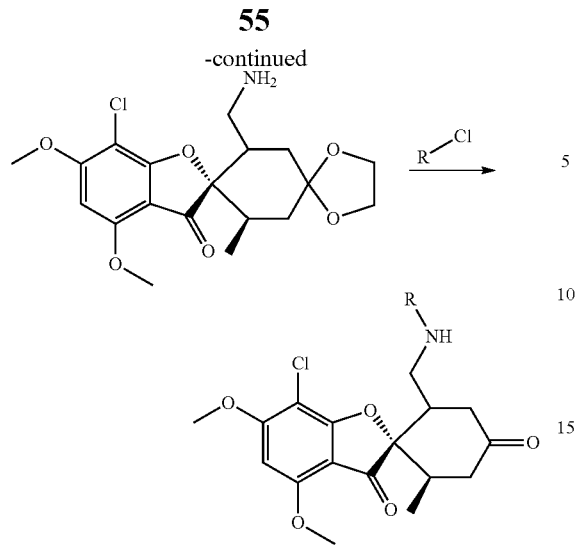

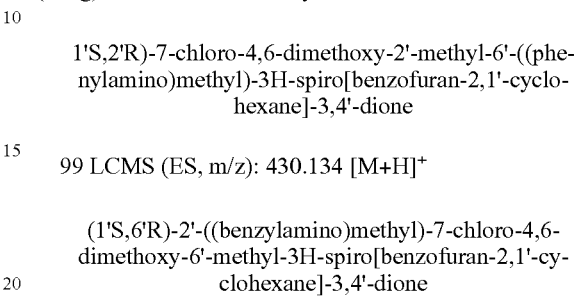

Example R=Ph

In a 250 mL round-bottomed flask charged with 9 g of enone (see 1.10) (27.9 mmo, 1.0 eq.) in 200 mL acetonitrile were added 1.9 g (30.8 mmol, 1.1 eq.) of nitromethane, 1.6 g (27.9 mmo, 1.0 eq.) of KF and 7.4 g (28.0 mmol, 1.0 eq.) of 18-crown-6. The solution was left under agitation for 1.5 h at 80° C. The reaction medium was cooled to ambient temperature and diluted in 500 mL of water. The solution was extracted with 3×300 mL ethyl acetate. The organic phases were combined, dried over anhydrous sodium sulfate, filtered and concentrated under reduced pressure. The residue was purified by chromatography on silica gel (AcOEt/PE 1:2). A pale yellow solid (m=7.6 g) was obtained with a yield of 71%.

In a 500 mL round-bottomed flask to a solution of the product previously obtained (5 g, 13.0 mmol, 1.0 eq.) in 100 mL of toluene were added 1.6 g (26.1 mmol, 2.0 eq.) of ethylene glycol and 225 mg (1.3 mmol, 0.1 eq.) of PTSA. The solution was heated to 80° C. and left under agitation for 4 h. The reaction mixture was then cooled to ambient temperature, washed with 2×100 mL saturated sodium bicarbonate solution then 100 mL of brine. The organic phase was dried over anhydrous sodium sulfate, filtered and concentrated under reduced pressure. A white solid (5.2 g) was obtained with a yield of 93%.

In a 500 mL round-bottomed flask charged with a solution of the product obtained previously (5.2 g, 12.1 mmol, 1.0 eq.) in ethanol (100 mL), were added 4.1 g (73.2 mmol, 6.0 eq.) of iron and 5 mL saturated NH$_4$Cl solution. The solution was then left under agitation at 70° C. for 4 h. The reaction mixture was filtered and the filtrate concentrated under reduced pressure. A pale yellow solid (4.7 g) was obtained with a yield of 97%.

In a 100 mL round-bottomed flask charged with a solution of the product previously obtained (2 g, 5.0 mmol, 1.0 eq.) in 50 mL of dichloromethane, were added 676 mg (5.5 mmol, 1.1 eq.) of phenylboronic acid, 915 mg (5.0 mmol, 1.0 eq.) of Cu(OAc)$_2$ and 5 mL of triethylamine. The reaction mixture was left under agitation at ambient temperature for 16 h, then washed with 3×20 mL of saturated sodium bicarbonate solution and 20 mL of brine. The organic phase was dried over anhydrous sodium sulfate, filtered and concentrated under reduced pressure. The residue was purified by chromatography on silica gel (AcOEt/PE 1:2). A pale yellow solid (1.6 g) was obtained with a yield of 66%.

In a 100 mL round-bottomed flask 15 mL of 2N HCl solution were added to a solution of the product previously obtained (1.57 g, 3.3 mmol, 1 eq.) in THF (30 mL). The reaction mixture was left under agitation for 16 h at 35° C. The pH of the solution was then adjusted to 7 through the addition of saturated sodium bicarbonate solution. The mixture was extracted with 3×30 mL of CH$_2$Cl$_2$. The organic phases were combined, dried over Na2SO4, filtered and concentrated under reduced pressure. The residue was purified by chromatography on silica gel (AcOEt/PE 1:2). A white solid (1.3 g) was obtained with a yield of 91%.

1'S,2'R)-7-chloro-4,6-dimethoxy-2'-methyl-6'-((phenylamino)methyl)-3H-spiro[benzofuran-2,1'-cyclohexane]-3,4'-dione 99 LCMS (ES, m/z): 430.134 [M+H]$^+$ (1'S,6'R)-2'-((benzylamino)methyl)-7-chloro-4,6-dimethoxy-6'-methyl-3H-spiro[benzofuran-2,1'-cyclohexane]-3,4'-dione 100 yellow solid; $^1$H NMR (CDCl$_3$, 400 MHz, δ, ppm): 7.30-7.20 (5H, m), 6.13 (1H, s), 4.04 (3H, s), 4.00 (3H, s), 3.76-3.70 (1H, m), 3.61 (1H, d), 2.90-2.75 (3H, m), 2.75-2.60 (2H, m), 2.65-2.45 (3H, m), 1.06 (3H, d); LCMS (ES, m/z): 444.30 [M+H]$^+$ N-(((1'S,2'R)-7-chloro-4,6-dimethoxy-2'-methyl-3,4'-dioxo-3H-spiro[benzofuran-2,1'-cyclohexane]-6'-yl)methyl)benzamide 101 white solid, yield 32%; $^1$H NMR (CDCl$_3$, 300 MHz, δ, ppm): 7.75-7.73 (2H, m), 7.54-7.51 (1H, m), 7.50-7.42 (2H, m), 6.35 (1H, 1s), 6.08 (1H, s), 4.02 (3H, s), 3.89 (3H, s), 3.77-3.66 (1H, m), 3.44-3.40 (1H, m), 2.91-2.83 (3H, m), 2.70-2.63 (1H, m), 2.60-2.49 (2H, m), 1.11 (3H, d); LCMS (ES, m/z): 458.20 [M+H]$^+$

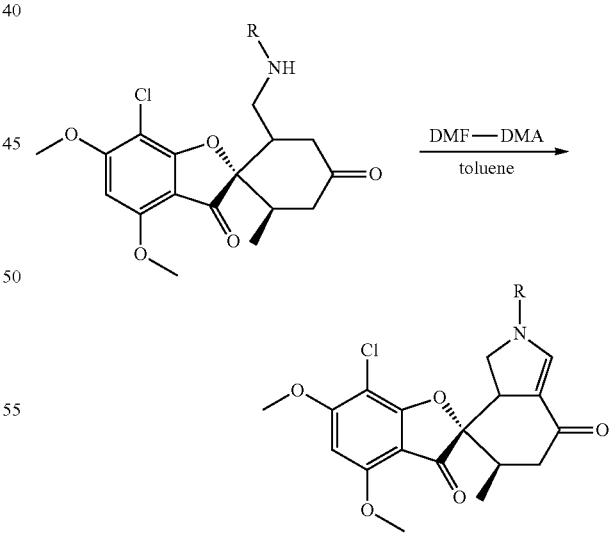

In a 50 mL round-bottomed flask 1.2 g (5.8 mmol, 5.0 eq.) of DMF-DMA were added to a solution of the product previously obtained (0.5 g, 1.2 mmol, 1.0 eq.) in 10 mL of toluene. The solution was heated under reflux and left under agitation for 5 days. The reaction mixture was cooled to ambient temperature and concentrated under reduced pressure. The residue was purified by chromatography on silica gel (AcOEt/PE 1:1). A pale yellow solid (60 mg) was obtained with a yield of 12%.

(2S,5'R)-7-chloro-4,6-dimethoxy-5'-methyl-2'-phenyl-3',3a',5',6'-tetrahydro-3H-spiro[benzofuran-2,4'-isoindole]-3,7'(2'H)-dione 102 pale yellow solid, yield 12%; $^1$H NMR (CDCl$_3$, 300 MHz, δ, ppm): 8.09 (1H, s), 7.28-7.34 (2H, m), 7.05-7.08 (1H, t, J=5.8 Hz), 6.91-6.93 (2H, d, J=6.0 Hz), 6.16 (1H, s), 4.23-4.25 (1H, t), 4.04 (3H, s), 4.03 (3H, s), 3.90-3.95 (1H, t, J=7.8 Hz), 3.59-3.61 (1H, t, J=7.8 Hz), 2.95-3.00 (1H, dd, J=9.1 Hz), 2.37-2.44 (2H, m), 1.29-1.31 (3H, d, J=5.4 Hz); LCMS (ES, m/z): 440 [M+H]$^+$ (2S,5'R)-2'-benzyl-7-chloro-4,6-dimethoxy-5'-methyl-3',3a',5',6'-tetrahydro-3H-spiro[benzofuran-2,4'-isoindole]-3,7'(2'H)-dione 103 pale yellow oil, yield 16%; $^1$H NMR (300 MHz, CD$_3$OD, δ, ppm): 8.35 (1H, s), 7.40-7.25 (5H, m), 6.38 (1H, s), 4.70 (2H, q, J=7.8 Hz), 4.04 (3H, s), 4.03-3.98 (1H, m), 3.95 (3H, s), 3.60 (1H, t, J=7.8 Hz), 3.13 (1H, t, J=7.8 Hz), 2.89 (1H, dd, J=9 Hz), 2.35-2.25 (2H, m), 1.24 (3H, d, J=5.4 Hz); LCMS (ES, m/z): 454.20 [M+H]$^+$ 1.12. Synthesis of Pyrroles at 4'

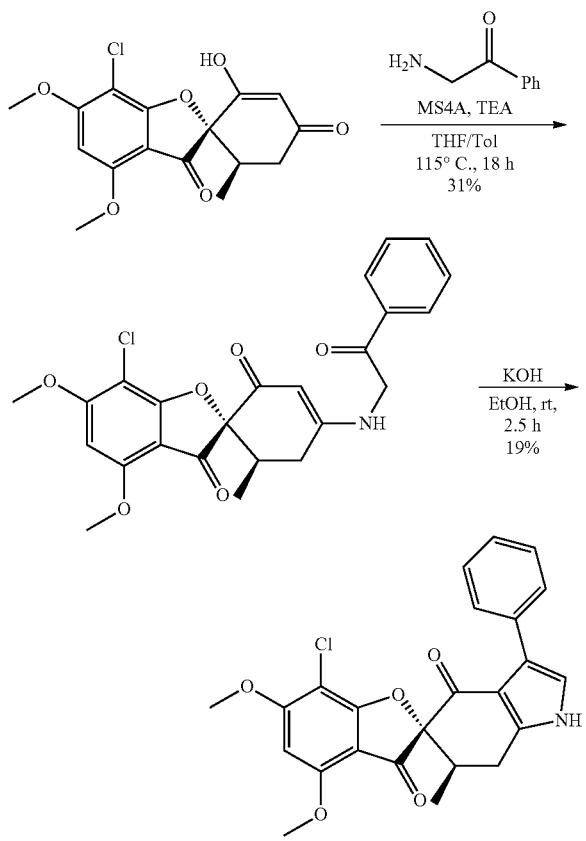

In a 50 mL round-bottomed flask a solution of 0.25 g (1.5 mmol, 1.0 eq.) of 2-aminoacetophenone hydrochloride and 0.20 mL (1.5 mmol, 1.0 eq.) of triethylamine in 1.5 mL THF was added to a mixture of griseofulvic acid (0.5 g, 1.5 mmol, 1.0 eq.) and 4A molecular sieve (0.25 g) in 3.5 mL of toluene. The mixture was heated under reflux (118° C.) for 18 h. After cooling to ambient temperature the reaction mixture was filtered on Dicalite® then concentrated under reduced pressure. The residue was purified by chromatography on silica gel (CH$_2$Cl$_2$/MeOH 98:2). An orange oil was obtained (m=0.21 g) with a yield of 31%. In a 50 mL round-bottomed flask 0.1 g (1.8 mmol, 3.9 eq.) of powder KOH were added to a suspension of the product obtained previously (0.21 g, 0.5 mmol, 1.0 eq.) in 4 mL of EtOH. The mixture was left under agitation for 2 h 30 at ambient temperature. The reaction mixture was acidified through the addition of 2% HCl and diluted in 10 mL of water and 10 mL of AcOEt. The aqueous phase was extracted with 2×20 mL AcOEt. The organic phases were combined, washed with 30 mL of brine, dried over sodium sulfate, filtered and concentrated under reduced pressure. The residue was purified by chromatography on silica gel (CH$_2$Cl$_2$/EtOAc 95:5). A yellow solid (38 mg) was obtained with a yield of 19%.

(2S,4'S,6'R)-7-chloro-4'-hydroxy-4,6-dimethoxy-6'-methyl-3'-phenyl-1',4',6',7'-tetrahydro-3H-spiro[benzofuran-2,5'-indol]-3-one 104 $^1$H NMR (CD$_3$CN, 400 MHz, δ, ppm): 1.05 (d, 3H, J=6.4 Hz), 3.03 (m, 2H), 3.31 (dd, 1H, J=17.6, 13.2 Hz), 3.92 (s, 3H), 4.04 (s, 3H), 6.34 (s, 1H), 6.92 (s, 1H) 7.29 (m, 3H), 7.54 (d, 2H, J=7.6 Hz), 9.78 (br s, 1H); LCMS (ES, m/z): 438.103 [M+H]$^+$ 105 $^1$H NMR (400 MHz, CDCl$_3$, ppm): δ 10.69 (bs, 1H), 9.54 (s, 1H), 7.32 (s, 1H), 6.10 (s, 1H), 4.02 (s, 3H), 3.90 (s, 3H), 3.54 (dd, 1H, J=18.5, 13.7 Hz), 3.08-2.97 (m, 2H), 1.12 (d, 3H, J=6.7 Hz); LCMS (ES, m/z): [M+H]$^+$ 1.14. Synthesis of Pyrrazoles at 4'

Method A:

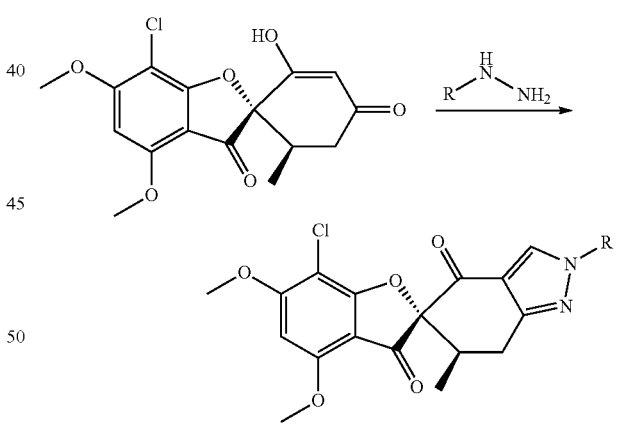

Example: R=Me

In a 100 mL round-bottomed flask 0.16 mL (2.9 mmol, 1.0 eq.) of methylhydrazine were added to a solution of griseofulvic acid (1 g, 2.9 mmol, 1.0 eq.) in THF (10 mL). The reaction mixture was left under agitation at 70° C. for 2 h. After cooling to ambient temperature, 2.0 mL (14.8 mmol, 5 eq.) of DMF-DMA were added and the reaction mixture left under agitation at 70° C. for 16 h. After cooling to ambient temperature the reaction mixture was concentrated under reduced pressure and diluted in 20 mL of AcOEt. The organic phase was washed with 30 mL of 0.1 N HCl, dried over sodium sulfate, filtered and concentrated under reduced pressure. The residue was purified by chromatography on silica gel (CH$_2$Cl$_2$/AcOEt 40:60). An off-white solid (0.62 g) was obtained with a yield of 56%.

(2S,6'R)-7-chloro-4,6-dimethoxy-2',6'-dimethyl-6',7'-dihydro-3H-spiro[benzofuran-2,5'-indazole]-3,4'(2'H)-dione R=Me 106 $^1$H NMR (CD$_3$CN, 400 MHz, δ, ppm): 1.04 (d, 3H, J=6.0 Hz), 2.95 (m, 2H), 3.25 (dd, 1H, J=16.4, 11.4 Hz), 3.91 (s, 3H), 3.93 (s, 3H), 4.05 (s, 3H), 6.36 (s, 1H), 7.98 (s, 1H); LCMS (ES, m/z): 377.083 [M+H]$^+$ (2S,6'R)-7-chloro-4,6-dimethoxy-6'-methyl-2'-phenyl-6',7'-dihydro-3H-spiro[benzofuran-2,5'-indazole]-3,4'(2'H)-dione R=Ph 107 beige solid, yield 33%; $^1$H NMR (CDCl$_3$, 400 MHz, δ, ppm): 8.39 (s, 1H), 7.72 (d, 2H, J=8.2 Hz), 7.51 (t, 2H, J=8.2 Hz), 7.40 (t, 1H, J=8.2 Hz), 6.13 (s, 1H), 4.04 (s, 3H), 3.95 (s, 3H), 3.58 (dd, 1H, J=16.3, 12.3 Hz), 3.13 (dd, 1H, J=16.3, 5.5 Hz), 3.07 (m, 1H), 1.17 (d, 3H, J=6.5 Hz); LCMS (ES, m/z): 439.098 [M+H]$^+$ (2S,6'R)-7-chloro-4,6-dimethoxy-6'-methyl-6',7'-dihydro-3H-spiro[benzofuran-2,5'-indazole]-3,4'(2'H)-dione R=H 108 off-white solid, yield 13%; $^1$H NMR (CDCl$_3$, 400 MHz, δ, ppm): 1.13 (d, 3H, J=6.4 Hz), 3.03 (m, 2H), 3.51 (dd, 1H, J=18.0, 13.6 Hz), 3.93 (s, 3H), 4.00 (br s, 1H), 4.02 (s, 3H), 6.11 (s, 1H), 8.00 (s, 1H); LCMS (ES, m/z): 388.067 [M+H]$^+$ Method B:

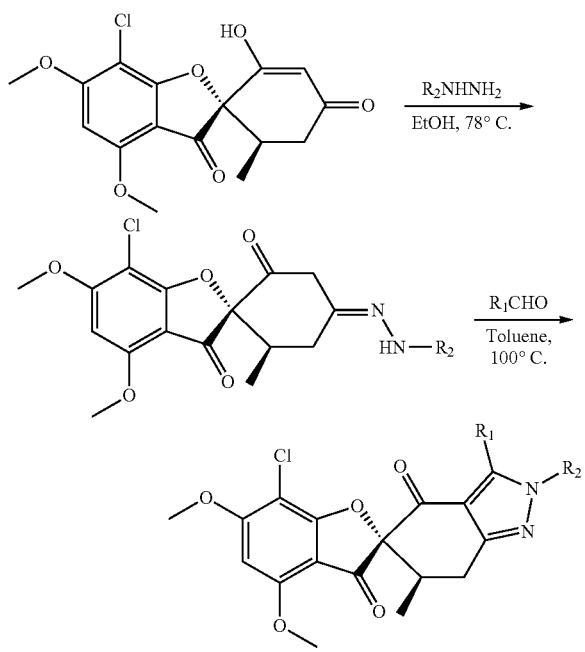

Example: R$_1$=2-MeOPh, R$_2$=Me

A 500 mL round-bottomed flask was charged with griseofulvic acid (10 g, 29.5 mmol, 1.0 eq.) and methylhydrazine (20 mL, 5.0 eq.) in 200 mL of ethanol. The reaction mixture was left under agitation and heated to 78° C. for 16 h. The reaction mixture was concentrated under reduced pressure and the residue purified by chromatography on silica gel (AcOEt/PE 1:5). A yellow solid (5 g) was obtained with a yield of 46%. A 500 mL round-bottomed flask was charged with the hydrazone intermediate previously obtained (1.2 g, 3.3 mmol, 1.0 eq.) and with 2-methoxybenzaldehyde (0.9 g, 6.6 mmol, 2.0 eq.) in 300 mL of toluene. The solution was left under agitation at 100° C. for 16 h. The mixture was then concentrated under reduced pressure and the residue purified by chromatography on silica gel (AcOEt/PE 1:10 to 1:1). A yellow solid (400 mg) was obtained with a yield of 25%.

(2S,6'R)-7-chloro-4,6-dimethoxy-3'-(2-methoxyphenyl)-2',6'-dimethyl-6',7'-dihydro-3H-spiro[benzofuran-2,5'-indazole]-3,4'(2'H)-dione 109 $^1$H NMR (CDCl$_3$, 400 MHz, δ, ppm): 7.5-7.2 (m, 2H), 7.1-6.9 (m, 2H), 6.07 (s split, 1H), 4.0-3.9 (2×s split, 6H), 3.82-3.70 (2×s split, 6H), 3.60-3.50 (m, 1H), 3.1-3.0 (m, 2H), 1.17-1.13 (m, 3H); LCMS (ES, m/z): 483.00 [M+H]$^+$ (2S,6'R)-7-chloro-4,6-dimethoxy-2',6'-dimethyl-3'-phenyl-6',7'-dihydro-3H-spiro[benzofuran-2,5'-indazole]-3,4'(2'H)-dione 110 yellow solid, yield 18%; $^1$H NMR (CDCl$_3$, 300 MHz, δ, ppm): 7.43 (s, 5H), 6.07 (s, 1H), 3.96 (s, 3H), 3.92 (s, 3H), 3.82 (s, 3H), 3.60-3.50 (m, 1H), 3.09-2.96 (m, 2H), 1.15 (d, 3H); LCMS (ES, m/z): 453.15 [M+H]$^+$ (2S,6'R)-7-chloro-4,6-dimethoxy-3'-(4-methoxyphenyl)-2',6'-dimethyl-6',7'-dihydro-3H-spiro[benzofuran-2,5'-indazole]-3,4'(2'H)-dione 111 yellow solid, yield 25%; $^1$H NMR (CDCl$_3$, 400 MHz, δ, ppm): 7.41 (d, 2H), 6.9 (d, 2H), 6.1 (s, 1H), 4.0 (s, 3H), 3.92 (s, 3H), 3.84 (2×s, 6H), 3.6-3.5 (m, 1H) 3.1-3.0 (m, 2H), 1.14 (d, 3H); LCMS (ES, m/z): 482.85 [M+H]$^+$ (2S,6'R)-7-chloro-4,6-dimethoxy-3'-(3-methoxyphenyl)-2',6'-dimethyl-6',7'-dihydro-3H-spiro[benzofuran-2,5'-indazole]-3,4'(2'H)-dione 112 yellow solid, yield 15%; LCMS (ES, m/z): 483.124 [M+H]$^+$ (2S,6'R)-7-chloro-3'-(3-chlorophenyl)-4,6-dimethoxy-2',6'-dimethyl-6',7'-dihydro-3H-spiro[benzofuran-2,5'-indazole]-3,4'(2'H)-dione 113 solid, yield 8%; $^1$H NMR (CDCl$_3$, 300 MHz, δ, ppm): 7.5-7.3 (m, 4H), 6.09 (s, 1H), 4.0 (s, 3H), 3.93 (s, 3H), 3.83 (s, 3H), 3.62-3.50 (m, 1H), 3.12-2.98 (m, 2H), 1.15 (d, 3H); LCMS (ES, m/z): 487.00 [M+H]$^+$ (2S,6'R)-7-chloro-3'-(4-chlorophenyl)-4,6-dimethoxy-2',6'-dimethyl-6',7'-dihydro-3H-spiro[benzofuran-2,5'-indazole]-3,4'(2'H)-dione 114 yellow solid, yield 56%; $^1$H NMR (CDCl$_3$, 400 MHz, δ, ppm): 0.5-7.4 (m, 4H), 6.1 (s, 1H), 4.03 (s, 3H), 3.93 (s, 3H), 3.83 (s, 3H), 3.60-3.50 (m, 1H), 3.08-3.0 (m, 2H), 1.15 (d, 3H); LCMS (ES, m/z): 486.95 [M+H]$^+$ (2S,6'R)-7-chloro-3'-(2-chlorophenyl)-4,6-dimethoxy-2',6'-dimethyl-6',7'-dihydro-3H-spiro[benzofuran-2,5'-indazole]-3,4'(2'H)-dione 115 yellow oil, yield 9%; $^1$H NMR (CDCl$_3$, 400 MHz, δ, ppm): 7.6-7.3 (m, 4H), 6.1 (s split, 1H), 4.0 (s split, 3H), 3.95

(s split, 3H), 3.85 (s split, 3H), 3.65-3.5 (m, 1H), 3.1-3.0 (m, 2H), 1.2-1.1 (d split, 3H); LCMS (ES, m/z): 486.80 [M+H]$^+$ tert-butyl 4-((2S,6'R)-7-chloro-4,6-dimethoxy-2',6'-dimethyl-3',4'-dioxo-2',4',6',7'-tetrahydro-3H-spiro[benzofuran-2,5'-indazole]-3'-yl)piperidine-1-carboxylate 116 white solid, yield 26%; $^1$H NMR (CDCl$_3$, 400 MHz, δ, ppm): 6.12 (s, 1H), 4.30-4.15 (m, 2H), 4.04 (s, 3H), 3.95 (s, 3H), 3.91 (s, 3H), 3.5-3.4 (m, 1H), 3.22-3.15 (m, 1H), 3.0-2.9 (m, 2H), 2.76-2.65 (m, 2H), 2.23-2.05 (m, 2H), 1.65-1.55 (m, 2H), 1.46 (s, 9H), 1.12 (d, 3H); LCMS (ES, m/z): 582.00 [M+Na]$^+$ (2S,6'R)-7-chloro-3'-(2-fluorophenyl)-4,6-dimethoxy-2',6'-dimethyl-6',7'-dihydro-3H-spiro[benzofuran-2,5'-indazole]-3,4'(2'H)-dione 117 white solid, yield 4%; $^1$H NMR (CDCl$_3$, 400 MHz, δ, ppm): 7.6-7.35 (m, 2H), 7.3-7.15 (m, 2H), 6.08 (s, 1H), 4.0 (s, 3H), 3.94 (s, 3H), 3.80 (s, 3H), 3.62-3.53 (m, 1H), 3.08-3.0 (m, 2H), 1.16 (d, 3H); LCMS (ES, m/z): 471.10 [M+H]$^+$ (2S,6'R)-7-chloro-3'-(3-fluorophenyl)-4,6-dimethoxy-2',6'-dimethyl-6',7'-dihydro-3H-spiro[benzofuran-2,5'-indazole]-3,4'(2'H)-dione 118 yield 4%; $^1$H NMR (CDCl$_3$, 400 MHz, δ, ppm): 7.45-7.40 (m, 1H), 7.25-7.12 (m, 3H), 6.09 (s, 1H), 4.0 (s, 3H), 3.93 (s, 3H), 3.83 (s, 3H), 3.62-3.53 (m, 1H), 3.08-3.0 (m, 2H), 1.16 (d, 3H); LCMS (ES, m/z): 470.90 [M+H]$^+$ (2S,6'R)-7-chloro-3'-(4-fluorophenyl)-4,6-dimethoxy-2',6'-dimethyl-6',7'-dihydro-3H-spiro[benzofuran-2,5'-indazole]-3,4'(2'H)-dione 119 pale yellow solid, yield 19%; $^1$H NMR (CDCl$_3$, 300 MHz, δ, ppm): 7.5-7.4 (m, 2H), 7.2-7.1 (m, 2H), 6.08 (s, 1H), 4.0 (s, 3H), 3.93 (s, 3H), 3.83 (s, 3H), 3.65-3.5 (m, 1H), 3.1-3.0 (m, 2H), 1.16 (d, 3H); LCMS (ES, m/z): 470.90 [M+H]$^+$ (2S,6'R)-7-chloro-4,6-dimethoxy-2',6'-dimethyl-3'-(tetrahydro-2H-pyran-4-yl)-6',7'-dihydro-3H-spiro[benzofuran-2,5'-indazole]-3,4'(2'H)-dione 120 solid, yield 12%; $^1$H NMR (CDCl$_3$, 300 MHz, δ, ppm): 6.12 (s, 1H), 4.1-3.9 (m, 2H), 4.0 (s, 3H), 3.94 (s, 3H), 3.92 (s, 3H), 3.5-3.3 (m, 4H), 3.0-2.9 (m, 2H), 2.5-2.2 (m, 2H), 1.55-1.55 (m, 2H), 1.16 (d, 3H); LCMS (ES, m/z): 461.15 [M+H]$^+$ (2S,6'R)-7-chloro-4,6-dimethoxy-2',6'-dimethyl-3'-(4-methylthiazol-2-yl)-6',7'-dihydro-3H-spiro[benzofuran-2,5'-indazole]-3,4'(2'H)-dione 121 pale yellow solid, yield 31%; $^1$H NMR (DMSO-d6, 300 MHz, δ, ppm): 7.62 (s, 1H), 6.50 (s, 1H), 4.20 (s, 3H), 4.05 (s, 3H), 4.02 (s, 3H), 3.25-3.15 (m, 1H), 3.1-2.95 (m, 2H), 2.50 (s, 3H), 0.97 (d, 3H); LCMS (ES, m/z): 474.05 [M+H]$^+$ (2S,6'R)-7-chloro-4,6-dimethoxy-2',6'-dimethyl-3'-(2-methylthiazol-4-yl)-6',7'-dihydro-3H-spiro[benzofuran-2,5'-indazole]-3,4'(2'H)-dione 122 beige solid, yield 21%; $^1$H NMR (CDCl$_3$, 400 MHz, δ, ppm): 8.57 (s, 1H), 6.11 (s, 1H), 4.23 (s, 3H), 4.03 (s, 3H), 3.94 (s, 3H), 3.57-3.49 (m, 1H), 3.1-3.0 (m, 2H), 2.76 (s, 3H), 1.16 (d, 3H); LCMS (ES, m/z): 473.80 [M+H]$^+$ (2S,6'R)-7-chloro-4,6-dimethoxy-2',6'-dimethyl-3'-((S)-tetrahydrofuran-3-yl)-6',7'-dihydro-3H-spiro[benzofuran-2,5'-indazole]-3,4'(2'H)-dione and (2 S,6'R)-7-chloro-4,6-dimethoxy-2',6'-dimethyl-3'-((R)-tetrahydrofuran-3-yl)-6',7'-dihydro-3H-spiro[benzofuran-2,5'-indazole]-3,4'(2'H)-dione 123 beige solid; $^1$H NMR (CDCl$_3$, 400 MHz, δ, ppm): 6.12 (s, 1H), 4.25-4.2 (m, 1H), 4.05 (s, 3H), 4.05-3.75 (2×s+m, 10H), 3.5-3.4 (m, 1H), 3.05-2.9 (m, 2H), 2.25-2.15 (m, 2H), 1.10 (d, 3H); LCMS (ES, m/z): 446.95 [M+H]$^+$ 124 second diastereomer, beige solid, yield 1%; $^1$H NMR (CDCl$_3$, 300 MHz, δ, ppm): 6.12 (s, 1H), 4.3-4.2 (m, 1H), 4.03 (s, 3H), 4.0-3.75 (2×s+m, 10H), 3.5-3.4 (m, 1H), 3.05-2.95 (m, 2H), 2.45-2.15 (dm, 2H), 1.15 (d, 3H); LCMS (ES, m/z): 447.00 [M+H]$^+$ (2S,6'R)-7-chloro-4,6-dimethoxy-2',6'-dimethyl-3'-(piperidin-4-yl)-6',7'-dihydro-3H-spiro[benzofuran-2,5'-indazole]-3,4'(2'H)-dione 125 $^1$H NMR (CDCl$_3$+D$_2$O, 400 MHz, δ, ppm): 6.14 (s, 1H), 4.05 (s, 3H), 3.95 (2×s, 6H), 3.35-3.3 (m, 4H), 3.1-2.9 (m, 4H), 2.7-2.35 (m, 2H), 1.9-1.7 (m, 2H), 1.12 (d, 3H); LCMS (ES, m/z): 460.00 [M+H]$^+$ (2S,3'R,6'R)-7-chloro-3'-(2-chlorophenyl)-4,6-dimethoxy-2',6'-dimethyl-6',7'-dihydro-3H-spiro[benzofuran-2,5'-indazole]-3,4'(2'H)-dione and (2S,3'S,6'R)-7-chloro-3'-(2-chlorophenyl)-4,6-dimethoxy-2',6'-dimethyl-6',7'-dihydro-3H-spiro[benzofuran-2,5'-indazole]-3,4'(2'H)-dione 126 orange solid, yield 20.3%; $^1$H NMR (CDCl$_3$, 400 MHz, δ, ppm): 1.14 (d, 3H, J=6.4 Hz), 2.98-3.05 (m, 2H), 3.57 (dd, 1H, J=17.5, 13.8 Hz), 3.72 (s, 3H), 3.90 (s, 3H), 3.97 (s, 3H), 6.04 (s, 1H), 7.33-7.46 (m, 4H); LCMS (ES, m/z): 487.03 [M+H]$^+$ 127 orange solid, yield 2.7%; $^1$H NMR (CDCl$_3$, 400 MHz, δ, ppm): 1.13 (d, 3H, J=6.3 Hz), 3.00-3.06 (m, 2H), 3.55 (m, 1H), 3.71 (s, 3H), 3.92 (s, 3H), 3.98 (s, 3H), 6.06 (s, 1H), 7.28-7.47 (m, 4H); LCMS (ES, m/z): 486.9 [M+H]$^+$ (2 S,6'R)-7-chloro-3'-(2,6-dichlorophenyl)-4,6-dimethoxy-2',6'-dimethyl-6',7'-dihydro-3H-spiro[benzofuran-2,5'-indazole]-3,4'(2'H)-dione 128 white solid, yield 5%; $^1$H (CDCl$_3$, 400 MHz, δ, ppm): 1.13 (d, 3H, J=5.2 Hz), 3.03 (m, 2H), 3.57 (m, 2H), 3.71 (s, 3H), 3.91 (s, 3H), 3.97 (s, 3H), 6.06 (s, 1H), 7.32-7.41 (m, 3H); LCMS (ES, m/z): 521.0 [M+H]$^+$ (2S,3'R,6'R)-7-chloro-3'-(2-bromophenyl)-4,6-dimethoxy-2',6'-dimethyl-6',7'-dihydro-3H-spiro[benzofuran-2,5'-indazole]-3,4'(2'H)-dione and (2S,3'S,6'R)-7-chloro-3'-(2-bromophenyl)-4,6-dimethoxy-2',6'-dimethyl-6',7'-dihydro-3H-spiro[benzofuran-2,5'-indazole]-3,4'(2'H)-dione 129 orange solid, yield 17%; $^1$H (CDCl$_3$, 400 MHz, δ, ppm): 1.14 (d, 3H, J=6.1 Hz), 3.00-3.04 (m, 2H), 3.59 (dd, 1H, J=18.5, 13.9 Hz), 3.71 (s, 3H), 3.90 (s, 3H), 3.97 (s, 3H), 6.05 (s, 1H), 7.31 (–m, 2H), 7.39 (m, 1H), 7.63 (d, 1H, J=7.8 Hz); LCMS (ES, m/z): 532.8 [M+H]$^+$ 130 yellow solid, yield 11%; $^1$H (CDCl$_3$, 400 MHz, δ, ppm): 1.13 (d, 3H, J=6.0 Hz), 2.99-3.09 (m, 2H), 3.55 (dd, 1H, J=17.7, 13.7 Hz), 3.70 (s, 3H), 3.92 (s, 3H), 3.98 (s, 3H), 6.06 (s, 1H), 7.30-7.34 (m, 3H), 7.66 (d, 1H, J=7.7 Hz); LCMS (ES, m/z): 532.9 [M+H]$^+$

(2S,6'R)-7-chloro-4,6-dimethoxy-2',6'-dimethyl-3'-(o-tolyl)-6',7'-dihydro-3H-spiro[benzofuran-2,5'-indazole]-3,4'(2'H)-dione 131 orange solid, yield 18%; $^1$H (CDCl$_3$, 400 MHz, δ, ppm): 1.14 (m, 3H), 2.03-2.12 (s split, 3H), 3.00-3.05 (m, 2H), 3.55 (m, 1H), 3.64-3.67 (s split, 3H), 3.91 (s split, 3H), 3.98 (s, 3H), 6.06 (s split, 1H), 7.11-7.34 (m, 4H); LCMS (ES, m/z): 466.9 [M+H]$^+$

(2S,6'R)-7-chloro-3'-(2,6-dimethylphenyl)-4,6-dimethoxy-2',6'-dimethyl-6',7'-dihydro-3H-spiro[benzofuran-2,5'-indazole]-3,4'(2'H)-dione 132 orange solid, yield 28%; $^1$H (CDCl$_3$, 400 MHz, δ, ppm): 1.13 (d, 3H, J=6.4 Hz), 1.92 (s, 3H), 2.02 (s, 3H), 3.00-3.06 (m, 2H), 3.54 (dd, 1H, J=17.6, 13.8 Hz), 3.59 (s, 3H), 3.90 (s, 3H), 3.97 (s, 3H), 6.05 (s, 1H), 7.04–d, 1H, J=7.6 Hz), 7.08 (d, 1H, J=7.6 Hz), 7.21 (t, 1H, J=7.6 Hz); LCMS (ES, m/z): 481.0 [M+H]$^+$

(2S,3'S,6'R)-3'-(2-bromophenyl)-7-chloro-2'-(tert-butyl)-4,6-dimethoxy-6'-methyl-6',7'-dihydro-3H-spiro[benzofuran-2,5'-indazole]-3,4'(2'H)-dione and

(2S,3'R,6'R)-3'-(2-bromophenyl)-7-chloro-2'-(tert-butyl)-4,6-dimethoxy-6'-methyl-6',7'-dihydro-3H-spiro[benzofuran-2,5'-indazole]-3,4'(2'H)-dione 133 orange solid, yield 15%; $^1$H (CDCl$_3$, 400 MHz, δ, ppm): 1.11 (d, 3H, J=6.4 Hz), 2.93-3.03 (m, 2H), 3.54 (td, 1H, J=14.1, 2.7 Hz), 3.89 (s, 3H), 3.96 (s, 3H), 6.04 (s, 1H), 7.22-7.27 (m, 2H), 7.32-7.36 (m, 1H), 7.56 (d, 1H, J=8.1 Hz); LCMS (ES, m/z): 575.2 [M+H]$^+$ 134 orange solid, yield 6%; $^1$H (CDCl$_3$, 400 MHz, δ, ppm): 1.11 (d, 3H, J=6.4 Hz), 1.49 (s, 9H), 3.01-3.07 (m, 2H), 3.51 (dd, 1H, J=17.5, 13.7 Hz), 3.89 (s, 3H), 3.96 (s, 3H), 6.03 (s, 1H), 7.21-7.30 (m, 3H), 7.60 (m, 1H); LCMS (ES, m/z): 575.2 [M+H]$^+$

(2S,3'S,6'R)-7-chloro-4,6-dimethoxy-2',6'-dimethyl-3'-(2-(trifluoromethyl)phenyl)-6',7'-dihydro-3H-spiro[benzofuran-2,5'-indazole]-3,4'(2'H)-dione and

(2S,3'R,6'R)-7-chloro-4,6-dimethoxy-2',6'-dimethyl-3'-(2-(trifluoromethyl)phenyl)-6',7'-dihydro-3H-spiro[benzofuran-2,5'-indazole]-3,4'(2'H)-dione 135 orange solid, yield 11%; $^1$H (CDCl$_3$, 400 MHz, δ, ppm): 1.13 (d, 3H, J=6.4 Hz), 2.95-3.04 (m, 2H), 3.54-3.60 (m, 1H), 3.62 (s, 3H), 3.90 (s, 3H), 3.96 (s, 3H), 6.04 (s, 1H), 7.32 (d, 1H, J=7.5 Hz), 7.56-7.66 (m, 2H), 7.74 (7.5 Hz); LCMS (ES, m/z): 521.1 [M+H]$^+$ 136 orange solid, yield 3%; $^1$H (CDCl$_3$, 400 MHz, δ, ppm): 1.13 (d, 3H, J=5.1 Hz), 3.02-3.08 (m, 2H), 3.54 (dd, 1H, J=17.4, 14.4 Hz), 3.61 (s, 3H), 3.91 (s, 3H), 3.97 (s, 3H), 6.05 (s, 1H), 7.29 (m, 1H), 7.58 (m, 2H), 7.80 (m, 1H); LCMS (ES, m/z): 521.1 [M+H]$^+$

(2S,3'S,6'R)-7-chloro-3'-(2-iodophenyl)-4,6-dimethoxy-2',6'-dimethyl-6',7'-dihydro-3H-spiro[benzofuran-2,5'-indazole]-3,4'(2'H)-dione and

(2S,3'R,6'R)-7-chloro-3'-(2-iodophenyl)-4,6-dimethoxy-2',6'-dimethyl-6',7'-dihydro-3H-spiro[benzofuran-2,5'-indazole]-3,4'(2'H)-dione 137 orange solid, yield 9%; $^1$H (CDCl$_3$, 400 MHz, δ, ppm): 1.14 (d, 3H, J=6.4 Hz), 2.96-3.05 (m, 2H), 3.57 (dd, 1H, J=17.8, 13.9 Hz), 3.68 (s, 3H), 3.90 (s, 3H), 3.97 (s, 3H), 6.05 (s, 1H), 7.12 (td, 1H, J=7.8, 1.6 Hz), 7.25 (dd, 1H, J=7.6, 1.6 Hz), 7.42 (td, 1H, J=7.6, 1.1 Hz), 7.88 (d, 1H, J=8.0 Hz); LCMS (ES, m/z): 579.2 [M+H]$^+$ 138 beige solid, yield 10%; $^1$H (CDCl$_3$, 400 MHz, δ, ppm): 1.13 (d, 3H, J=6.4 Hz), 3.01-3.08 (m, 2H), 3.55 (dd, 1H, J=17.5, 13.7 Hz), 3.67 (s, 3H), 3.92 (s, 3H), 3.97 (s, 3H), 6.06 (s, 1H), 7.12 (td, 1H, J=7.8, 1.6 Hz), 7.21 (dd, 1H, J=7.6, 1.6 Hz), 7.37 (t, 1H, J=7.6 Hz), 7.91 (d, 1H, J=7.9 Hz); LCMS (ES, m/z): 579.2 [M+H]$^+$

(2S,3'S,6'R)-3'-(2-bromophenyl)-7-chloro-2'-isopropyl-4,6-dimethoxy-6'-methyl-6',7'-dihydro-3H-spiro[benzofuran-2,5'-indazole]-3,4'(2'H)-dione and

(2S,3'R,6'R)-3'-(2-bromophenyl)-7-chloro-2'-isopropyl-4,6-dimethoxy-6'-methyl-6',7'-dihydro-3H-spiro[benzofuran-2,5'-indazole]-3,4'(2'H)-dione 139 beige solid, yield 20%; $^1$H (CDCl$_3$, 400 MHz, δ, ppm): 1.13 (d, 3H, J=6.4 Hz), 1.43 (d, 3H, J=6.6 Hz), 1.52 (d, 3H, J=6.6 Hz), 2.97-3.07 (m, 2H), 3.58 (dd, 1H, J=15.5, 11.7 Hz), 3.90 (s, 3H), 3.97 (s, 3H), 4.18 (sept., 1H, J=6.6 Hz), 6.05 (s, 1H), 7.24 (dd, 1H, J=7.6, 1.7 Hz), 7.29 (td, 1H, J=7.8, 1.7 Hz), 7.38 (t, 1H, J=7.4 Hz), 7.62 (d, 1H, J=7.8 Hz); LCMS (ES, m/z): 561.1 [M+H]$^+$ 140 orange solid, yield 12%; $^1$H (CDCl$_3$, 400 MHz, δ, ppm): 1.13 (d, 3H, J=6.4 Hz), 1.37 (d, 3H, J=6.6 Hz), 1.56 (d, 3H, J=6.6 Hz), 3.04-3.10 (m, 2H), 3.56 (dd, 1H, J=17.6, 13.7 Hz), 3.91 (s, 3H), 3.87 (s, 3H), 4.15 (sept., 1H, J=6.6 Hz), 6.05 (s, 1H), 7.20 (dd, 1H, J=7.3, 2.0 Hz), 7.28-7.35 (m, 2H), 7.66 (dd, 1H, J=7.9, 1.3 Hz); LCMS (ES, m/z): 561.2 [M+H]$^+$

(2S,3'S,6'R)-3'-(2-bromophenyl)-7-chloro-2'-cyclohexyl-4,6-dimethoxy-6'-methyl-6',7'-dihydro-3H-spiro[benzofuran-2,5'-indazole]-3,4'(2'H)-dione and

(2 S,3'R,6'R)-3'-(2-bromophenyl)-7-chloro-2'-cyclohexyl-4,6-dimethoxy-6'-methyl-6',7'-dihydro-3H-spiro[benzofuran-2,5'-indazole]-3,4'(2'H)-dione 141 orange solid, yield 16%; $^1$H (CDCl$_3$, 400 MHz, δ, ppm): 1.13 (d, 3H, J=6.5 Hz), 1.20 (m, 2H), 1.64 (m, 1H), 1.81-1.87 (m, 3H), 1.97-2.06 (m, 3H), 2.96-3.06 (m, 2H), 3.57 (m, 1H), 3.77 (m, 1H), 3.97 (s, 3H), 3.90 (s, 3H), 6.05 (s, 1H), 7.22 (dd, 1H, J=7.5, 1.7 Hz), 7.29 (td, 1H, J=7.7, 1.7 Hz), 7.38 (td, 1H, J=7.5, 1.2 Hz), 7.63 (1H, dd, J=8.0, 1.0 Hz); LCMS (ES, m/z): 601.2 [M+H]$^+$ 142 orange solid, yield 16%; $^1$H (CDCl$_3$, 400 MHz, δ, ppm): 1.13 (d, 3H, J=6.4 Hz), 1.56 (m, 1H), 1.19-1.23 (m, 2H), 1.63 (m, 1H), 1.73-1.93 (m, 5H), 2.10 (m, 2H), 3.02-3.09 (m, 2H), 3.56 (dd, 1H, J=17.5, 13.7 Hz), 3.70 (m, 1H), 3.90 (s, 3H), 3.97 (s, 3H), 6.05 (s, 1H), 7.19 (dd, 1H, J=7.2, 2.0 Hz), 7.27-7.36 (m, 2H), 7.66 (dd, 1H, J=7.8, 1.4 Hz); LCMS (ES, m/z): 601.2 [M+H]$^+$ Method C:

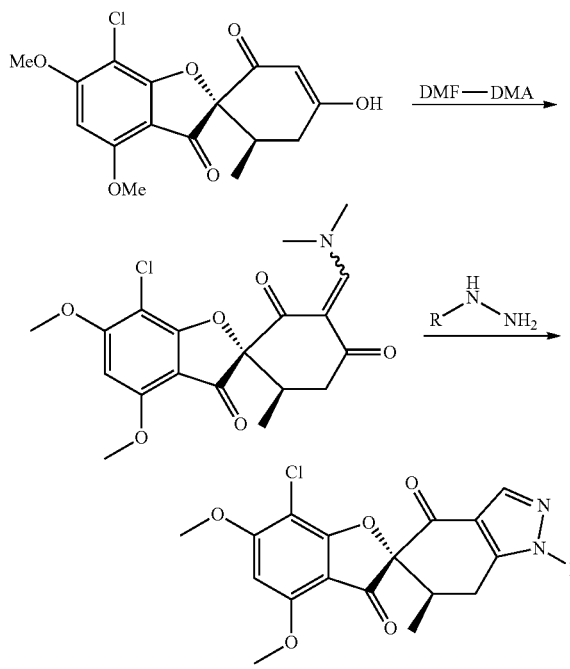

Example: R=Me

In a 250 mL round-bottomed flask containing 17 g (50.2 mmol, 1.0 eq.) of griseofulvic acid and 51 mL of DMF were added 16.80 mL (125 mmol, 2.5 eq.) of DMF-DMA at ambient temperature. A yellow suspension was first obtained then clear yellow. After an agitation time of 1 h 30 at ambient temperature the formation of the product was completed. The solution was concentrated in a rotary evaporator and 90 mL of $CH_2Cl_2$ were added to the crude product. 4 washings were performed with 50 mL of brine. The organic phase was then dried over $MgSO_4$, filtered and concentrated under reduced pressure. A yellow foam (m=20 g) was obtained with a yield of 100%.

In a 100 mL round-bottomed flask 0.97 mL (10.2 mmol, 4 eq.) of $H_2SO_4$ and 0.2 mL (3.8 mmol, 1.5 eq.) of methylhydrazine were added to a solution of the product previously obtained (1 g, 2.5 mmol, 1.0 eq.) in 25 mL EtOH. The mixture was left under agitation at 50° C. for 2 h, cooled to ambient temperature and concentrated under reduced pressure. The residue was diluted in 30 mL of ethyl acetate then washed with 2×50 mL 0.1 NHCl. The organic phase was dried over sodium sulfate, filtered and concentrated under reduced pressure. The residue was purified by chromatography on silica gel ($CH_2Cl_2$/AcOEt 80:20). A white solid (m=0.72 g) was obtained with a yield of 75%.

(2S,4'S,6'R)-7-chloro-4'-hydroxy-4,6-dimethoxy-1',6'-dimethyl-1',4',6',7'-tetrahydro-3H-spiro[benzofuran-2,5'-indazol]-3-one R=Me 143 $^1$H NMR ($CD_3CN$, 400 MHz, δ, ppm): 1.06 (d, 3H, J=6.8 Hz), 2.98 (m, 1H), 3.07 (dd, 1H, J=16.7, 5.8 Hz), 3.22 (dd, 1H, J=16.7, 11.8 Hz), 3.83 (s, 3H), 3.93 (s, 3H), 4.05 (s, 3H), 6.36 (s, 1H), 7.78 (s, 1H); LCMS (ES, m/z): 377.083 [M+H]$^+$ (2S,4'S,6'R)-7-chloro-4'-hydroxy-4,6-dimethoxy-6'-methyl-1'-phenyl-1',4',6',7'-tetrahydro-3H-spiro[benzofuran-2,5'-indazol]-3-one R=Ph 144 beige solid, yield 57%; $^1$H NMR ($CDCl_3$, 400 MHz, δ, ppm): 8.09 (s, 1H), 7.56 (m, 4H), 7.47 (m, 1H), 6.14 (s, 1H), 4.05 (s, 3H), 3.97 (s, 3H), 3.70 (dd, 1H, J=16.0, 11.2 Hz), 3.04 (m, 1H), 2.97 (dd, 1H, J=16.0, 5.4 Hz), 1.13 (d, 3H, J=6.5 Hz); LCMS (ES, m/z): 439.098 [M+H]$^+$ 1.15. Formation of Sulfones at 2'

Method A

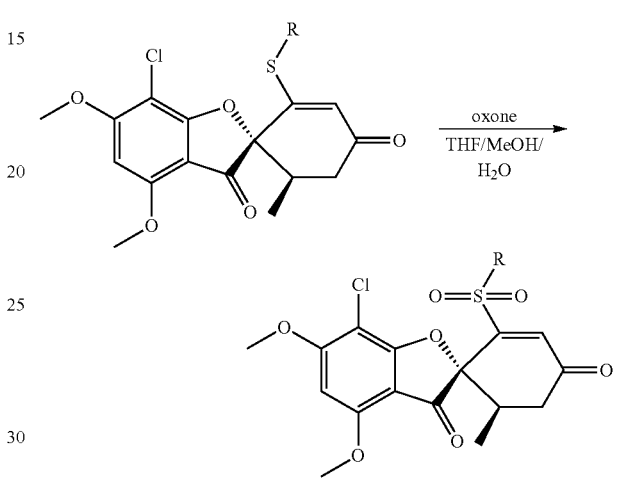

Example: R=Bn

Synthesis of the Sulfide:

In a 100 mL round-bottomed flask, thiol (RSH) (5.6 mmol, 2 eq.) was added to a 1 g solution of (1'R,6'R)-2',7-dichloro-4,6-dimethoxy-6'-methyl-3H-spiro[benzofuran-2,1'-cyclohex[2]ene]-3,4'-dione (1 g, 2.8 mmol, 1 eq.) and 1.05 mL of 1,8-diazabicyclo[5.4.0]undec-7-ene (7.0 mmol, 2.5 eq.) dissolved in 10 mL of 1,4-dioxane. The mixture was brought to 100° C. for 16 h. The reaction mixture was then cooled to ambient temperature and diluted in water and dichloromethane. The organic phase was washed with saturated $NaHCO_3$ solution, dried over $MgSO_4$, filtered and concentrated under reduced pressure. The residue was purified by chromatography on silica gel (eluting with dichloromethane/methanol).

Synthesis of Sulfone:

In a 250 ml round-bottomed flask, 4.6 g of oxone monopersulfate (13.0 mmol) dissolved in 46 ml of water were added to a solution of the sulfide (768 mg, 1.7 mmol) in 15 mL of methanol (15 mL) and 15 mL of THF. The reaction mixture was left under agitation at ambient temperature for 16 h. The solids were filtered and rinsed with methanol. The filtrate was concentrated under reduced pressure then diluted in AcOEt and water. The aqueous phase was extracted with AcOEt. The organic phases were combined, dried over $MgSO_4$, filtered and concentrated under reduced pressure. The residue was purified by chromatography on silica gel ($CH_2Cl_2$/AcOEt 98:2). A beige solid (0.26 g) was obtained with a yield of 32%.

Method B:

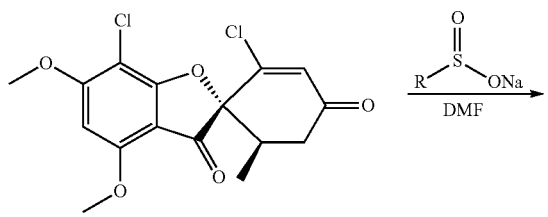

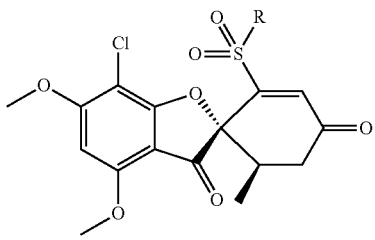

Example R=Ph (70504)

In a 50 mL round-bottomed flask, 46 mg (0.28 mmol, 1 eq.) of sodium benzenesulfinate were added to a solution of 100 mg of (1'R,6'R)-2',7-dichloro-4,6-dimethoxy-6'-methyl-3H-spiro[benzofuran-2,1'-cyclohex[2]ene]-3,4'-dione (0.28 mmol, 1 eq.) in 1 mL of DMF. The mixture was left under agitation at ambient temperature for 16 h. Water was added to the reaction medium and the precipitate obtained was filtered, rinsed with water and dried under reduced pressure. A white solid was obtained with a yield of 86%.

(1'R,6'R)-2'-(benzylsulfonyl)-7-chloro-4,6-dimethoxy-6'-methyl-3H-spiro[benzofuran-2,1'-cyclohex[2]ene]-3,4'-dione 145 $^1$H NMR (CDCl$_3$, 400 MHz, δ, ppm): 0.96 (d, 3H, J=6.8 Hz), 2.39 (dd, 1H, J=17.6, 4.8 Hz), 2.74 (m, 1H), 3.07 (dd, 1H, J=17.6, 14.0 Hz), 3.99 (s, 3H), 4.06 (s, 3H), 4.49 (d, 1H, J=13.6 Hz), 4.69 (d, 1H, J=13.6 Hz), 6.19 (s, 1H), 6.52 (s, 1H), 7.37 (m, 3H), 7.49 (m, 2H); LCMS (ES, m/z): 477.07 [M+H]$^+$ (1'R,6'R)-7-chloro-2'-(2-(dimethylamino)ethylsulfonyl)-4,6-dimethoxy-6'-methyl-3H-spiro[benzofuran-2,1'-cyclohex[2]ene]-3,4'-dione 146 pale yellow solid, yield 11%; 1H NMR (CDCl$_3$, 400 MHz, δ, ppm): 0.95 (d, 3H, J=6.8 Hz), 2.27 (s, 6H), 2.50 (dd, 1H, J=17.6, 4.8 Hz), 2.66 (dt, 1H, J=13.2, 5.2 Hz), 2.87 (m, 2H), 3.18 (m, 2H), 3.77 (ddd, 1H, J=14.4, 8.8, 6.0 Hz), 3.98 (s, 3H), 4.03 (s, 3H), 6.16 (s, 1H), 6.88 (s, 1H); LCMS (ES, m/z): 458.096 [M+H]$^+$ (1'R,6'R)-7-chloro-4,6-dimethoxy-6'-methyl-2'-(phenylsulfonyl)-3H-spiro[benzofuran-2,1'-cyclohex[2]ene]-3,4'-dione 147 pale yellow solid, yield 13%; $^1$H NMR (CDCl$_3$, 400 MHz, δ, ppm): 0.83 (d, 1H, J=6.8 Hz), 2.44 (dd, 1H, J=17.2, 4.8 Hz), 2.77 (m, 1H), 3.11 (dd, 1H, J=17.2, 14.0 Hz), 4.00 (s, 3H), 4.05 (s, 3H), 6.18 (s, 1H), 7.11 (s, 1H), 7.54 (t, 2H, J=7.6 Hz), 7.65 (t, 1H, J=7.6 Hz), 7.83 (d, 2H, J=7.2 Hz); LCMS (ES, m/z): 463.054 [M+H]$^+$ (1'R,6'R)-7-chloro-4,6-dimethoxy-6'-methyl-2'-(methylsulfonyl)-3H-spiro[benzofuran-2,1'-cyclohex[2]ene]-3,4'-dione 148 pale yellow solid, yield 12%; $^1$H NMR (CDCl$_3$, 400 MHz, δ, ppm): 0.97 (d, 3H, J=6.8 Hz), 2.52 (dd, 1H, J=17.2, 4.4 Hz), 2.94 (m, 1H), 3.17 (dd, 1H, J=17.2, 14.0 Hz), 3.22 (s, 3H), 3.98 (s, 3H), 4.03 (s, 3H), 6.16 (s, 1H), 6.98 (s, 1H); LCMS (ES, m/z): 401.038 [M+H]$^+$ 1.16. Synthesis of Pyridines and Dihydropyridines at 2' and 4'

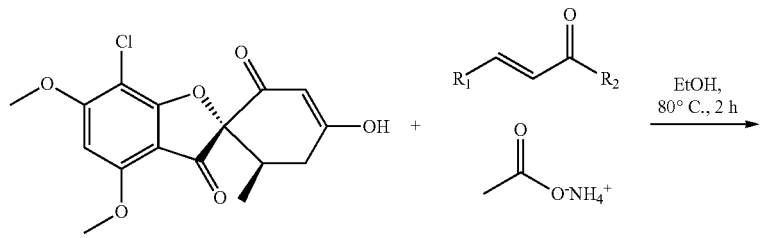

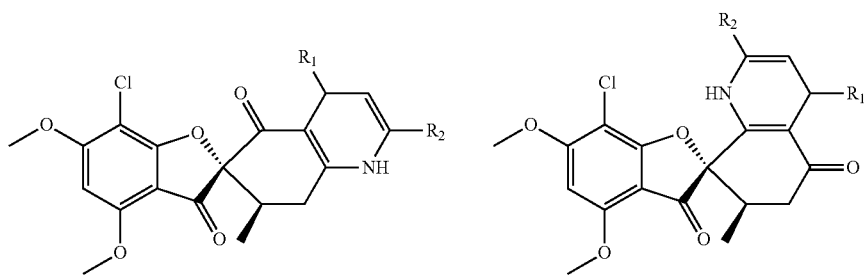

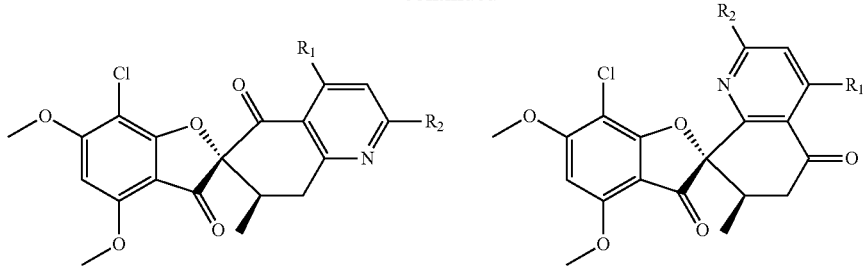

Example: R₁=Ph, R₂=CO₂Me

In a 25 ml round-bottomed flask, a mixture was formed of (1'S,6'R)-7-chloro-4'-hydroxy-4,6-dimethoxy-6'-methyl-3H-spiro[benzofuran-2,1'-cyclohex[3]ene]-2',3-dione (1 g, 2.95 mmol), methyl (E)-2-oxo-4-phenylbut-3-enoate (Chen, Y.-J. and coll. *J. Org. Chem.*, 2006, 71, 6592) (0.67 g, 3.5 mmol) and ammonium acetate (0.34 g, 4.4 mmol) in ethanol (10 mL). The mixture was heated to 80° C. for 2 hours then concentrated under reduced pressure. The residue was purified by chromatography on silica gel. No more than 3 isomers were isolated with yields of 1% to 13%. The mixture fractions were combined and used in the following oxidation step.

In a 250 mL round-bottomed flask, a solution of CAN (12.2 g, 22.3 mmol) in water (11.3 mL) was added dropwise to a mixture of the isomers obtained previously (4.5 g, 8.9 mmol) dissolved in acetone (30 mL) under agitation at 0° C. The reaction mixture was left under agitation at 0° C. for 3 h then concentrated under reduced pressure. The residue was dissolved in ethyl acetate and water. The aqueous phase was extracted with 3×50 mL AcOEt. The organic phases were combined, washed with saturated NaHCO₃ solution then with brine solution, dried over MgSO₄, filtered and concentrated under reduced pressure. The residue was purified by chromatography on silica gel. The 2 isomers were obtained with yields of 7% to 22%.

(2S,4'R,7'R)-methyl 7-chloro-4,6-dimethoxy-7'-methyl-3,5'-dioxo-4'-phenyl-4',5',7',8'-tetrahydro-1'H,3H-spiro[benzofuran-2,6'-quinoline]-2'-carboxylate
and
(2S,4'S,7'R)-methyl 7-chloro-4,6-dimethoxy-7'-methyl-3,5'-dioxo-4'-phenyl-4',5',7',8'-tetrahydro-1'H,3H-spiro[benzofuran-2,6'-quinoline]-2'-carboxylate 149 yellow solid, yield 12%; ¹H NMR (CDCl₃, 400 MHz, δ, ppm): 0.95 (d, 3H, J=6.4 Hz), 2.25 (dd, 1H, J=16.4, 5.2 Hz), 2.83 (m, 1H), 3.43 (dd, 1H, J=16.0, 12.4 Hz), 3.55 (s, 3H), 3.71 (s, 3H), 3.87 (s, 3H), 4.65 (d, 1H, J=5.2 Hz), 5.85 (s, 1H), 6.02 (d, 1H, J=5.2 Hz), 6.62 (s, 1H), 7.05 (m, 1H), 7.18 (m, 4H); LCMS (ES, m/z): 509.99 [M+H]⁺

150 yellow solid, yield 14%; ¹H NMR (CDCl₃, 400 MHz, δ, ppm): 0.96 (d, 3H, J=6.8 Hz), 2.46 (dd, 1H, J=17.2, 5.6 Hz), 2.81 (m, 1H), 3.26 (dd, 1H, J=17.2, 12.4 Hz), 3.75 (s, 3H), 3.84 (s, 3H), 3.90 (s, 3H), 4.51 (d, 1H, J=5.6 Hz), 5.98 (s, 1H), 6.08 (d, 1H, J=5.6 Hz), 6.66 (s, 1H), 7.10 (m, 1H), 7.18 (m, 4H); LCMS (ES, m/z): 510.00 [M+H]⁺

(2S,7'R)-methyl 7-chloro-4,6-dimethoxy-7'-methyl-3,5'-dioxo-4'-phenyl-4',5',6',7'-tetrahydro-1'H,3H-spiro[benzofuran-2,8'-quinoline]-2'-carboxylate 151 beige solid, yield 1%; ¹H NMR (CDCl₃, 400 MHz, δ, ppm): 0.86 (d, 1H, J=5.6 Hz), 2.32 (d, 1H, J=12.8 Hz), 2.89 (m, 2H), 3.66 (s, 3H), 3.95 (s, 3H), 3.99 (s, 3H), 4.76 (d, 1H, J=5.6 Hz), 6.04 (d, 1H, J=5.6 Hz), 6.13 (s, 1H), 6.52 (s, 1H), 7.09 (m, 1H), 7.22 (m, 4H); LCMS (ES, m/z): 509.99 [M+H]⁺

(2S,7'R)-methyl 7-chloro-4,6-dimethoxy-7'-methyl-3,5'-dioxo-4'-phenyl-7',8'-dihydro-3H,5'H-spiro[benzofuran-2,6'-quinoline]-2'-carboxylate 152 yellow solid, yield 22%; ¹H NMR (CDCl₃, 400 MHz, δ, ppm): 1.15 (d, 3H, J=6.8 Hz), 3.05 (m, 1H), 3.50 (dd, 1H, J=18.0, 5.6 Hz), 3.94 (m, 4H), 3.99 (s, 3H), 4.04 (s, 3H), 6.09 (s, 1H), 7.17 (m, 2H), 7.35 (m, 3H), 7.93 (s, 1H); LCMS (ES, m/z): 507.98 [M+H]⁺

(2S,7'R)-methyl 7-chloro-4,6-dimethoxy-7'-methyl-3,5'-dioxo-4'-phenyl-6',7'-dihydro-3H,5'H-spiro[benzofuran-2,8'-quinoline]-2'-carboxylate 153 orange solid, yield 7%; ¹H NMR (CDCl₃, 400 MHz, δ, ppm): 1.13 (d, 3H, J=6.8 Hz), 2.71 (dd, 1H, J=16.8, 4.8 Hz), 3.04 (m, 1H), 4.49 (dd, 1H, J=16.8, 13.6 Hz), 3.87 (s, 3H), 3.96 (s, 3H), 4.06 (s, 3H), 6.18 (s, 1H), 7.26 (m, 2H), 7.43 (m, 3H), 7.95 (s, 1H); LCMS (ES, m/z): 508.01 [M+H]⁺

(2S,4'S,7'R)-methyl 7-chloro-4,6-dimethoxy-7'-methyl-4'-(naphthalen-2-yl)-3,5'-dioxo-4',5',7',8'-tetrahydro-1'H,3H-spiro[benzofuran-2,6'-quinoline]-2'-carboxylate and
(2S,4'R,7'R)-methyl 7-chloro-4,6-dimethoxy-7'-methyl-4'-(naphthalen-2-yl)-3,5'-dioxo-4',5',7',8'-tetrahydro-1'H,3H-spiro[benzofuran-2,6'-quinoline]-2'-carboxylate 154 yellow solid, yield 10%; ¹H NMR (CDCl₃, 400 MHz, δ, ppm): 1.03 (d, 3H, J=6.4 Hz), 2.57 (dd, 1H, J=17.2, 6.0 Hz), 2.88 (m, 1H), 3.36 (dd, 1H, J=17.2, 12.0 Hz), 3.82 (s, 3H), 3.92 (s, 3H), 3.96 (s, 3H), 4.75 (d, 1H, J=5.6 Hz), 6.05 (s, 1H), 6.20 (d, 1H, J=5.6 Hz), 6.81 (s, 1H), 7.41 (m, 3H), 7.65 (s, 1H), 7.73 (m, 3H); LCMS (ES, m/z): 560.0 [M+H]⁺

155 white solid, yield 13%; ¹H NMR (CDCl₃, 400 MHz, δ, ppm): 1.01 (d, 3H, J=6.4 Hz), 2.35 (dd, 1H, J=16.0, 4.8 Hz), 2.92 (m, 1H), 3.45 (s, 3H), 3.54 (dd, 1H, J=16.4, 12.8 Hz), 3.77 (s, 3H), 3.91 (s, 3H), 4.89 (d, 1H, J=5.2 Hz), 5.83 (s, 1H), 6.15 (d, 1H, J=4.4 Hz), 6.74 (s, 1H), 7.38 (m, 3H), 7.73 (m, 4H); LCMS (ES, m/z): 560.0 [M+H]⁺

(2S,7'R)-methyl 7-chloro-4,6-dimethoxy-7'-methyl-4'-(naphthalen-2-yl)-3,5'-dioxo-7',8'-dihydro-3H,5'H-spiro[benzofuran-2,6'-quinoline]-2'-carboxylate 156 yellow solid, yield 9%; ¹H NMR (CDCl₃, 400 MHz, δ, ppm): 1.17 (d, 3H, J=6.4 Hz), 3.08 (m, 1H), 3.54 (dd, 1H, J=18.0, 5.6 Hz), 3.96 (m, 7H), 4.05 (s, 3H), 6.07 (s, 1H), 7.22 (d, 1H, J=8.4 Hz), 7.47 (m, 2H), 7.71 (s, 1H), 7.81 (m, 3H), 8.02 (s, 1H); LCMS (ES, m/z): 558.0 [M+H]$^+$ (2S,7'R)-methyl 7-chloro-4,6-dimethoxy-7'-methyl-4'-(naphthalen-2-yl)-3,5'-dioxo-6',7'-dihydro-3H,5'H-spiro[benzofuran-2,8'-quinoline]-2'-carboxylate 157 yellow solid, yield 4%; $^1$H NMR (CDCl$_3$, 400 MHz, δ, ppm): 1.15 (d, 3H, J=6.8 Hz), 2.74 (dd, 1H, J=16.8, 4.8 Hz), 3.07 (m, 1H), 3.53 (dd, 1H, J=16.4, 13.2 Hz), 3.88 (s, 3H), 3.98 (s, 3H), 4.08 (s, 3H), 6.18 (s, 1H), 7.33 (dd, 1H, J=8.4, 1.6 Hz), 7.52 (m, 2H), 7.77 (s, 1H), 1.87 (m, 3H), 8.05 (s, 1H); LCMS (ES, m/z): 558.0 [M+H]$^+$ (2S,4'R,7'R)-methyl 4'-(biphenyl-4-yl)-7-chloro-4,6-dimethoxy-7'-methyl-3,5'-dioxo-4',5',7',8'-tetrahydro-1'H,3H-spiro[benzofuran-2,6'-quinoline]-2'-carboxylate and (2S,4'S,7'R)-methyl 4'-(biphenyl-4-yl)-7-chloro-4,6-dimethoxy-7'-methyl-3,5'-dioxo-4',5',7',8'-tetrahydro-1'H,3H-spiro[benzofuran-2,6'-quinoline]-2'-carboxylate 158 white solid, yield 13%; $^1$H NMR (CDCl$_3$, 400 MHz, δ, ppm): 1.05 (d, 3H, J=6.4 Hz), 2.35 (dd, 1H, J=16.0, 4.8 Hz), 2.94 (m, 1H), 3.54 (dd, 1H, J=16.0 Hz, 12.4 Hz), 3.78 (s, 3H), 3.79 (s, 3H), 3.94 (s, 3H), 4.79 (d, 1H, J=5.2 Hz), 5.97 (s, 1H), 6.14 (d, 1H, J=4.8 Hz), 6.68 (s, 1H), 7.29 (m, 3H), 7.38 (m, 2H), 7.50 (m, 4H); LCMS (ES, m/z): 586.0 [M+H]$^+$ 159 beige solid, yield 9%; $^1$H NMR (CDCl$_3$, 400 MHz, δ, ppm): 1.03 (d, 3H, J=6.4 Hz), 2.55 (dd, 1H, J=16.8, 5.6 Hz), 2.92 (m, 1H), 3.34 (dd, 1H, J=17.2, 12.0 Hz), 3.83 (s, 3H), 3.92 (s, 3H), 3.97 (s, 3H), 4.63 (d, 1H, J=5.6 Hz), 6.06 (s, 1H), 6.18 (d, 1H, J=5.6 Hz), 6.77 (s, 1H), 7.31 (m, 2H), 7.40 (m, 2H), 7.47 (m, 2H), 7.54 (m, 2H); LCMS (ES, m/z): 586.0 [M+H]$^+$ (2S,7'R)-methyl 4'-(biphenyl-4-yl)-7-chloro-4,6-dimethoxy-7'-methyl-3,5'-dioxo-6',7'-dihydro-3H,5'H-spiro[benzofuran-2,8'-quinoline]-2'-carboxylate 160 yellow solid, yield 20%; $^1$H NMR (CDCl$_3$, 400 MHz, δ, ppm): 1.15 (d, 3H, J=6.6 Hz), 2.75 (dd, 1H, J=16.7, 5.0 Hz), 3.06 (m, 1H), 3.52 (dd, 1H, J=16.7, 13.4 Hz), 3.88 (s, 3H), 3.96 (s, 3H), 4.07 (s, 3H), 6.18 (s, 1H), 7.36 (m, 3H), 7.45 (t, 2H, J=7.0 Hz), 7.66 (m, 4H), 7.89 (s, 1H); LCMS (ES, m/z): 584.2 [M+H]$^+$ (2S,7'R)-methyl 7-chloro-4'-(4-fluorophenyl)-4,6-dimethoxy-7'-methyl-3,5'-dioxo-4',5',7',8'-tetrahydro-1'H,3H-spiro[benzofuran-2,6'-quinoline]-2'-carboxylate 161 beige solid, yield 4%; $^1$H NMR (CDCl$_3$, 400 MHz, δ, ppm): 1.02 (d, 3H, J=6.8 Hz), 2.52 (dd, 1H, J=17.2, 5.6 Hz), 2.86 (m, 1H), 3.32 (dd, 1H, J=17.2, 12.4 Hz), 3.83 (s, 3H), 3.91 (s, 3H), 3.98 (s, 3H), 4.57 (d, 1H, J=5.6 Hz), 6.06 (s, 1H), 6.12 (dd, 1H, J=5.6, 1.6 Hz), 6.76 (s, 1H), 6.93 (m, 2H), 7.21 (m, 2H); LCMS (ES, m/z): 527.8 [M+H]$^+$ (2S,7'R)-methyl 7-chloro-4'-(4-fluorophenyl)-4,6-dimethoxy-7'-methyl-3,5'-dioxo-4',5',6',7'-tetrahydro-1'H,3H-spiro[benzofuran-2,8'-quinoline]-2'-carboxylate 162 white solid, yield 4%; $^1$H NMR (CDCl$_3$, 400 MHz, δ, ppm): 0.93 (d, 3H, J=6.0 Hz), 2.40 (m, 1H), 2.95 (m, 2H), 3.75 (s, 3H), 4.02 (s, 3H), 4.06 (s, 3H), 4.81 (d, 1H, J=5.6 Hz), 6.07 (dd, 1H, J=5.6, 1.6 Hz), 6.20 (s, 1H), 6.62, (br s, 1H), 6.98 (m, 2H), 7.23 (m, 2H); LCMS (ES, m/z): 527.8 [M+H]$^+$ (2S,7'R)-methyl 7-chloro-4'-(4-fluorophenyl)-4,6-dimethoxy-7'-methyl-3,5'-dioxo-6',7'-dihydro-3H, 5'H-spiro[benzofuran-2,8'-quinoline]-2'-carboxylate 163 yellow solid, yield 51%; $^1$H NMR (CDCl$_3$, 400 MHz, δ, ppm): 1.13 (d, 3H, J=6.8 Hz), 2.71 (dd, 1H, J=16.8, 4.8 Hz), 3.04 (m, 1H), 3.48 (dd, 1H, J=16.8, 13.6 Hz), 3.87 (s, 3H), 3.96 (s, 3H), 4.06 (s, 3H), 6.18 (s, 1H), 7.12 (m, 2H), 7.24 (m, 2H), 7.91 (s, 1H); LCMS (ES, m/z): 526 [M+H]$^+$ (2S,7'R)-methyl 7-chloro-4'-(4-fluorophenyl)-4,6-dimethoxy-7'-methyl-3,5'-dioxo-7',8'-dihydro-3H, 5'H-spiro[benzofuran-2,6'-quinoline]-2'-carboxylate 164 yellow solid, yield 19%; $^1$H NMR (CDCl$_3$, 400 MHz, δ, ppm): 1.15 (d, 3H, J=6.4 Hz), 3.04 (m, 1H), 3.50 (dd, 1H, J=18.0, 5.6 Hz), 3.91 (m, 4H), 4.00 (s, 3H), 4.04 (s, 3H), 6.10 (s, 1H), 7.04 (m, 2H), 7.15 (m, 2H), 7.89 (s, 1H); LCMS (ES, m/z): 526 [M+H]$^+$ (2S,4'S,7'R)-methyl 7-chloro-4,6-dimethoxy-7'-methyl-3,5'-dioxo-4'-(thiophen-3-yl)-4',5',7',8'-tetrahydro-1'H,3H-spiro[benzofuran-2,6'-quinoline]-2'-carboxylate and (2S,4'R,7'R)-methyl 7-chloro-4,6-dimethoxy-7'-methyl-3,5'-dioxo-4'-(thiophen-3-yl)-4',5',7',8'-tetrahydro-1'H,3H-spiro[benzofuran-2,6'-quinoline]-2'-carboxylate 165 beige solid, yield 2%; $^1$H NMR (CDCl$_3$, 400 MHz, δ, ppm): 1.02 (d, 3H, J=6.8 Hz), 2.31 (dd, 1H, J=16.4, 5.2 Hz), 2.90 (m, 1H), 3.46 (dd, 1H, J=16.0, 12.4 Hz), 3.76 (s, 3H), 3.80 (s, 3H), 3.96 (s, 3H), 4.86 (d, 1H, J=5.2 Hz), 5.98 (s, 1H), 6.15 (dd, 1H, J=5.6, 1.6 Hz), 6.72 (s, 1H), 6.96 (d, 1H, J=4.8 Hz), 7.01 (d, 1H, J=2.4 Hz), 7.16 (dd, 1H, J=4.8, 2.8 Hz); LCMS (ES, m/z): 516 [M+H]$^+$ 166 yellow solid, yield 2%; $^1$H NMR (CDCl$_3$, 400 MHz, δ, ppm): 1.02 (d, 3H, J=6.8 Hz), 2.48 (dd, 1H, J=17.2, 6.0 Hz), 2.85 (m, 1H), 3.28 (dd, 1H, J=17.2, 12.0 Hz), 3.84 (s, 3H), 3.91 (s, 3H), 3.98 (s, 3H), 4.73 (d, 1H, J=5.6 Hz), 6.07 (s, 3H), 6.18 (dd, 1H, J=5.6, 1.6 Hz), 6.77 (s, 1H), 7.00 (m, 2H), 7.18 (dd, 1H, J=4.8, 3.2 Hz); LCMS (ES, m/z): 516 [M+H]$^+$ (2S,7'R)-methyl 7-chloro-4,6-dimethoxy-7'-methyl-3,5'-dioxo-4'-(thiophen-3-yl)-7',8'-dihydro-3H,5'H-spiro[benzofuran-2,6'-quinoline]-2'-carboxylate 167 yellow solid, yield 18%; $^1$H NMR (CDCl$_3$, 400 MHz, δ, ppm): 1.15 (d, 3H, J=6.8 Hz), 3.05 (m, 1H), 3.49 (dd, 1H, J=18.0, 5.6 Hz), 3.93 (m, 4H), 4.01 (s, 3H), 4.04 (s, 3H), 6.10 (s, 1H), 6.95 (dd, 1H, J=4.8, 1.2 Hz), 7.28 (m, 2H), 7.33 (m, 1H), 7.98 (s, 1H); LCMS (ES, m/z): 514 [M+H]$^+$ (2S,7'R)-methyl 7-chloro-4,6-dimethoxy-7'-methyl-3,5'-dioxo-4'-(thiophen-3-yl)-6',7'-dihydro-3H,5'H-spiro[benzofuran-2,8'-quinoline]-2'-carboxylate 168 yellow solid, yield 4%; $^1$H NMR (CDCl$_3$, 400 MHz, δ, ppm): 1.13 (d, 3H, J=6.8 Hz), 2.75 (dd, 1H, J=16.8, 4.8 Hz), 3.03 (m, 1H), 3.48 (dd, 1H, J=16.4, 13.2 Hz), 3.88 (s, 3H), 3.95 (s, 3H), 4.06 (s, 3H), 6.18 (s, 1H) 7.07 (m, 1H), 7.39 (m, 2H), 8.00 (s, 1H); LCMS (ES, m/z): 514 [M+H]$^+$ (2S,7'R)-isopropyl 7-chloro-4,6-dimethoxy-7'-methyl-3,5'-dioxo-4'-phenyl-4',5',7',8'-tetrahydro-1'H,3H-spiro[benzofuran-2,6'-quinoline]-2'-carboxylate 169 beige solid, yield 9%; $^1$H NMR (CDCl$_3$, 400 MHz, δ, ppm): 1.01 (d, 3H, J=6.8 Hz), 1.25 (d, 3H, J=6.0 Hz), 1.28 (d, 3H, J=6.4 Hz), 2.32 (dd, 1H, J=16.4, 5.2 Hz), 2.90 (m, 1H), 3.51 (dd, 1H, J=16.0, 12.0 Hz), 3.56 (s, 3H), 3.94 (s, 3H), 4.72 (d, 1H, J=5.6 Hz), 5.09 (sept., 1H, J=6.4 Hz), 5.89 (s, 1H), 6.07 (dd, 1H, J=5.2, 1.2 Hz), 6.74 (s, 1H), 7.13 (m, 1H), 7.26 (m, 4H); LCMS (ES, m/z): 538 [M+H]$^+$ (2S,7'R)-isopropyl 7-chloro-4,6-dimethoxy-7'-methyl-3,5'-dioxo-4'-phenyl-7',8'-dihydro-3H,5'H-spiro[benzofuran-2,6'-quinoline]-2'-carboxylate 170 yellow solid, yield 60%; $^1$H NMR (CDCl$_3$, 400 MHz, δ, ppm): 1.15 (d, 3H, J=6.8 Hz), 1.41 (d, 3H, J=3.6 Hz), 1.42 (d, 3H, J=3.6 Hz), 3.04 (m, 1H), 3.52 (dd, 1H, J=18.0, 6.0 Hz), 3.91 (m, 4H), 3.99 (s, 3H), 3.35 (sept., 1H, J=5.2 Hz), 6.08 (s, 1H), 7.18 (m, 2H), 7.36 (m, 3H), 7.84 (s, 1H); LCMS (ES, m/z): 536 [M+H]$^+$ (2S,7'R)-isopropyl 7-chloro-4,6-dimethoxy-7'-methyl-3,5'-dioxo-4'-phenyl-6',7'-dihydro-3H,5'H-spiro[benzofuran-2,8'-quinoline]-2'-carboxylate 171 yellow solid, yield 31%; $^1$H NMR (CDCl$_3$, 400 MHz, δ, ppm): 1.16 (d, 3H, J=6.8 Hz), 1.24 (d, 3H, J=6.4 Hz), 1.29 (d, 3H, J=6.0 Hz), 2.70 (dd, 1H, J=16.4, 4.8 Hz), 3.06 (m, 1H), 3.58 (dd, 1H, J=16.4, 14.0 Hz), 3.95 (s, 3H), 4.06 (s, 3H), 5.14 (sept., 1H, J=6.4 Hz), 6.18 (s, 1H), 7.25 (m, 2H), 7.43 (m, 3H), 7.88 (s, 1H); LCMS (ES, m/z): 536 [M+H]$^+$ (2S,7'R)-butyl 7-chloro-4,6-dimethoxy-7'-methyl-3,5'-dioxo-4'-phenyl-4',5',7',8'-tetrahydro-1'H,3H-spiro[benzofuran-2,6'-quinoline]-2'-carboxylate 172 beige solid, yield 5%; $^1$H NMR (CDCl$_3$, 400 MHz, δ, ppm): 0.92 (t, 3H, J=7.6 Hz), 1.01 (d, 3H, J=6.8 Hz), 1.36 (sex., 2H, J=7.6 Hz), 1.63 (quint., 2H, J=6.8 Hz), 2.31 (dd, 1H, J=16.0, 5.2 Hz), 2.90 (m, 1H), 3.50 (dd, 1H, J=16.0, 12.0 Hz), 3.56 (s, 3H), 3.95 (s, 3H), 4.13 (m, 1H), 4.23 (m, 1H), 4.72 (d, 1H, J=5.2 Hz), 5.89 (s, 1H), 6.08 (d, 1H, J=5.2 Hz), 6.73 (s, 1H), 7.12 (m, 1H), 7.24 (m, 4H); LCMS (ES, m/z): 552 [M+H]$^+$ (2S,7'R)-butyl 7-chloro-4,6-dimethoxy-7'-methyl-3,5'-dioxo-4'-phenyl-7',8'-dihydro-3H,5'H-spiro[benzofuran-2,6'-quinoline]-2'-carboxylate 173 yellow solid, yield 26%; $^1$H NMR (CDCl$_3$, 400 MHz, δ, ppm): 0.97 (t, 3H, J=7.2 Hz), 1.15 (d, 3H, J=6.4 Hz), 1.46 (sex., 2H, J=7.2 Hz), 1.80 (quint., 2H, J=6.8 Hz), 3.05 (m, 1H), 3.52 (dd, 1H, J=18.0, 5.6 Hz), 3.94 (m, 4H), 4.00 (s, 3H), 4.44 (m, 2H), 6.09 (s, 1H), 7.17 (m, 2H), 7.36 (m, 3H), 7.87 (s, 1H); LCMS (ES, m/z): 550 [M+H]$^+$ (2S,7'R)-butyl 7-chloro-4,6-dimethoxy-7'-methyl-3,5'-dioxo-4'-phenyl-6',7'-dihydro-3H,5'H-spiro[benzofuran-2,8'-quinoline]-2'-carboxylate 174 yellow solid, yield 29%; $^1$H NMR (CDCl$_3$, 400 MHz, δ, ppm): 0.88 (t, 3H, J=7.6 Hz), 1.15 (d, 3H, J=6.8 Hz), 1.34 (sex., 2H, J=6.8 Hz), 1.62 (quint., 2H, J=6.4 Hz), 2.69 (dd, 1H, J=16.4, 4.8 Hz), 3.06 (m, 1H), 3.57 (dd, 1H, J=16.4, 14.0 Hz), 3.96 (s, 3H), 4.06 (s, 3H), 4.25 (t, 2H, J=6.0 Hz), 6.17 (s, 1H), 7.25 (m, 2H), 7.43 (m, 3H), 7.93 (s, 1H); LCMS (ES, m/z): 550 [M+H]$^+$ 1.17. Synthesis of Tetrahydropyrimidines at 4'

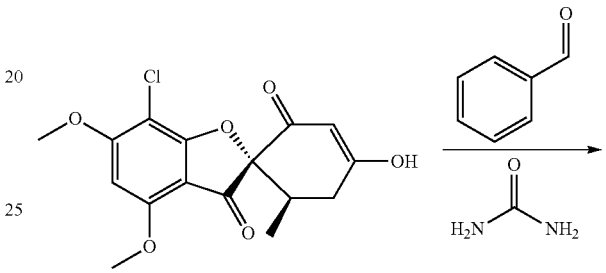

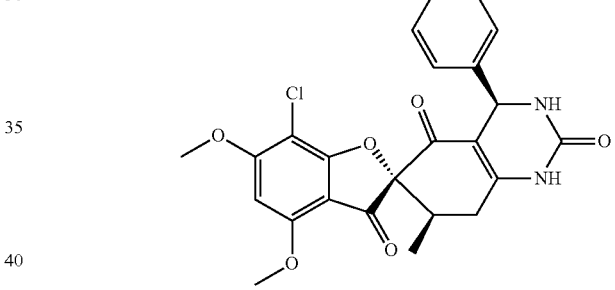

A 50 mL round-bottomed flask was charged with 0.5 g (1.5 mmol, 1 eq.) of griseofulvic acid, 0.15 mL (1.5 mmol, 1 eq.) of benzaldehyde, 0.13 g (2.2 mmol, 1.5 eq.) of urea and 32 mg (0.6 mmol, 0.4 eq.) of ammonium chloride in 1 mL of ethanol. The mixture was brought to 100° C. for 18 h. The mixture was cooled to ambient temperature. The precipitate was filtered and the filtrate concentrated under reduced pressure. The residue was purified by chromatography on silica gel (CH$_2$Cl$_2$/MeOH 98:2 to 96:4). A brown solid (26 mg) was obtained with a yield of 4%.

(2S,7'R)-7-chloro-4,6-dimethoxy-7'-methyl-4'-phenyl-3',4',7',8'-tetrahydro-1'H,3H-spiro[benzofuran-2,6'-quinazoline]-2',3,5'-trione 175 $^1$H NMR (CD$_3$CN, 400 MHz, δ, ppm): 0.97 (d, 3H, J=6.4 Hz), 2.55 (dd, 1H, J=17.4, 5.3 Hz), 2.92 (m, 1H), 3.18 (dd, 1H, J=17.2, 11.9 Hz), 3.87 (s, 3H), 4.00 (s, 3H), 5.33 (d, 1H, J=3.3 Hz), 6.25 (br s, 1H), 6.28 (s, 1H), 7.29 (m, 5H), 7.97 (br s, 1H); LCMS (ES, m/z): 469.02 [M+H]$^+$ 1.18. Synthesis of Tetrahydropyridines at 4'

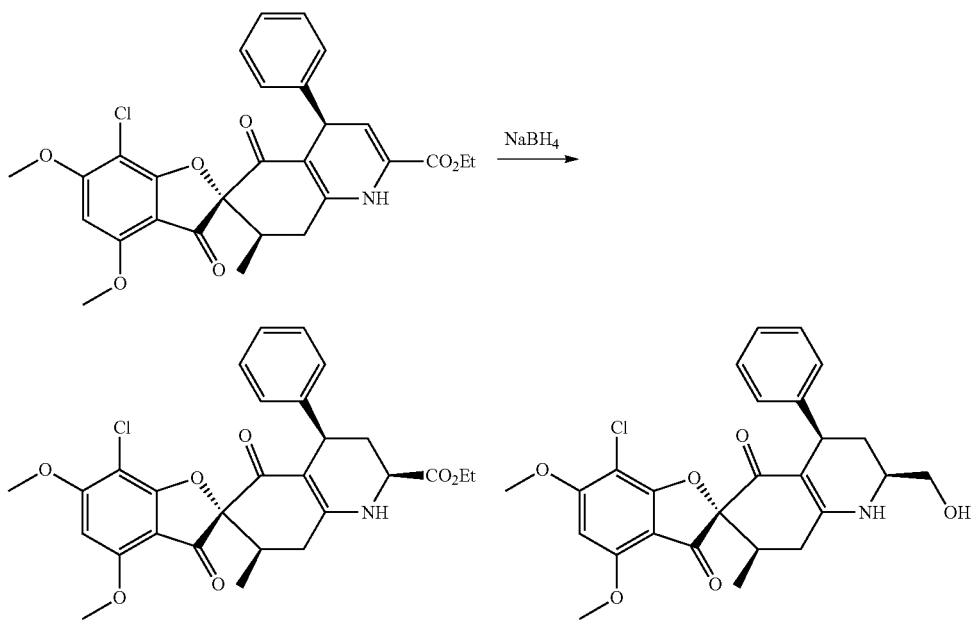

In a 50 mL round-bottomed flask 0.24 g (6.5 mmol, 6.6 eq.) of sodium borohydride was added to a solution of (2S,4'R,7'R)-methyl 7-chloro-4,6-dimethoxy-7'-methyl-3,5'-dioxo-4'-phenyl-4',5',7',8'-tetrahydro-1'H,3H-spiro[benzofuran-2,6'-quinoline]-2'-carboxylate (0.5 g, 1.0 mmol, 1 eq.) in 5 mL of methanol. The mixture was left under agitation at ambient temperature for 18 h. 5 equivalents of sodium borohydride were added and the mixture left under agitation for a further 18 h. The mixture was then concentrated under reduced pressure and the residue purified by chromatography on silica gel (CH$_2$Cl$_2$/MeOH 98:2). A white solid (2.3 mg) was obtained with a yield of 0.5%.

(2S,7'R)-methyl 7-chloro-4,6-dimethoxy-7'-methyl-3,5'-dioxo-4'-phenyl-2',3',4',5',7',8'-hexahydro-1'H,3H-spiro[benzofuran-2,6'-quinoline]-2'-carboxylate 176 $^1$H NMR (CDCl$_3$, 400 MHz, δ, ppm): 1.04 (d, 3H, J=6.8 Hz), 2.29 (m, 2H), 2.51 (dt, 1H, J=13.2, 3.6 Hz), 2.88 (m, 1H), 3.17 (s, 3H), 3.57 (dd, 1H, J=16.0, 12.4 Hz), 3.74 (s, 3H), 3.95 (s, 3H), 3.98 (m, 1H), 4.08 (m, 1H), 5.40 (m, 1H), 5.97 (s, 1H), 7.03 (t, 1H, J=7.2 Hz), 7.08 (d, 2H, J=7.2 Hz), 7.16 (t, 2H, J=7.6 Hz); LCMS (ES, m/z): 512.1 [M+H]$^+$ (2S,7'R)-7-chloro-2'-(hydroxymethyl)-4,6-dimethoxy-7'-methyl-4'-phenyl-3',4',7',8'-tetrahydro-1'H,3H-spiro[benzofuran-2,6'-quinoline]-3,5'(2'H)-dione 177 beige solid, yield 2%; $^1$H NMR (CDCl$_3$, 400 MHz, δ, ppm): 0.92 (d, 3H, J=6.8 Hz), 1.69 (m, 2H), 1.95 (m, 1H), 2.01 (dd, 1H, J=16.0, 5.2 Hz), 2.69 (m, 1H), 3.08 (m, 1H), 3.16 (dd, 1H, J=10.8, 4.0 Hz), 3.28 (dd, 1H, J=15.2, 13.2 Hz), 3.37 (m, 1H), 3.79 (m, 4H), 3.89 (s, 3H), 5.75 (br s, 1H), 5.95 (s, 1H), 6.97-7.03 (m, 3H), 7.11 (t, 2H, J=7.6 Hz); LCMS (ES, m/z): 483.99 [M+H]$^+$ 1.19. Functionalization at 2' by a Hydrazine and Coupling of Pyrazole at 2'

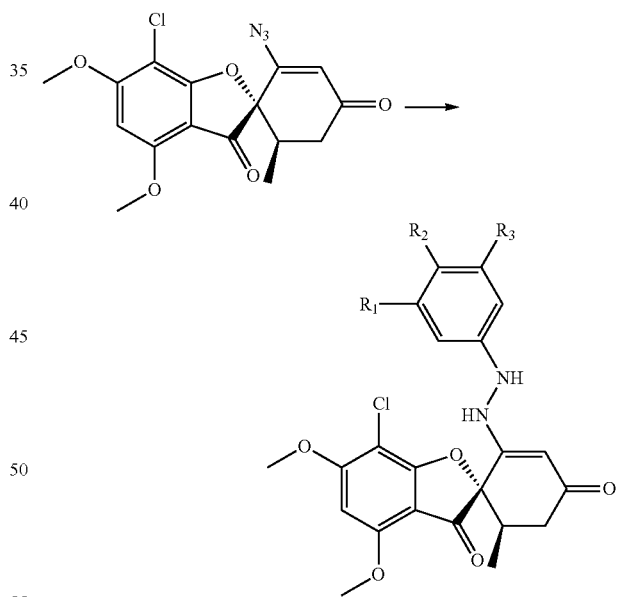

Example: R$_1$=R$_2$=R$_3$=H

To the azide (400 mg; 1.10 mmol) in solution in pyridine (4 ml) the addition was made of aniline (205 mg; 2.20 mmol). The mixture was heated under microwave radiation at 90° C. for 90 min. The pyridine was then evaporated and the syrup obtained was purified by chromatography on silica to give 178 mg of a mixture of the expected product (56%) and starting product (33%). This mixture was re-purified by preparative HPLC (SunFire, C18 OBD, 19×100) to give 51 mg (9.5%) of the desired product in the form of orange crystals.

(1'S,6'R)-7-chloro-4,6-dimethoxy-6'-methyl-2'-(2-phenylhydrazinyl)-3H-spiro[benzofuran-2,1'-cyclohex[2]ene]-3,4'-dione 178 $^1$H NMR (CDCl$_3$, 400 MHz, δ, ppm): 0.96 (m, 3H); 2.50 (m, 1H); 2.82 (m, 1H); 3.13 (m, 1H); 3.90 (s, 3H); 4.00 (s, 3H); 5.48 (s, 1H); 6.07 (s, 1H); 6.58 (m, 2H); 6.84 (m, 1H); 7.17 (m, 2H); HRMS (ESI+, m/z): 429.1207 [M+H]$^+$ (1'S,6'R)-7-chloro-4,6-dimethoxy-2'-(2-(4-methoxyphenyl)hydrazinyl)-6'-methyl-3H-spiro[benzofuran-2,1'-cyclohex[2]ene]-3,4'-dione 179 orange crystals, 9% yield; $^1$H NMR (DMSO-d$_6$, 400 MHz, δ, ppm): 0.74 (m, 3H); 2.40 (m, 1H); 2.70 (m, 2H); 3.63 (s, 3H); 3.88 (s, 3H); 4.00 (s, 3H); 5.74 (s, 1H); 6.40 (s, 1H); 6.56 (m, 2H); 6.70 (m, 2H); HRMS (ESI+, m/z): 459.1310 [M+H]$^+$ (1'S,6'R)-7-chloro-4,6-dimethoxy-6'-methyl-2'-(2-(4-(trifluoromethyl)phenyl) hydrazinyl)-3H-spiro[benzofuran-2,1'-cyclohex[2]ene]-3,4'-dione 180 white crystals 24% yield; $^1$H NMR (DMSO-d$_6$, 400 MHz, δ, ppm): 0.78 (m, 3H); 1.24 (s, 1H); 2.78 (m, 2H); 3.86 (s, 3H); 4.00 (s, 3H); 4.28 (s, 2H); 6.40 (s, 1H); 6.61 (m, 2H); 7.38 (m, 2H); 7.62 (s, 1H); HRMS (ESI+, m/z): 497.1085 [M+H]$^+$ (1'S,6'R)-7-chloro-2'-(2-(3,5-dichlorophenyl)hydrazinyl)-4,6-dimethoxy-6'-methyl-3H-spiro[benzofuran-2,1'-cyclohex[2]ene]-3,4'-dione 181 yellow crystals, 12.5% yield; $^1$H NMR (DMSO-d$_6$, 400 MHz, δ, ppm): 0.76 (m, 3H); 1.24 (s, 1H) 2.80 (m, 2H); 3.88 (s, 3H); 4.01 (s, 3H); 4.56 (s, 2H); 5.76 (s, 1H); 6.42 (s, 1H); 6.46 (s, 2H); 6.74 (m, 1H); 7.55 (s, 1H); HRMS (ESI+, m/z): 497.0427 [M+H]$^+$ (1'S,6'R)-2'-(2-(4-tert-butylphenyl)hydrazinyl)-7-chloro-4,6-dimethoxy-6'-methyl-3H-spiro[benzofuran-2,1'-cyclohex[2]ene]-3,4'-dione 182 beige crystals, 26% yield; $^1$H NMR (DMSO-d$_6$, 400 MHz, δ, ppm): 0.75 (m, 3H); 1.18 (s, 9H); 2.72 (m, 2H); 3.80 (broad s, 2H); 3.86 (s, 3H); 3.99 (s, 3H); 6.40 (s, 1H); 6.50 (m, 2H); 7.09 (m, 2H); HRMS (ESI+, m/z): 485.1833 [M+H]$^+$ (1'S,6'R)-2'-(2-(biphenyl-4-yl)hydrazinyl)-7-chloro-4,6-dimethoxy-6'-methyl-3H-spiro[benzofuran-2,1'-cyclohex[2]ene]-3,4'-dione 183 beige crystals, 14.3% yield; $^1$H NMR (DMSO-d$_6$, 400 MHz, δ, ppm): 0.78 (m, 3H); 2.67-80 (m, 2H); 3.86 (s, 3H); 3.99 (m, 5H); 6.41 (s, 1H); 6.63 (m, 2H); 7.24 (m, 1H); 7.32 (broad s, 1H); 7.37 (m, 4H); 7.53 (m, 2H); HRMS (ESI+, m/z): 505.1520 [M+H]$^+$ (1'S,6'R)-7-chloro-2'-(2-(3,5-di-tert-butylphenyl)hydrazinyl)-4,6-dimethoxy-6'-methyl-3H-spiro[benzofuran-2,1'-cyclohex[2]ene]-3,4'-dione 184 yellow crystals, 4.4% yield; $^1$H NMR (DMSO-d$_6$, 400 MHz, δ, ppm): 0.74 (m, 3H); 1.18 (s, 18H); 2.33-2.74 (m, 3H); 3.86 (s, 3H); 3.98 (s, 3H); 6.38 (s, 1H); 6.46 (s, 2H); 6.80 (s, 1H); 7.25 (broad s, 1H); HRMS (ESI+, m/z): 541.2460 [M+H]$^+$

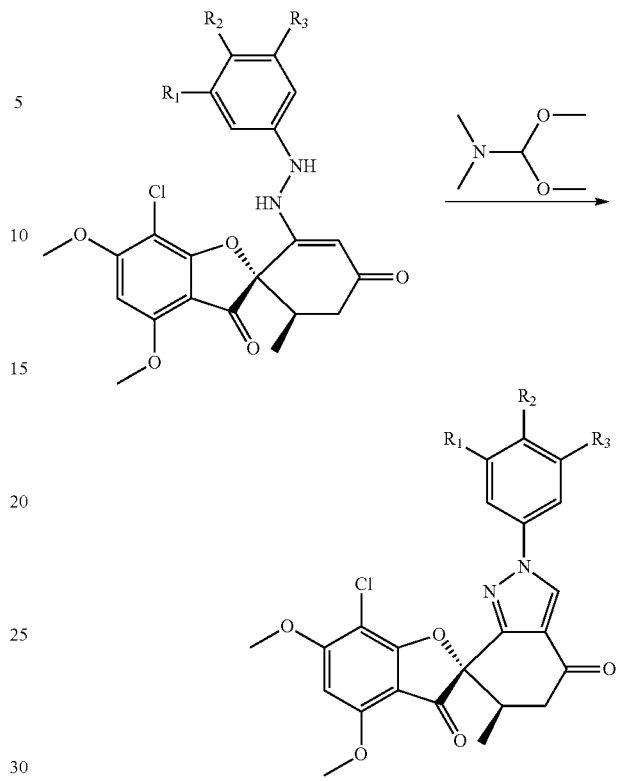

Example: R$_1$=R$_3$=H, R$_2$=CF$_3$

To hydrazine (100 mg; 0.20 mmol) in solution in THF (2 ml) was added 1,1-dimethoxy-N,N-dimethylmethanamine (240 mg; 2.0 mmol) and this mixture was heated to 100° C. for 1 hour. The THF was evaporated and the residue obtained was purified by chromatography on silica to give the coupling product in the form of a yellow solid (79 mg, 77%).

(2S,6'R)-7-chloro-4,6-dimethoxy-6'-methyl-2'-(4-(trifluoromethyl)phenyl)-5',6'-dihydro-3H-spiro[benzofuran-2,7'-indazole]-3,4'(2'H)-dione 185 $^1$H NMR (DMSO-d$_6$, 400 MHz, δ, ppm): 0.80 (m, 3H); 2.91-3.08 (m, 3H); 3.93 (s, 6H); 6.36 (s, 1H); 7.38 (m, 2H); 7.56 (m, 2H); 8.13 (s, 1H); HRMS (ESI+, m/z): 507.0931 [M+H]$^+$ (2S,6'R)-2'-(4-tert-butylphenyl)-7-chloro-4,6-dimethoxy-6'-methyl-5',6'-dihydro-3H-spiro[benzofuran-2,7'-indazole]-3,4'(2'H)-dione 186 white crystals, 20.4% yield; $^1$H NMR (DMSO-d$_6$, 400 MHz, δ, ppm): 0.77 (m, 3H); 1.16 (s, 9H); 2.87-3.03 (m, 3H); 3.92 (s, 6H); 6.35 (s, 1H); 7.03 (broad s, 2H); 7.18 (m, 2H); 8.04 (s, 1H); HRMS (ESI+, m/z): 495.1685 [M+H]$^+$ (2S,6'R)-7-chloro-2'-(3,5-di-tert-butylphenyl)-4,6-dimethoxy-6'-methyl-5',6'-dihydro-3H-spiro[benzofuran-2,7'-indazole]-3,4'(2'H)-dione 187 orange crystals, 71% yield; $^1$H NMR (CD$_3$OD, 400 MHz, δ, ppm): 0.86 (m, 3H); 1.17 (broad s, 18H); 2.58 (m, 1H); 2.99-3.12 (m, 2H); 3.92 (s, 3H); 3.94 (s, 3H); 6.29 (s, 1H); 6.68 (broad s, 1H); 7.19 (broad s, 1H); 7.13 (m, 1H); 7.86 (s, 1H); HRMS (ESI+, m/z): 551.2307 [M+H]$^+$ (2 S,6'R)-2'-(biphenyl-4-yl)-7-chloro-4,6-dimethoxy-6'-methyl-5',6'-dihydro-3H-spiro[benzofuran-2,7'-indazole]-3,4'(2'H)-dione 188 white crystals, 69% yield; $^1$H NMR (DMSO-d$_6$, δ, ppm): 0.81 (m, 3H); 2.94 (m, 1H); 3.05 (m, 1H); 3.30 (m, 1H); 3.66 (s, 3H); 3.92 (s, 3H); 6.27 (s, 1H); 7.19 (broad s, 2H); 7.40-7.52 (m, 7H); 8.10 (s, 1H); HRMS (ESI+, m/z): 515.1364 [M+H]$^+$ 1.20. Functionalization with Various Nitrogenous Derivatives at 2'

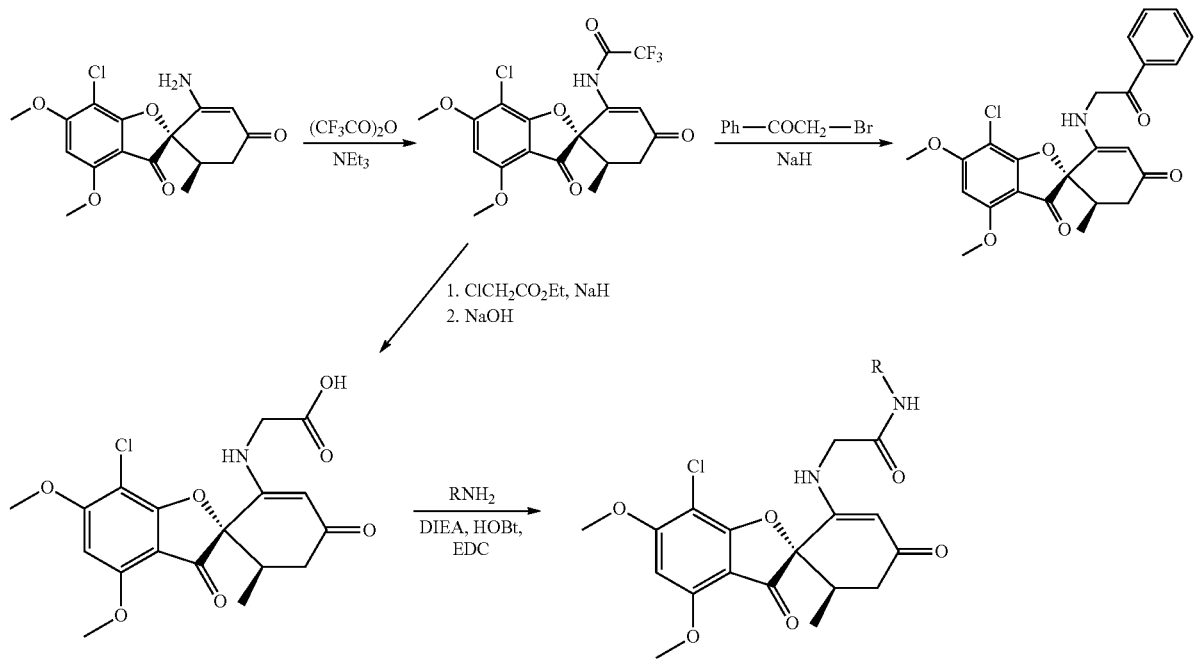

The starting amine (12 g; 3535 mmol) in solution in dichloromethane (100 ml) and in the presence of triethylamine (9.9 ml; 71.1 mmol) was treated with trifluoroacetic anhydride (5.44 ml; 39.1 mmol). After an agitation time of 3 days at ambient temperature the medium was diluted with dichloromethane and washed with water. The organic phases were combined, dried and evaporated to obtain a syrup. This was purified by chromatography on silica and crystallised in a heptane/ether mixture to give the expected product in the form of white crystals (13.7 g; 77%).

N-((1'S,6'R)-7-chloro-4,6-dimethoxy-6'-methyl-3,4'-dioxo-3H-spiro[benzofuran-2,1'-cyclohex[2]ene]-2'-yl)-2,2,2-trifluoroacetamide 189 $^1$H NMR (CDCl$_3$, 400 MHz, δ, ppm): 0.94 (m, 3H); 2.49 (m, 1H)=; 2.92 (m, 1H); 3.02 (m, 1H); 4.01 (s, 3H); 4.08 (s, 3H); 6.22 (s, 1H); 7.19 (s, 1H); 7.63 (broad s, 1H; HRMS (ESI+, m/z): 434.0607 [M+H]$^+$ To the preceding compound (1.4 g; 3.23 mmol) in solution in DMF (8 ml) at 0° C. was added sodium hydride (142 mg; 3.55 mmol). The mixture was agitated 2 minutes at 0° C. after which the addition was made of 2-bromo-1-phenylethanone (642 mg; 3.23 mmol). The mixture was agitated 5 minutes at ambient temperature then heated to 120° C. for 2 h. The medium was then diluted with ethyl acetate and washed with water. The organic phases were combined, dried and evaporated leading to a syrup. This was purified by chromatography on silica and recrystallized in ethyl acetate/ether mixture to give the expected product in the form of beige crystals (129 mg; 8.3%).

(1'S,6'R)-7-chloro-4,6-dimethoxy-6'-methyl-2'-(2-oxo-2-phenylethylamino)-3H-spiro[benzofuran-2,1'-cyclohex[2]ene]-3,4'-dione 190 $^1$H NMR (dmso-d$_6$, 400 MHz, δ, ppm): 0.76 (m, 3H); 2.20 (m, 1H); 2.54 (m, 1H); 2.77 (m, 1H); 3.96 (s, 3H); 4.08 (s, 3H); 4.58 (m, 2H); 5.01 (s, 1H); 6.56 (s, 2H); 7.54 (m, 2H); 7.68 (m, 1H); 8.00 (m, 2H); HRMS (ESI+, m/z): 456.1207 [M+H]$^+$ A mixture of the preceding fluorinated compound (2 g; 4.61 mmol) and ethyl 2-chloroacetate in solution in DMF (10 ml) was treated at 0° C. with sodium hydride (221 mg; 5.33 mmol). The mixture was agitated 30 minutes at 0° C., then for 24 h at 70° C. and a further 24 h at 120° C. Potassium iodide was then added (765 mg; 4.61 mmol) and the mixture heated an additional 72 h. The medium was then diluted with ethyl acetate and washed with water. The organic phases were combined, dried and evaporated leading to a brown syrup. This was purified by chromatography on silica to give the expected product in the form of a yellow oil (1.2 g; 35%). This compound (1.2 g; 2.30 mmol) in solution in ethanol (8 ml) at ambient temperature was treated with a solution composed of 277 mg (6.93 mmol) of sodium hydroxide in 2 ml of water. After an agitation time of one hour, the ethanol was evaporated and the residue diluted with dichloromethane, washed with 1N HCl and then with water. The organic phases were combined, dried and evaporated to obtain an orange syrup. This was crystallised in an ether/methanol mixture to give beige crystals. Re-crystallisation in acetonitrile allowed the compound to be obtained in the form of white crystals (450 mg; 47%).

2-((1'S,6'R)-7-chloro-4,6-dimethoxy-6'-methyl-3,4'-dioxo-3H-spiro[benzofuran-2,1'-cyclohex[2]ene]-2'-ylamino)acetic acid 191 $^1$H NMR (dmso-d$_6$, 400 MHz, δ, ppm): 0.72 (m, 3H); 2.18 (m, 1H); 2.54 (m, 1H); 2.73 (m, 1H); 3.67 (m, 2H); 3.94 (s, 3H); 4.06 (s, 3H); 4.84 (s, 1H) 6.53 (s, 1H); 6.79 (m, 1H); HRMS (ESI+, m/z): 396.0834 [M+H]$^+$ Example: R=Ph To the preceding compound (100 mg; 0.25 mmol) in solution in dichloromethane (5 ml) were added the amine (28 mg; 0.30 mmol), DIEA (0.132 ml; 0.76 mmol), HOBt (58 mg; 0.38 mmol) and EDC (73 mg; 0.38 mmol). The mixture was left under agitation at ambient temperature for 2 h after which the medium was diluted with dichloromethane and washed with water. The organic phases were combined, dried and evaporated leading to an orange syrup. This was purified by chromatography on silica to give the expected product which crystallised in ether in the form of white crystals (34 mg; 26%).

2-((1'S,6'R)-7-chloro-4,6-dimethoxy-6'-methyl-3,4'-dioxo-3H-spiro[benzofuran-2,1'-cyclohex[2]ene]-2'-ylamino)-N-phenylacetamide 192 $^1$H NMR (dmso-d$_6$, 400 MHz, δ, ppm): 0.73 (m, 3H); 2.18 (m, 1H); 2.53 (m, 1H); 2.75 (m, 1H); 3.79 (m, 2H); 3.96 (s, 3H); 4.07 (s, 3H); 4.93 (s, 1H); 6.55 (s, 1H); 6.82 (m, 1H); 7.06 (m, 1H); 7.31 (m, 2H); 7.54 (m, 2H); HRMS (ESI+, m/z): 493.1128 [M+Na]$^+$

2-((1'S,6'R)-7-chloro-4,6-dimethoxy-6'-methyl-3,4'-dioxo-3H-spiro[benzofuran-2,1'-cyclohex[2]ene]-2'-ylamino)-N-hexylacetamide 193 yellow crystals, 38% yield; $^1$H NMR (DMSO-d$_6$, 400 MHz, δ, ppm): 0.72 (m, 3H); 0.85 (m, 3H); 1.23-1.36 (m, 8H); 2.18 (m, 1H); 2.53 (m, 1H); 2.75 (m, 1H); 3.03 (m, 2H); 3.52 (m, 2H); 3.95 (s, 3H); 4.06 (s, 3H); 4.85 (s, 1H); 6.54 (s, 1H); 6.64 (t, 1H); 7.93 (m, 1H); HRMS (ESI+, m/z): 501.1760 [M+Na]$^+$

2-((1'S,6'R)-7-chloro-4,6-dimethoxy-6'-methyl-3,4'-dioxo-3H-spiro[benzofuran-2,1'-cyclohex[2]ene]-2'-ylamino)-N-(naphthalen-1-yl)acetamide 194 white crystals, 26%; $^1$H NMR (DMSO-d$_6$, 400 MHz, δ, ppm): 0.75 (broad s, 3H); 2.23-2.78 (m, 3H); 3.95-4.06 (m, 8H); 5.07 (s, 1H); 6.55 (s, 1H); 6.85 (broad s, 1H); 7.50 (m, 3H); 7.73 (m, 2H); 7.95 (s, 1H); 8.06 (s, 1H); HRMS (ESI+, m/z): 521.1479 [M+H]$^+$

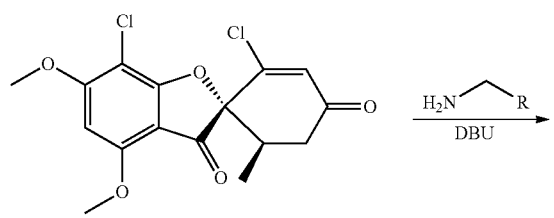

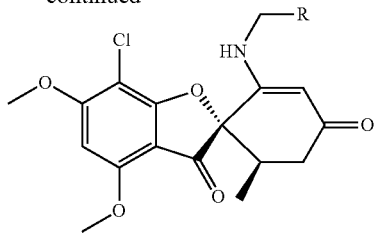

Example: R=Py

Pyridin-2-ylmethanamine (5.60 mmol; 2.0 equiv.), (1'R, 6'R)-2',7-dichloro-4,6-dimethoxy-6'-methyl-3H-spiro[benzofuran-2,1'-cyclohex[2]ene]-3,4'-dione (2.80 mmol, 1.0 equiv) and DBU (7.00 mmol, 2.5 equiv) were dissolved in dioxane (35 mL). The mixture was brought to 100° C. for 16 hours then concentrated under reduced pressure. The residue was purified on silica gel (CH$_2$Cl$_2$/AcOEt 75:25 to 0:100, then EtOAc/MeOH 100:0 to 90:10) to obtain the amino derivatives with yields ranging from 2 to 87%.

(1'S,6'R)-7-chloro-4,6-dimethoxy-6'-methyl-2'-(pyridin-2-ylmethylamino)-3H-spiro[benzofuran-2,1'-cyclohex[2]ene]-3,4'-dione 195 yellow solid, 250 mg (21%); $^1$H NMR (400 MHz, DMSO-d$_6$, ppm): δ 0.73 (d, 3H, J=6.6 Hz), 2.14 (dd, 1H, J=17.0, 4.9 Hz), 2.48 (d, 1H, 13.7 Hz), 2.71-2.80 (m, 1H), 3.96 (s, 3H), 4.06 (s, 3H), 4.26 (d, 2H, J=5.2 Hz), 4.87 (s, 1H), 6.55 (s, 1H), 7.11 (d, 1H, J=7.9 Hz), 7.26 (t, 1H, J=6.2 Hz), 7.40 (t, 1H, J=5.7 Hz), 7.77 (t, 1H, J=7.8 Hz), 8.50 (d, 1H, 4.7).
LCMS (ES, m/z): 429.0 [M+H]$^+$.

(1'S,6'R)-7-chloro-4,6-dimethoxy-6'-methyl-2'-(pyridin-3-ylmethylamino)-3H-spiro[benzofuran-2,1'-cyclohex[2]ene]-3,4'-dione 196 yellow solid, 96 mg (8%); $^1$H NMR (400 MHz, DMSO-d$_6$, ppm): δ 00.71 (d, 3H, J=6.6 Hz), 2.13 (dd, 1H, J=16.8, 4.9 Hz), 2.44 (d, 1H, 13.0 Hz), 2.69-2.78 (m, 1H), 3.97 (s, 3H), 4.06 (s, 3H), 4.25 (m, 2H), 4.97 (s, 1H), 6.54 (s, 1H), 7.35 (dd, 1H, J=7.5, 5.0 Hz), 7.41 (t, 1H, J=5.9 Hz), 7.54 (t, 1H, J=7.9 Hz), 8.38 (s, 1H), 8.44 (d, 1H, 4.6); LCMS (ES, m/z): 429.0 [M+H]$^+$.

(1'S,6'R)-7-chloro-4,6-dimethoxy-6'-methyl-2'-(pyridin-4-ylmethylamino)-3H-spiro[benzofuran-2,1'-cyclohex[2]ene]-3,4'-dione 197 orange solid, 93 mg (8%); $^1$H NMR (400 MHz, DMSO-d$_6$, ppm): δ 0.72 (d, 3H, J=6.6 Hz), 2.13 (dd, 1H, J=16.8, 5.1 Hz), 2.47 (m, 1H), 2.72-2.79 (m, 1H), 3.97 (s, 3H), 4.06 (s, 3H), 4.24 (d, 2H, J=5.6 Hz), 4.81 (s, 1H), 6.55 (s, 1H), 7.13 (d, 2H, J=5.1 Hz), 7.41 (t, 1H, J=6.0 Hz), 7.41 (t, 1H, J=7.9 Hz), 8.49 (s, 2H, J=5.0 Hz); LCMS (ES, m/z): 429.0 [M+H]$^+$.

tert-butyl 4-(((1'S,6'R)-7-chloro-4,6-dimethoxy-6'-methyl-3,4'-dioxo-3H-spiro[benzofuran-2,1'-cyclohex[2]ene]-2'-ylamino)methyl)piperidine-1-carboxylate 198 yellow solid, 68 mg (5%); $^1$H NMR (400 MHz, DMSO-d$_6$, ppm): δ 0.69 (d, 3H, J=6.7 Hz), 0.91 (td, 2H, J=11.8, 3.4 Hz), 1.38 (s, 9H), 1.49 (dd, 2H, J=28.8, 12.6 Hz), 2.13 (dd, 1H, J=16.9, 5.0 Hz), 2.42-2.48 (m, 1H), 2.56-2.78 (m, 3H), 2.85 (t, 2H, J=6.6 Hz), 3.83-3.91 (m, 2H), 3.94 (s, 3H), 4.05 (s, 3H), 5.03 (s, 1H), 6.52 (s, 1H), 6.83 (t, 1H, J=6.0 Hz); LCMS (ES, m/z): 535.1 [M+H]+.

(1'S,6'R)-7-chloro-4,6-dimethoxy-6'-methyl-2'-((piperidin-4-ylmethyl)amino)-3H-spiro[benzofuran-2,1'-cyclohex[2]ene]-3,4'-dione 199 yellow solid, 82 mg (67%); 1H NMR (400 MHz, DMSO-d6, ppm): δ 0.70 (d, 3H, J=6.7 Hz), 1.11-1.30 (m, 3H), 1.62 (d, 1H, J=13.8 Hz), 1.72 (d, 1H, J=13.8 Hz), 1.78-1.90 (m, 2H), 2.15 (dd, 1H, J=16.6, 5.0 Hz), 2.66-2.95 (m, 6H), 3.94 (s, 3H), 4.06 (s, 3H), 5.07 (s, 1H), 6.53 (s, 1H), 6.88 (t, 1H, J=6.2 Hz); LCMS (ES, m/z): 434.9 [M+H]+.

methyl 4-(((1'S,6'R)-7-chloro-4,6-dimethoxy-6'-methyl-3,4'-dioxo-3H-spiro[benzofuran-2,1'-cyclohex[2]ene]-2'-ylamino)methyl)benzoate 200 orange solid, 82 mg (6%); 1H NMR (400 MHz, DMSO-d6, ppm): δ 00.72 (d, 3H, J=6.7 Hz), 2.12 (dd, 1H, J=16.8, 5.0 Hz), 2.40-2.47 (m, 1H), 2.70-2.78 (m, 1H), 3.83 (s, 3H), 3.97 (s, 3H), 4.06 (s, 3H), 4.28 (d, 2H, J=6.2 Hz), 4.83 (s, 1H), 6.54 (s, 1H), 7.30 (d, 2H, J=8.1 Hz), 7.44 (t, 1H, J=6.2 Hz), 7.91 (d, 1H, J=8.1 Hz); LCMS (ES, m/z): 485.9 [M+H]+.

(1'S,6'R)-7-chloro-2'-(furan-2-ylmethylamino)-4,6-dimethoxy-6'-methyl-3H-spiro[benzofuran-2,1'-cyclohex[2]ene]-3,4'-dione 201 orange solid, 129 mg (11%); 1H NMR (400 MHz, DMSO-d6, ppm): δ 0.70 (d, 3H, J=6.9 Hz), 2.14 (dd, 1H, J=16.9, 5.0 Hz), 2.42-2.48 (m, 1H), 2.69-2.77 (m, 1H), 3.95 (s, 3H), 4.05 (s, 3H), 4.17 (d, 2H, J=6.0 Hz), 5.11 (s, 1H), 6.17 (d, 1H, J=3.0 Hz), 6.38 (s, 1H), 6.52 (s, 1H), 7.22 (t, 1H, J=5.7 Hz), 7.57 (s, 1H); LCMS (ES, m/z): 418.0 [M+H]+.

(1'S,6'R)-2'-(4-bromobenzylamino)-7-chloro-4,6-dimethoxy-6'-methyl-3H-spiro[benzofuran-2,1'-cyclohex[2]ene]-3,4'-dione 202 orange solid, 245 mg (17%); 1H NMR (400 MHz, DMSO-d6, ppm): δ 0.71 (d, 3H, J=6.7 Hz), 2.12 (dd, 1H, J=16.9, 5.2 Hz), 2.41-2.46 (m, 1H), 2.69-2.77 (m, 1H), 3.96 (s, 3H), 4.06 (s, 3H), 4.15-4.19 (m, 2H), 4.85 (s, 1H), 6.54 (s, 1H), 7.12 (d, 2H, J=8.4 Hz), 7.40 (t, 1H, J=6.2 Hz), 7.52 (d, 1H, J=8.4 Hz); LCMS (ES, m/z): 505.9 [M+H]+.

(1'S,6'R)-7-chloro-2'-(4-hydroxybenzylamino)-4,6-dimethoxy-6'-methyl-3H-spiro[benzofuran-2,1'-cyclohex[2]ene]-3,4'-dione 203 light brown solid, 901 mg (39%); 1H NMR (400 MHz, CDCl3, ppm): δ 0.70 (d, 3H, J=6.6 Hz), 2.11 (dd, 1H, J=16.8, 5.1 Hz), 2.40-2.46 (m, 1H), 2.66-2.75 (m, 1H), 2.66-2.75 (m, 1H), 3.96 (s, 3H), 4.05 (s, 3H), 4.07 (sl, 2H), 4.89 (s, 1H), 6.53 (s, 1H), 6.68 (d, 2H, J=8.3 Hz), 6.96 (d, 2H, J=8.3 Hz), 7.33 (t, 1H, J=6.0 Hz), 9.30 (sl, 1H); LCMS (ES, m/z): 443.11 [M+H]+.

(1'S,6'R)-2'-(4-benzylpiperidin-1-yl)-7-chloro-4,6-dimethoxy-6'-methyl-3H-spiro[benzofuran-2,1'-cyclohex[2]ene]-3,4'-dione 204 yellow solid, 292 mg (42%); 1H NMR (400 MHz, DMSO-d6, ppm): δ 0.67 (d, 3H, J=6.7 Hz), 0.98-1.12 (m, 1H), 1.13-1.21 (m, 1H), 1.36 (dl, 1H, J=12.3), 1.52 (dl, 1H, J=12.6 Hz), 1.63-1.75 (m, 1H), 2.19 (dd, 1H, J=17.2, 4.9 Hz), 2.35-2.44 (m, 1H), 2.45-2.48 (m, 2H), 2.55-2.64 (m, 1H), 2.68-2.77 (m, 1H), 2.77-2.88 (m, 1H), 2.99 (dl, 1H, J=13.8 Hz), 3.95 (s, 3H), 4.05 (s, 3H), 5.21 (s, 1H), 6.52 (s, 1H), 7.10-7.18 (m, 3H), 7.22-7.28 (m, 2H); LCMS (ES, m/z): 496.0 [M+H]+.

(1'S,6'R)-7-chloro-4,6-dimethoxy-6'-methyl-2'-(methyl(2-(methyl(pyridin-2-yl)amino)ethyl)amino)-3H-spiro[benzofuran-2,1'-cyclohex[2]ene]-3,4'-dione 205 yellow solid, 15 mg (2%); 1H NMR (400 MHz, CDCl3, ppm): δ 0.84 (d, 3H, J=6.7 Hz), 2.30 (dd, 1H, J=16.7, 4.1 Hz), 2.75-2.83 (m, 1H), 2.84 (s, 1H), 2.88 (s, 1H), 2.90-2.95 (m, 1H), 3.19-3.25 (m, 2H), 3.61-3.79 (m, 2H), 3.97 (s, 3H), 4.03 (s, 3H), 5.42 (s, 1H), 6.14 (s, 1H), 6.40 (d, 1H, J=8.6 Hz), 6.52 (dd, 1H, J=6.9, 5.1 Hz), 7.39-7.44 (m, 1H), 8.06 (dd, 1H, J=4.8, 1.5 Hz); LCMS (ES, m/z): 486.0 [M+H]+.

6-(3-((1'S,6'R)-7-chloro-4,6-dimethoxy-6'-methyl-3,4'-dioxo-3H-spiro[benzofuran-2,1'-cyclohex[2]ene]-2'-ylamino)propylamino)-2,4-dimethyl-1,2,4-triazine-3,5(2H,4H)-dione 206 yellow solid, 86 mg (11%); 1H NMR (400 MHz, DMSO-d6, ppm): δ 0.70 (d, 3H, J=6.7 Hz), 1.63-1.71 (m, 2H), 2.14 (dd, 1H, J=16.8, 5.0 Hz), 2.43-2.48 (m, 1H), 2.66-2.77 (m, 1H), 2.95-3.02 (m, 2H), 3.03-3.09 (m, 2H), 3.17 (s, 3H), 3.34 (s, 3H), 3.94 (s, 3H), 4.05 (s, 3H), 5.01 (s, 1H), 6.51 (s, 1H), 6.69 (t, 1H, J=5.8 Hz), 6.73 (t, 1H, J=5.8 Hz); LCMS (ES, m/z): 534.0 [M+H]+.

(1'S,6'R)-7-chloro-4,6-dimethoxy-6'-methyl-2'-(4-(4-(trifluoromethyl)pyridin-2-yloxy)piperidin-1-yl)-3H-spiro[benzofuran-2,1'-cyclohex[2]ene]-3,4'-dione 207 yellow solid, 144 mg (18%); 1H NMR (400 MHz, CDCl3, ppm): δ 0.86 (d, 3H, J=6.7 Hz), 1.69-1.79 (m, 1H), 1.80-1.97 (m, 2H), 2.01-2.10 (m, 1H), 2.36 (dd, 1H, J=17.0, 4.3 Hz), 2.77-2.86 (m, 1H), 2.89-3.05 (m, 3H), 3.15-3.23 (m, 1H), 3.28-3.36 (m, 1H), 3.98 (s, 3H), 4.03 (s, 3H), 5.22 (m, 1H), 5.48 (s, 1H), 6.14 (s, 1H), 6.90 (s, 1H), 7.03 (d, 1H, J=5.3 Hz), 8.22 (d, 1H, 5.3); LCMS (ES, m/z): 567.0 [M+H]+.

2,4-dibutyl-6-(3-((1'S,6'R)-7-chloro-4,6-dimethoxy-6'-methyl-3,4'-dioxo-3H-spiro[benzofuran-2,1'-cyclohex[2]ene]-2'-ylamino)propylamino)-1,2,4-triazine-3,5(2H,4H)-dione 208 colourless solid, 97 mg (22%); 1H NMR (400 MHz, CDCl3, ppm): δ 0.89 (d, 3H, J=6.3 Hz), 0.94 (td, 6H, J=7.3, 2.0 Hz), 1.28-1.41 (m, 4H), 1.56-1.70 (m, 4H), 1.77-1.91 (m, 1H), 2.37 (dd, 1H, J=15.6, 3.6 Hz), 2.86-2.96 (m, 2H), 3.02-3.17 (m, 2H), 3.18-3.28 (m, 2H), 3.73-3.87 (m, 2H), 3.93 (t, 2H, J=7.4 Hz), 3.98 (s, 3H), 4.04 (s, 3H), 4.65 (t, 1H, J=5.5 Hz), 5.28 (s, 1H), 6.17 (s, 1H); LCMS (ES, m/z): 618.1 [M+H]+.

(1'S,6'R)-7-chloro-2'-((6-chloropyridin-3-yl)methylamino)-4,6-dimethoxy-6'-methyl-3H-spiro[benzofuran-2,1'-cyclohex[2]ene]-3,4'-dione 209 light brown solid, 812 mg (87%); $^1$H NMR (400 MHz, DMSO-$d_6$, ppm): δ 0.71 (d, 3H, J=6.7 Hz), 2.13 (dd, 1H, J=16.9, 5.0 Hz), 2.41-2.47 (m, 1H), 2.71-2.78 (m, 1H), 3.96 (s, 3H), 4.06 (s, 3H), 4.26 (d, 2H, J=5.4 Hz), 4.93 (s, 1H), 6.54 (s, 1H), 7.40 (t, 1H, J=6.0 Hz), 7.50 (t, 1H, J=8.3 Hz), 7.60-7.63 (m, 1H), 8.20 (s, 1H); LCMS (ES, m/z): 462.07 [M+H]$^+$.

(1'S,6'R)-7-chloro-4,6-dimethoxy-6'-methyl-2'-(4-(4-methylpiperazin-1-yl)benzylamino)-3H-spiro[benzofuran-2,1'-cyclohex[2]ene]-3,4'-dione 210 orange solid, 71 mg (15%); $^1$H NMR (400 MHz, CDCl$_3$, ppm): δ 0.90 (d, 3H, J=6.0 Hz), 2.32-2.41 (m, 1H), 2.36 (s, 3H), 2.57 (t, 4H, J=4.5 Hz), 2.85-3.02 (m, 2H), 3.20 (t, 4H, J=4.5 Hz), 3.98 (s, 3H), 4.02 (s, 3H), 4.00-4.13 (m, 2H), 4.71 (t, 1H, J=4.5 Hz), 5.33 (s, 1H), 6.14 (s, 1H), 6.86 (d, 2H, J=8.4 Hz), 7.08 (d, 2H, J=8.4 Hz); LCMS (ES, m/z): 526.9 [M+H]$^+$ (1'S,6'R)-7-chloro-4,6-dimethoxy-6'-methyl-2'-(4-(2-morpholinoethoxy)benzylamino)-3H-spiro[benzofuran-2,1'-cyclohex[2]ene]-3,4'-dione 211 yellow solid, 148 mg (24%); $^1$H NMR (400 MHz, CDCl$_3$, ppm): δ 0.90 (d, 3H, J=6.5 Hz), 2.34-2.40 (m, 1H), 2.57 (t, 4H, J=4.5 Hz), 2.79 (t, 2H, J=5.7 Hz), 2.86-2.97 (m, 2H), 3.73 (t, 4H, J=4.7 Hz), 3.98 (s, 3H), 4.03 (s, 3H), 4.06-4.12 (m, 4H), 4.78 (t, 1H, J=5.1 Hz), 6.16 (s, 1H), 6.84 (d, 2H, J=8.7 Hz), 7.09 (d, 2H, J=8.7 Hz); LCMS (ES, m/z): 557.0 [M+H]$^+$

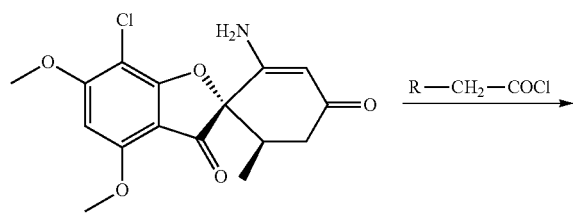

Example: R=Ph (1'S,6'R)-2'-amino-7-chloro-4,6-dimethoxy-6'-methyl-3H-spiro[benzofuran-2,1'-cyclohex[2]ene]-3,4'-dione (2.96 mmol; 1.0 equiv.), 2-phenylethanoic acid chloride (4.44 mmol, 1.5 equiv.) and triethylamine (8.88 mmol, 3 equiv.) were dissolved in dichloromethane (20 mL). The mixture was left under agitation at ambient temperature for 16 hours. The reaction was then halted through the addition of silica. The residue was purified on silica gel (CH$_2$Cl$_2$/AcOEt 98:2 to 90:10) to obtain the amide derivatives with yields ranging from 3 to 37%.

N-((1'S,6'R)-7-chloro-4,6-dimethoxy-6'-methyl-3,4'-dioxo-3H-spiro[benzofuran-2,1'-cyclohex[2]ene]-2'-yl)-2-phenylacetamide 212 white solid, 408 mg (30%); $^1$H NMR (400 MHz, DMSO-$d_6$, ppm): δ 0.69 (d, 3H, J=6.7 Hz), 2.30 (dd, 1H, J=17.4, 5.0 Hz), 2.52-2.58 (m, 1H), 2.79-2.87 (m, 1H), 3.68 (d, 1H, J=15.2), 3.75 (d, 1H, J=15.2), 3.97 (s, 3H), 4.10 (s, 3H), 6.57 (s, 1H), 6.94 (s, 1H), 7.14-7.26 (m, 5H); LCMS (ES, m/z): 456.0 [M+H]$^+$.

2-(4-bromophenyl)-N-((1'S,6'R)-7-chloro-4,6-dimethoxy-6'-methyl-3,4'-dioxo-3H-spiro[benzofuran-2,1'-cyclohex[2]ene]-2'-yl)acetamide 213 white solid, 585 mg (37%); $^1$H NMR (400 MHz, DMSO-$d_6$, ppm): δ 0.69 (d, 3H, J=6.6 Hz), 2.30 (dd, 1H, J=17.3, 5.0 Hz), 2.52-2.57 (m, 1H), 2.78-2.87 (m, 1H), 3.71 (s, 2H), 3.97 (s, 3H), 4.09 (s, 3H), 6.57 (s, 1H), 6.92 (s, 1H), 7.14 (d, 2H, J=8.3 Hz), 7.42 (d, 2H, J=8.3 Hz); LCMS (ES, m/z): 431.8 [M−H]$^−$.

N-((1'S,6'R)-7-chloro-4,6-dimethoxy-6'-methyl-3,4'-dioxo-3H-spiro[benzofuran-2,1'-cyclohex[2]ene]-2'-yl)-2-(2,5-dimethylphenyl)acetamide 214 white solid, 329 mg (23%); $^1$H NMR (400 MHz, DMSO-$d_6$, ppm): δ 0.67 (d, 3H, J=6.7 Hz), 1.99 (s, 3H), 2.17 (s, 3H), 2.30 (dd, 1H, J=17.3, 4.9 Hz), 2.53-2.59 (m, 1H), 2.78-2.85 (m, 1H), 3.66 (d, 1H, J=16.5), 3.70 (d, 1H, J=16.5), 3.98 (s, 3H), 4.11 (s, 3H), 6.56 (s, 1H), 6.82-6.89 (m, 2H), 6.92 (s, 1H), 6.95 (s, 1H), 8.00 (s, 1H); LCMS (ES, m/z): 484.0 [M+H]$^+$.

2-(4-(benzyloxy)phenyl)-N-((1'S,6'R)-7-chloro-4,6-dimethoxy-6'-methyl-3,4'-dioxo-3H-spiro[benzofuran-2,1'-cyclohex[2]en]-2'-yl)acetamide 215 yellow solid, 58 mg (3%); $^1$H NMR (400 MHz, DMSO-$d_6$, ppm): δ 0 0.68 (d, 3H, J=6.7 Hz), 2.30 (dd, 1H, J=17.4, 5.2 Hz), 2.53-2.57 (m, 1H), 2.79-2.87 (m, 1H), 3.59 (d, 1H, J=15.5), 3.66 (d, 1H, J=15.5), 3.97 (s, 3H), 4.05 (s, 3H), 5.06 (s, 2H), 6.56 (s, 1H), 6.86 (d, 2H, J=8.6 Hz), 6.94 (s, 1H), 7.08 (d, 2H, J=8.6 Hz), 7.38-7.47 (m, 5H), 8.52 (s, 1H); LCMS (ES, m/z): 462.0 [M+H]$^+$.

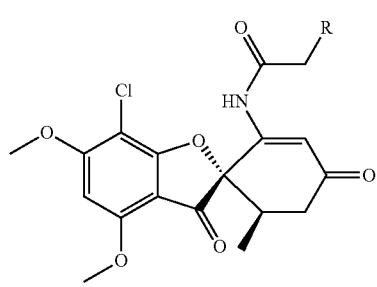

1.21. Functionalization at 4'

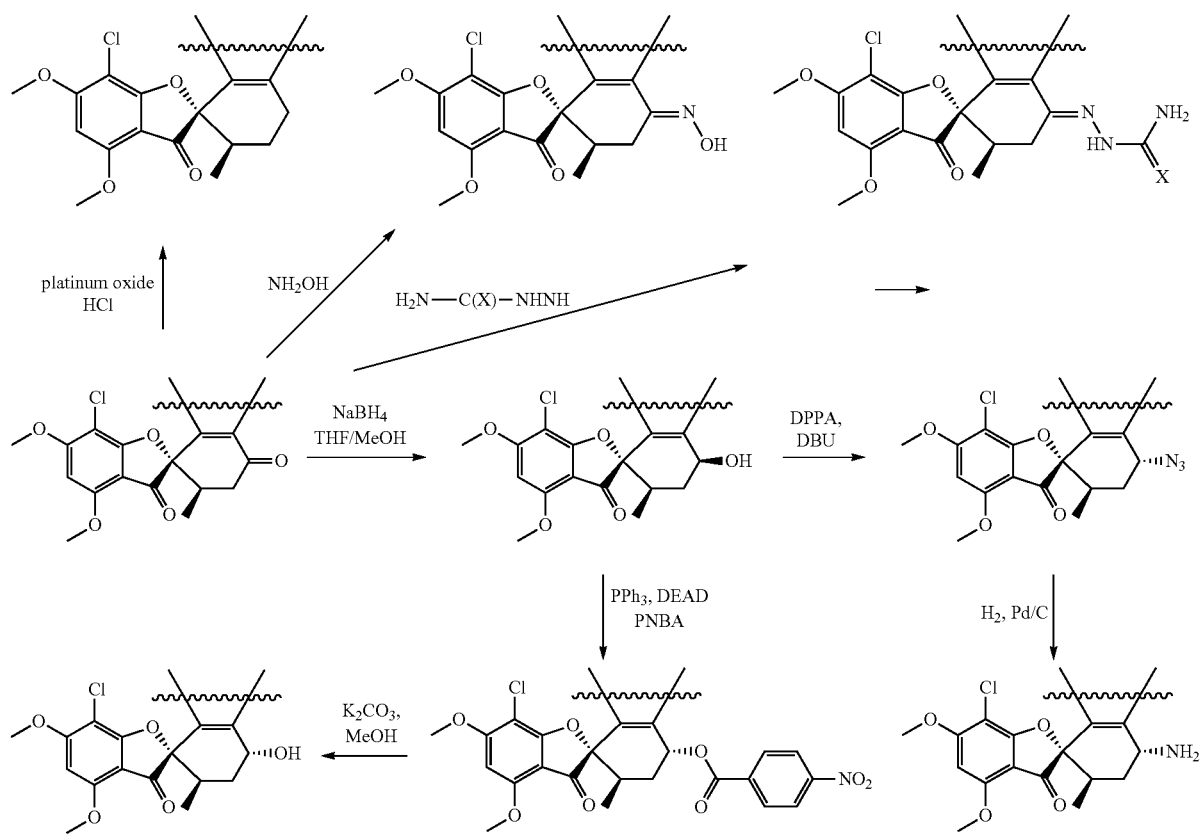

N.B. The stereochemistry of the carbon atom carrying the OH function after reduction of the carbonyl using NaBH₄ was not determined. Arbitrary stereochemistry is indicated in this scheme to evidence clearly that each of the two possible stereochemistries can be obtained via different synthesis pathways and can lead to derivatives substituted differently at this position with a given stereochemistry.

Decarbonylation:

A mixture of platinum oxide (25 mg; 0.1 equiv.), hydrochloric acid (4 M dioxane; 2.8 mL; 10 equiv.) and carbonylated derivative (500 mg; 1.0 equiv.) was left under agitation in a hydrogen atmosphere (1 atm) in methanol (10 mL) at ambient temperature for 18 hours. The reaction medium was then filtered on DICALITE® with ethyl acetate and the solvents evaporated. The residue was purified on silica gel (CH$_2$Cl$_2$/AcOEt 95:5) to give the desired decarbonylated derivative in the form of a pale yellow solid with a yield of 18%.

(2S,7'R)-7-chloro-4,6-dimethoxy-7'-methyl-2'-phenyl-6',7'-dihydro-3H,5'H-spiro[benzofuran-2,8'-quinolin]-3-one 216 pale yellow solid, 16% yield; $^1$H NMR (400 MHz, CDCl$_3$, ppm): δ 7.75 (d, 2H, J=6.6 Hz), 7.55 (d, 1H, J=8.2 Hz), 7.49 (d, 1H, J=8.2 Hz), 7.34-7.26 (m, 3H), 6.09 (s, 1H), 4.02 (s, 3H), 3.91 (s, 3H), 2.93 (m, 2H), 2.59 (m, 2H), 1.87 (m, 1H), 1.06 (d, 3H, J=6.0 Hz); LCMS (ES, m/z): 435.90 [M+H]$^+$ Forming of an Oxime:

A mixture of ketone (1.41 g; 1.0 equiv.), hydroxylamine hydrochloride (3.5 equiv.) and sodium acetate (4.0 equiv) in ethanol (40 mL) and dimethylsulfoxide (20 mL) was left under agitation at 75° C. for 24 hours. The reaction medium was diluted in ethyl acetate (150 mL) and the organic phase successively washed with a saturated aqueous solution of bicarbonate (100 mL), of sodium hydroxide and brine (100 mL). The organic phase was dried over magnesium sulfate, filtered and the solvents evaporated under reduced pressure. The residue was purified on silica gel (CH$_2$Cl$_2$/AcOEt 90:10) to give the corresponding oxime with a yield of 28%.

(2'S,6R,E)-7'-chloro-4-(hydroxyimino)-4',6'-dimethoxy-6-methyl-2-phenyl-3,4,5,6-tetrahydro-2H,3'H-2,7'-spirobi[benzofuran]-3'-one 217 yellow solid, 28% yield; $^1$H NMR (400 MHz, CDCl$_3$, ppm): δ 7.30 (m, 3H), 7.22 (m, 2H), 6.08 (s, 1H), 5.71 (m, 1H), 3.99 (s, 3H), 3.96 (s, 3H), 3.36 (dd, 1H, J=15.0, 10.0 Hz), 3.19 (dd, 1H, J=16.0, 4.0 Hz), 2.87 (dd, 1H, J=15.0, 8.0 Hz), 2.74 (m, 2H), 1.00 (d, 3H, J=6.4 Hz); LCMS (ES, m/z): 456.22 [M+H]$^+$ Forming of a Hydrazone:

(1'S,6'R)-7-chloro-4,6-dimethoxy-6'-methyl-2'-(pyridin-2-ylmethylamino)-3H-spiro[benzofuran-2,1'-cyclohex[2]ene]-3,4'-dione (0.755 mmol, 1 equiv.), hydrazinecarbothioamide (0.831 mmol, 1.1 equiv) and 2 mL of concentrated hydrochloric acid were dissolved in ethanol (20 mL). The reaction mixture was left under agitation at 70° C. for 3 h and then concentrated under reduced pressure. The residue was neutralised with saturated aqueous NaHCO₃ solution. The mixture formed was extracted with CH₂Cl₂ and the organic phase dried over Na₂SO₄, filtered and concentrated. The residue was purified on silica gel (CH₂Cl₂/MeOH 100:0 to 90:10) and led to the thiosemicarbazone and semicarbazone with respective yields of 3% and 35%.

(Z)-2-((1'S,6'R)-7-chloro-4,6-dimethoxy-6'-methyl-3-oxo-2'-(pyridin-2-ylmethylamino)-3H-spiro[benzofuran-2,1'-cyclohex[2]ene]-4'-ylidene)hydrazinecarbothioamide 218 yellow solid, 13 mg (3%); $^1$H NMR (400 MHz, CDCl₃, ppm): δ 0.94 (m, 3H), 2.37-2.45 and 3.05-3.14 (m, 1H), 2.60-2.75 (m, 2H), 3.96 (s, 3H), 4.05 and 4.06 (2s, 3H), 4.17-4.36 (m, 2H), 5.76 and 6.42 (2t, 1H, J=4.6 Hz), 6.18 (s, 1H), 6.33 and 6.49 (2sl, 1H), 7.13-7.25 (m, 3H), 7.61-7.68 (m, 1H), 8.45 (dd, 1H, J=15.0, 4.6 Hz), 8.60 and 8.95 (2sl, 1H); LCMS (ES, m/z): 501.9 [M+H]⁺.

(Z)-2-((1'S,6'R)-7-chloro-4,6-dimethoxy-6'-methyl-3-oxo-2'-(pyridin-2-ylmethylamino)-3H-spiro[benzofuran-2,1'-cyclohex[2]ene]-4'-ylidene)hydrazinecarboxamide 219 yellow solid, 131 mg (35%); $^1$H NMR (400 MHz, CDCl₃, ppm): δ 0.94 (m, 3H), 2.37-2.54 (m, 1H), 2.60-2.75 (m, 1H), 3.11 (m, 1H), 3.97 (s, 1H), 4.04 and 4.05 (2s, 3H), 4.16-4.34 (m, 2H), 5.30 (s, 3H), 5.31-5.41 (m, 1H), 5.93 (sl, 1H), 6.14 (d, 1H), 7.12-7.18 (m, 2H), 7.39 and 7.81 (2sl, 1H), 7.64 (m, 1H), 8.47 (dd, 1H, J=16.2, 4.6 Hz); LCMS (ES, m/z): 586.0 [M+H]⁺.

Reduction of the Carbonyl:

The carbonylated derivative (1.0 g; 1.0 equiv.) was diluted in a 1:1 THF/MeOH mixture (20 mL). NaBH₄ (100 mg, 1.0 eq.) was added to the solution at ambient temperature. The resulting reaction mixture was left under agitation at 25° C. for 1 h. The reaction medium was diluted in ethyl acetate (100 mL) and the organic phase successively washed with a saturated aqueous solution of bicarbonate (100 mL), of sodium hydroxide and brine (100 mL). The organic phase was dried over magnesium sulfate, filtered and the solvents evaporated under reduced pressure. The residue was purified on silica gel (CH₂Cl₂/AcOEt 1:1) to give the desired alcohol with a yield of 86%.

Alcohol Inversion:

DEAD (465 mg; 1.3 equiv.) was added to a solution of the alcohol (800 mg; 1.0 equiv.), triphenylphosphine (805 mg; 1.5 equiv.) and PNBA (377 mg; 1.1 equiv.) in THF (10 mL). The mixture was left under agitation 4 hours at ambient temperature. The solvents were evaporated and the residue purified on silica gel (cyclohexane/CH₂Cl₂/AcOEt 10:10:1) to give the desired ester in the form of a white solid with a yield of 82%. This product (1.135 g; 1.0 equiv.) was dissolved in a 1:1 THF/MeOH mixture (30 mL) to which potassium carbonate (306 mg; 1.05 equiv.) was added. After an agitation time of 3 hours the solvents were evaporated and the residue purified on silica gel (CH₂Cl₂/AcOEt 90:10) to give the inverted alcohol in the form of a white solid with a yield of 63%.

(2S,5'S,7'R)-7-chloro-5'-hydroxy-4,6-dimethoxy-2',7'-dimethyl-6',7'-dihydro-3H,5'H-spiro[benzofuran-2,8'-quinolin]-3-one and (2S,5'R,7'R)-7-chloro-5'-hydroxy-4,6-dimethoxy-2',7'-dimethyl-6',7'-dihydro-3H,5'H-spiro[benzofuran-2,8'-quinolin]-3-one R=Me 220 (obtained by reduction of the carbonyl) white solid, 86% yield; $^1$H NMR (400 MHz, CDCl₃, ppm): δ 7.82 (d, 1H, J=8.0 Hz), 7.06 (d, 1H, J=8.0 Hz), 6.12 (s, 1H), 4.82 (m, 1H), 4.04 (s, 3H), 3.95 (s, 3H), 2.52 (m, 2H), 2.35 (s, 3H), 2.19 (m, 1H), 1.02 (d, 3H, J=6.5 Hz); LCMS (ES, m/z): 389.94 [M+H]⁺

221 (obtained by inversion of the alcohol), white solid, 63% yield; $^1$H NMR (400 MHz, CDCl₃, ppm): δ 7.58 (d, 1H, J=8.0 Hz), 7.05 (d, 1H, J=8.2 Hz), 6.4 (bs, 1H), 6.11 (s, 1H), 4.90 (m, 1H), 4.03 (s, 3H), 3.95 (s, 3H), 2.98 (m, 1H), 2.78 (td, J=4.0, 14.0 Hz), 2.36 (s, 3H), 1.93 (dt, 1H, J=3.0, 14.00 Hz), 1.03 (d, 3H, J+7.0 Hz); LCMS (ES, m/z): 389.94 [M+H]⁺

(2S,5'S,7'R)-7-chloro-5'-hydroxy-4,6-dimethoxy-7'-methyl-2'-phenyl-6',7'-dihydro-3H,5'H-spiro[benzofuran-2,8'-quinolin]-3-one and (2S,5'R,7'R)-7-chloro-5'-hydroxy-4,6-dimethoxy-7'-methyl-2'-phenyl-6',7'-dihydro-3H,5'H-spiro[benzofuran-2,8'-quinolin]-3-one R=Ph 222 (obtained by reduction of the carbonyl), white solid, 63% yield; $^1$H NMR (400 MHz, CDCl₃, ppm): δ 8.01 (d, 1H, J=8.3 Hz), 7.78 (m, 2H), 7.68 (d, 1H, J=8.3 Hz), 7.32 (m, 3H), 6.12 (s, 1H), 4.89 (m, 1H), 4.06 (s, 3H), 3.94 (s, 3H), 2.62 (m, 2H), 2.27 (m, 1H), 2.13 (bs, 1H), 1.08 (d, 3H, J=6.0 Hz); LCMS (ES, m/z): 452.00 [M+H]⁺

223 (obtained by inversion of the alcohol), white solid, 83% yield; $^1$H NMR (400 MHz, CDCl₃, ppm): δ 7.76 (m, 2H), 7.71 (d, 1H, J=8.4 Hz), 7.61 (d, 1H, J=8.4 Hz), 7.32 (m, 3H), 6.08 (s, 1H), 4.96 (t, 1H, J=3.0 Hz), 4.01 (s, 3H), 3.89 (s, 3H), 3.05 (m, 1H), 2.87 (td, 1H, J=14.1, 3.6 Hz), 1.98 (m, 1H), 1.07 (d, 3H, J=6.7 Hz); LCMS (ES, m/z): 452.00 [M+H]⁺

(2'S,6R)-7'-chloro-4-hydroxy-4',6'-dimethoxy-6-methyl-2-phenyl-3,4,5,6-tetrahydro-2H,3'H-2,7'-spirobi[benzofuran]-3'-one 224 (reduction of 3) white solid, 31% yield; $^1$H NMR (400 MHz, CDCl₃, ppm): δ 7.29-7.17 (m, 5H), 5.80 (s, 1H), 5.52 (dd, 1H, J=10.5, 7.5 Hz), 4.47 (m, 1H), 3.86 (s, 3H, 3.69 (s, 3H), 3.16 (dd, 1H, J=15.5, 10.7 Hz), 2.89 (dd, 1H, J=15.5, 7.4 Hz), 2.66 (m, 1H), 2.44 (m, 1H), 2.17 (m, 1H), 2.08 (m, 1H), 0.86 (d, 3H, J=6.9 Hz); LCMS (ES, m/z): 424.90 [M-OH]⁺

2-((2'S,6R)-7'-chloro-4-hydroxy-4',6'-dimethoxy-6-methyl-3'-oxo-2-phenyl-3,4,5,6-tetrahydro-2H,3'H-2,7'-spirobi[benzofuran]-2-yl)ethyl acetate 225 (reduction of 13) white solid, 79% yield; $^1$H NMR (400 MHz, CDCl₃, ppm): δ 7.37 (d, 2H, J=7.7 Hz), 7.17 (t, 2H, J=7.7 Hz), 7.05 (t, 1H, J=7.7 Hz), 5.44 (s, 1H), 4.43 (m, 1H), 4.27 (m, 2H), 3.31 (s, 3H), 3.17 (s, 3H), 3.09 (d, 1H, J=15.4 Hz), 2.90 (d, 1H, J=15.4 Hz), 2.36 (m, 1H), 2.28 (m, 2H), 1.87 (m, 1H), 1.65 (s, 3H), 0.98 (d, 3H, J=6.7 Hz); LCMS (ES, m/z): 511.00 [M-OH]⁺

(1'S,6'R)-7-chloro-4'-hydroxy-4,6-dimethoxy-6'-methyl-2'-((pyridin-2-ylmethyl)amino)-3H-spiro[benzofuran-2,1'-cyclohex[2]en]-3-one 226 (obtained by reduction of the carbonyl), orange solid, 28 mg (15%); $^1$H NMR (400 MHz, DMSO-d₆, ppm): δ 1.10 (d, 3H, J=6.6 Hz), 2.08-2.18 (m, 1H), 2.60 (sl, 1H), 2.80 (sl, 1H), 3.84 (s, 3H), 3.89 (s, 3H), 4.22-4.36 (m, 2H), 4.74 (s, 1H), 5.57 (d, 1H, J=6.4 Hz), 6.13 (sl, 1H), 6.37 (s, 1H), 7.21 (dl, 1H, J=6.1 Hz), 7.27 (t, 1H, J=6.1 Hz), 7.77 (t, 1H, 7.4), 8.45 (d, 1H, J=4.4 Hz); LCMS (ES, m/z): 431.1 [M+H]⁺

(1'S,6'R)-7-chloro-4'-hydroxy-4,6-dimethoxy-6'-methyl-2'-((4-(4-methylpiperazin-1-yl)benzyl)amino)-3H-spiro[benzofuran-2,1'-cyclohex[2]en]-3-one 227 (obtained by reduction of the carbonyl), colourless solid, 31 mg (26%); $^1$H NMR (400 MHz, CDCl$_3$, ppm): δ 1.23 (d, 3H, J=6.9 Hz), 2.36 (s, 3H), 2.44 (dl, 1H, J=16.1 Hz), 2.58 (t, 4H, J=4.8 Hz), 2.75-2.85 (m, 1H), 3.01-3.12 (m, 1H), 3.20 (t, 4H, J=4.8 Hz), 3.85 (s, 3H), 3.91 (s, 3H), 4.11 (qd, 2H, J=14.6, 5.3 Hz), 5.01 (sl, 1H), 5.16 (s, 1H), 5.78 (s, 1H), 6.11 (s, 1H), 6.85 (d, 2H, J=8.5 Hz), 7.07 (d, 2H, J=8.5 Hz).

LCMS (ES, m/z): 528.1 [M+H]$^+$

Azide Substitution:

DBU (448 mg, 1.5 equiv.) was added to a solution of the alcohol (765 mg; 1.0 equiv.) and DPPA (810 mg; 1.5 equiv.) in THF (5 mL). The mixture was left under agitation at 60° C. for 2 hours and thirty minutes. The solvents were evaporated in vacuo and the residue purified on silica gel (CH$_2$Cl$_2$/Cylcohexane/AcOEt 50:50:5) to give the azide in the form of a white foam with a yield of 68%.

(2S,7'R)-5'-azido-7-chloro-4,6-dimethoxy-2',7'-dimethyl-6',7'-dihydro-3H,5'H-spiro[benzofuran-2,8'-quinolin]-3-one 228 white solid, 68% yield; $^1$H NMR (400 MHz, CDCl$_3$, ppm): δ 7.48 (d, 1H, J=8.0 Hz), 7.08 (d, 1H, J=8.0 Hz), 6.12 (s, 1H), 4.75 (m, 1H), 4.04 (s, 3H), 3.95 (s, 3H), 2.92 (m, 1H), 2.85 (td, 1H, J=13.0, 4.0 Hz), 2.38 (s, 3H), 1.87 (m, 1H), 1.01 (d, 3H, J=7.0 Hz); LCMS (ES, m/z): 414.94 [M+H]$^+$ Reduction of the Azide:

A mixture of the azide (500 mg, 1.0 equiv.) and palladium on carbon (10 weight %, 257 mg, 0.2 equiv.) was left under agitation in a hydrogen atmosphere (1 atm) for 1 hour. The reaction medium was then filtered on DICALITE® with ethyl acetate and the solvents evaporated. The residue was purified on silica gel (CH$_2$Cl$_2$/MeOH 95:5) to give the amine in the form of a white solid with a yield of 55%.

(2 S,7'R)-5'-amino-7-chloro-4,6-dimethoxy-2',7'-dimethyl-6',7'-dihydro-3H,5'H-spiro[benzofuran-2,8'-quinolin]-3-one 229 white solid, 55% yield; $^1$H NMR (400 MHz, CDCl$_3$, ppm): δ 7.54 (d, 1H, J=8.0 Hz), 7.02 (d, 1H, J=8.0 Hz), 6.11 (s, 1H), 4.15 (m, 1H), 4.03 (s, 3H), 3.95 (s, 3H), 2.87 (m, 1H), 2.80 (td, 1H, J=13.0, 4.0 Hz), 2.33 (s, 3H), 1.77 (bs, 2H), 1.75 (m, 1H), 1.03 (d, 3H, J=7.0 Hz); LCMS (ES, m/z): 388.97 [M+H]$^+$

(2S,7'R)-5'-amino-7-chloro-4,6-dimethoxy-7'-methyl-2'-phenyl-6',7'-dihydro-3H,5'H-spiro[benzofuran-2,8'-quinolin]-3-one R=Ph: 230 pale yellow solid, 61% yield; $^1$H NMR (400 MHz, CDCl$_3$, ppm): δ 7.99 (d, 1H, J=8.3 Hz), 7.75 (dd, 2H, 7.8, 2.0 Hz), 7.61 (d, 1H, J=8.3 Hz), 7.33-7.24 (m, 3H), 6.06 (s, 1H), 5.26 (s, 2H), 4.00 (dd, 1H, 10.8, 5.7 Hz), 3.98 (s, 3H), 3.85 (s, 3H), 2.61 (m, 1H), 2.48 (ddd, 1H, J=15.2, 13.0, 10.8 Hz), 2.05 (ddd, 1H, J=13.0, 7.5, 2.5 Hz), 1.04 (d, 3H, J=6.7 Hz); LCMS (ES, m/z): 450.90 [M+H]$^+$ 1.22. Functionalization at 2'

Reduction of the Carbonyl:

See procedure for carbonyl reduction at 4' (see: 1.21)

Inversion of the Alcohol:

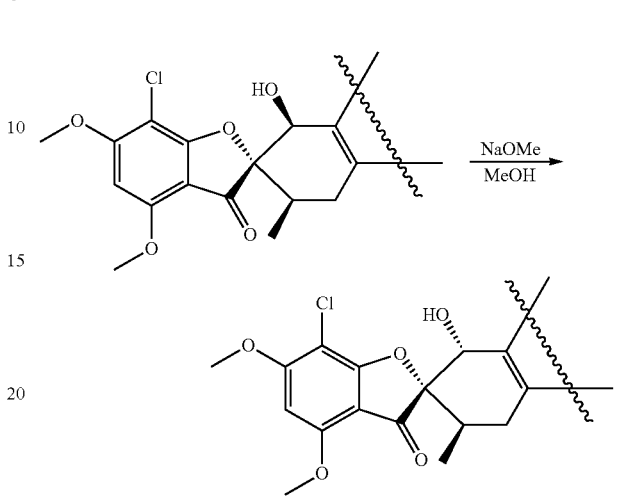

A 100 mL round-bottomed flask was charged with 1.0 g (1.8 mmol, 1 eq.) of 252 and 0.1 g (1.8 mmol, 1.04 eq.) of sodium methylate in 10 mL of methanol. The mixture was left under agitation at ambient temperature for 5 h, then acidified through the addition of 1N HCl solution. The precipitate was filtered, rinsed with cold methanol and dried. A beige solid (0.37 g) was obtained with a yield of 41%.

The following compounds were obtained by reducing the carbonyl unless otherwise indicated (when they were obtained by inversion of the alcohol).

(2S,7'R)-7-chloro-5'-hydroxy-4,6-dimethoxy-7'-methyl-3-oxo-7',8'-dihydro-3H,5'H-spiro[benzofuran-2,6'-quinoline]1'-oxide 231 white solid, 21% yield; $^1$H NMR (400 MHz, DMSO-d6, ppm): δ 8.20 (m, 1H), 7.32 (m, 2H), 6.55 (d, 1H, J=6.8 Hz), 6.42 (s, 1H), 5.1 (d, 1H, J=6.5 Hz), 4.02 (s, 3H), 3.87 (s, 3H), 3.20 (m, 1H), 2.73-2.60 (m, 2H), 0.87 (d, 3H, J=6.0 Hz); LCMS (ES, m/z): 391.90 [M+H]$^+$

(2S,7'R)-7-chloro-3,5'-dihydroxy-4,6-dimethoxy-7'-methyl-7',8'-dihydro-3H,5'H-spiro[benzofuran-2,6'-quinoline]1'-oxide 232 pale yellow solid, 82% yield; $^1$H NMR (400 MHz, DMSO-d6, ppm): δ 8.22 (dd, 1H, J=5.2, 2.2 Hz), 7.32 (m, 2H), 6.28 (s, 1H), 6.20 (d, 1H, J=5.9 Hz), 5.34 (m, 2H), 4.45 (bs, 1H), 3.84 (s, 3H), 3.80 (s, 3H), 2.98 (m, 2H), 2.64 (m, 1H), 1.20 (d, 3H, J=6.9 Hz); LCMS (ES, m/z): 394.00 [M+H]$^+$

(2S,7'R)-7-chloro-5'-hydroxy-4,6-dimethoxy-7'-methyl-7',8'-dihydro-3H,5'H-spiro[benzofuran-2,6'-quinolin]-3-one 233 pale yellow solid, 40% yield; $^1$H NMR (400 MHz, CD$_3$CN, ppm): δ 8.44 (d, 1H, J=4.7 Hz), 7.81 (d, 1H, J=8.0 Hz), 7.23 (dd, 1H, J=8.0, 4.7 Hz), 6.32 (s, 1H), 5.15 (d, 1H, J=6.0 Hz), 4.37 (d, 1H, J=6.0 Hz), 4.03 (s, 3H), 3.91 (s, 3H), 3.19 (dd, 1H, J=17.8, 12.0 Hz), 3.09 (dd, 1H, J=17.8, 6.4 Hz), 2.68 (m, 1H), 0.93 (d, 3H, J=6.6 Hz); LCMS (ES, m/z): 376.00 [M+H]+

(2S,4'S,6'R)-7-chloro-4'-hydroxy-4,6-dimethoxy-3'-(2-methoxyphenyl)-2',6'-dimethyl-2',4',6',7'-tetrahydro-3H-spiro[benzofuran-2,5'-indazol]-3-one and (2S,4'R,6'R)-7-chloro-4'-hydroxy-4,6-dimethoxy-3'-(3-methoxyphenyl)-2',6'-dimethyl-2',4',6',7'-tetrahydro-3H-spiro[benzofuran-2,5'-indazol]-3-one 234 off-white solid, yield 57%; $^1$H NMR (400 MHz, CDCl$_3$, ppm): δ 7.40-7.42 (1H, q), 7.21-7.38 (1H, dd), 7.00-7.07 (1H, t), 6.96-6.98 (1H, d, J=8.4 Hz), 6.05 (1H, s), 5.21-5.23 (1H, d, J=8.8 Hz), 3.99 (3H, s), 3.93 (3H, s), 3.85 (2H, s), 3.79 (1H, s), 3.73 (2H, s), 3.65 (1H, s), 3.12-3.24 (1H, m), 2.90-2.96 (1H, m), 2.70-2.72 (1H, m), 1.28-1.29 (3H, s); LCMS (ES, m/z): 485 [M+H]+

235 white solid, yield 46%; $^1$H NMR (300 MHz, CDCl$_3$, ppm): 7.45-7.3 (m, 1H), 7.0-6.0 (m, 3H), 6.06 (s, 1H), 5.25 (s, 1H), 4.0-3.9 (2s, 6H), 3.8-3.75 (2s, 6H), 3.2-3.1 (m, 1H), 3.0-2.9 (m, 1H), 2.7-2.6 (m, 1H), 2.10 (m, 1H), 1.10 (d, 3H); LCMS (ES, m/z): 485 [M+H]+

(2 S,6'R)-7-chloro-4'-hydroxy-4,6-dimethoxy-3'-(4-methoxyphenyl)-2',6'-dimethyl-2',4',6',7'-tetrahydro-3H-spiro[benzofuran-2,5'-indazol]-3-one 236 yellow solid, yield 60%; $^1$H NMR (400 MHz, CDCl$_3$, ppm): 7.35 (d, 2H), 6.95 (d, 2H) 6.06 (s, 1H), 5.25 (s, 1H), 4.0 (s, 3H), 3.93 (s, 3H), 3.83 (s, 3H), 3.77 (s, 3H), 3.2-3.1 (m, 1H), 2.95-2.9 (m, 1H), 2.7-2.6 (m, 1H), 2.0 (m, 1H), 1.1 (d, 3H); LCMS (ES, m/z): 485.00 [M+H]+

(2S,6'R)-7-chloro-3'-(2-chlorophenyl)-4'-hydroxy-4,6-dimethoxy-2',6'-dimethyl-2',4',6',7'-tetrahydro-3H-spiro[benzofuran-2,5'-indazol]-3-one 237 yellow solid, yield 50%; $^1$H NMR (400 MHz, CDCl$_3$, ppm): 7.52 (d, 1H), 7.40-7.25 (m, 3H), 6.06 (s, 1H), 5.25 (m split, 1H), 4.0 (s, 3H), 3.94 (s split, 3H), 3.65 (s split, 3H), 3.25-3.15 (m, 1H), 2.95-2.83 (m, 1H), 2.72-2.62 (m, 1H), 1.80-1.65 (m, 1H), 1.04 (d split, 3H); LCMS (ES, m/z): 488.80 [M+H]+

(2S,6'R)-7-chloro-3'-(3-chlorophenyl)-4'-hydroxy-4,6-dimethoxy-2',6'-dimethyl-2',4',6',7'-tetrahydro-3H-spiro[benzofuran-2,5'-indazol]-3-one 238 beige solid, 60% yield; $^1$H NMR (300 MHz, CDCl$_3$, ppm): 7.41 (s, 1H), 7.35-7.25 (m, 3H), 6.05 (s, 1H), 5.20 (s, 1H), 4.0 (s, 3H), 3.93 (s, 3H), 3.75 (s, 3H), 3.1-3.0 (m, 1H), 2.9-2.8 (m, 1H), 2.65-2.5 (m, 2H), 1.1 (d, 3H); LCMS (ES, m/z): 488.90 [M+H]+

(2S,6'R)-7-chloro-3'-(4-chlorophenyl)-4'-hydroxy-4,6-dimethoxy-2',6'-dimethyl-2',4',6',7'-tetrahydro-3H-spiro[benzofuran-2,5'-indazol]-3-one 239 white solid, yield 40%; $^1$H NMR (300 MHz, DMSO-d$_6$, ppm): 7.45 (m, 4H), 6.37 (s, 1H), 5.4 (1s, 1H), 5.20 (s, 1H), 3.98 (s, 3H), 3.85 (s, 3H), 3.65 (s, 3H), 3.1-3.0 (m, 1H), 2.9-2.5 (m, 3H), 0.82 (d, 3H); LCMS (ES, m/z): 488.95 [M+H]+

(2S,6'R)-7-chloro-3'-(3-fluorophenyl)-4'-hydroxy-4,6-dimethoxy-2',6'-dimethyl-2',4',6',7'-tetrahydro-3H-spiro[benzofuran-2,5'-indazol]-3-one 240 white solid, yield 57%; $^1$H NMR (300 MHz, CDCl$_3$, ppm): 7.45-7.05 (m, 4H), 6.05 (s, 1H), 5.22 (s, 1H), 4.0 (s, 3H), 3.90 (2s, 3H), 3.83 (s, 3H), 3.10-3.00 (m, 1H), 2.92-2.85 (m, 1H), 2.65-2.55 (m, 1H), 2.38 (m, 1H), 1.06 (d, 3H); LCMS (ES, m/z): 472.85 [M+H]+

(2S,6'R)-7-chloro-3'-(4-fluorophenyl)-4'-hydroxy-4,6-dimethoxy-2',6'-dimethyl-2',4',6',7'-tetrahydro-3H-spiro[benzofuran-2,5'-indazol]-3-one 241 white solid, yield 40%; $^1$H NMR (CDCl$_3$, 300 MHz, δ, ppm): 7.45-7.35 (m, 2H), 7.15-7.10 (m, 2H), 6.05 (s, 1H), 5.21 (s, 1H), 4.0 (s, 3H), 3.91 (2s, 3H), 3.75 (s, 3H), 3.15-3.00 (m, 1H), 3.00-2.85 (m, 1H), 2.65-2.55 (m, 1H), 2.4-2.2 (m, 1H), 1.08 (d, 3H); LCMS (ES, m/z): 472.90 [M+H]+

(2 S,6'R)-7-chloro-4'-hydroxy-4,6-dimethoxy-2',6'-dimethyl-3'-phenyl-2',4',6',7'-tetrahydro-3H-spiro[benzofuran-2,5'-indazol]-3-one 242 beige solid, yield 50%; $^1$H NMR (CDCl$_3$, 400 MHz, δ, ppm): 7.5-7.4 (m, 5H), 6.08 (s, 1H), 5.27 (s, 1H), 4.0 (s, 3H), 3.95 (s, 3H), 3.8 (s, 3H), 3.2-3.1 (m, 1H), 3.0-2.9 (m, 1H), 2.7-2.6 (m, 1H), 2.0 (m, 1H), 1.1 (d, 3H); LCMS (ES, m/z): 454.95 [M+H]+ tert-butyl 4-((2S,6'R)-7-chloro-4'-hydroxy-4,6-dimethoxy-2',6'-dimethyl-3-oxo-2',4',6',7'-tetrahydro-3H-spiro[benzofuran-2,5'-indazole]-3'-yl)piperidine-1-carboxylate 243 white solid, yield 40%; $^1$H NMR (CD$_3$OD, 400 MHz, δ, ppm): 6.36 (s, 1H), 5.15 (s, 1H), 4.25-4.10 (m, 2H), 4.04 (s, 3H), 3.95 (s, 3H), 3.82 (s, 3H), 3.10-2.90 (m, 2H), 2.90-2.80 (m, 2H), 2.75-2.65 (m, 1H), 2.60-2.50 (m, 1H), 2.25-2.15 (m, 1H), 2.05-1.90 (m, 1H), 1.75-1.65 (m, 2H), 1.40 (s, 9H), 0.90 (d, 3H); LCMS (ES, m/z): 561.90 [M+H]+

(2S,6'R)-7-chloro-4'-hydroxy-4,6-dimethoxy-2',6'-dimethyl-3'-(piperidin-4-yl)-2',4',6',7'-tetrahydro-3H-spiro[benzofuran-2,5'-indazol]-3-one 244 $^1$H NMR (CD$_3$OD, 400 MHz, δ, ppm): 6.38 (s, 1H), 5.18 (s, 1H), 4.04 (s, 3H), 3.95 (s, 3H), 3.84 (s, 3H), 3.55-3.40 (m, 2H), 3.30-3.05 (m, 3H), 3.0-2.9 (m, 1H), 2.80-2.70 (m, 1H), 2.60-2.40 (m, 2H), 2.05-1.90 (m, 2H), 0.90 (d, 3H); LCMS (ES, m/z): 462 [M+H]+

(2 S,6'R)-7-chloro-4'-hydroxy-4,6-dimethoxy-2',6'-dimethyl-3'-(4-methylthiazol-2-yl)-2',4',6',7'-tetrahydro-3H-spiro[benzofuran-2,5'-indazol]-3-one 245 white solid, yield 20%; $^1$H NMR (CDCl$_3$, 400 MHz, δ, ppm): 6.97 (s, 1H), 6.10 (s, 1H), 5.37 (s, 1H), 4.16 (s, 3H), 3.99 (s, 3H), 3.90 (s, 3H), 3.30-3.18 (m, 1H), 2.85-2.77 (m, 1H), 2.70-2.58 (m, 1H), 2.42 (s, 3H), 1.02 (d, 3H); LCMS (ES, m/z): 498 [M+Na]+

(2S,6'R)-7-chloro-4'-hydroxy-4,6-dimethoxy-2',6'-dimethyl-3'-(2-methylthiazol-4-yl)-2',4',6',7'-tetrahydro-3H-spiro[benzofuran-2,5'-indazol]-3-one 246 white solid, yield 75%; $^1$H NMR (CDCl$_3$, 400 MHz, δ, ppm): 6.80 (s, 1H), 6.07 (s, 1H), 5.30 (s, 1H), 4.03 (s, 3H), 3.98 (s, 3H), 3.90 (s, 3H), 3.25-3.18 (m, 1H), 2.81-2.77 (m, 1H), 2.70-2.50 (s+m, 4H), 1.02 (d, 3H); LCMS (ES, m/z): 475.85 [M+H]$^+$ (2S,6'R)-7-chloro-4'-hydroxy-4,6-dimethoxy-2',6'-dimethyl-2',4',6',7'-tetrahydro-3H-spiro[benzofuran-2,5'-indazol]-3-one 247 white solid, yield 50%; $^1$H NMR (CD$_3$CN, 400 MHz, δ, ppm): 0.90 (d, 3H, J=6.8 Hz), 2.56 (m, 1H), 2.80 (m, 2H), 3.75 (1 Hd, 1H, J=6.0 Hz), 3.82 (s, 3H), 3.93 (s, 3H), 4.03 (s, 3H), 5.11 (d, 1H, J=6.0 Hz), 6.31 (s, 1H), 7.34 (s, 1H); LCMS (ES, m/z): 378.96 [M+H]$^+$ (2S,6'R)-7-chloro-4'-hydroxy-4,6-dimethoxy-6'-methyl-2'-phenyl-2',4',6',7'-tetrahydro-3H-spiro[benzofuran-2,5'-indazol]-3-one 248 solid, yield 60%; $^1$H NMR (DMSO-d6, 400 MHz, δ, ppm): 8.24 (s, 1H), 7.82-7.80 (m, 2H), 7.50-7.45 (m, 2H), 7.30-7.25 (m, 1H), 6.45 (s, 1H), 5.95 (1s, 1H), 5.10 (s, 1H), 4.05 (s, 3H), 3.90 (s, 3H), 2.9-2.8 (m, 2H), 2.7-2.6 (m, 1H), 0.85 (d, 3H); LCMS (ES, m/z): 441.15 [M+H]$^+$ (2S,7'R)-7-chloro-5'-hydroxy-4,6-dimethoxy-2',7'-dimethyl-7',8'-dihydro-3H,5'H-spiro[benzofuran-2,6'-quinolin]-3-one 249 beige solid, yield 92%; $^1$H NMR (CD$_3$CN, 400 MHz, δ, ppm): 0.92 (d, 3H, J=6.4 Hz), 2.49 (s, 3H), 2.65 (m, 1H), 3.02 (dd, 1H, J=17.6, 6.4 Hz), 3.14 (dd, 1H, J=17.6, 11.9 Hz), 3.92 (s, 3H), 4.03 (s, 3H), 5.12 (d, 1H, J=5.5 Hz), 5.12 (d, 1H, J=5.5 Hz), 6.32 (s, 1H), 7.09 (d, 1H, J=8.3 Hz), 7.68 (d, 1H, J=8.3 Hz); LCMS (ES, m/z): 389.9 [M+H]$^+$ (2 S,7'R)-7-chloro-2'-ethyl-5'-hydroxy-4,6-dimethoxy-7'-methyl-7',8'-dihydro-3H,5'H-spiro[benzofuran-2,6'-quinolin]-3-one 250 white solid, yield 44%; $^1$H NMR (CD$_3$CN, 400 MHz, δ, ppm): 0.93 (d, 3H, J=6.8 Hz), 1.29 (t, 3H, J=7.6 Hz), 2.66 (m, 1H), 2.78 (q, 2H, J=7.6 Hz), 3.03 (dd, 1H, J=18.0, 6.4 Hz), 3.16 (dd, 1H, J=18.0, 12.0 Hz), 3.92 (s, 3H), 4.03 (s, 3H), 4.26 (d, 1H, J=6.0 Hz), 5.12 (d, 1H, J=6.0 Hz), 6.32 (s, 1H), 7.11 (d, 1H, J=8.0 Hz), 7.71 (d, 1H, J=8.0 Hz); LCMS (ES, m/z): 403.95 [M+H]$^+$ (2S,7'R)-7-chloro-5'-hydroxy-4,6-dimethoxy-2',7'-dimethyl-3-oxo-7',8'-dihydro-3H,5'H-spiro[benzofuran-2,6'-quinoline]1'-oxide 251 brown solid, yield 27%; $^1$H NMR (CD$_3$CN, 400 MHz, δ, ppm): 0.98 (d, 3H, J=6.4 Hz), 2.45 (s, 3H), 2.62 (m, 1H), 2.80 (dd, 1H, J=18.8, 11.6 Hz), 3.33 (dd, 1H, J=18.0, 5.2 Hz), 3.92 (s, 3H), 4.04 (s, 3H), 4.49 (m, 1H), 5.12 (m, 1H), 6.33 (s, 1H), 7.29 (d, 1H, J=8.6 Hz), 7.32 (d, 1H, J=8.6 Hz); LCMS (ES, m/z): 405.95 [M+H]$^+$ (2S,5'S,7'R)-methyl 7-chloro-5'-hydroxy-4,6-dimethoxy-7'-methyl-3-oxo-4'-phenyl-7',8'-dihydro-3H,5'H-spiro[benzofuran-2,6'-quinoline]-2'-carboxylate and (2S,5'R7'R)-methyl 7-chloro-5'-hydroxy-4,6-dimethoxy-7'-methyl-3-oxo-4'-phenyl-7',8'-dihydro-3H,5'H-spiro[benzofuran-2,6'-quinoline]-2'-carboxylate 252 white solid, yield 28%; $^1$H NMR (CDCl$_3$, 400 MHz, δ, ppm): 1.14 (d, 3H, J=6.8 Hz), 2.44 (d, 1H, J=4.4 Hz), 2.65 (m, 1H), 3.33 (dd, 1H, J=18.0, 6.0 Hz), 3.64 (dd, 1H, J=18.0, 10.8 Hz), 3.90 (s, 3H), 3.97 (s, 3H), 4.02 (s, 3H), 5.43 (d, 1H, J=4.0 Hz), 6.04 (s, 1H), 7.41 (m, 5H), 7.90 (s, 1H); LCMS (ES, m/z): 509.95 [M+H]$^+$ 253 (obtained by inversion of the alcohol)$^1$H NMR (CDCl$_3$, 400 MHz, δ, ppm): 0.95 (d, 3H, J=6.4 Hz), 2.25 (br s, 1H), 2.61 (m, 1H), 3.28 (dd, 1H, J=18.0, 5.2 Hz), 3.39 (dd, 1H, J=18.0, 12.4 Hz), 3.94 (s, 3H), 3.96 (s, 3H), 4.03 (s, 3H), 5.59 (m, 1H), 6.05 (s, 1H), 7.41 (m, 5H), 7.91 (s, 1H); LCMS (ES, m/z): 510 [M+H]$^+$ (2S,7'R)-7-chloro-5'-hydroxy-4,6-dimethoxy-7'-methyl-3-oxo-4'-phenyl-7',8'-dihydro-3H,5'H-spiro[benzofuran-2,6'-quinoline]-2'-carboxamide 254 white solid, yield 31%; $^1$H NMR (CDCl$_3$, 400 MHz, δ, ppm): 1.13 (d, 3H, J=6.8 Hz), 2.40 (d, 1H, J=4.8 Hz), 2.67 (m, 1H), 3.19 (dd, 1H, J=17.6, 6.0 Hz), 3.57 (dd, 1H, J=17.6, 11.2 Hz), 5.46 (d, 1H, J=4.0 Hz), 5.62 (br s, 1H), 6.03 (s, 1H), 7.40 (m, 5H), 7.93 (br s, 1H), 7.95 (s, 1H); LCMS (ES, m/z): 495 [M+H]$^+$ (2S,7'R)-methyl 7-chloro-5'-hydroxy-4,6-dimethoxy-7'-methyl-3-oxo-4'-(thiophen-3-yl)-7',8'-dihydro-3H,5'H-spiro[benzofuran-2,6'-quinoline]-2'-carboxylate 255 beige solid, yield 69%; $^1$H NMR (CDCl$_3$, 400 MHz, δ, ppm): 1.23 (d, 3H, J=7.2 Hz), 2.59 (m, 1H), 3.20 (d, 1H, J=3.6 Hz), 3.39 (dd, 1H, J=18.0, 6.0 Hz), 3.56 (dd, 1H, J=18.0, 9.2 Hz), 3.93 (s, 3H), 3.98 (s, 3H), 4.02 (s, 3H), 5.27 (d, 1H, J=3.2 Hz), 6.06 (s, 1H), 7.29 (m, 1H), 7.43 (dd, 1H, J=5.2, 3.2 Hz), 7.63 (m, 1H), 7.99 (s, 1H); LCMS (ES, m/z): 516 [M+H]$^+$ (2S,7'R)-methyl 7-chloro-4'-(4-fluorophenyl)-5'-hydroxy-4,6-dimethoxy-7'-methyl-3-oxo-7',8'-dihydro-3H,5'H-spiro[benzofuran-2,6'-quinoline]-2'-carboxylate 256 white solid, yield 91%; $^1$H NMR (CDCl$_3$, 400 MHz, δ, ppm): 1.16 (d, 3H, J=7.2 Hz), 2.60 (m, 1H), 2.66 (d, 1H, J=4.8 Hz), 3.33 (dd, 1H, J=18.0, 6.4 Hz), 3.60 (dd, 1H, J=18.0, 10.4 Hz), 3.90 (s, 3H), 3.98 (s, 3H), 4.02 (s, 3H), 5.27 (d, 1H, J=4.4 Hz), 6.05 (s, 1H), 7.09 (t, 2H, J=8.4 Hz), 7.37 (m, 2H), 7.87 (s, 1H); LCMS (ES, m/z): 528 [M+H]$^+$ (2S,7'R)-isopropyl 7-chloro-5'-hydroxy-4,6-dimethoxy-7'-methyl-3-oxo-4'-phenyl-7',8'-dihydro-3H,5'H-spiro[benzofuran-2,6'-quinoline]-2'-carboxylate 257 white solid, yield 42%; $^1$H NMR (CDCl$_3$, 400 MHz, δ, ppm): 1.14 (d, 3H, J=6.8 Hz), 1.39 (d, 3H, J=4.4 Hz), 1.41 (d, 3H, J=4.4 Hz), 2.46 (d, 1H, J=4.4 Hz), 2.62 (m, 1H), 3.35 (dd, 1H, J=17.6, 6.0 Hz), 3.63 (dd, 1H, J=17.6, 10.8 Hz), 3.90 (s, 3H), 3.97 (s, 3H), 5.33 (sept., 1H, J=6.4 Hz), 5.37 (d, 1H, J=4.4 Hz), 6.04 (s, 1H), 7.40 (m, 5H), 7.81 (s, 1H); LCMS (ES, m/z): 538 [M+H]$^+$ (2S,7'R)-butyl 7-chloro-5'-hydroxy-4,6-dimethoxy-7'-methyl-3-oxo-4'-phenyl-7',8'-dihydro-3H,5'H-spiro[benzofuran-2,6'-quinoline]-2'-carboxylate 258 white solid, yield 35%; $^1$H NMR (CDCl$_3$, 400 MHz, δ, ppm): 0.97 (t, 3H, J=7.2 Hz), 1.41 (d, 3H, J=7.2 Hz), 1.45 (sex., 2H, J=7.6 Hz), 1.79 (quint., 2H, J=7.2 Hz), 2.45 (d, 1H, J=4.4 Hz), 2.64 (m, 1H), 3.34 (dd, 1H, J=18.0, 6.0 Hz), 3.63 (dd, 1H, J=18.0, 11.2 Hz), 3.90 (s, 3H), 3.97 (s, 3H), 4.42 (t, 2H, J=6.8 Hz), 5.40 (d, 1H, J=4.4 Hz), 6.04 (s, 1H), 7.40 (m, 5H), 7.84 (s, 1H); LCMS (ES, m/z): 552 [M+H]+

(2S,7'R)-methyl 4'-([1,1'-biphenyl]-4-yl)-7-chloro-5'-hydroxy-4,6-dimethoxy-7'-methyl-3-oxo-6',7'-dihydro-3H,5'H-spiro[benzofuran-2,8'-quinoline]-2'-carboxylate 259 white solid, yield 75%; 1H NMR (CDCl3, 400 MHz, δ, ppm): 1.09 (d, 3H, J=6.8 Hz), 2.31 (m, 1H), 2.47 (m, 1H), 2.63 (m, 1H), 3.88 (s, 3H), 3.96 (s, 3H), 4.07 (s, 3H), 4.33 (d, 1H, J=10.0 Hz), 5.10 (m, 1H), 6.18 (s, 1H), 7.39 (m, 1H), 7.47 (m, 2H), 7.67 (m, 6H), 8.04 (s, 1H); LCMS (ES, m/z): 586 [M+H]+

Substitution of the Alcohol:

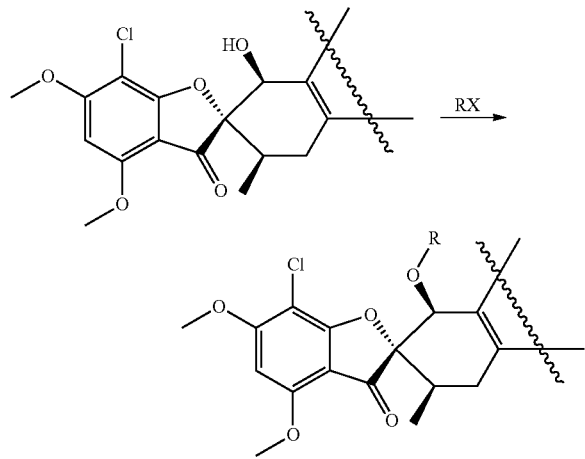

Example: R=Bn

In a 50 mL round-bottomed flask, 8.3 mg (0.2 mmol, 1.2 eq.) of sodium hydride was added to a solution of (2S,5'S,7'R)-7-chloro-5'-hydroxy-4,6-dimethoxy-2',7'-dimethyl-7',8'-dihydro-3H,5'H-spiro[benzofuran-2,6'-quinolin]-3-one (68 mg, 0.17 mmol, 1 eq.) in 1 mL of DMF. The mixture was left under agitation at ambient temperature for 3 min. 23 μL (0.19 mmol, 1.1 eq.) of benzyl bromide were added to the solution and the mixture left under agitation at ambient temperature for 1 h. 5 mL of water were added to the mixture and the aqueous phase extracted with AcOEt. The organic phases were combined, dried over Na2SO4, filtered and concentrated under reduced pressure. The residue was purified by chromatography on silica gel (CH2Cl2/MeOH 99:1 to 98:2). After precipitation in dioxane/4N HCl a white solid (16 mg) was obtained with a yield of 18%.

(2S,7'R)-7-chloro-4,5',6-trimethoxy-2',7'-dimethyl-7',8'-dihydro-3H,5'H-spiro[benzofuran-2,6'-quinolin]-3-one 260 white solid, yield 41%; 1H NMR (CD3CN, 400 MHz, δ, ppm): 0.82 (d, 3H, J=6.3 Hz), 2.49 (s, 3H), 2.57 (m, 1H), 2.81 (dd, 1H, J=17.6, 12.6 Hz), 3.01 (dd, 1H, J=17.6, 6.3 Hz), 3.44 (s, 3H), 4.00 (s, 3H), 4.03 (s, 3H), 4.80 (s, 1H), 6.36 (s, 1H), 7.11 (d, 1H, J=8.6 Hz), 7.66 (d, 1H, J=8.6 Hz); LCMS (ES, m/z): 403.98 [M+H]+

(2S,7'R)-5'-(benzyloxy)-7-chloro-4,6-dimethoxy-2',7'-dimethyl-7',8'-dihydro-3H,5'H-spiro[benzofuran-2,6'-quinolin]-3-one 261 1H NMR (CD3CN, 400 MHz, δ, ppm): 0.82 (m, 3H), 2.71 (s, 3H), 2.85 (m, 1H), 3.52 (m, 1H), 3.98 (s, 3H), 4.03 (s, 3H), 4.45 (d, 1H, J=10.6 Hz), 4.83 (d, 1H, J=10.6 Hz), 5.21 (s, 1H), 6.49 (s, 1H), 7.08 (m, 2H), 7.25 (m, 3H), 7.68 (m, 1H), 8.24 (m, 1H); LCMS (ES, m/z): 480.02 [M+H]+

EXAMPLE 2

Cytotoxic Activity of the Compounds of the Invention

Culture of Lines and Measurement of Cell Viability:

The lines N1E115 (ATCC, CRL2263), MDA-MB-231 (ATCC, HTB26) and HSC-1 (Health Science Research Resources Bank, JCRB1015) were cultured in DMEM medium (Dulbecco's Modified Eagle Medium) supplemented with 2 mM of L-Glutamine (Sigma, G7513) and 10% foetal calf serum (Hyclone, SH30109.03) or 20% for the HSC-1 cells. The HCC-1937 (ATCC, CRL2336) and A549 (ATCC, CCL185) lines were cultured in RPMI medium (Roswell Park Memorial Institute Medium) supplemented with 10% foetal calf serum and 2 mM of L-Glutamine. Finally, the SCC114 (DSMZ, ACC662) line was cultured in MEM medium (Minimum Essential Medium Eagle) supplemented with 10% foetal calf serum and 2 mM of L-Glutamine. Initially, in 96-well plates (Perkin Elmer, 6005668), the cells were seeded in their respective culture media with 750 cells per well for N1E115; 1000 cells per well for SCC114 and A549; 2000 cells per well for HCC-1937 and HSC-1; 2500 cells per well for MDA-MB-231. Cascade dilution of each compound was performed in dimethylsulfoxide (DMSO) (Sigma, D8418) from 10 mM stock solutions in 100% DMSO. Each of the dilutions was added to the cells 24 hours after seeding. Under these conditions the final solvent concentration was 0.1% DMSO. Reading of cell proliferation was conducted 72 hours after addition of products with the ATPLite kit (Perkin Elmer, 6016947) and following the manufacturer's directions except in the case of the HCC-1937 line for which this reading was carried out 48 hours after treatment. Analysis of proliferation results was performed by comparing with conditions in which solely the vehicle was added to the cells. The dose-response curves obtained were analysed using Prism 4.03 software (GraphPad Software Inc.) to determine the concentration of each compound allowing 50% inhibition of cell proliferation ($IC_{50}$).

As examples, the cytotoxic properties of some compounds of the invention evaluated on the lines A549 (lung cancer cell line), MDA-MB-231 line (mammary adenocarcinoma cell line), N1E115 (mouse brain neuroblastoma cell line), HCC-1937 line (primary ductam breast carcinoma cell line), HSC-1 (cutaneous squamous carcinoma cell line) and SCC114 line (oral squamous carcinoma cell line) are reported in Table 1, as compared with griseofulvin used as control product. The concentration values are expressed in micromolar units (μM).

TABLE 1

| | $IC_{50}$ (μM) | | | | | |
|---|---|---|---|---|---|---|
| Compound | N1E-115 | MDA-MB-231 | SCC114 | HCC1937 | HSC-1 | A549 |
| Griseofulvin | >10 | >10 | 6.4 | >10 | >10 | >10 |
| GF-15* | 1.1 | 1 | 0.98 | >10 | 4.3 | 2.9 |
| 97 | | | 0.021 | | 0.14 | |
| 130 | | | 0.14 | | 0.25 | |
| 35 | | 0.25 | 0.17 | >10 | 0.38 | |
| 34 | | 0.18 | 0.21 | >10 | 0.45 | 0.072 |
| 165 | | 0.17 | 0.23 | >10 | 0.5 | |
| 149 | 0.21 | 0.34 | 0.23 | >10 | 0.72 | 0.24 |
| 95 | 1 | 0.54 | 0.25 | 0.43 | 0.32 | 0.25 |

TABLE 1-continued

| Compound | N1E-115 | MDA-MB-231 | SCC114 | HCC1937 | HSC-1 | A549 |
|---|---|---|---|---|---|---|
| 252 | 0.2 | 0.38 | 0.32 | >10 | 0.52 | 0.25 |
| 217 | 0.73 | 0.63 | 0.33 | >10 | 1.3 | 0.36 |
| 255 |  | 0.22 | 0.38 | >10 | 0.77 |  |
| 5 | 0.25 | 0.86 | 0.38 | >10 |  | 0.95 |
| 145 | 3 | 2 | 0.385 | 1.4 | 1.4 | 1.5 |
| 98 |  |  | 0.41 |  | 0.76 |  |
| 249 | 0.26 | 0.34 | 0.42 | >10 | 0.88 | 0.55 |
| 164 |  | 1.4 | 0.43 | >10 | >10 | 0.45 |
| 37 |  | 0.27 | 0.47 | >10 | 1.4 |  |
| 135 |  |  | 0.51 |  | 1.3 |  |
| 257 |  | 0.43 | 0.51 | >10 | 2.4 |  |
| 256 |  | 0.33 | 0.51 | >10 | 0.84 |  |
| 3 | 0.21 | 0.45 | 0.52 | >10 | 6 | 0.25 |
| 250 | 1.4 | 0.35 | 0.54 | >10 | 1.9 | 1.4 |
| 46 | 0.22 |  | 0.57 | >10 | 0.79 | 0.86 |
| 205 |  | 11.2 | 0.62 |  | >10 | 9.2 |
| 152 | 0.62 | 1.6 | 0.71 | >10 | 10 | 0.48 |
| 93 | 3.6 | 1.5 | 0.72 | >10 | 0.62 | 2.3 |
| 115 |  | 0.64 | 0.73 | >10 | 1.3 |  |
| 126 |  |  | 0.73 |  | 2.3 |  |
| 14 |  | 0.46 | 0.74 | >10 | 0.86 | 0.44 |

*compound 15 of *J. Med. Chem.* 2009, 3342-3347
nd = not determined

The invention claimed is:

1. A compound of formula (I):

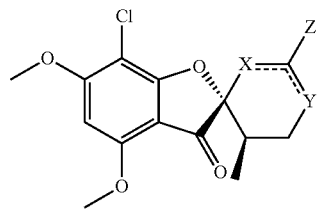

(I)

or a pharmaceutically acceptable salt thereof,
wherein:

represents

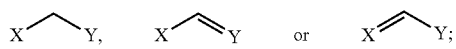

and

Y, together with Z and the carbon atom which carries Y and Z, forms an optionally substituted first carbocycle or first heterocycle,

represents

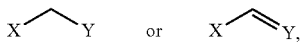

and X is $C=O$, $C=S$, $CH_2$, $CH-OR_1$, $CHN_3$, $CHNR_2R_3$, $C=N-OR_4$ or $C=N-NR_5R_6$; or X, together with Z and the carbon atom which carries X and Z, forms an optionally substituted second carbocycle or second heterocycle,

represents

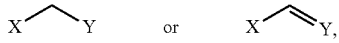

and Y is $C=O$, $C=S$, $CH_2$, $CH-OR_7$, $CHN_3$, $CHNR_8R_9$, $C=N-OR_{10}$ or $C=N-NR_{11}R_{12}$, wherein:

$R_1$ to $R_5$ and $R_7$ to $R_{11}$ each independently represent a hydrogen atom or a $(C_1-C_6)$alkyl, aryl, $(C_1-C_6)$alkyl-aryl or aryl-$(C_1-C_6)$alkyl group; and $R_6$ and $R_{12}$ each independently represent a hydrogen atom or a $(C_1-C_6)$alkyl, aryl, $(C_1-C_6)$alkyl-aryl, aryl-$(C_1-C_6)$alkyl, $C(O)NH_2$ or $C(S)NH_2$ group, and the compound is not one of the following compounds:

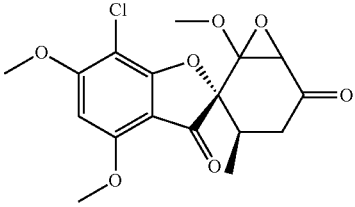

and

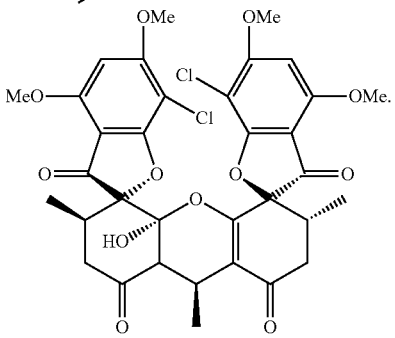

2. The compound according to claim 1, wherein:

Y, together with Z and the carbon atom which carries Y and Z, forms an optionally substituted first carbocycle or first heterocycle,

represents

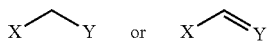

and
X is C=O or CH—OR$_1$; or
X, together with Z and the carbon atom which carries X and Z, forms an optionally substituted second carbocycle or second heterocycle,

represents

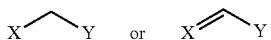

and Y is C=O or CH—OR$_7$.

3. The compound according to claim 1, wherein the compound comprises the first or second heterocycle comprising 1 or 2 heteroatoms selected from N, O and S and comprising 1 or 2 saturated, unsaturated or aromatic fused rings, each ring having 3 to 8 members.

4. The compound according to claim 1, wherein the compound comprises the first or second heterocycle selected from epoxide, aziridine, furan, dihydrofuran, tetrahydrofuran, pyrrole, pyroline, pyrrolidine, pyrazole, pyrazoline, pyrazolidine, imidazole, imidazoline, imizadolidine, pyridine, dihydropyridine, tetrahydropyridine, piperidine, pyrimidine, pyridazine, pyrazine, dihydropyrimidine, dihydropyridazine, dihydropyrazine, tetrahydropyrimidine, tetrahydropyridazine, tetrahydropyrazine, hexahydropyrimidine, hexahydropyridazine, piperazine, pyran, dihydropyran, tetrahydropyran, azepine, dihydroazepine, tetrahydroazepine, azepane, indole, benzofuran, benzopyrans, dihydrobenzopyrans, quinoline, dihydroquinolines, tetrahydroquinoline, isoquinoline, dihydroisoquinolines and tetrahydroisoquinoline.

5. The compound according to claim 4, wherein the first or second heterocycle is selected from furan, dihydrofuran, pyrrole, pyroline, pyrazole, pyrazoline, imidazole, imidazoline, pyridine, dihydropyridine, tetrahydropyridine, pyrimidine, pyridazine, pyrazine, dihydropyrimidine, dihydropyridazine, dihydropyrazine, tetrahydropyrimidine, tetrahydropyridazine, tetrahydropyrazine, pyran, dihydropyran, indole, benzofuran, benzopyrans, quinoline, dihydroquinolines, isoquinoline and dihydroisoquinolines.

6. The compound according to claim 1, wherein the substituents on the first or second heterocycle, or first or second carbocycle are selected from a halogen atom; an oxo group (=O); —CN; —OR$_{18}$; —NR$_{19}$R$_{20}$; —SR$_{21}$; —S(O)R$_{22}$; —S(O)$_2$R$_{23}$; —C(O)R$_{24}$; —C(O)OR$_{25}$; —C(O)NR$_{26}$R$_{27}$; —C(O)SR$_{28}$; —S(O)$_2$NR$_{29}$R$_{30}$; —NR$_{31}$S(O)$_2$R$_{32}$; —NR$_{33}$C(O)NR$_{34}$R$_{35}$; —C(=NR$_{36}$)NR$_{37}$R$_{38}$; —NR$_{39}$C(=NR$_{42}$)NR$_{43}$R$_{44}$; (C$_1$-C$_6$)alkyl optionally substituted with one or more substituents selected from a halogen atom, NR$_{45}$R$_{46}$, SR$_{47}$, OR$_{48}$ and aryl; (C$_2$-C$_6$)alkenyl; (C$_2$-C$_6$)alkynyl; and a carbocycle, heterocycle or biaryl optionally substituted with one or more substituents selected from a halogen atom, OR$_{49}$, NR$_{50}$R$_{51}$, C(O)R$_{52}$, C(O)OR$_{53}$, C(O)NR$_{54}$R$_{55}$, an aryl and a (C$_1$-C$_6$)alkyl group optionally substituted with one or more substituents selected from a halogen atom, OR$_{56}$ and NR$_{57}$R$_{58}$, wherein:

R$_{18}$ to R$_{47}$ and R$_{49}$ to R$_{56}$ each independently represent a hydrogen atom or a (C$_1$-C$_6$)alkyl, aryl, (C$_1$-C$_6$)alkyl-aryl or aryl-(C$_1$-C$_6$)alkyl group;

R$_{48}$ represents a hydrogen atom or a (C$_1$-C$_6$)alkyl, aryl, (C$_1$-C$_6$)alkyl-aryl, aryl-(C$_1$-C$_6$)alkyl or —C(O)—(C$_1$-C$_6$)alkyl group; and R$_{57}$ and R$_{58}$ each independently represent a hydrogen atom or a (C$_1$-C$_6$)alkyl, aryl, (C$_1$-C$_6$)alkyl-aryl or aryl-(C$_1$-C$_6$)alkyl group, or together with the nitrogen atom which carries them, form a heterocycle which may contain another heteroatom, and, wherein the first or second heterocycle comprises one or more nitrogen atoms, which are optionally substituted with an oxygen atom forming a N$^+$—O$^-$ group for a nitrogen atom engaged in a double bond, or optionally substituted with an OH or (C$_1$-C$_6$)alkyl group for a nitrogen atom not engaged in a double bond.

7. The compound according to claim 6, wherein the substituents on the first or second heterocycle, or first or second carbocycle are selected from a halogen atom; an oxo group (=O); —CN; —OR$_{18}$; —NR$_{19}$R$_{20}$; —SR$_{21}$; —S(O)R$_{22}$; —S(O)$_2$R$_{23}$; —C(O)R$_{24}$; —C(O)OR$_{25}$; —C(O)NR$_{26}$R$_{27}$; —C(O)SR$_{28}$; —S(O)$_2$NR$_{29}$R$_{30}$; —NR$_{31}$S(O)$_2$R$_{32}$; —NR$_{33}$C(O)NR$_{34}$R$_{35}$; —C(=NR$_{36}$)NR$_{37}$R$_{38}$; —NR$_{39}$C(=NR$_{42}$)NR$_{43}$R$_{44}$; (C$_1$-C$_6$)alkyl optionally substituted with one or more substituents selected from a halogen atom, NR$_{45}$R$_{46}$, SR$_{47}$, OR$_{48}$ and aryl; (C$_2$-C$_6$)alkenyl; (C$_2$-C$_6$)alkynyl; and an aryl, heteroaryl, saturated carbocycle, saturated heterocycle or biaryl group optionally substituted with one or more substituents selected from a halogen atom, OR$_{49}$, NR$_{50}$R$_{51}$, C(O)R$_{52}$, C(O)OR$_{53}$, C(O)NR$_{54}$R$_{55}$, an aryl and a (C$_1$-C$_6$)alkyl group optionally substituted with one or more substituents selected from a halogen atom, OR$_{56}$ and NR$_{57}$R$_{58}$, wherein:

R$_{18}$ to R$_{47}$ and R$_{49}$ to R$_{56}$ each independently represent a hydrogen atom or a (C$_1$-C$_6$)alkyl, aryl, (C$_1$-C$_6$)alkyl-aryl or aryl-(C$_1$-C$_6$)alkyl group;

R$_{48}$ represents a hydrogen atom or a (C$_1$-C$_6$)alkyl, aryl, (C$_1$-C$_6$)alkyl-aryl, aryl-(C$_1$-C$_6$)alkyl or —C(O)—(C$_1$-C$_6$)alkyl group; and R$_{57}$ and R$_{58}$ each independently represents a hydrogen atom or a (C$_1$-C$_6$)alkyl, aryl, (C$_1$-C$_6$)alkyl-aryl or aryl-(C$_1$-C$_6$)alkyl group, or together with the nitrogen atom which carries them, form a heterocycle which may contain another heteroatom, and, wherein the first or second heterocycle comprises one or more nitrogen atoms, which are optionally substituted with an oxygen atom forming a N$^+$—O$^-$ group for a nitrogen atom engaged in a double bond, or optionally substituted with an OH or (C$_1$-C$_6$)alkyl group for a nitrogen atom not engaged in a double bond.

8. The compound according to claim 7, wherein the substituents on the first or second heterocycle, or first or second carbocycle are selected from a halogen atom; an oxo group (=O); —CN; —OR$_{18}$; —NR$_{19}$R$_{20}$; —SR$_{21}$; —S(O)R$_{22}$; —S(O)$_2$R$_{23}$; —C(O)R$_{24}$; —C(O)OR$_{25}$; —C(O)NR$_{26}$R$_{27}$; —C(O)SR$_{28}$; —S(O)$_2$NR$_{29}$R$_{30}$; —NR$_{31}$S(O)$_2$R$_{32}$; —NR$_{33}$C(O)NR$_{34}$R$_{35}$; —C(=NR$_{36}$)NR$_{37}$R$_{38}$; —NR$_{39}$C(=NR$_{42}$)NR$_{43}$R$_{44}$; (C$_1$-C$_6$)alkyl optionally substituted with one or more substituents selected from NR$_{45}$R$_{46}$, OR$_{48}$ and aryl; (C$_2$-C$_6$)alkenyl; (C$_2$-C$_6$)alkynyl; and a phenyl, naphthyl, thiophene, thiazole, piperidine, morpholine, piperazine, tetrahydropyran, tetrahydrofuran or biphenyl group optionally substituted with one or more substituents selected from a halogen atom, OR$_{49}$, NR$_{50}$R$_{51}$, C(O)R$_{52}$, C(O)OR$_{53}$, C(O)NR$_{54}$R$_{55}$, an aryl and a (C$_1$-C$_6$)alkyl group optionally substituted with one or more substituents selected from a halogen atom, $OR_{56}$ and $NR_{57}R_{58}$, wherein:

$R_{18}$ to $R_{47}$ and $R_{49}$ to $R_{56}$ each independently represent a hydrogen atom or a ($C_1$-$C_6$)alkyl or aryl group;

$R_{48}$ represents a hydrogen atom or a ($C_1$-$C_6$)alkyl or —C(O)—($C_1$-$C_6$)alkyl group; and $R_{57}$ and $R_{58}$ each independently represent a hydrogen atom or a ($C_1$-$C_6$)alkyl or aryl group, or together with the nitrogen atom which carries them, form a heterocycle selected from morpholine, piperazine and piperidine, and, when it is a wherein the first or second heterocycle comprises one or more nitrogen atoms, which are optionally substituted with an oxygen atom forming a $M^+$-$O^-$ group for a nitrogen atom engaged in a double bond, or optionally substituted with an OH or ($C_1$-$C_6$)alkyl group for a nitrogen atom not engaged in a double bond.

9. The compound according to claim 1, having the following formula (I-YZ):

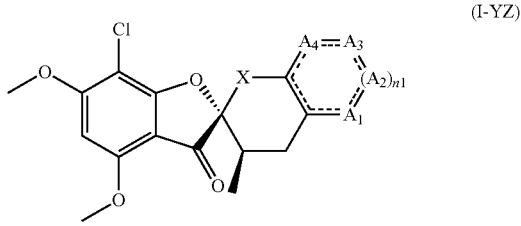

(I-YZ)

wherein:

⁝⁝⁝⁝ represents a single or double bond, it not being possible for two successive ⁝⁝⁝⁝ bonds to represent a double bond at the same time;

X is C=O, C=S, $CH_2$, CH—$OR_1$, $CHN_3$, $CHNR_2R_3$, C=N—$OR_4$ or C=N—$NR_5R_6$, n1 equals 0 or 1;

$A_1$ represents:

N when one of the ⁝⁝⁝⁝ bonds starting from $A_1$ is a double bond, or $NRa$, $N^+O^-$ or O when the two ⁝⁝⁝⁝ bonds starting from $A_1$ are single bonds;

$A_2$ represents:

CRb when one of the ⁝⁝⁝⁝ bonds starting from $A_2$ is a double bond, or

CRbRb' or C=O when the two ⁝⁝⁝⁝ bonds starting from $A_2$ are single bonds;

$A_3$ represents:

N or CRc when one of the ⁝⁝⁝⁝ bonds starting from $A_3$ is a double bond, or

NRc or CRcRc' when the two ⁝⁝⁝⁝ bonds starting from $A_3$ are single bonds; and $A_4$ represents:

CRz when one of the ⁝⁝⁝⁝ bonds starting from $A_4$ is a double bond, or

CRzRz' when the two ⁝⁝⁝⁝ bonds starting from $A_4$ are single bonds, wherein:

Ra represents a hydrogen atom or an OH, ($C_1$-$C_6$)alkyl, aryl, aryl-($C_1$-$C_6$)alkyl or C(O)O—($C_1$-$C_6$)alkyl group; and Rb, Rb', Rc, Rc', Rz, and Rz' each independently represent a hydrogen atom; a halogen atom; —CN; —$OR_{18}$; —$NR_{19}R_{20}$; —$SR_{21}$; —S(O)$R_{22}$; —S(O)$_2R_{23}$; —C(O)$R_{24}$; —C(O)O$R_{25}$; —C(O)NR$_{26}$R$_{27}$; —C(O)S$R_{28}$; S(O)$_2$NR$_{29}$R$_{30}$; —NR$_{31}$S(O)$_2R_{32}$; —NR$_{33}$C(O)NR$_{34}$R$_{35}$; —C(=NR$_{36}$)NR$_{37}$R$_{38}$; —NR$_{39}$C(=NR$_{42}$)NR$_{43}$R$_{44}$; ($C_1$-$C_6$)alkyl optionally substituted with one or more substituents selected from a halogen atom, NR$_{45}$R$_{46}$, SR$_{47}$, OR$_{48}$ and aryl; ($C_2$-$C_6$)alkenyl; ($C_2$-$C_6$)alkynyl; or a carbocycle, heterocycle or biaryl optionally substituted with one or more substituents selected from a halogen atom, OR$_{49}$, NR$_{50}$R$_{51}$, C(O)R$_{52}$, C(O)OR$_{53}$, C(O)NR$_{54}$R$_{55}$, an aryl and a ($C_1$-$C_6$)alkyl group optionally substituted with one or more substituents selected from a halogen atom, OR$_{56}$ and NR$_{57}$R$_{58}$.

10. The compound according to claim 9, wherein Rb, Rb', Rc, Rc', Rz, and Rz' each independently represent a hydrogen atom; a halogen atom; —CN; —$OR_{18}$; —$NR_{19}R_{20}$; —$SR_{21}$; —S(O)$R_{22}$; —S(O)$_2R_{23}$; —C(O)$R_{24}$; —C(O)O$R_{25}$; —C(O)NR$_{26}$R$_{27}$; —C(O)S$R_{28}$; —S(O)$_2$NR$_{29}$R$_{30}$; —NR$_{31}$S(O)$_2R_{32}$; —NR$_{33}$C(O)NR$_{34}$R$_{35}$; —C(=NR$_{36}$)NR$_{37}$R$_{38}$; —NR$_{39}$C(=NR$_{42}$)NR$_{43}$R$_{44}$; ($C_1$-$C_6$)alkyl optionally substituted with one or more substituents selected from among NR$_{45}$R$_{46}$, OR$_{48}$ and aryl; ($C_2$-$C_6$)alkenyl; ($C_2$-$C_6$)alkynyl; or an aryl, heteroaryl, saturated carbocycle, saturated heterocycle or biaryl group optionally substituted with one or more substituents selected from a halogen atom, OR$_{49}$, NR$_{50}$R$_{51}$, C(O)R$_{52}$, C(O)OR$_{53}$, C(O)NR$_{54}$R$_{55}$, an aryl and a ($C_1$-$C_6$)alkyl group optionally substituted with one or more substituents selected from a halogen atom, OR$_{56}$ and NR$_{57}$R$_{58}$.

11. The compound according to claim 10, wherein:

X is C=O or CH—$OR_1$, and

Rb, Rb', Rc, Rc', Rz, and Rz' each independently represent a hydrogen atom; a halogen atom; —CN; —$OR_{18}$, —$NR_{19}R_{20}$; —C(O)$R_{24}$; —C(O)$R_{25}$; —C(O)NR$_{26}$R$_{27}$; ($C_1$-$C_6$)alkyl optionally substituted with one or more substituents selected from NR$_{45}$R$_{46}$, OR$_{48}$ and aryl; or a phenyl, naphthyl, thiophene, thiazole, piperidine, morpholine, piperazine, tetrahydropyran, tetrahydrofuran or biphenyl group optionally substituted with one or more substituents selected from a halogen atom, OR$_{49}$, NR$_{50}$R$_{51}$, C(O)R$_{52}$, C(O)OR$_{53}$, C(O)NR$_{54}$R$_{55}$, an aryl and a ($C_1$-$C_6$)alkyl group optionally substituted with one or more substituents selected from a halogen atom, OR$_{56}$ and NR$_{57}$R$_{58}$.

12. The compound according to claim 1, having the following formula (I-XZ):

(I-XZ)

wherein:

⁝⁝⁝⁝ represents a single or double bond, it not being possible for two successive ⁝⁝⁝⁝ bonds to represent a double bond at the same time;

Y is C=O, C=S, $CH_2$, CH—$OR_7$, $CHN_3$, $CHNR_8R_9$, C=N—$OR_{10}$ or C=N—$NR_{11}R_{12}$;

n2, n3 and n4 each independently equal 0 or 1;

$A_5$ represents:

N or CRe when one of the ⁝⁝⁝⁝ bonds starting from $A_5$ is a double bond, or

NRa, O or CReRe' when the two ⁝⁝⁝⁝ bonds starting from $A_5$ are single bonds;

$A_6$ represents:
  CRb when one of the ---- bonds starting from $A_6$ is a double bond, or
  NRa, CRbRb' or C=O when the two ---- bonds starting from $A_6$ are single bonds;

$A_7$ represents:
  CRc when one of the ---- bonds starting from $A_7$ is a double bond, or
  CRcRc' when the two ---- bonds starting from $A_7$ are single bonds;

$A_8$ represents:
  CRd when one of the ---- bonds starting from $A_8$ is a double bond, or
  CRdRd' when the two ---- bonds starting from $A_8$ are single bonds, or

represents

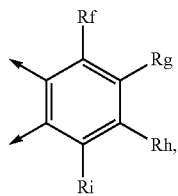

and
  $A_9$ represents:
    CRz when one of the ---- bonds starting from $A_9$ is a double bond, or
    CRzRz' when the two ---- bonds starting from $A_9$ are single bonds, wherein:
  Ra represent a hydrogen atom or an OH, $(C_1-C_6)$alkyl, aryl, aryl-$(C_1-C_6)$alkyl or C(O)O—$(C_1-C_6)$alkyl group;
  Rb, Rb', Rc, Rc', Rd, Rd', Re, Re', Rf, Rg, Rh, Ri, Rz, and Rz' each independently represent a hydrogen atom; a halogen atom; —CN; —$OR_{18}$, —$NR_{19}R_{20}$; —$SR_{21}$; —$S(O)R_{22}$; —$S(O)_2R_{23}$; —$C(O)R_{24}$; —$C(O)OR_{25}$; —$C(O)NR_{26}R_{27}$; —$C(O)SR_{28}$; —$S(O)_2NR_{29}R_{30}$; —$NR_{31}S(O)_2R_{32}$; —$NR_{33}C(O)NR_{34}R_{35}$; —$C(NR_{36})NR_{37}R_{38}$; —$NR_{39}C(=NR_{42})NR_{43}R_{44}$; $(C_1-C_6)$alkyl optionally substituted with one or more substituents selected from among a halogen atom, $NR_{45}R_{46}$, $SR_{47}$, $OR_{48}$ and aryl; $(C_2-C_6)$alkenyl; $(C_2-C_6)$alkynyl; or a carbocycle, heterocycle or biaryl optionally substituted with one or more substituents selected from among a halogen atom, $OR_{49}$, $NR_{50}R_{51}$, $C(O)R_{52}$, $C(O)OR_{53}$, $C(O)NR_{54}R_{55}$, an aryl and a $(C_1-C_6)$alkyl group optionally substituted with one or more substituents selected from among a halogen atom, $OR_{56}$ and $NR_{57}R_{58}$.

13. The compound according to claim 12, wherein:
Y is C=O, CH—$OR_7$, $CHN_3$, $CHNR_8R_9$, C=N—$OR_{10}$ or C=N—$NR_{11}R_{12}$, and
Rb, Rb', Rc, Rc', Rd, Rd', Re, Re', Rf, Rg, Rh, Ri, Rz, and Rz' each independently represent a hydrogen atom; a halogen atom; —CN; —$OR_{18}$; —$NR_{19}R_{20}$; —$SR_{21}$; —$S(O)R_{22}$; —$S(O)_2R_{23}$; —$C(O)R_{24}$; —$C(O)OR_{25}$; —$C(O)NR_{26}R_{27}$; —$C(O)SR_{28}$; —$S(O)_2NR_{29}R_{30}$; —$NR_{31}S(O)_2R_{32}$; —$NR_{33}C(O)NR_{34}R_{35}$; —$C(=NR_{36})NR_{37}R_{38}$; —$NR_{39}C(=NR_{42})NR_{43}R_{44}$; $(C_1-C_6)$alkyl optionally substituted with one or more substituents selected from a halogen atom, $NR_{45}R_{46}$, $SR_{47}$, $OR_{48}$ and aryl; $(C_2-C_6)$alkenyl; $(C_2-C_6)$alkynyl; or an aryl, heteroaryl, saturated carbocycle, saturated heterocycle or biaryl group optionally substituted with one or more substituents selected from a halogen atom, $OR_{49}$, $NR_{50}R_{51}$, $C(O)R_{52}$, $C(O)OR_{53}$, $C(O)NR_{54}R_{55}$, an aryl and a $(C_1-C_6)$alkyl group optionally substituted with one or more substituents selected from a halogen atom, $OR_{56}$ and $NR_{57}R_{58}$.

14. The compound according to claim 13, wherein:
Y is C=O or CH—$OR_7$, and
Rb, Rb', Rc, Rc', Rd, Rd', Re, Re', Rf, Rg, Rh, Ri, Rz, and Rz' each independently represent a hydrogen atom; a halogen atom; —CN; —$OR_{18}$; —$NR_{19}R_{20}$; —$C(O)R_{24}$; —$C(O)OR_{25}$; —$C(O)NR_{26}R_{27}$; $(C_1-C_6)$alkyl optionally substituted with one or more substituents selected from $NR_{45}R_{46}$, $OR_{48}$ and aryl; or a phenyl, naphthyl, thiophene, thiazole, piperidine, morpholine, piperazine, tetrahydropyran, tetrahydrofuran or biphenyl group optionally substituted with one or more substituents selected from a halogen atom, $OR_{49}$, $NR_{50}R_{51}$, $C(O)R_{52}$, $C(O)OR_{53}$, $C(O)NR_{54}R_{55}$, an aryl and a $(C_1-C_6)$ alkyl group optionally substituted with one or more substituents selected from a halogen atom, $OR_{56}$ and $NR_{57}R_{58}$.

15. The compound according to claim 12, wherein:
when n2=1, then $A_5$=N, O or NRa and/or $A_6$=NRa, and
when n2=0, then $A_5$=N, O or NRa.

16. The compound according to claim 12, wherein when n3=0, then n2=n4.

17. The compound according to claim 12, wherein n3=0 and n2=n4=1; or n3=1, and n2 and/or n4=0.

18. The compound according to claim 1, having one of the general formulas (I-YZ-1) to (I-YZ-14) or (I-XZ-1) to (I-XZ-19) below:

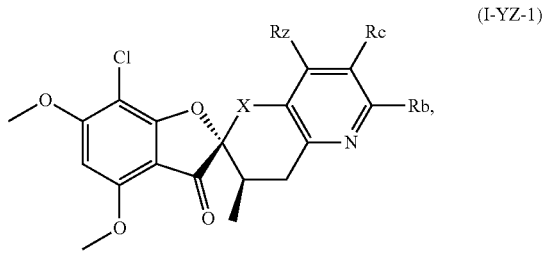
(I-YZ-1)

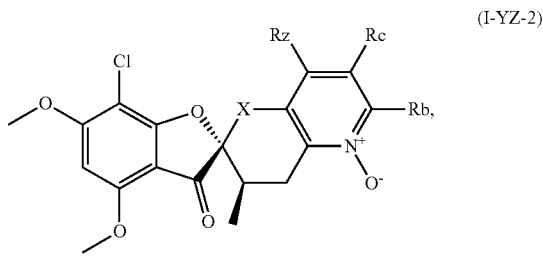
(I-YZ-2)

(I-YZ-3)
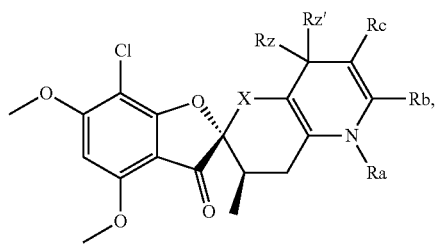
(I-YZ-4)
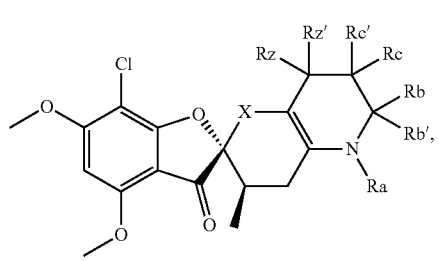
(I-YZ-5)
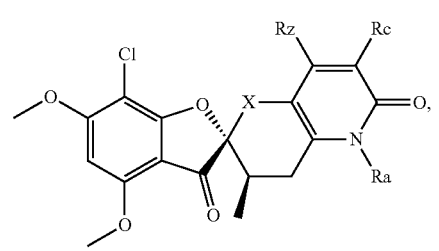
(I-YZ-6)
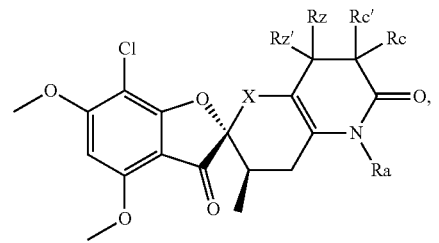
(I-YZ-7)
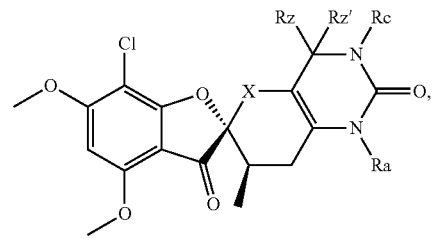
(I-YZ-8)
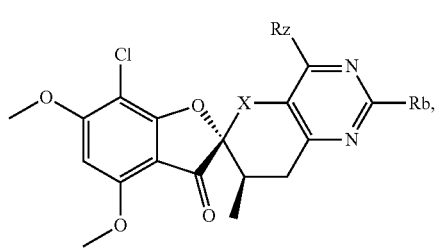
(I-YZ-9)
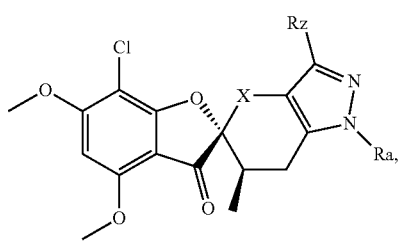
(I-YZ-10)
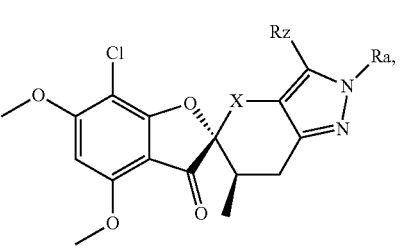
(I-YZ-11)
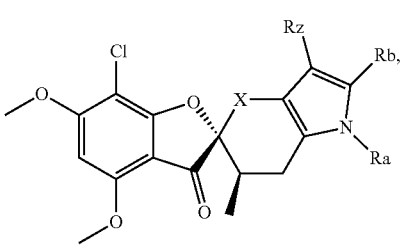
(I-YZ-12)
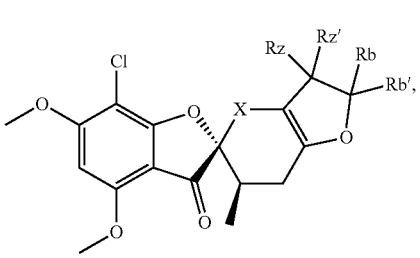
(I-YZ, 13)
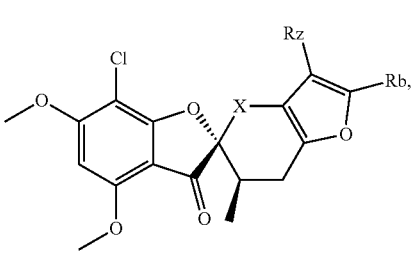
(I-YZ-14)
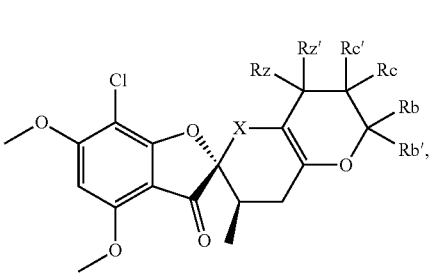

-continued (I-XZ-1)

(I-XZ-2)

(I-XZ-3)

(I-XZ-4)

(I-XZ-5)

-continued (I-XZ-6)

(I-XZ-7)

(I-XZ-8)

(I-XZ-9)

(I-XZ-10)

(I-XZ-11)

-continued (I-XZ-12)
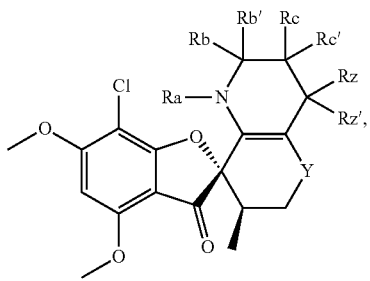

(I-XZ-13)
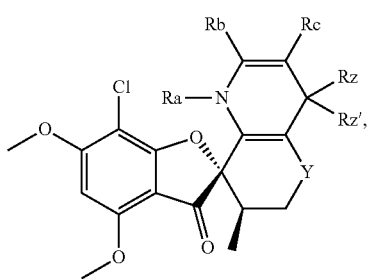

(I-XZ-14)
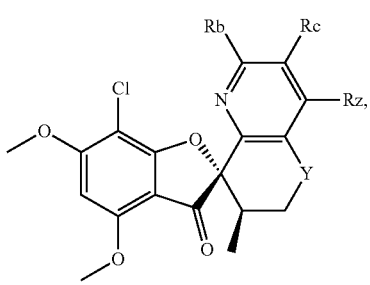

(I-XZ-15)
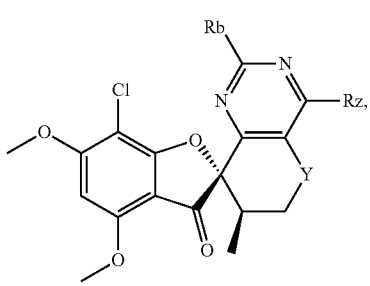

(I-XZ-16)
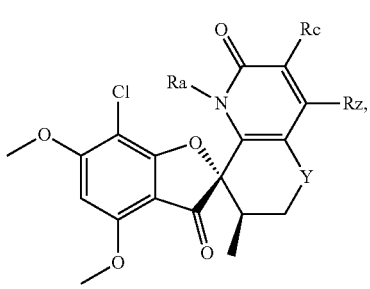

-continued (I-XZ-17)
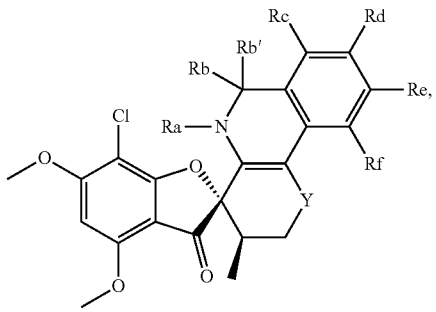

(I-XZ-18)
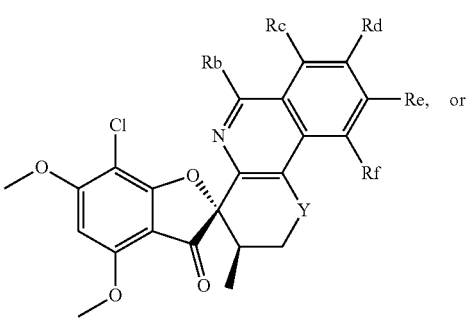

(I-XZ-19)
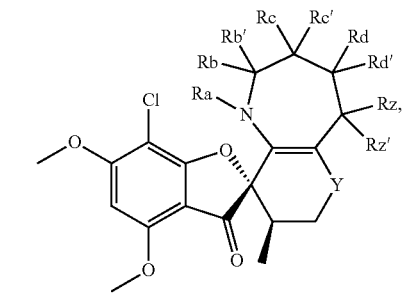

wherein:
Ra represents a hydrogen atom or an OH, $(C_1-C_6)$alkyl, aryl, aryl-$(C_1-C_6)$alkyl or $C(O)O$—$(C_1-C_6)$alkyl group; and Rb, Rb', Rc, Rc', Rd, Rd', Re, Rf, Rz and Rz' each independently represent a hydrogen atom; a halogen atom; —CN; —OR$_{18}$; —NR$_{19}$R$_{20}$; —SR$_{21}$; —S(O)R$_{22}$; —S(O)$_2$R$_{23}$; —C(O)R$_{24}$; —C(O)OR$_{25}$; —C(O)NR$_{26}$R$_{27}$; —C(O)SR$_{28}$; —S(O)$_2$NR$_{29}$R$_{30}$; —NR$_{31}$S(O)$_2$R$_{32}$; —NR$_{33}$C(O)NR$_{34}$R$_{35}$; —C(=NR$_{36}$)NR$_{37}$R$_{38}$; —NR$_{39}$C(=NR$_{42}$)NR$_{43}$R$_{44}$; $(C_1-C_6)$alkyl optionally substituted with one or more substituents selected from a halogen atom, NR$_{45}$R$_{46}$, SR$_{47}$, OR$_{48}$ and aryl; $(C_2-C_6)$alkenyl; $(C_2-C_6)$alkynyl; or a carbocycle, heterocycle or biaryl optionally substituted with one or more substituents selected from a halogen atom, OR$_{49}$, NR$_{50}$R$_{51}$, C(O)R$_{52}$, C(O)OR$_{53}$, C(O)NR$_{54}$R$_{55}$, an aryl and a $(C_1-C_6)$alkyl group optionally substituted with one or more substituents selected from a halogen atom, OR$_{56}$ and NR$_{57}$R$_{58}$.

19. The compound according to claim 18, wherein Rb, Rb', Rc, Rc', Rd, Rd', Re, Rf, Rz and Rz' each independently represent a hydrogen atom; a halogen atom; —CN; —OR$_{18}$; —NR$_{19}$R$_{20}$; —SR$_{21}$; —S(O)R$_{22}$; —S(O)$_2$R$_{23}$; —C(O)R$_{24}$; —C(O)OR$_{25}$; —C(O)NR$_{26}$R$_{27}$; C(O)SR$_{28}$; —S(O)$_2$NR$_{29}$R$_{30}$; —NR$_{31}$S(O)$_2$R$_{32}$; —NR$_{33}$C(O)NR$_{34}$R$_{35}$; —C(=NR$_{36}$)NR$_{37}$R$_{38}$; NR$_{39}$C(=NR$_{42}$)NR$_{43}$R$_{44}$; $(C_1-C_6)$ alkyl optionally substituted with one or more substituents selected from a halogen atom, $NR_{45}R_{46}$, $SR_{47}$, $OR_{48}$ and aryl; $(C_2-C_6)$alkenyl; $(C_2-C_6)$alkynyl; or an aryl, heteroaryl, saturated carbocycle, saturated heterocycle or biaryl group optionally substituted with one or more substituents selected from a halogen atom, $OR_{49}$, $NR_{50}R_{51}$, $C(O)R_{52}$, $C(O)OR_{53}$, $C(O)NR_{54}R_{55}$, an aryl and a $(C_1-C_6)$alkyl group optionally substituted with one or more substituents selected from a halogen atom, $OR_{56}$ and $NR_{57}R_{58}$.

20. The compound according to claim 19, wherein Rb, Rb', Rc, Rc', Rd, Rd', Re, Rf, Rz and Rz' each independently represent a hydrogen atom; a halogen atom; —CN; —$OR_{18}$; —$NR_{19}R_{20}$; —$C(O)R_{24}$; —$C(O)OR_{25}$; —$C(O)NR_{26}R_{27}$; $(C_1-C_6)$alkyl optionally substituted with one or more substituents selected from $NR_{45}R_{46}$, $OR_{48}$ and aryl; or a phenyl, naphthyl, thiophene, thiazole, piperidine, morpholine, piperazine, tetrahydropyran, tetrahydrofuran or biphenyl group optionally substituted with one or more substituents selected from a halogen atom, $OR_{49}$, $NR_{50}R_{51}$, $C(O)R_{52}$, $C(O)OR_{53}$, $C(O)NR_{54}R_{55}$, an aryl and a $(C_1-C_6)$alkyl group optionally substituted with one or more substituents selected from a halogen atom, $OR_{56}$ and $NR_{57}R_{58}$.

21. The compound according to claim 1, selected from:

| Compound N° | Structures |
|---|---|
| 9 | 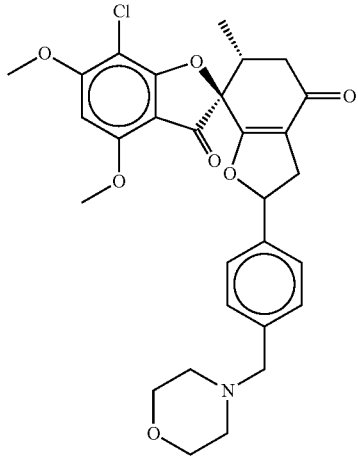 |
| 10 | 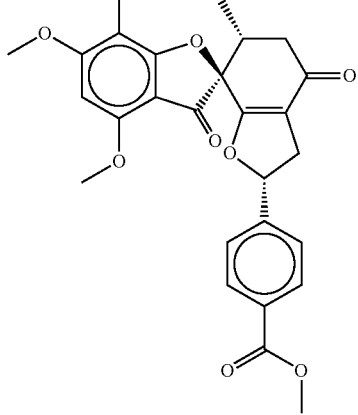 |
| 11 | 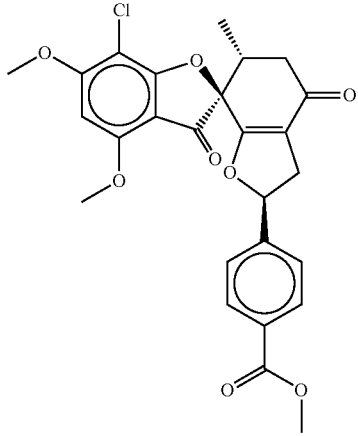 |
| Compound N° | Structures |
|---|---|
| 12 | 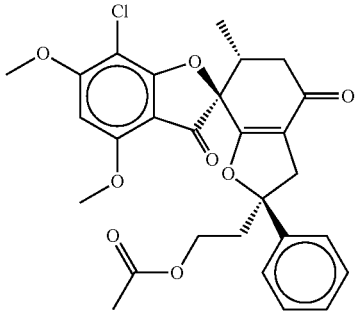 |
| 13 | 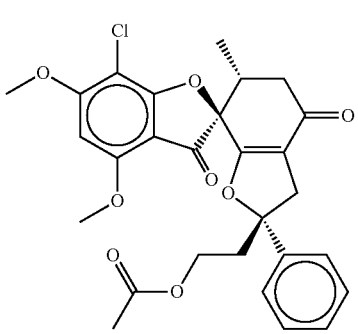 |
| 14 | 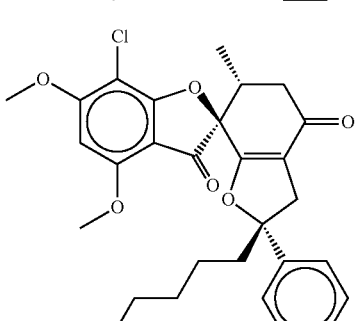 |
| 15 | 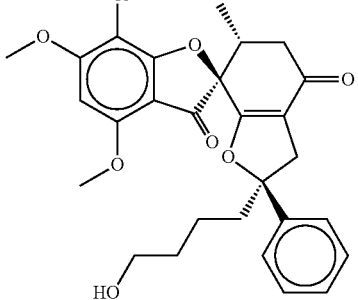 |
| 16 | 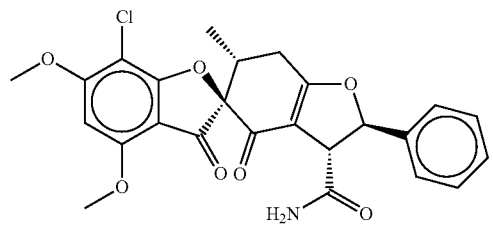 |

| Compound N° | Structures |
|---|---|
| 17 | 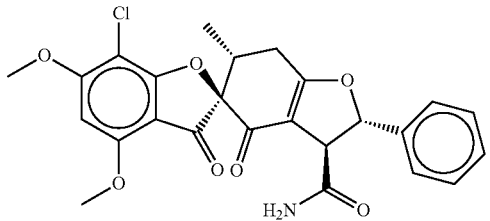 |
| 18 | 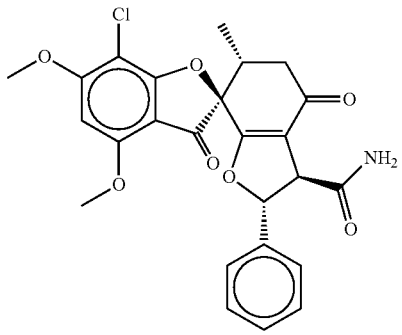 |
| 19 | 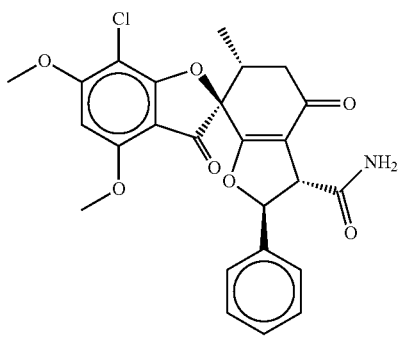 |
| 20 | 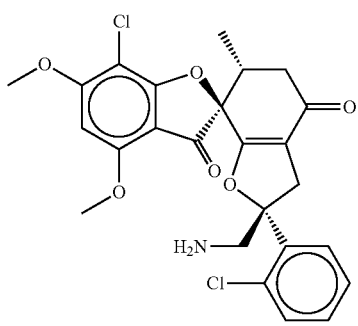 |
| 21 | 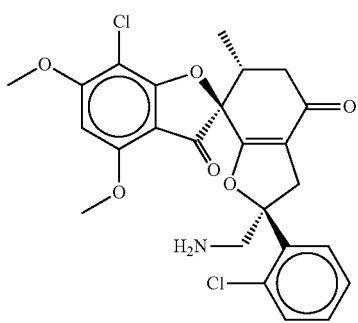 |
| Compound N° | Structures |
|---|---|
| 22 | 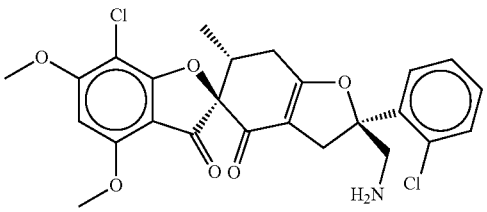 |
| 23 | 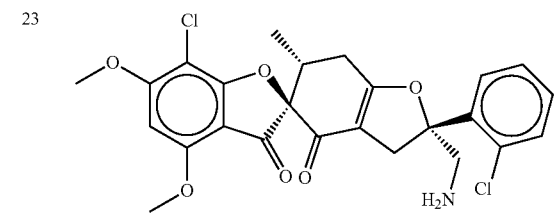 |
| 24 | 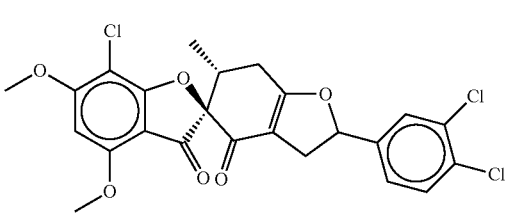 |
| 25 | 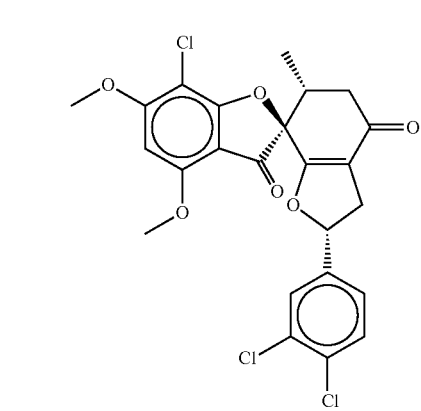 |
| 26 | 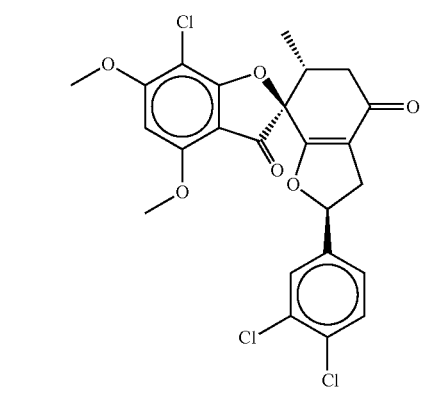 |

| Compound N° | Structures |
|---|---|
| 27 | 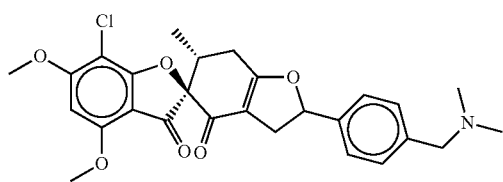 |
| 28 | 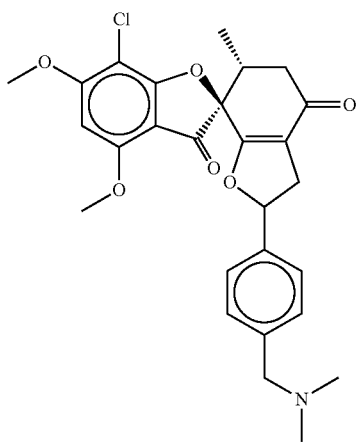 |
| 29 | 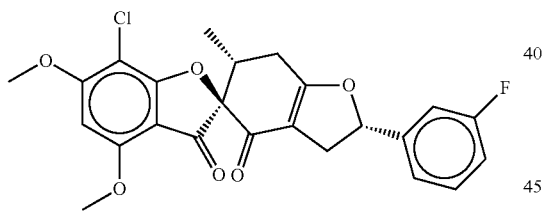 |
| 30 | 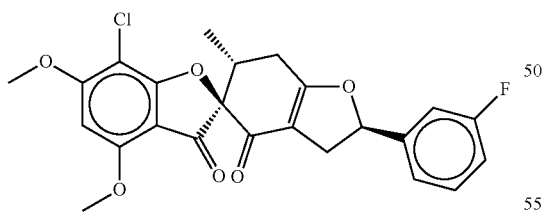 |
| 31 | 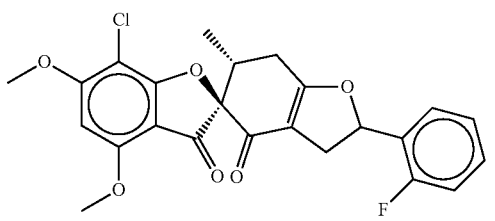 |
| Compound N° | Structures |
|---|---|
| 32 | 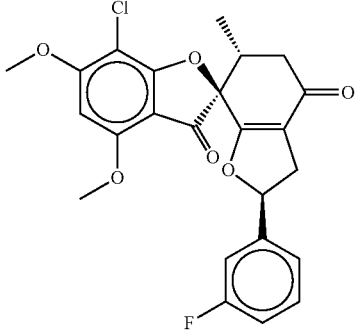 |
| 33 | 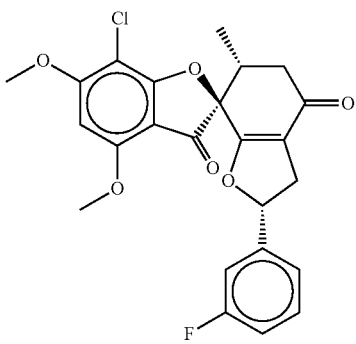 |
| 34 | 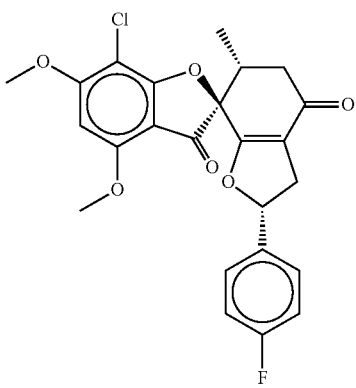 |
| 35 | 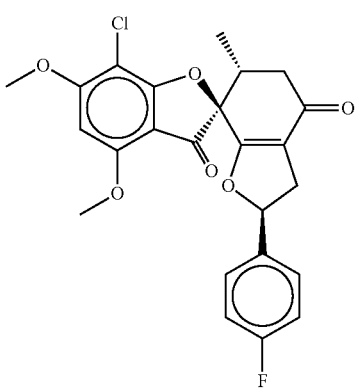 |

| Compound N° | Structures |
|---|---|
| 36 | 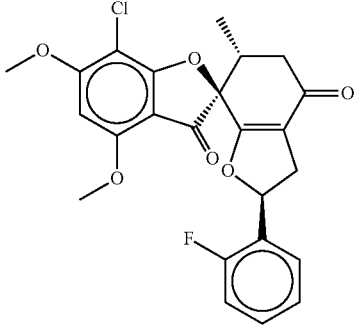 |
| 37 | 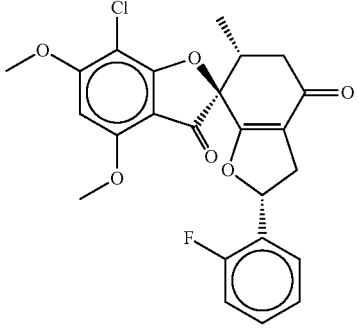 |
| 38 | 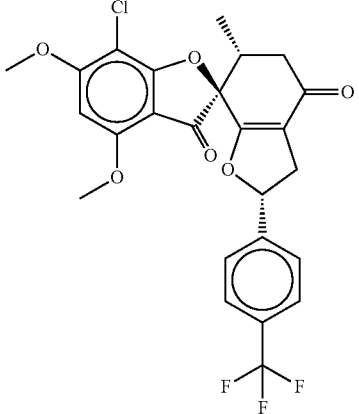 |
| 39 | 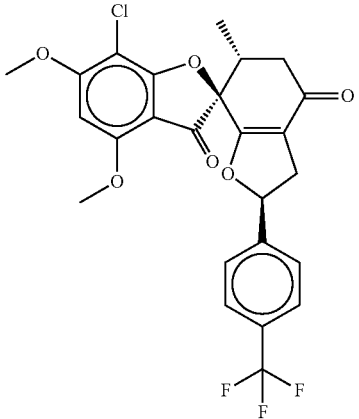 |
| Compound N° | Structures |
|---|---|
| 40 | 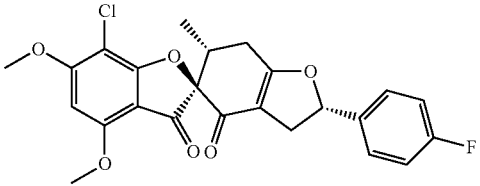 [SMILES: COc1cc(OC)c2c(c1Cl)O[C@@]1(C(=O)C3=C(C[C@H]1C)O[C@H](c1ccc(F)cc1)C3)C2=O] |
| 41 | 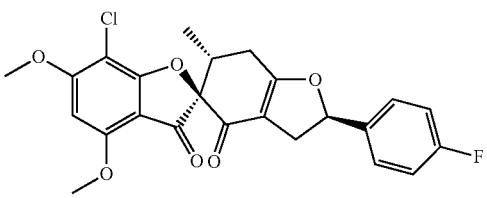 [SMILES: COc1cc(OC)c2c(c1Cl)O[C@@]1(C(=O)C3=C(C[C@H]1C)O[C@@H](c1ccc(F)cc1)C3)C2=O] |
| 42 | 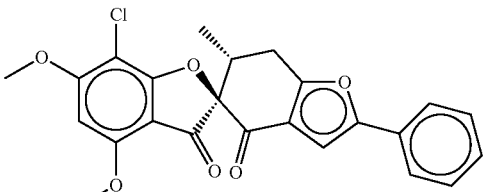 |
| 43 | 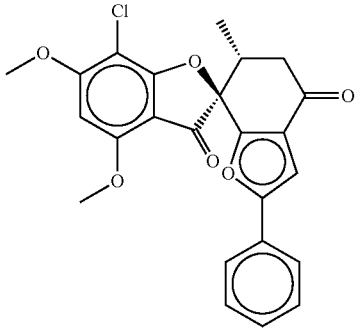 |
| 44 | 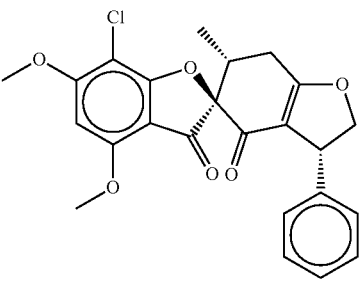 |
| 45 | 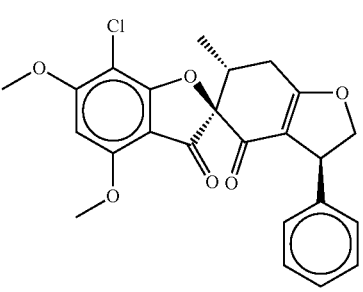 |

| Compound N° | Structures |
|---|---|
| 46 | 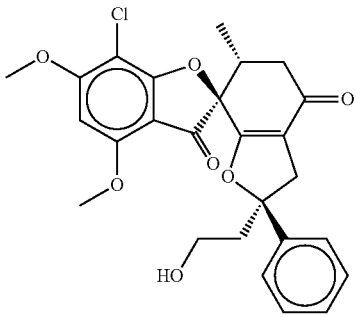 |
| 47 | 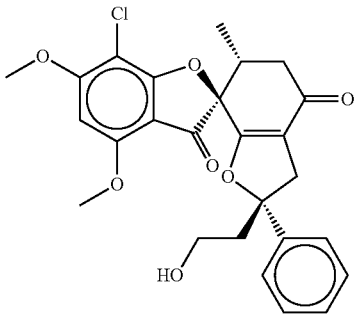 |
| 48 | 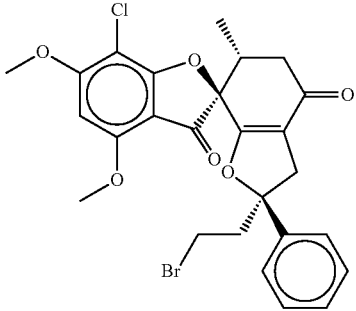 |
| 49 | 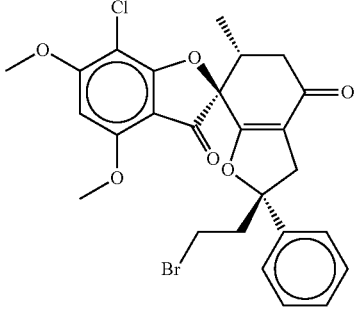 |
| Compound N° | Structures |
|---|---|
| 50 | 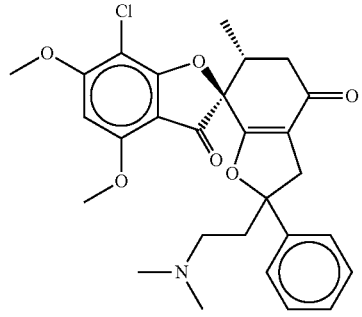 |
| 51 | 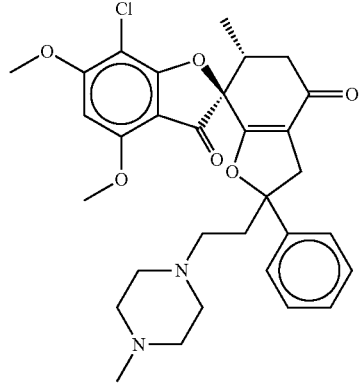 |
| 52 | 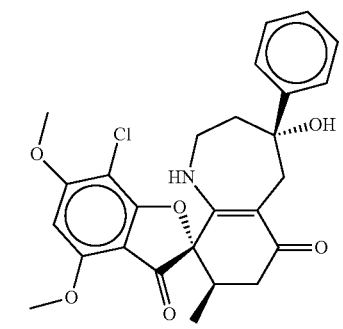 |
| 53 | 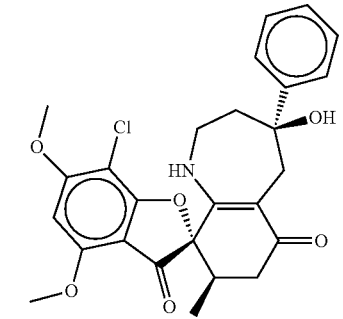 |

125
-continued
| Compound N° | Structures |
|---|---|
| 54 | 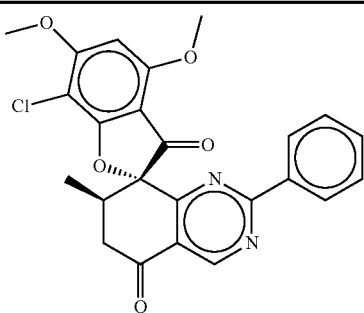 |
| 55 | 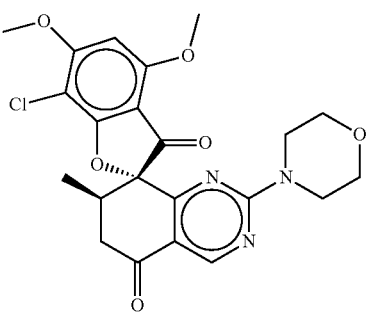 |
| 56 | 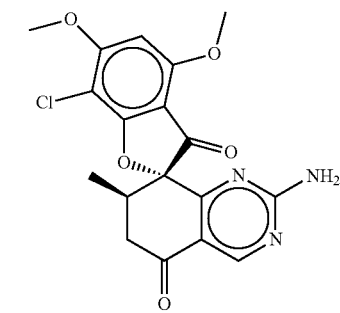 |
| 57 | 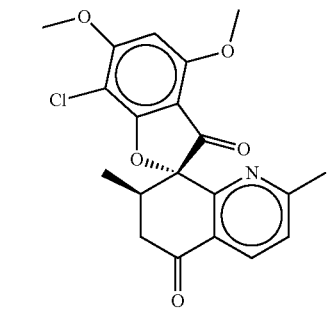 |
| 58 | 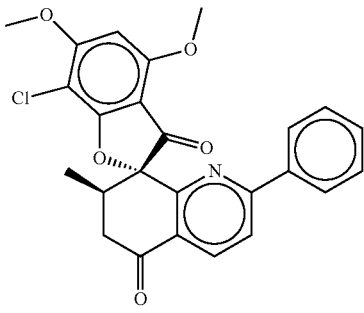 |
126
-continued
| Compound N° | Structures |
|---|---|
| 59 | 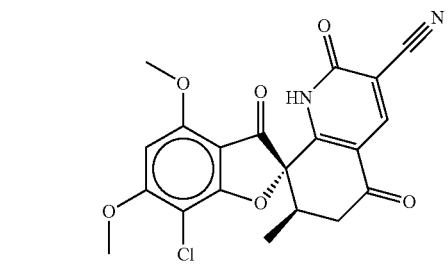 |
| 60 | 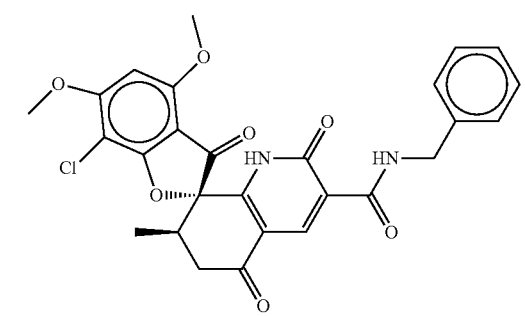 |
| 61 | 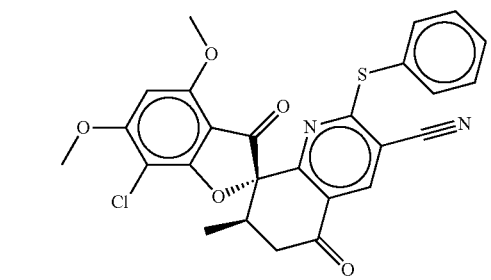 |
| 62 | 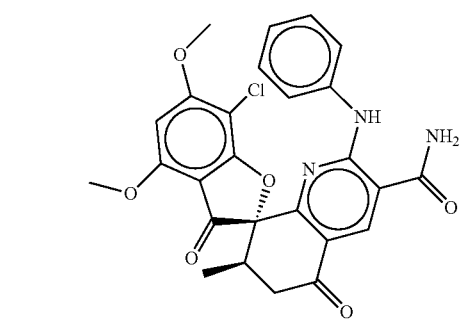 |
| 72 | 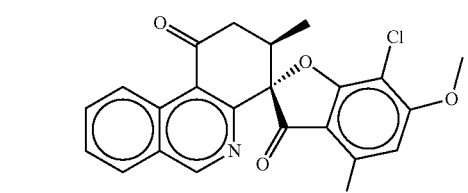 |

| Compound N° | Structures |
|---|---|
| 73 | 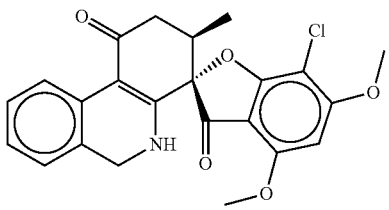 |
| 74 | 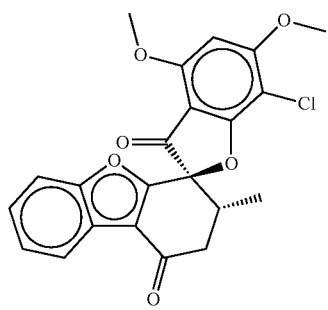 |
| 75 | 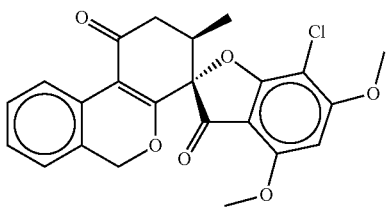 |
| 83 | 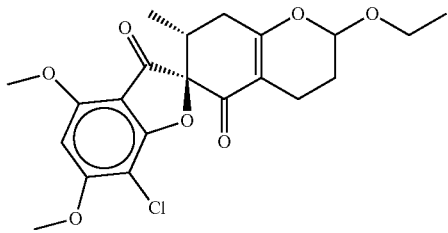 |
| 84 | 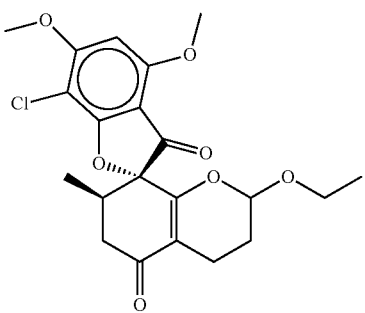 |
| Compound N° | Structures |
|---|---|
| 85 | 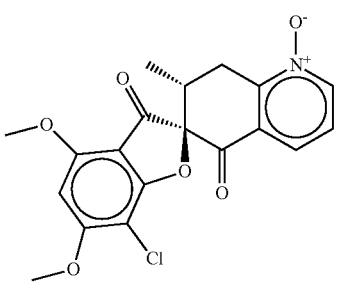 |
| 86 | 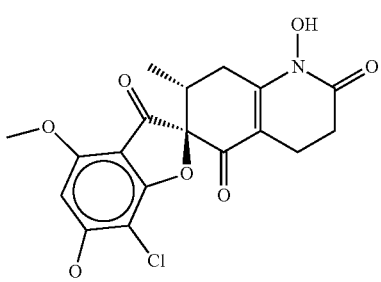 |
| 87 | 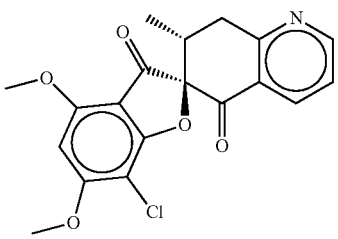 |
| 88 | 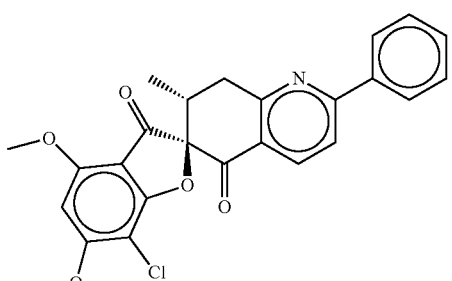 |
| 89 | 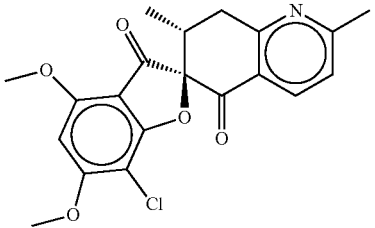 |

| Compound N° | Structures |
|---|---|
| 90 | 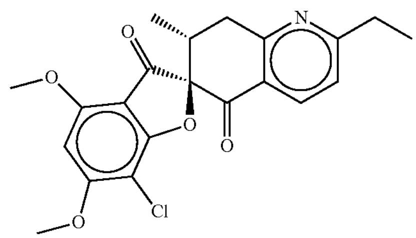 |
| 91 | 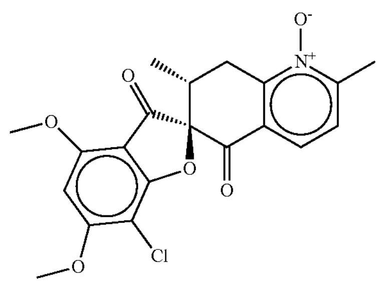 |
| 92 | 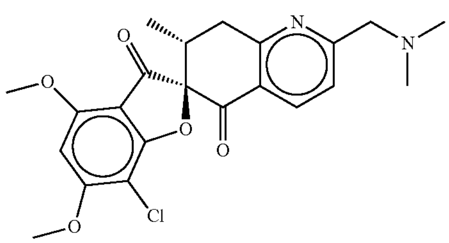 |
| 94 | 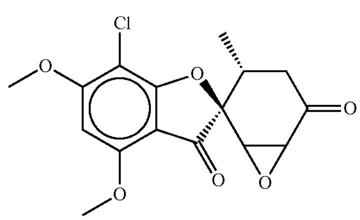 |
| 102 | 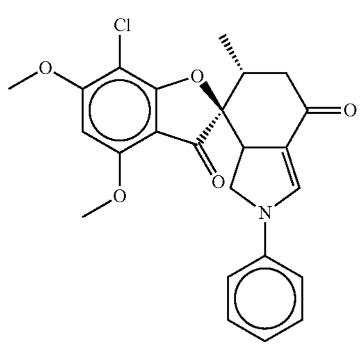 |
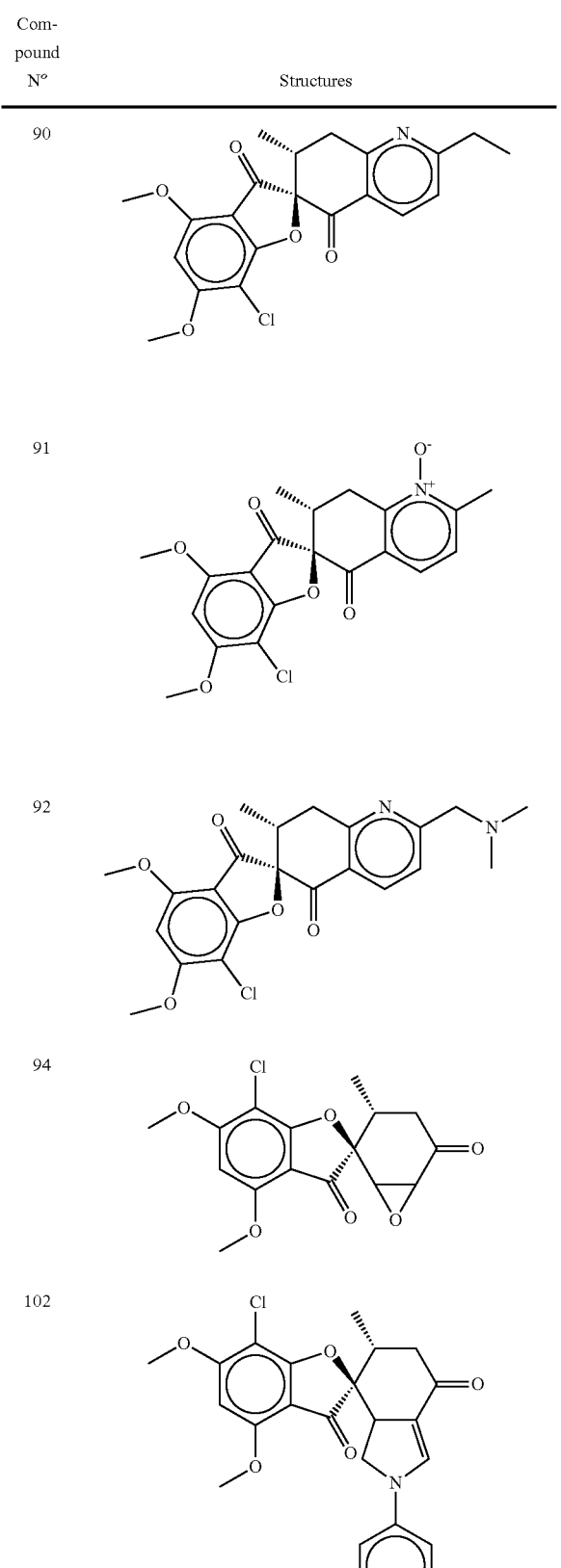
| Compound N° | Structures |
|---|---|
| 103 | 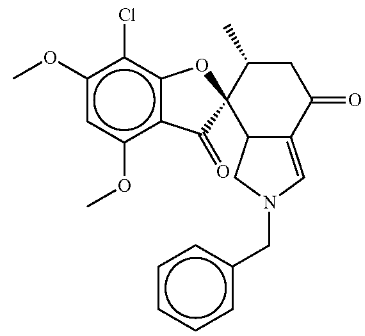 |
| 104 | 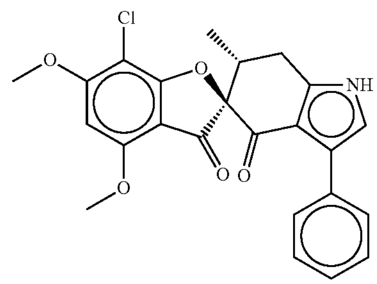 |
| 105 | 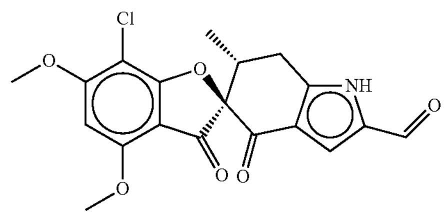 |
| 106 | 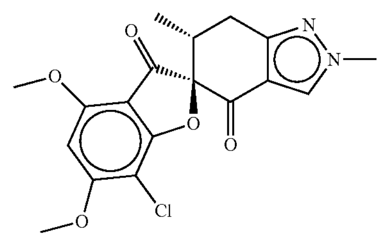 |
| 107 | 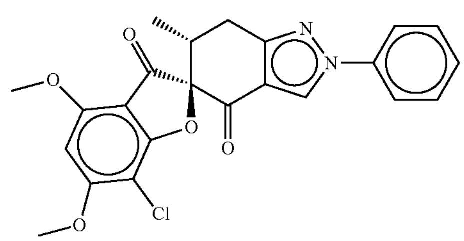 |
| 108 | 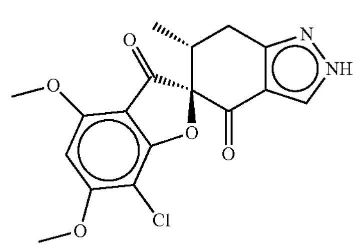 |
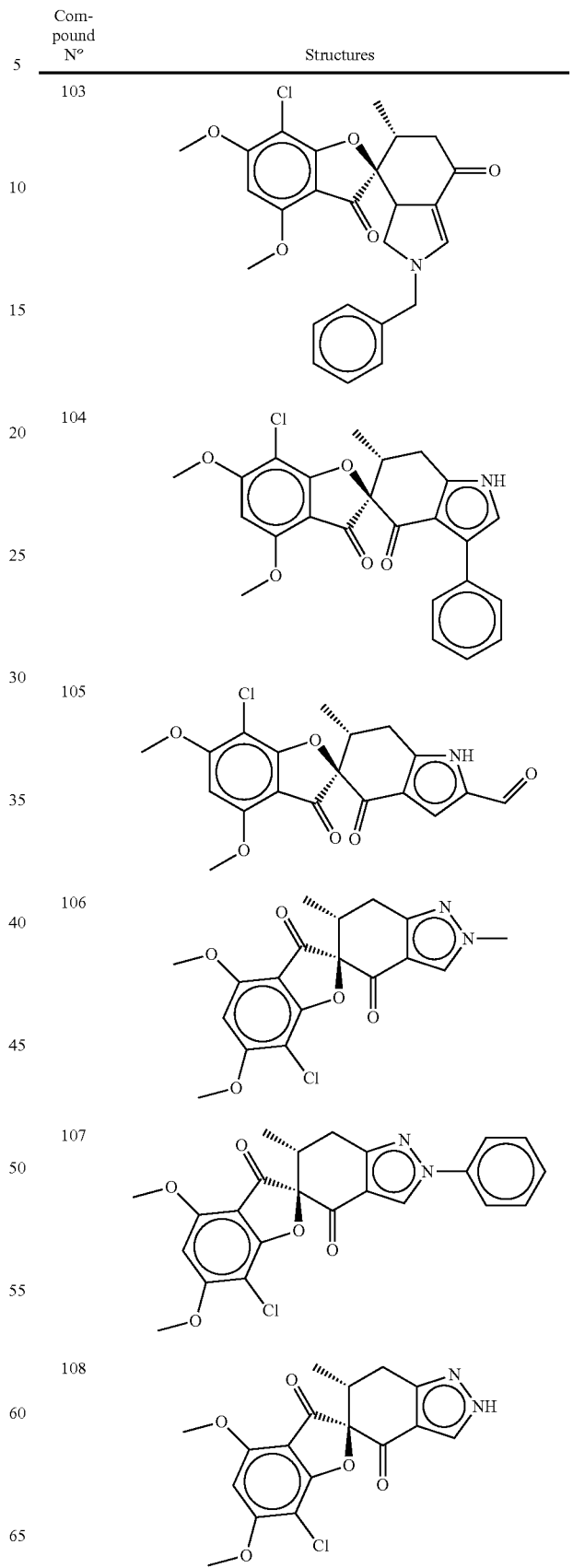

| Compound N° | Structures |
|---|---|
| 109 | 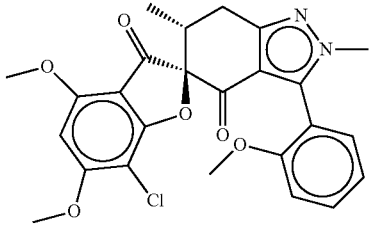 |
| 110 | 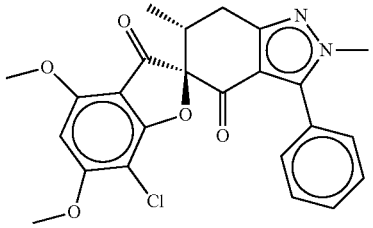 |
| 111 | 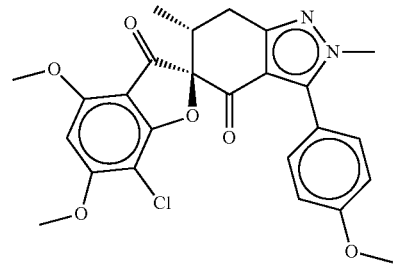 |
| 112 | 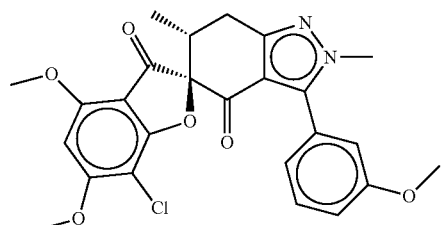 |
| 113 | 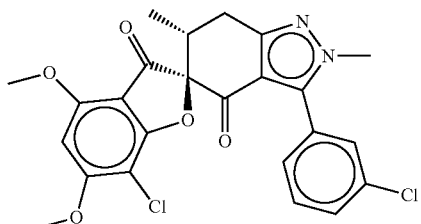 |
| 114 | 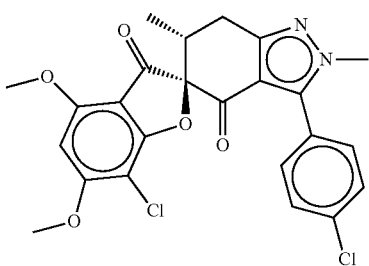 |
| Compound N° | Structures |
|---|---|
| 115 | 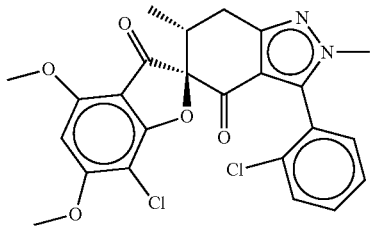 |
| 116 | 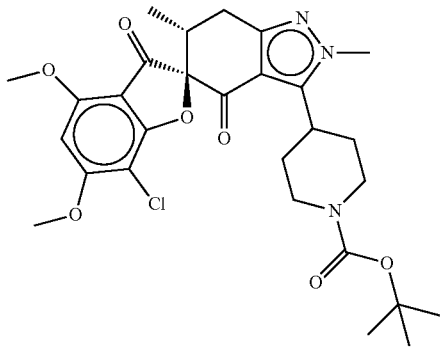 |
| 117 | 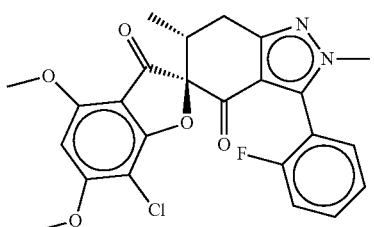 |
| 118 | 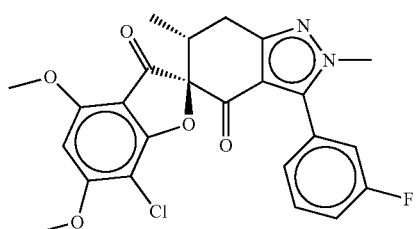 |
| 119 | 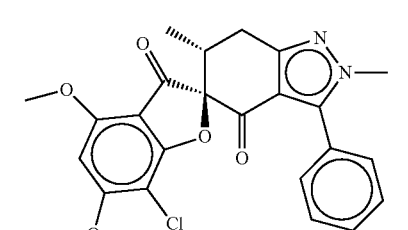 |

| Compound Nº | Structures |
|---|---|
| 120 | 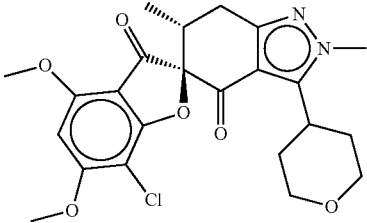 |
| 121 | 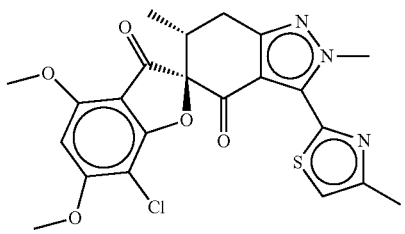 |
| 122 | 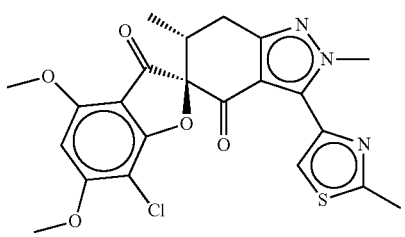 |
| 123 | 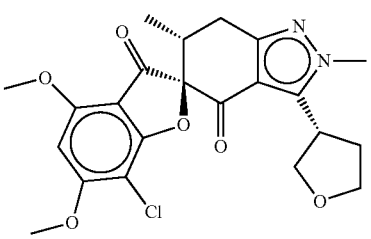 |
| 124 | 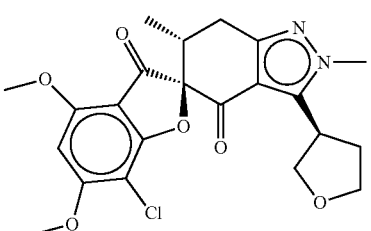 |
| 125 | 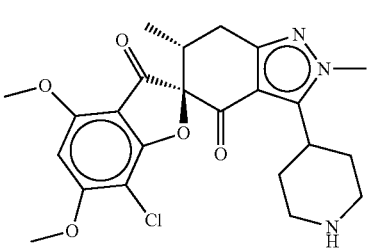 |
| Compound Nº | Structures |
|---|---|
| 126 | 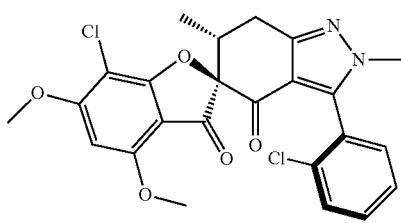 |
| 127 | 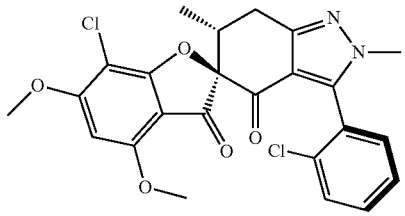 |
| 128 | 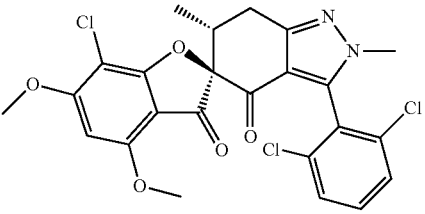 [SMILES: COc1cc(OC)c2c(c1Cl)O[C@]1(C2=O)C(=O)c2c(nn(C)c2-c2c(Cl)cccc2Cl)C[C@H]1C] |
| 129 | 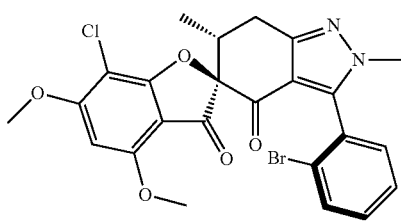 |
| 130 | 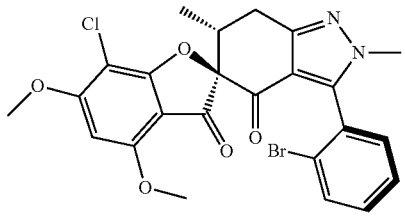 |
| 131 | 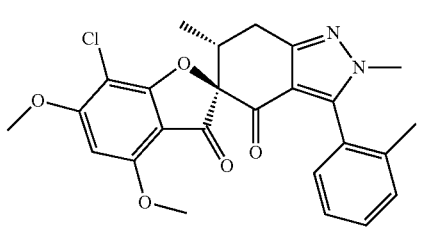 |

| Compound N° | Structures |
|---|---|
| 132 | 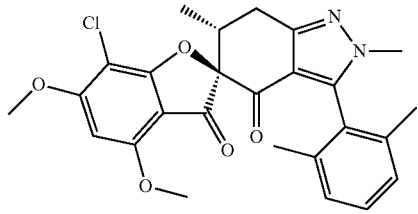 |
| 133 | 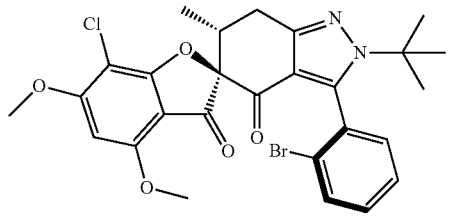 |
| 134 | 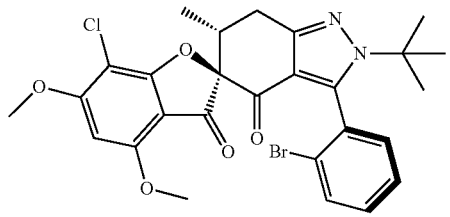 |
| 135 | 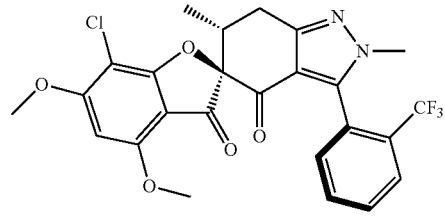 |
| 136 | 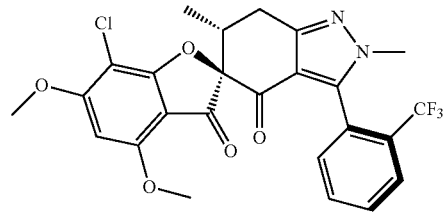 |
| 137 | 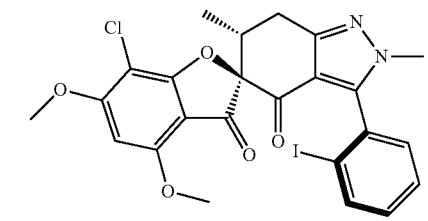 |
| Compound N° | Structures |
|---|---|
| 138 | 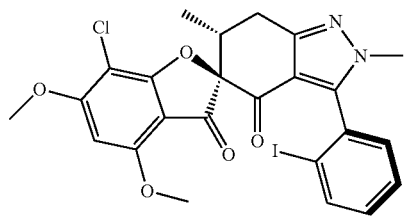 |
| 139 | 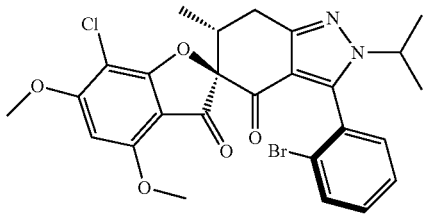 |
| 140 | 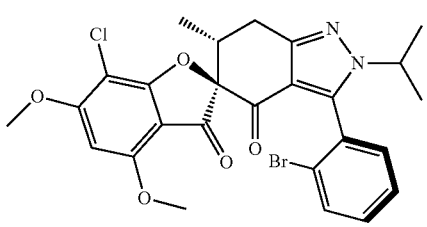 |
| 141 | 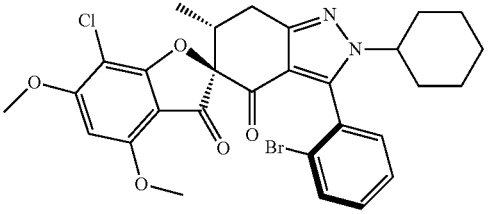 |
| 142 | 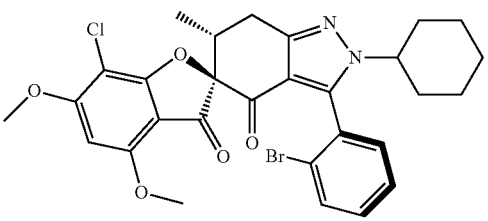 |
| 143 | 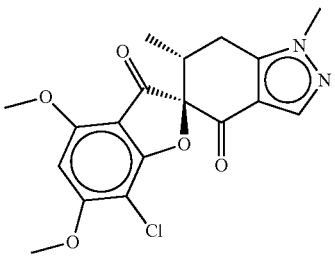 |

| Compound N° | Structures |
|---|---|
| 144 | 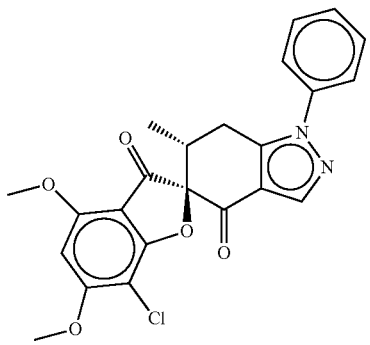 |
| 149 | 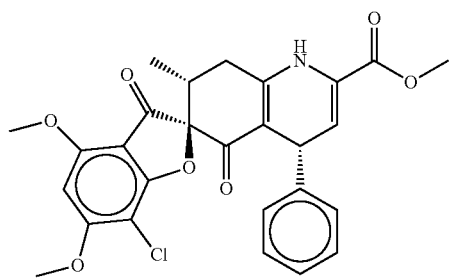 |
| 150 | 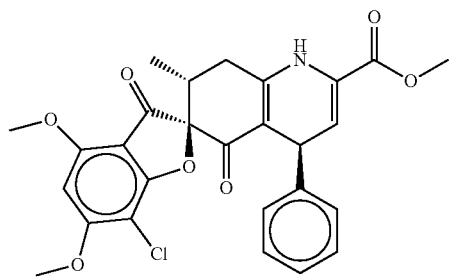 |
| 151 | 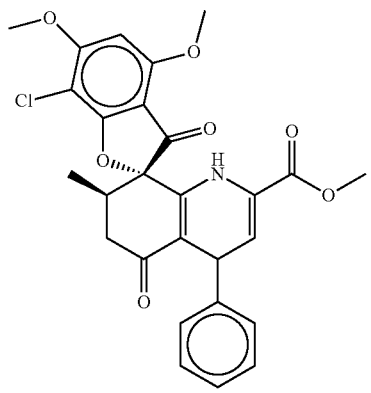 |
| Compound N° | Structures |
|---|---|
| 152 | 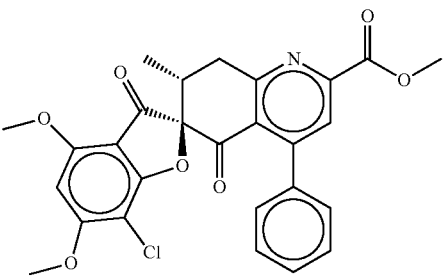 |
| 153 | 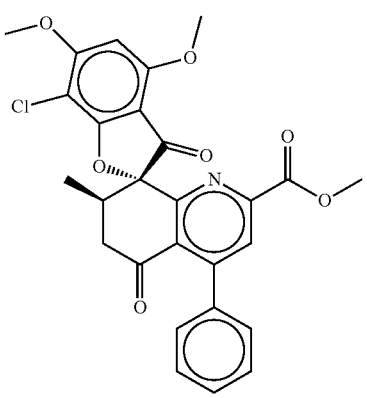 |
| 154 | 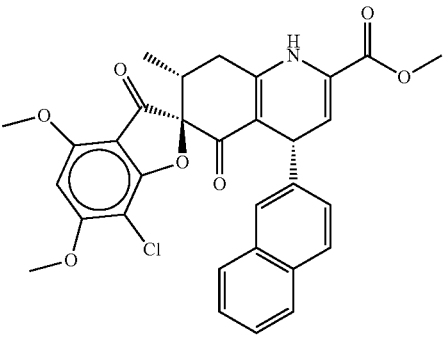 |
| 155 | 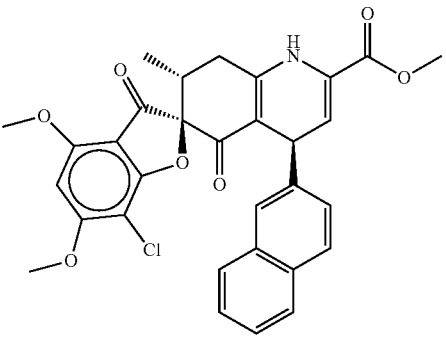 |

| Compound N° | Structures |
|---|---|
| 156 | 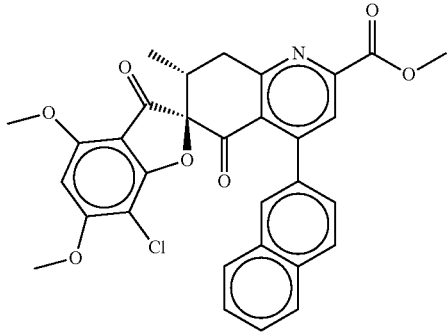 |
| 157 | 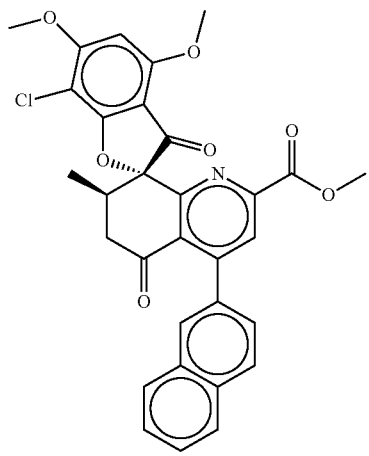 |
| 158 | 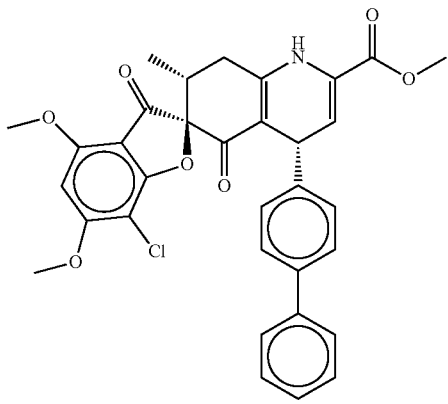 |
| Compound N° | Structures |
|---|---|
| 159 | 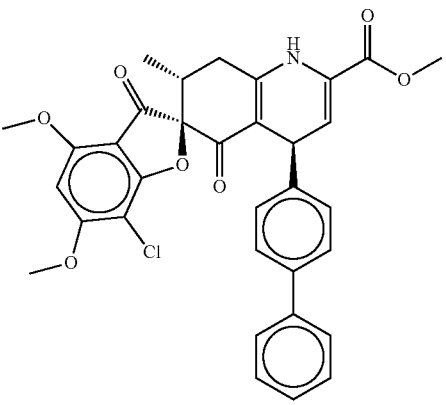 |
| 160 | 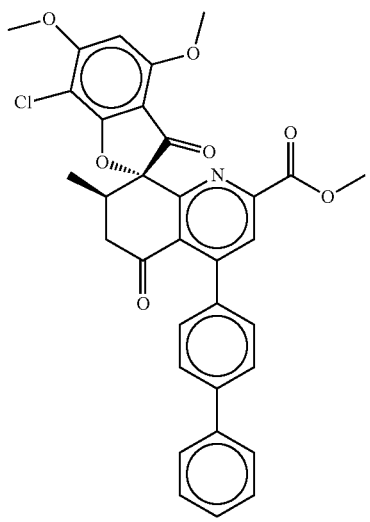 |
| 161 | 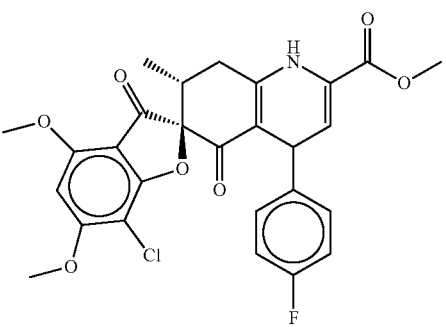 |

| 141 -continued | 142 -continued |
|---|---|
| Compound N° / Structures | Compound N° / Structures |
| 162, 163, 164, 165 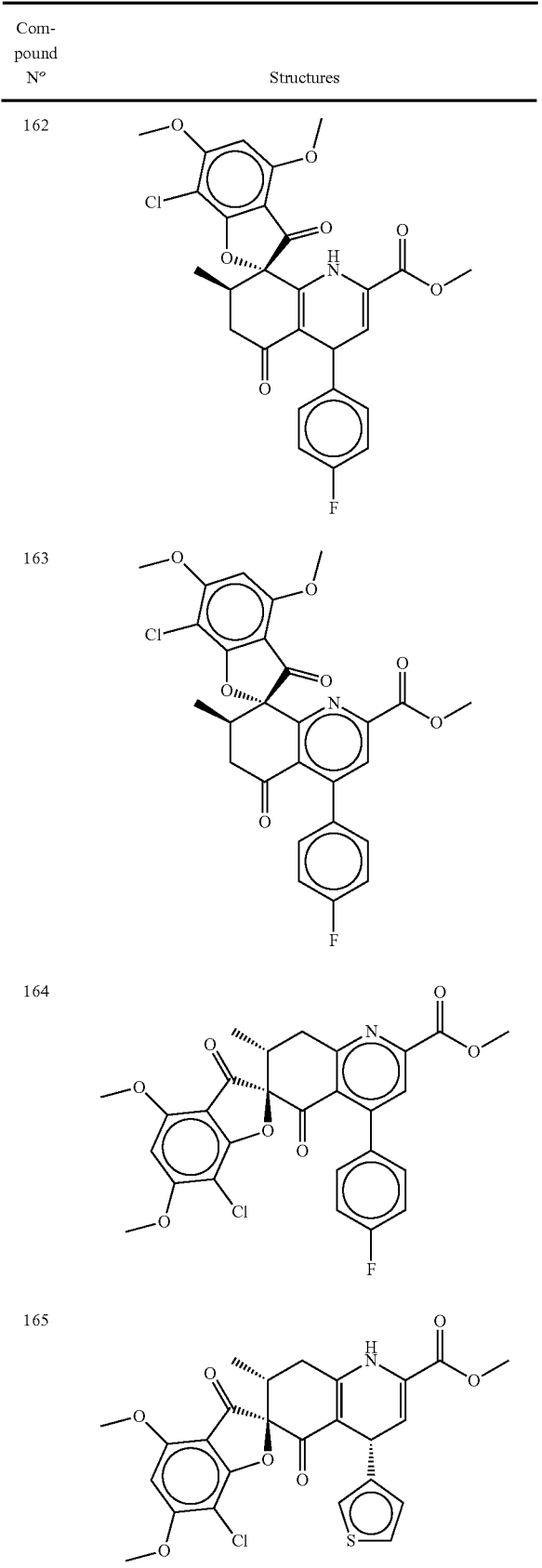 | 166, 167, 168, 169, 170 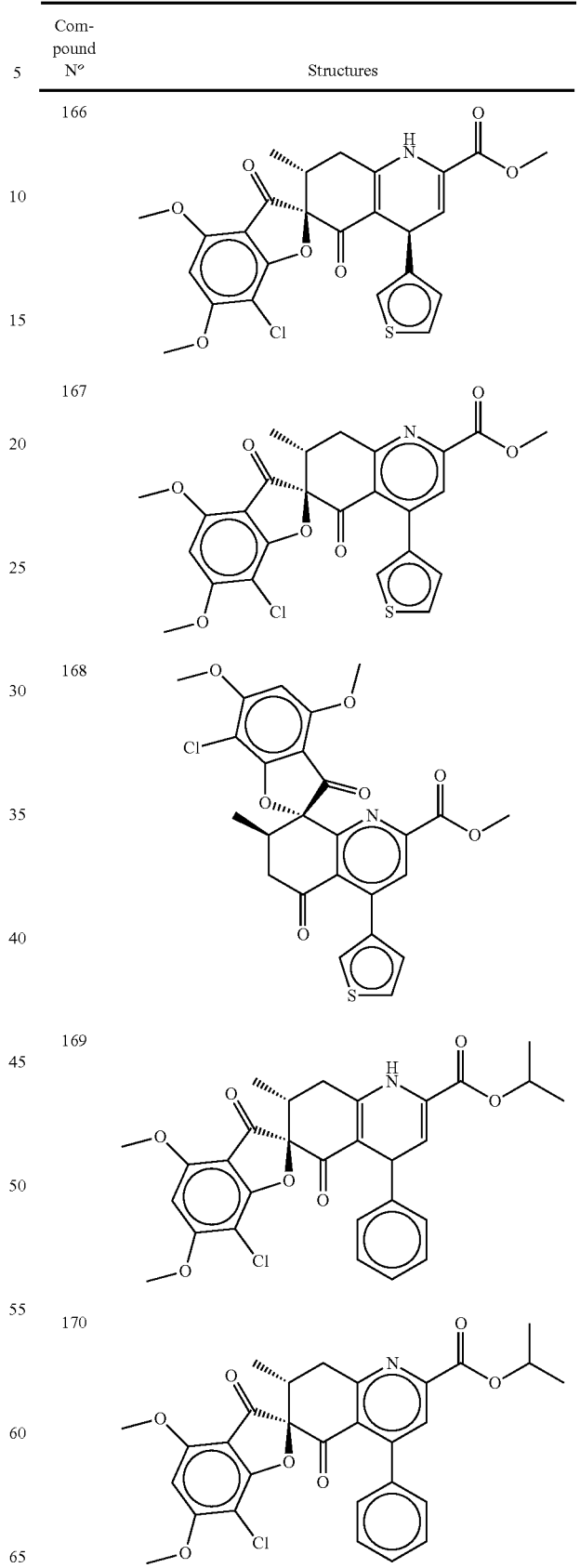 |

-continued
| Compound N° | Structures |
|---|---|
| 171 | 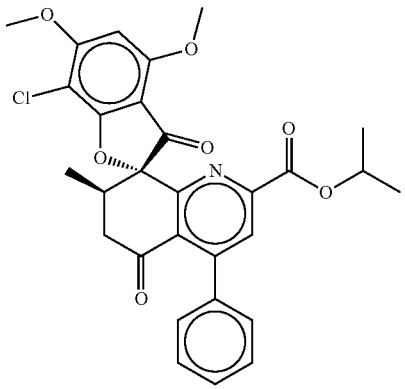 |
| 172 | 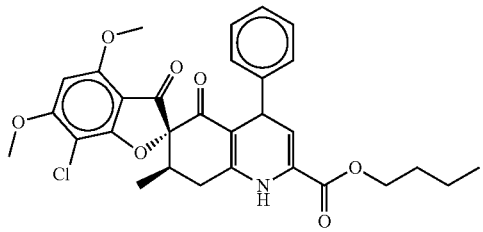 |
| 173 | 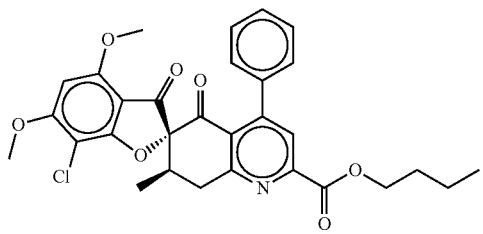 |
| 174 | 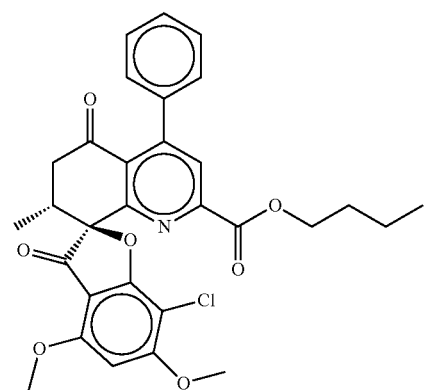 |
| 175 | 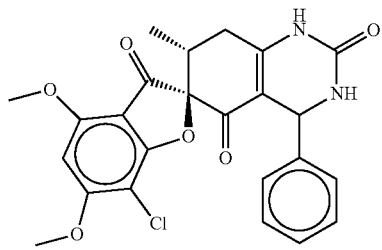 |
-continued
| Compound N° | Structures |
|---|---|
| 176 | 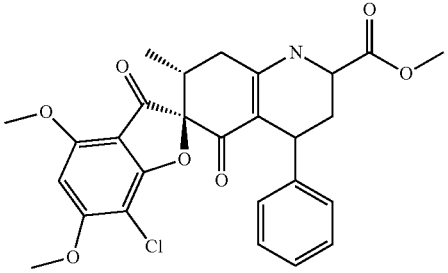 |
| 177 | 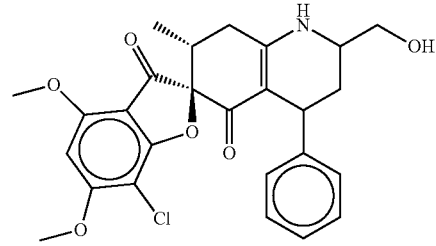 |
| 185 | 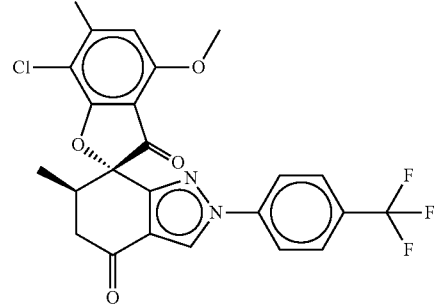 |
| 186 | 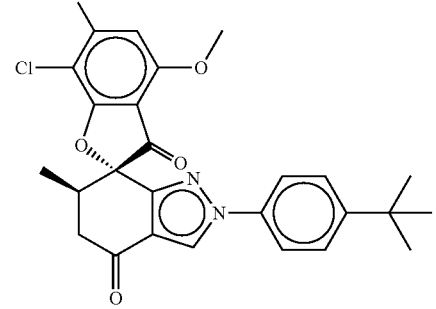 |
| 187 | 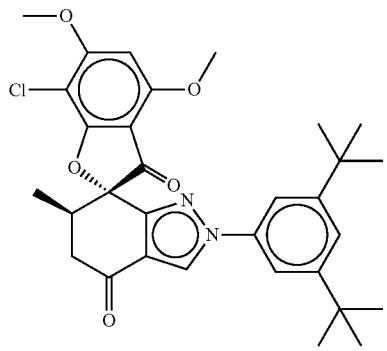 |

| Compound N° | Structures |
|---|---|
| 188 | 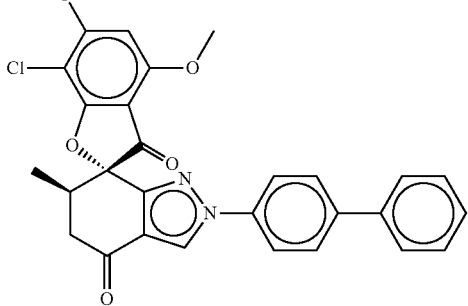 |
| 216 | 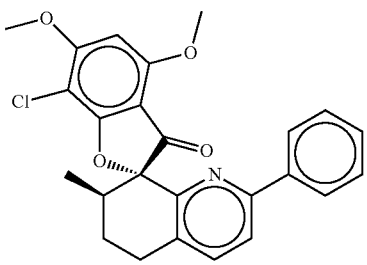 |
| 217 | 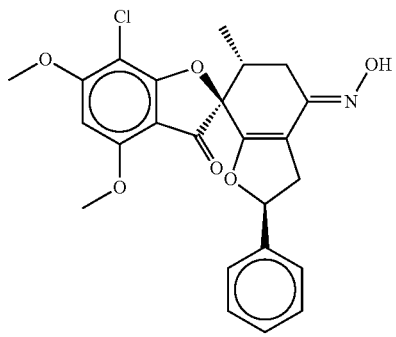 |
| 220 | 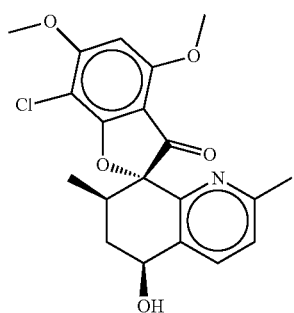 |
| Compound N° | Structures |
|---|---|
| 221 | 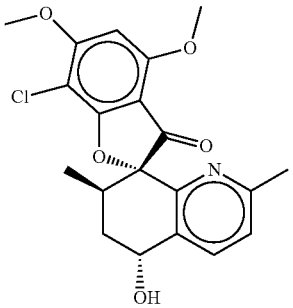 |
| 222 | |
| 223 | 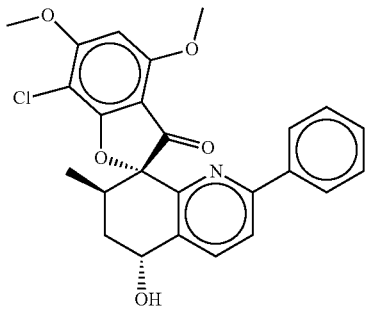 |
| 224 | 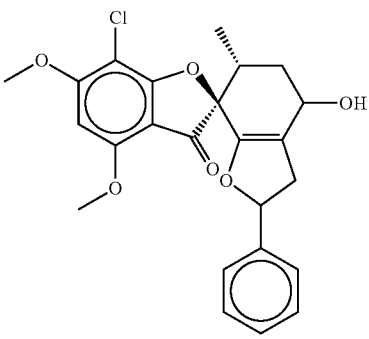 |

| Compound N° | Structures |
|---|---|
| 225 | 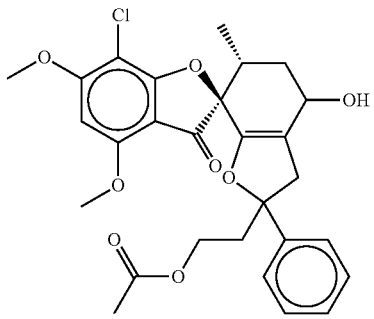 |
| 228 | 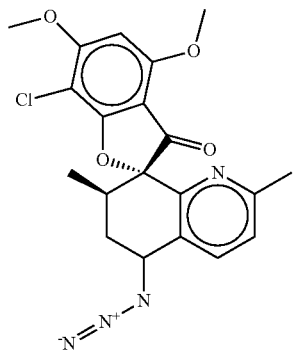 |
| 229 | 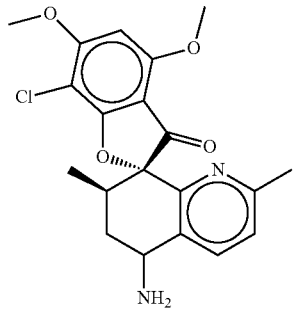 |
| 230 | 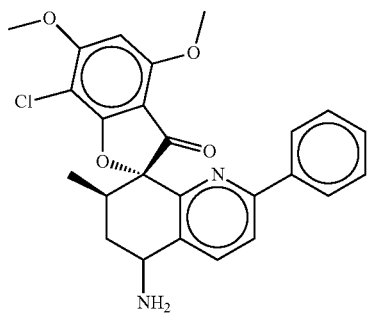 |
| Compound N° | Structures |
|---|---|
| 231 | 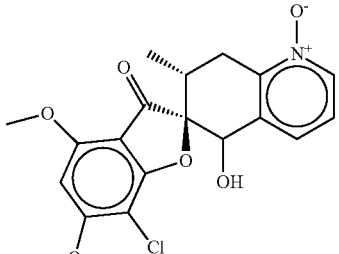 |
| 232 | 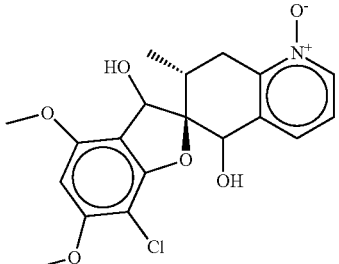 |
| 233 | 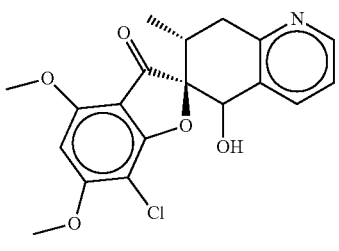 |
| 234 | 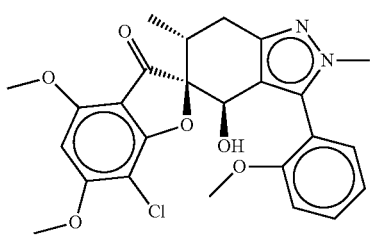 |
| 235 | 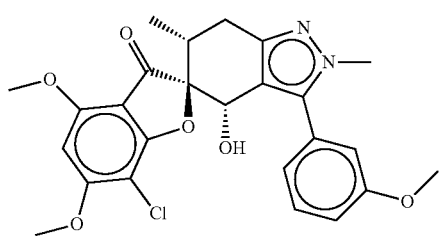 |
| 236 | 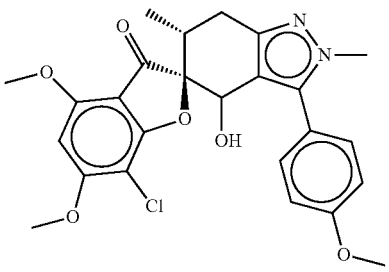 |

| Compound N° | Structures |
|---|---|
| 237 | 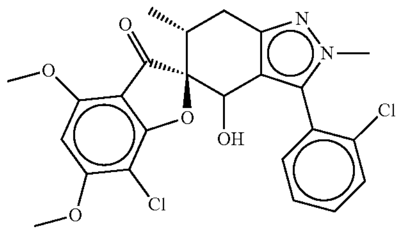 |
| 238 | 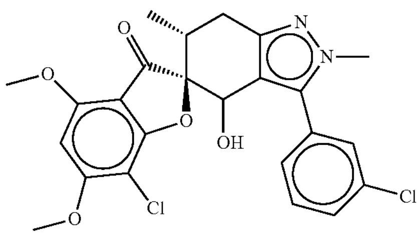 |
| 239 | 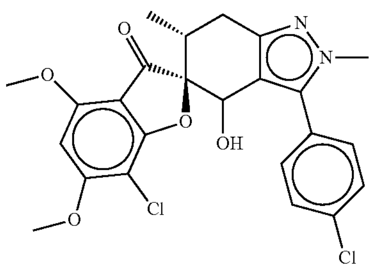 |
| 240 | 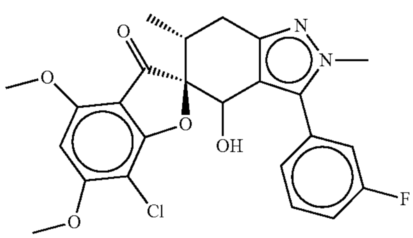 |
| 241 | 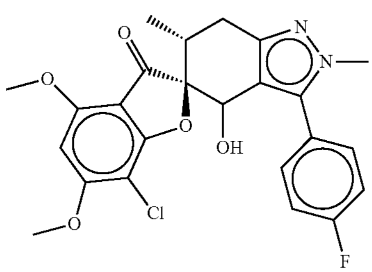 |
| 242 | 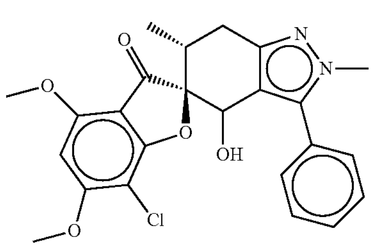 |
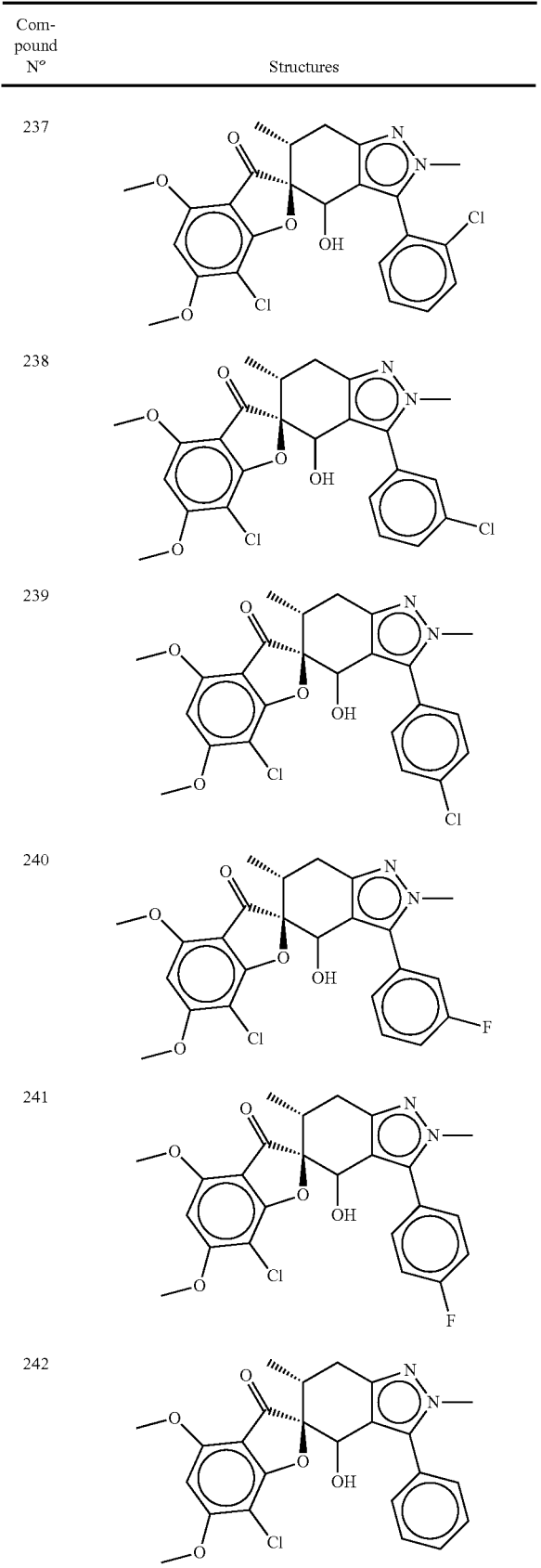
| Compound N° | Structures |
|---|---|
| 243 | |
| 244 | |
| 245 | |
| 246 | |
| 247 | |
| 248 | |
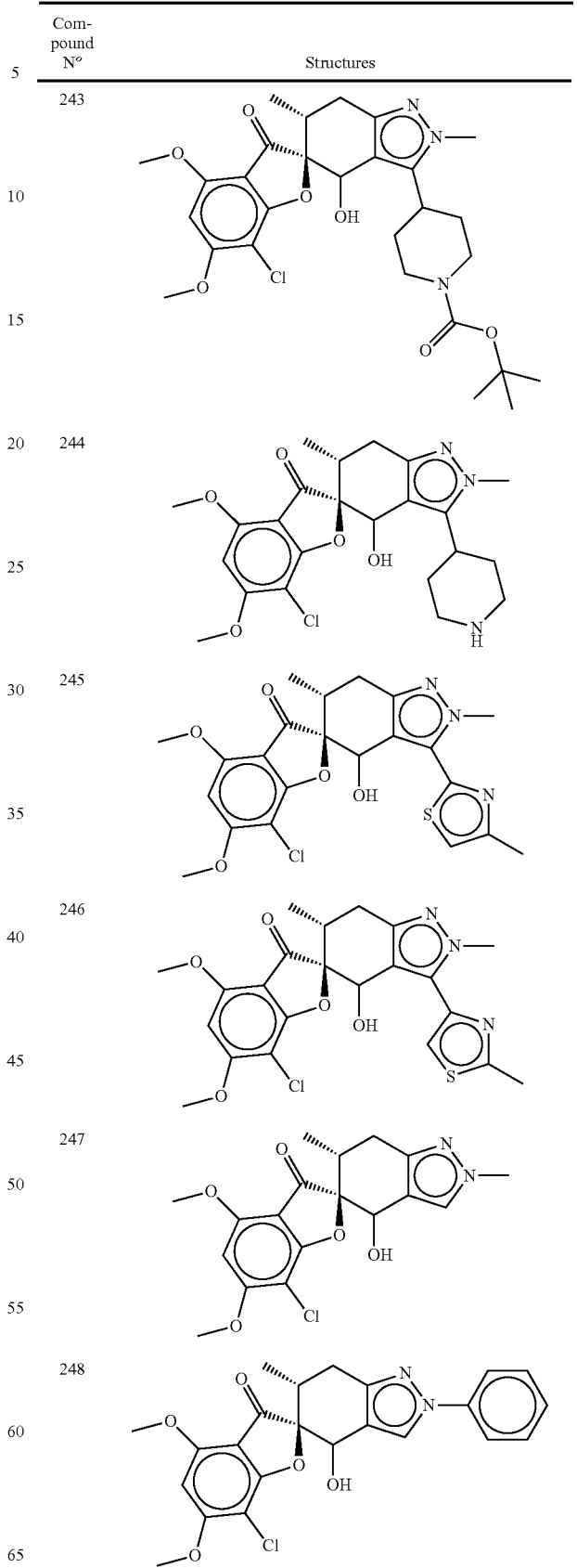

-continued
| Compound N° | Structures |
|---|---|
| 249 | 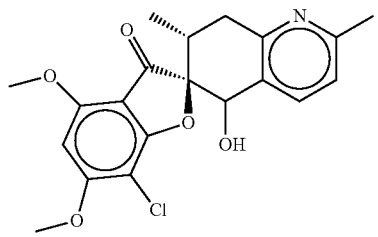 |
| 250 | 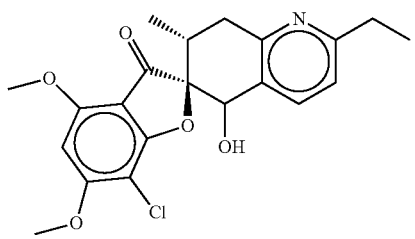 |
| 251 | 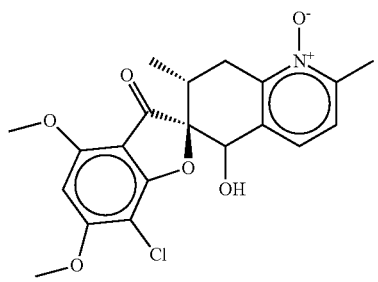 |
| 252 | 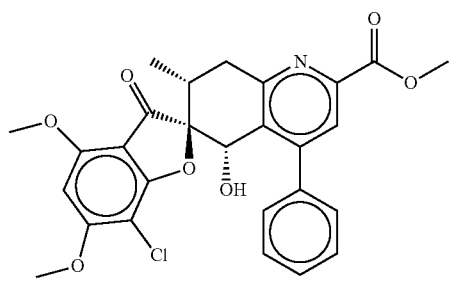 |
| 253 | 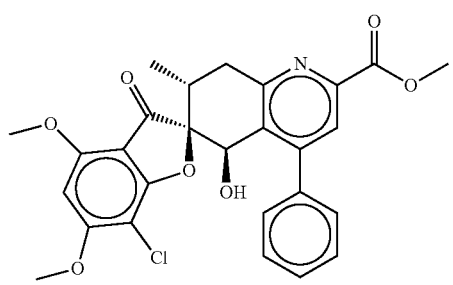 |
-continued
| Compound N° | Structures |
|---|---|
| 254 | 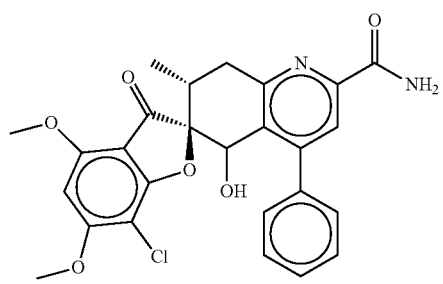 |
| 255 | 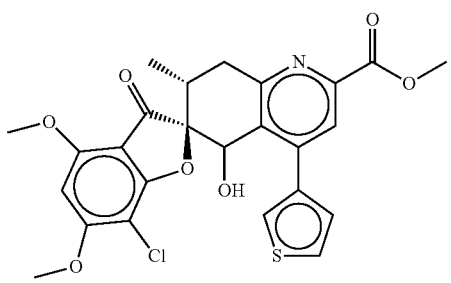 |
| 256 | 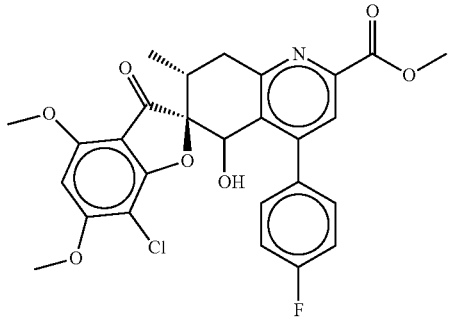 |
| 257 | 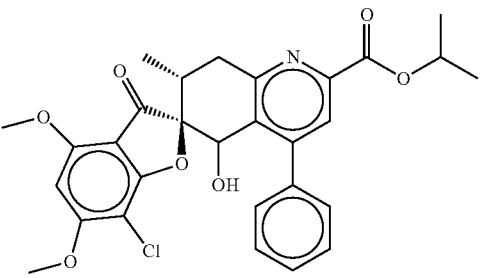 |
| 258 | 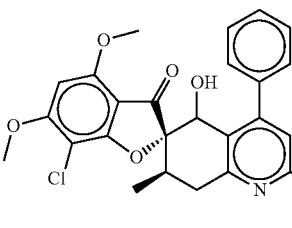 |

-continued

| Compound N° | Structures |
|---|---|
| 259 | 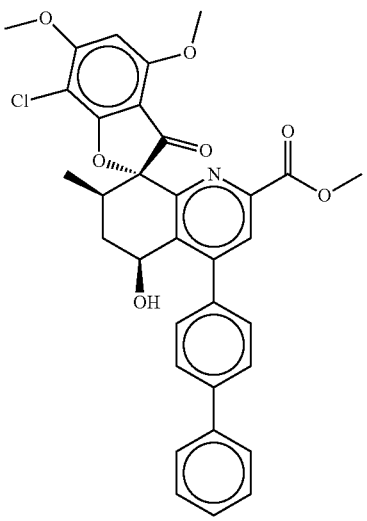 |
| 260 | 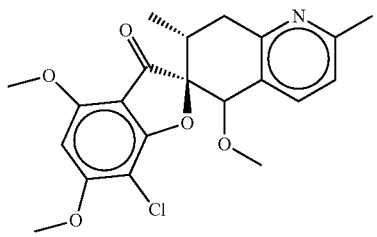 |
| 261 | 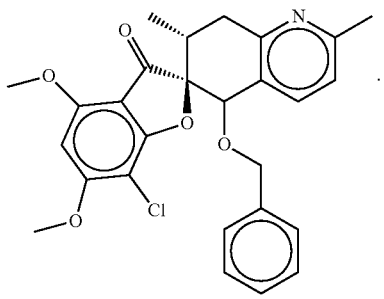 |

22. A pharmaceutical composition comprising at least one compound of formula (I):

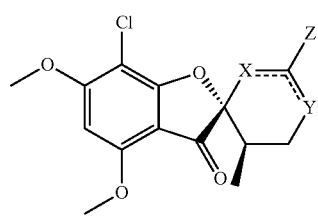

or a pharmaceutically acceptable salt thereof, wherein:

represents

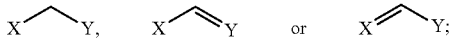

and

Y, together with Z and the carbon atom which carries Y and Z, forms an optionally substituted first carbocycle or first heterocycle,

represents

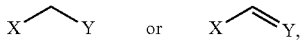

and X is $C=O$, $C=S$, $CH_2$, $CH-OR_1$, $CHN_3$, $CHNR_2R_3$, $C=N-OR_4$ or $C=N-NR_5R_6$; or X, together with Z and the carbon atom which carries X and Z, forms an optionally substituted second carbocycle or second heterocycle,

represents

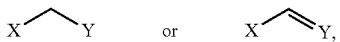

and Y is $C=O$, $C=S$, $CH_2$, $CH-OR_7$, $CHN_3$, $CHNR_8R_9$, $C=N-OR_{10}$ or $C=N-NR_{11}R_{12}$, and wherein:

$R_1$ to $R_5$ and $R_7$ to $R_{11}$ each independently representing a hydrogen atom or a $(C_1$-$C_6)$alkyl, aryl, $(C_1$-$C_6)$alkyl-aryl or aryl-$(C_1$-$C_6)$alkyl group; and $R_6$ and $R_{12}$ each independently representing a hydrogen atom or a $(C_1$-$C_6)$alkyl, aryl, $(C_1$-$C_6)$alkyl-aryl, aryl-$(C_1$-$C_6)$alkyl, $C(O)NH_2$ or $C(S)NH_2$ group;

and at least one pharmaceutically acceptable excipient.

23. A method for treating cancerous and pre-cancerous hyperproliferative pathologies selected from lung cancer, breast cancer, brain cancer and skin cancer, comprising the administration to a person in need thereof of an efficient dose of a compound of formula (I):

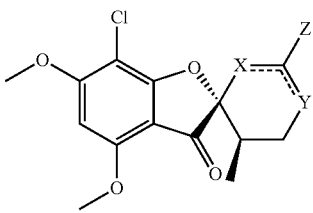

(I)

or a pharmaceutically acceptable salt thereof, wherein:

represents

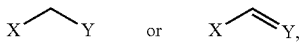

and

Y, together with Z and the carbon atom which carries Y and Z, forms an optionally substituted first carbocycle or first heterocycle,

represents

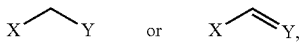

and X is $C=O$, $C=S$, $CH_2$, $CH-OR_1$, $CHN_3$, $CHNR_2R_3$, $C=N-OR_4$ or $C=N-NR_5R_6$; or X, together with Z and the carbon atom which carries X and Z, forms an optionally substituted second carbocycle or second heterocycle,

represents

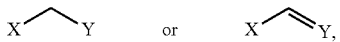

and Y is $C=O$, $C=S$, $CH_2$, $CH-OR_7$, $CHN_3$, $CHNR_8R_9$, $C=N-OR_{10}$ or $C=N-NR_{11}R_{12}$, and wherein:

$R_1$ to $R_5$ and $R_7$ to $R_{11}$ each independently representing a hydrogen atom or a ($C_1$-$C_6$)alkyl, aryl, ($C_1$-$C_6$)alkyl-aryl or aryl-($C_1$-$C_6$)alkyl group; and $R_6$ and $R_{12}$ each independently representing a hydrogen atom or a ($C_1$-$C_6$)alkyl, aryl, ($C_1$-$C_6$)alkyl-aryl, aryl-($C_1$-$C_6$)alkyl, $C(O)NH_2$ or $C(S)NH_2$ group.

24. The method according to claim 23, wherein the cancerous or pre-cancerous hyperproliferative pathology is skin cancer selected from actinic keratosis, solar keratosis, keratinocyte intraepithelial neoplasia, cutaneous papilloma, in situ squamous cell carcinoma, squamous cell carcinoma, pre-cancerous skin lesions, basal cell carcinoma, Bowen's disease, Dubreuilh's melanoma, condylomas, Merkel's cell tumour, Paget's disease, and cutaneous-mucosal lesions caused by human papilloma virus.

25. The method according to claim 24, wherein the skin cancer is basal cell carcinoma in surface and nodular forms.

* * * * *